US010184933B2

(12) United States Patent
Weinberger et al.

(10) Patent No.: US 10,184,933 B2
(45) Date of Patent: Jan. 22, 2019

(54) COMPOSITIONS, SYSTEMS AND METHODS FOR GENE EXPRESSION NOISE DRUG SCREENING AND USES THEREOF

(71) Applicant: The J. David Gladstone Institutes, San Francisco, CA (US)

(72) Inventors: Leor Weinberger, Oakland, CA (US); Roy Dar, Champaign, IL (US)

(73) Assignee: The J. David Gladstone Industries, San Francisco, CA (US)

( * ) Notice: Subject to any disclaimer, the term of this patent is extended or adjusted under 35 U.S.C. 154(b) by 18 days.

(21) Appl. No.: 15/026,225

(22) PCT Filed: Oct. 1, 2014

(86) PCT No.: PCT/US2014/058687
§ 371 (c)(1),
(2) Date: Mar. 30, 2016

(87) PCT Pub. No.: WO2015/051035
PCT Pub. Date: Apr. 9, 2015

(65) Prior Publication Data
US 2016/0245796 A1 Aug. 25, 2016

Related U.S. Application Data

(60) Provisional application No. 62/023,645, filed on Jul. 11, 2014, provisional application No. 61/885,464, filed on Oct. 1, 2013.

(51) Int. Cl.
*C12Q 1/68* (2018.01)
*G01N 33/50* (2006.01)
*C12Q 1/6897* (2018.01)
*C12Q 1/70* (2006.01)
*A61K 31/22* (2006.01)
*A61K 31/496* (2006.01)
*A61K 38/19* (2006.01)

(52) U.S. Cl.
CPC ......... *G01N 33/5023* (2013.01); *A61K 31/22* (2013.01); *A61K 31/496* (2013.01); *A61K 38/191* (2013.01); *C12Q 1/6897* (2013.01); *C12Q 1/703* (2013.01); *G01N 2333/16* (2013.01)

(58) Field of Classification Search
None
See application file for complete search history.

(56) References Cited

U.S. PATENT DOCUMENTS

2008/0118494 A1 5/2008 Kutsch et al.

FOREIGN PATENT DOCUMENTS

| WO | WO 2010/049182 A2 | 5/2010 |
| WO | WO 2010/049182 A3 | 5/2010 |
| WO | WO 2013/019710 A1 | 2/2013 |
| WO | WO 2013/148197 A1 | 10/2013 |

OTHER PUBLICATIONS

Boehm, Daniela et al., "BET bromodomain-targeting compounds reactive HIV from latency via a Tat-independent mechanism," Cell Cycle, Feb. 1, 2013, vol. 12, Issue 3, pp. 452-462.
Gallastegui, E. et al., "Combination of Biological Screening in a Cellular Model of Viral Latency and Virtual Screening Identifies Novel Compounds That Reactivate HIV-1," Journal of Virology, Apr. 2012, vol. 86, Issue 7, pp. 3795-3808.
Miller-Jensen, K. et al., "Genetic Selection for Context-Dependent Stochastic Phenotypes: Sp1 and TATA Mutations Increase Phenotypic Noise in HIV-1 Gene Expression," PLOS Computational Biology, Jul. 2013, vol. 9, Issue 7, e1003135.
Turano, A. et al., "Inhibitory Effect of Papaverine on HIV Replication in Vitro," AIDS Research and Human Retroviruses, Apr. 1989, vol. 5, No. 2, pp. 183-192.
Weinberger, L. et al., "Expression Noise and Acetylation Profiles Distinguish HDAC Functions," Molecular Cell, Jul. 27, 2012, vol. 47, pp. 193-202.
Blazkova, J. et al., "CpG Methylation Controls Reactivation of HIV from Latency," PLoS Pathog. Aug. 21, 2009 (Aug. 21, 2009), vol. 5, No. 8:e1000554, pp. 1-14.
Dar, R. et al., "Transcriptional burst frequency and burst size are equally modulated across the human genome," Proc. Natl .Acad. Sci,. Oct. 11, 2012 (Oct. 11, 2012), vol. 109, No. 43, pp. 17454-17459.
Weinberger, Leor;, et al., International Preliminary Report on Patentability for International Appl. No. PCT/US2014/058687, filed Oct. 1, 2014, dated Jan. 7, 2015, 3 pgs.
Weinberger, Leor, et al.. Written Opinion of the international Searching Authority for International Appl. No. PCT/US2014/058687, filed Oct. 1, 2014, dated Jan. 7, 2015, 130pgs.
Dar, R. et al., "Screening for Noise.in Gene Expression Identifies Drug Synergies," Science, Jun. 5, 2014 (Jun. 5, 2014); vol. 344, No. 6190, pp. 1392-1396.
Li, Z. et al., "The BET bromodomain inhibitor JQ1 activates HIV latency through antagonizing Brd4 inhibition of Tat-transactivation," Nucleic Acids Res. Oct. 18, 2012 (Oct. 18, 2014). vol. 41, No. 1, pp. 277-287.
Shishido. T. et al., "Selected Drugs with Reported Secondary Cell-Differentiating Capacity Prime Latent HIV-1 Infection.for Reactivation," J. Virol. Jun. 13, 2012 (Jun. 13, 2012), vol. 86, No. 17, pp. 9055-9069.
Dar, R. et al. (2012) Transcriptional burst frequency and burst size are equally modulated across the human genome. PNAS, 109(43): 17454-17459.

(Continued)

*Primary Examiner* — James S Ketter
(74) *Attorney, Agent, or Firm* — Taylor English Duma LLP; Siegfried J. W. Ruppert

(57) ABSTRACT

HIV-1's ability to enter a transcriptionally dormant state and establish a reservoir of latently infected cells is considered the major barrier to eradicating the virus from infected patients. Stochastic noise (i.e. fluctuations) in an HIV-1 transcriptional positive-feedback loop is one mechanism that enables HIV-1 to establish latency. Here, Applicants demonstrate that small-molecule modulation of noise in HIV-1 gene expression radically perturbs HIV-1 latency.

45 Claims, 41 Drawing Sheets

(56) References Cited

OTHER PUBLICATIONS

Dar, R. et al. (2014) Screening for Noise in Gene Expression Identifies Drug Synergies. Science, 344 (6190): 1392-1396. doi: 10 1126/science. 1250220.

Shishido, T. et al. (2012) Selected Drugs with Reported Secondary Cell-Differentiating Capacity Prime Latent HIV-1 Infection for Reactivation. Journal of Virology, 86 (17):9055-9069.

Li, Z et al. (2013) The BET bromodoman inhibitor JQ1 activates HIV latency through antagonizing Brd4 inhibition of Tat-transactivation Nucleic Acids Research, 41 (1) 277-287. doi 10.1093/nar/gks976.

Blazkova J. et al. (2009) CoG Methylation Controls Reactivation of HIV Latency. PloS Pathogens 5(8):e1000554. doi: 10.1371/journal.ppat. 1000554.

Written Opinion of the International Searching Authority for International App. No. PCT/US2014/058687, dated Jan. 7, 2015, 10 pages.

International Search Report for International App. No. PCT/US2014/058687, dated Jan. 7, 2015, 3 pages.

Step 1: Screening For Compounds That Modulate Variability Without Changing Mean Expression
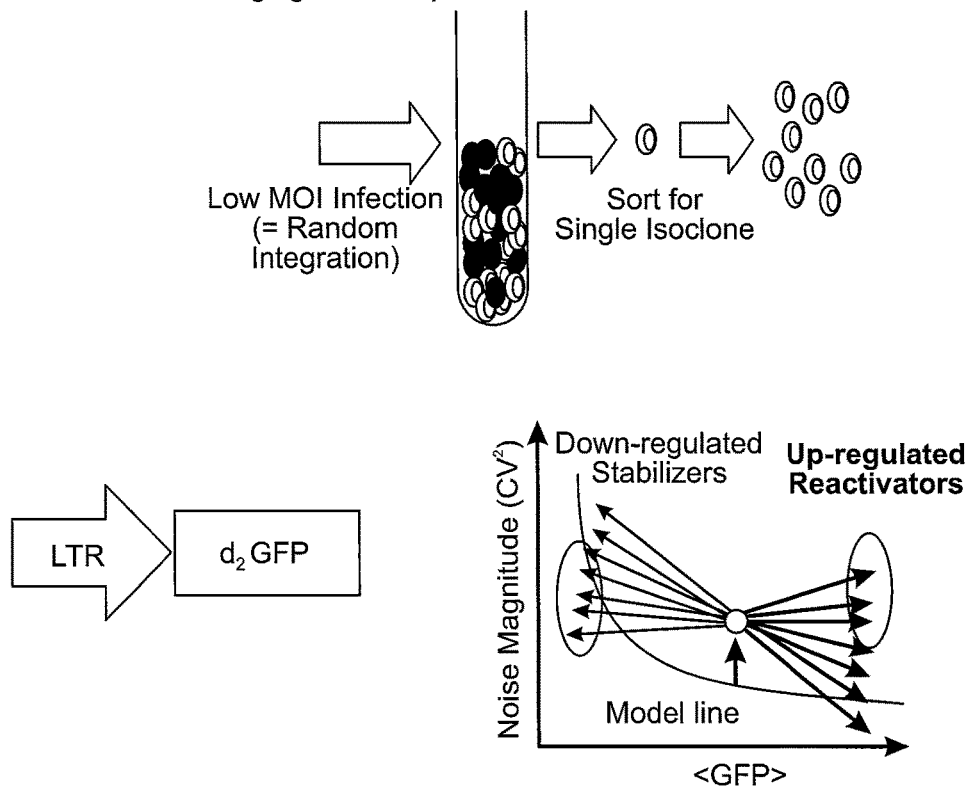
Step 2: Screening For Synergistic Reactivation of Latent HIV-1 Using Hits from Step 1
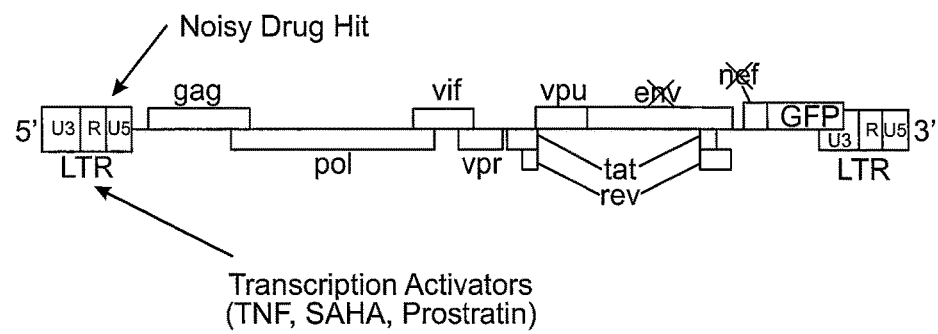
FIG. 5

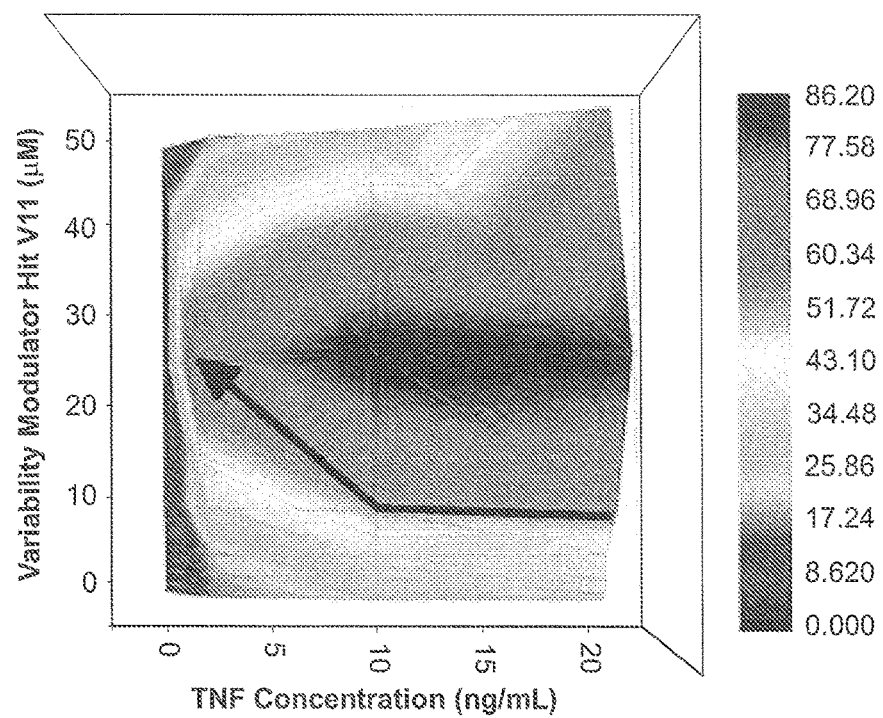
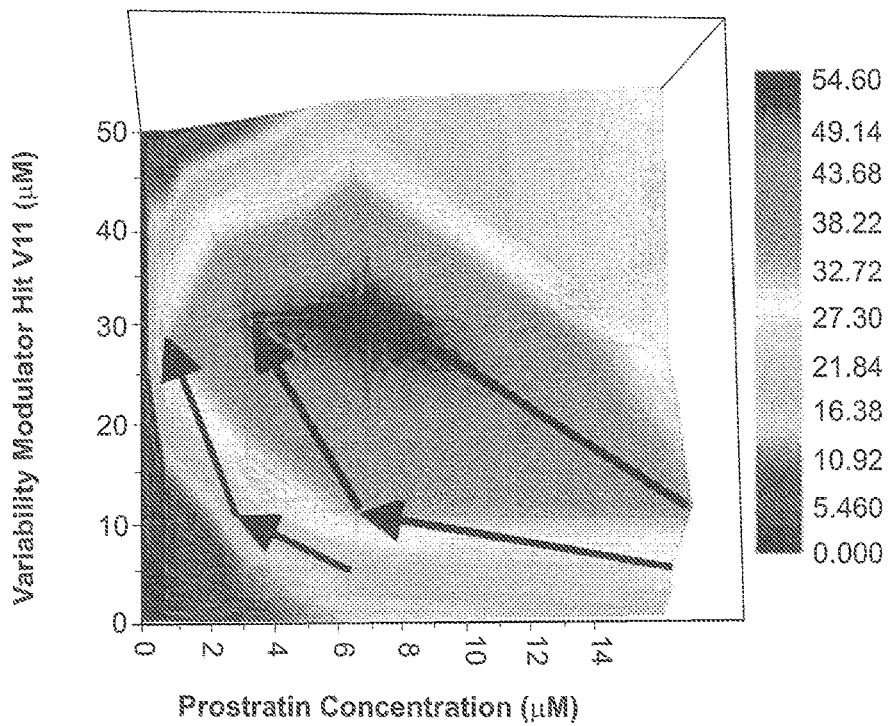
FIG. 7D

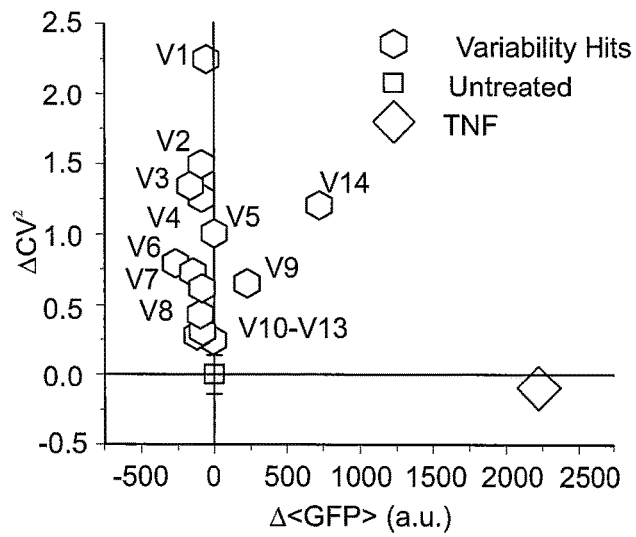

FIG. 8A

| VM ID # | Compound | Description |
|---|---|---|
| V1 | docetaxel | Microtubule Inhibitor, Chemotherapy |
| V2 | ethinyl estradiol | Activates ESR1 which binds Sp1 and p300 |
| V3 | estramustine | ESR1 agonist, also a Microtubule inhibitor |
| V4 | felbinac | Antiinflammatory |
| V6 | bezafibrate | Antilipemic agent that lowers cholesterol and triglycerides |
| V7 | mebendazole | Microtubule inhibitor |
| V9 | mercaptopurine | Purine nucleotide synthesis inhibitor and alters DNA/RNA synthesis, Inhibits IL-23 |
| V10 | dutasteride | Inhibits an estrogen antagonist(DHT) |
| V11 | cetirizine hydrochloride | Anti-histamine. Inhibitor of CCL11. Binds to CCR3. |
| V12 | acetophenazine maleate | Inhibitor of Dopamine Receptor D1 and D2 |
| V13 | oxytetracycline | Inhibitor of CCL5. Antibiotic, binds ribosomes and modulator of translational. |
| V14 | artemisinin | Antimalarial. Inhibitor of CDK2 (control of cell cycle) and SP1 |

FIG. 8B

| # | Overall Compound # in Screen | Alias | Formula | Bioactivity | # of +Σ in Cv2 of d₂GFP | # of +Σ in Cv2 of mCherry |
|---|---|---|---|---|---|---|
| 1 | 1396 | estramustine | 'C23H31Cl2NO3' | 'antineoplastic' | 24 | 0 |
| 2 | 1457 | griseofulvin | 'C17H17ClO6' | 'antifungal, inhibits mitosis in metaphase' | 19 | 1 |
| 3 | 1239 | telmisartan | 'C33H30N4O2' | 'antihypertensive, angiotensin II blocker' | 17 | 0 |
| 4 | 103 | docetaxel | 'C43H59NO17' | 'antineoplastic' | 17 | 0 |
| 5 | 160 | riboflavin | 'C17H20N4O6' | 'Vitamin B2; Vitamin cofactor; LD50(rat) 560 mg/kg ip' | 13 | 0 |
| 6 | 295 | pantothenic acid(d) na salt | 'C9H16NNaO5' | 'vitamin B5' | 12 | 1 |
| 7 | 1378 | mercaptopurine | 'C5H4N4S' | 'antineoplastic, purine antimetabolite' | 11 | 0 |
| 8 | 1395 | pemetrexed | 'C20H19N5Na2O6' | 'antineoplastic, thymidylate synthase inhibitor' | 11 | 0 |
| 9 | 487 | ethinyl estradiol | 'C20H24O2' | 'estrogen, plus progestogen as oral contraceptive' | 9 | 0 |
| 10 | 1851 | irinotecan hydrochloride | 'C33H39ClN4O6' | 'antineoplastic; topoisomerase I inhibitor' | 8 | 0 |
| 11 | 1294 | dutasteride | 'C27H30F6N2O2' | '5-alpha-reductase inhibitor' | 7 | 0 |
| 12 | 435 | felbinac | 'C14H12O2' | 'antiinflammatory' | 7 | 0 |
| 13 | 1293 | vincristine sulfate | 'C46H58N4O14S' | 'antineoplastic' | 7 | 1 |
| 14 | 1494 | thiram | 'C6H12N2S4' | 'antifungal' | 6 | 0 |
| 15 | 154 | bezafibrate | 'C19H20ClNO4' | 'antihyperlipidemic' | 6 | 0 |
| 16 | 542 | Indomethacin | 'C19H16ClNO4' | 'antiinflammatory, antipyretic, analgesic' | 6 | 1 |
| 17 | 86 | mebendazole | 'C16H13N3O3' | 'anthelmintic' | 5 | 0 |
| 18 | 722 | ouabain | 'C29H44O12' | 'antiarrhythmic, cardiotonic, hypertensive, Na/K ATPase inhibitor' | 5 | 0 |
| 19 | 1317 | sulfaquinoxaline sodium | 'C14H11N4NaO2S' | 'antibacterial' | 5 | 1 |

FIG. 10

| | | | | | | |
|---|---|---|---|---|---|---|
| 20 | 32 | oxybutynin chloride | 'C22H32ClNO3' | 'anticholinergic' | 5 | 0 |
| 21 | 211 | oxyphencyclimine | 'C20H29ClN2O3' | 'anticholinergic' | 5 | 0 |
| 22 | 1443 | saxagliptin hydrochloride | 'C18H25N3O2' | 'antidiabetic' | 5 | 1 |
| 23 | 1482 | phenylmercuric acetate | 'C8H8HgO2' | 'antifungal' | 5 | 0 |
| 24 | 174 | troclosene potassium | 'C3Cl2KN3O3' | 'antiinfective' | 5 | 0 |
| 25 | 1845 | artemisinin | 'C15H22O5' | 'antimalarial' | 5 | 0 |
| 26 | 419 | cytarabine | 'C9H13N3O5' | 'antineoplastic, antiviral; antimetabolite' | 5 | 1 |
| 27 | 663 | thioguanine | 'C5H5N5S' | 'antineoplastic, purine antimetabolite' | 5 | 0 |
| 28 | 1456 | hydroquinone | 'C6H6O2' | 'antioxidant' | 5 | 0 |
| 29 | 1158 | acetophenazine maleate | 'C27H33N3O6S' | 'antipsychotic' | 5 | 0 |
| 30 | 521 | hexylresorcinol | 'C12H18O2' | 'anthelmintic, topical antiseptic' | 4 | 0 |
| 31 | 1328 | oxytetracycline | 'C22H25ClN2O9' | 'antibacterial' | 4 | 0 |
| 32 | 367 | cefadroxil | 'C16H17N3O5S' | 'antibacterial' | 4 | 1 |
| 33 | 200 | tolnaftate | 'C19H17NOS' | 'antifungal' | 4 | 0 |
| 34 | 1247 | phenylbutyric acid | 'C10H11NaO2' | 'antihyperammonemic,antineoplastic' | 4 | 0 |
| 35 | 210 | atorvastatin calcium | 'C33H33CaFNO5' | 'antihyperlipidemic, HMGCoA reductase inhibitor' | 4 | 0 |
| 36 | 1530 | carboplatin | 'C6H12N2O4Pt' | 'antineoplastic, convulsant' | 4 | 0 |
| 37 | 1238 | 5-azacytidine | 'C8H12N4O5' | 'antineoplastic, pyrimidine antimetabolite' | 4 | 1 |
| 38 | 278 | levodopa | 'C9H11NO4' | 'antiparkinsonian' | 4 | 1 |
| 39 | 1275 | lamivudine | 'C8H11N3O3S' | 'antiviral' | 4 | 0 |
| 40 | 1230 | sotalol hydrochloride | 'C12H21ClN2O3S' | 'beta-adrenergic agonist' | 4 | 0 |
| 41 | 1191 | clavulanate lithium | 'C8H10LiNO5' | 'beta-lactamase inhibitor' | 4 | 0 |

FIG. 10 Cont'd

| | | | | | |
|---|---|---|---|---|---|
| 42 | 449 | digoxin sodium | 'C41H64O14' | 'cardiac stimulant' | 4 | 1 |
| 43 | 176 | monofluorophosphate sphate | 'FNa2O3P' | 'carries prophylactic' | 4 | 1 |
| 44 | 31 | dexpanthenol | 'C9H19NO4' | 'cholinergic' | 4 | 1 |
| 45 | 1179 | rabeprazole sodium | 'C18H20N3NaO3S' | 'gastric acid secretion inhibitor' | 4 | 0 |
| 46 | 1286 | cetirizine hydrochloride | 'C21H27Cl3N2O3' | 'H1 antihistamine' | 4 | 0 |
| 47 | 1455 | trilostane | 'C20H27NO3' | 'adrenocortical suppressant, antineoplastic, steroid biosynthesis inhibitor' | 3 | 0 |
| 48 | 1436 | modafinil | 'C15H15NO2S' | 'analeptic' | 3 | 0 |
| 49 | 1479 | thiabendazole | 'C10H7N3S' | 'anthelmintic' | 3 | 0 |
| 50 | 1386 | adapalene | 'C28H28O3' | 'anti-acne' | 3 | 0 |
| 51 | 114 | sulfameter | 'C11H12N4O3S' | 'antibacterial' | 3 | 0 |
| 52 | 959 | Fluoxetine hydrochloride | 'C17H19ClF3NO' | 'antidepressant' | 3 | 0 |
| 53 | 201 | trimethobenza mide hydrochloride | 'C21H29ClN2O5' | 'antiemetic' | 3 | 1 |
| 54 | 1371 | Metoclopramide hydrochloride | 'C14H23Cl2N3O2' | 'antiemetic' | 3 | 1 |
| 55 | 514 | guanethidine sulfate | 'C10H24N4O4S' | 'antihypertensive, mitotic agent' | 3 | 0 |
| 56 | 1664 | trichlormethine | 'C6H13Cl4N' | 'antineoplastic, cytotoxic' | 3 | 0 |
| 57 | 1510 | sucralfate | 'C12H46Al16Na8O75S8' | 'antiulcer' | 3 | 0 |
| 58 | 1087 | valganciclovir hydrochloride | 'C14H23ClN6O5' | 'antiviral' | 3 | 0 |
| 59 | 1207 | bemotrizinol | 'C38H49N3O5' | 'sunscreen' | 3 | 1 |
| 60 | 1444 | parachlorophenol | 'C6H5ClO' | 'topical antibacterial (topical)' | 3 | 0 |

FIG. 10 Cont'd

| | | | | | |
|---|---|---|---|---|---|
| 61 | 1459 | (A±)-Verapamil hydrochloride | 'C27H39ClN2O4' | 'adrenegic blocker, Ca channel blocker, coronary vasodilator, antiarrhythmic' | 2 | 1 |
| 62 | 573 | oxidopamine hydrochloride | 'C8H12ClNO3' | 'adrenergic agonist (opthalmic)' | 2 | 0 |
| 63 | 1408 | fomepizole | 'C4H6N2' | 'alcohol dehydrogenase inhibitor, antidote' | 2 | 1 |
| 64 | 126 | Xylazine hydrochloride | 'C12H16N2S' | 'analgesic' | 2 | 1 |
| 65 | 1160 | diperodon hydrochloride | 'C22H28ClN3O4' | 'analgesic, anesthetic' | 2 | 0 |
| 66 | 1203 | zomepirac sodium | 'C15H14ClNO3' | 'analgesic, antiinflammatory' | 2 | 1 |
| 67 | 1518 | closantel | 'C22H14Cl2I2N2O2' | 'anthelmintic' | 2 | 0 |
| 68 | 78 | fenbendazole | 'C15H13N3O2S' | 'anthelmintic' | 2 | 0 |
| 69 | 183 | finasteride | 'C23H36N2O2' | 'anti-androgen, alpha-reductase inhibitor' | 2 | 0 |
| 70 | 603 | Procainamide hydrochloride | 'C13H22ClN3O' | 'antiarrhythmic' | 2 | 0 |
| 71 | 921 | celecoxib | 'C17H14F3N3O2S' | 'antiarthritic, cyclooxygenase2 inhibitor' | 2 | 0 |
| 72 | 1182 | colistin sulfate | 'C52H102N16O21S2' | 'antibacterial' | 2 | 0 |
| 73 | 1265 | imipenem | 'C12H19N3O5S' | 'antibacterial' | 2 | 0 |
| 74 | 1269 | cefoxitin sodium | 'C16H16N3NaO7S2' | 'antibacterial' | 2 | 0 |
| 75 | 922 | azithromycin | 'C38H72N2O12' | 'antibacterial' | 2 | 0 |
| 76 | 399 | clidinium bromide | 'C22H26BrNO3' | 'anticholinergic' | 2 | 0 |
| 77 | 127 | Tolazamide | 'C14H21N3O3S' | 'antidiabetic' | 2 | 0 |
| 78 | 388 | chlorpheniramine maleate | 'C20H23ClN2O4' | 'antihistaminic' | 2 | 0 |
| 79 | 1521 | colesevalam hydrochloride (high mol wt copolymer @10mg/ml) | 'C31H72ClN4O' | 'antihyperlipidemic, cholesterol sequestrant' | 2 | 0 |

FIG. 10 Cont'd

| | | | | | |
|---|---|---|---|---|---|
| 80 | 1330 | Pargyline hydrochloride | 'C11H14ClN' | 'antihypertensive' | 2 | 0 |
| 81 | 525 | hydralazine hydrochloride | 'C8H9ClN4' | 'antihypertensive' | 2 | 0 |
| 82 | 1446 | anastrozole | 'C17H19N5' | 'antineoplastic' | 2 | 0 |
| 83 | 101 | vinorelbine | 'C45H54N4O8' | 'antineoplastic' | 2 | 0 |
| 84 | 215 | bleomycin (bleomycin b2 shown) | 'C58H94N20O26S4' | 'antineoplastic' | 2 | 0 |
| 85 | 107 | dasatinib | 'C22H28ClN7O3S' | 'antineoplastic' | 2 | 0 |
| 86 | 356 | busulfan | 'C6H14O6S2' | 'antineoplastic, alkylating agent' | 2 | 1 |
| 87 | 99 | vorinostat | 'C14H20N2O3' | 'antineoplastic, histone deacetylase inhibitor' | 2 | 1 |
| 88 | 929 | selamectin | 'C43H63NO11' | 'antiparasitic, antimite' | 2 | 0 |
| 89 | 1277 | idoxuridine | 'C9H11IN2O5' | 'antiviral' | 2 | 0 |
| 90 | 978 | carvedilol | 'C24H26N2O4' | 'beta-adrenergic blocker' | 2 | 0 |
| 91 | 549 | Isoproterenol (±)- hydrochloride | 'C11H18ClNO3' | 'bronchodilator' | 2 | 0 |
| 92 | 1414 | racephedrine hydrochloride | 'C10H16ClNO' | 'bronchodilator, decongestant' | 2 | 0 |
| 93 | 412 | vardenafil hydrochloride | 'C23H33ClN6O4S' | 'erectile dysfunction, PD5 inhibitor' | 2 | 0 |
| 94 | 1906 | guaiacol | 'C7H8O2' | 'expectorant' | 2 | 0 |
| 95 | 940 | clobetasol propionate | 'C25H32ClFO5' | 'glucocorticoid, antiinflammatory' | 2 | 0 |
| 96 | 718 | mycophenolic acid | 'C17H20O6' | 'immune suppressant, antineoplastic, antiviral' | 2 | 1 |
| 97 | 494 | fludrocortisone acetate | 'C23H31FO6' | 'mineralocorticoid' | 2 | 0 |
| 98 | 1442 | zaleplon | 'C17H15N5O' | 'sedative, hypnotic' | 2 | 0 |
| 99 | 1411 | nitroglycerin | 'C3H5N3O9' | 'vasodilator (coronary)' | 2 | 0 |

FIG. 10 Cont'd

| | | | | |
|---|---|---|---|---|
| 100 | 1169 | riboflavin 5-phosphate sodium | 'C17H20N4NaO9P' | 'vitamin, enzyme cofactor' | 2 | 0 |
| 101 | 956 | acetriazoic acid | 'C9H6I3NO3' | 'X-ray contrast medium' | 2 | 1 |
| 102 | 448 | digitoxin | | Inhibitor of Sodium/potassium -transporting ATPase alpha1 chain, the active enzyme that catalyzes the hydrolysis of ATP | 4 | 2 |
| 103 | 1682 | carnitine hydrochloride | | Regulates Energy Metabolism, required for transport of fatty acids from cytosol into mitochondria for generation of metabolic energy | 4 | 2 |
| 104 | 701 | albendazole | | Mitochondrial Inhibitor, inhibits both respiration and glycolysis leading to a decrease in cellular ATP | 2 | 2 |
| 105 | 1083 | taurine | | Mitosis, chromosome segregation, and cell cycle blocker arresting the cell cycle at the G2/M phase | 8 | 3 |
| 106 | 938 | Taxol | | Inhibitor of DNA synthesis, nuclear division | 6 | 6 |
| 107 | 296 | mitomycin c | | purine nucleoside antimetabolite, DNA synthesis inhibition by inhibiting synthesis of nucleic acids, implications to cell growth and division | 6 | 3 |
| 108 | 91 | clofarabine | | An essential amino acid involved in many things.... cell division is one. | 5 | 2340 |
| 109 | 1303 | arginine hydrochloride | | Inhibits DNA replication and cell division, alkylating agent adds an alkyl group (CnH2n+1) to DNA | 3 | 3 |
| 110 | 1509 | tetramizole hydrochloride | | DNA synthesis and methylation inhibitor, Chemodrug | 11 | 7 |
| 111 | 1228 | thiostrepton | | Inhibitor of DNA and RNA synthesis, antineoplastic | 12 | 5 |
| 112 | 1815 | lonidamine | | modulates apoptosis in some cells; functions in many metabolic activities; | 11 | 13 |
| 113 | 10 | melphalan | | Inhibits growth and microtubule assembly in humans, reduces ATP production, treatment of a variety of worm infestations | 8 | 3 |

FIG. 10 Cont'd

| | | | | |
|---|---|---|---|---|
| 114 | 1137 | fludarabine phosphate | Antibiotic; inhibiting the proinflammatory transcription factor NF-kappa B (NF-κB), PXR activator and affects transcription, Bacterial RNA Pol Inhibitor | 3 | 3 |
| 115 | 18 | methotrexate(+/-) | phosphatase inhibitor, Posttranslational Modifier | | 2 |
| 116 | 248 | rifaximin | Inhibits Translation | 2 | 2 |
| 117 | 271 | Arecoline hydrobromide | Anthelmintic | 7 | 2 |
| 118 | 1301 | zalcitabine | HIV RTInhibitor, nucleoside analog reverse transcriptase inhibitor (NARTI) | 6 | 13 |
| 119 | 854 | erythrosine sodium | Potentially fluorescent... | 5 | 5 |
| 120 | 185 | nikethamide | | 3 | 10 |
| 121 | 1121 | oxfendazole | | 3 | 7 |
| 122 | 381 | editol | | 2 | 5 |
| 123 | 1288 | doxapram hydrochloride | | 2 | 5 |
| 124 | 740 | aminacrine | matrix substance for MALDI-MS | 2 | 3 |
| 125 | 1434 | dobutamine hydrochloride | | 2 | 2 |
| 126 | 1439 | rutin | | 2 | 2 |

FIG. 10 Cont'd

| # | VE ID in Screen | Alias | Synergy with TNF in JLat 8.6 | Synergy with Prostratin in JLat 8.6 | Formula | Molwt | Bioactivity |
|---|---|---|---|---|---|---|---|
| 1 | V1 | docetaxel | Yes | Yes | 'C43H59NO17' | | 'antineoplastic' |
| 2 | V2 | ethinyl estradiol | Yes | Yes | 'C20H24O2' | | 'estrogen, plus progestogen as oral contraceptive' |
| 3 | V3 | estramustine | No | No | 'C23H31Cl2NO3' | | 'antineoplastic' |
| 4 | V4 | felbinac | Yes | Yes | 'C14H12O2' | 308.82977 | 'beta-adrenergic agonist' |
| 5 | V6 | bezafibrate | Yes | Yes | 'C19H20ClNO4' | 273.3563 | 'analeptic' |
| 6 | V7 | mebendazole | Yes | Yes | 'C16H13N3O3' | 371.26354 | 'antineoplastic, convulsant' |
| 7 | V8 | thiamylal sodium | Yes | Yes | | 186.18777 | 'antihyperammonemic,antineoplastic' |
| 8 | V9 | mercaptopurine | Yes | Yes | 'C5H4N4S' | 663.08388 | 'anthelmintic' |
| 9 | V10 | dutasteride | Yes | Yes | 'C27H30F6N2O2' | | '5-alpha-reductase inhibitor' |
| 10 | V11 | cetirizine hydrochloride | Yes | Yes | 'C21H27Cl3N2O3' | 195.69393 | 'antihypertensive' |
| 11 | V12 | acetophenazine maleate | Yes | Yes | 'C27H33N3O6S' | 552.39869 | 'antihyperlipidemic, cholesterol sequestrant' |
| 12 | V13 | oxytetracycline | Yes | Yes | 'C22H25ClN2O9' | 556.86627 | 'X-ray contrast medium' |
| 13 | V14 | artemisinin | Yes | Yes | 'C15H22O5' | 390.82961 | 'antiviral' |
| 14 | V17 | hydralazine hydrochloride | Yes | No | 'C8H9ClN4' | 769.98166 | 'antiparasitic, antimite' |
| 15 | V18 | Indomethacin | Yes | No | 'C19H16ClNO4' | | 'antiinflammatory, antipyretic, analgesic' |
| 16 | V20 | atorvastatin calcium | Yes | No | 'C33H33CaFNO5' | | 'antihyperlipidemic, HMGCoA reductase inhibitor' |
| 17 | V21 | guanethidine sulfate | Yes | No | 'C10H24N4O4S' | | 'antihypertensive, mitotic agent' |
| 18 | V22 | pantothenic acid(d) na salt | Yes | No | 'C9H16NNaO5' | | 'vitamin B5' |

FIG. 11

| | | | | | | |
|---|---|---|---|---|---|---|
| 19 | V23 | saxagliptin | Yes | No | 'C18H25N3O2' | 128.55915 | 'topical antibacterial (topical)' |
| 20 | V24 | (Å±)-Verapamil hydrochloride | Yes | Yes | 'C27H39ClN2O4' | 471.38393 | 'antineoplastic, thymidylate synthase inhibitor' |
| 21 | V25 | oxidopamine hydrochloride | No | Yes | 'C8H12ClNO3' | 271.79279 | 'antiarrhythmic' |
| 22 | V26 | trilostane | Yes | No | 'C20H27NO3' | | |
| 23 | V27 | fomepizole hydrochloride | Yes | No | 'C4H6N2' | 424.92868 | 'antiemetic' |
| 24 | V28 | modafinil | Yes | Yes | 'C15H15NO2S' | 466.98219 | 'glucocorticoid, antiinflammatory' |
| 25 | V29 | Xylazine hydrochloride | No | No | 'C12H16N2S' | 393.95824 | 'anticholinergic' |
| 26 | V30 | diperodon hydrochloride | Yes | No | 'C22H28ClN3O4' | 194.27606 | 'anthelmintic, topical antiseptic' |
| 27 | V31 | zomepirac sodium | Yes | Yes | 'C15H14ClNO3' | 449.43962 | 'antibacterial' |
| 28 | V33 | thiabendazole | No | Yes | 'C10H7N3S' | 412.53356 | 'anti-acne' |
| 29 | V34 | closantel | Yes | Yes | 'C22H14Cl2I2N2O2' | 305.342 | 'sedative, hypnotic' |
| 30 | V35 | hexylresorcinol | Yes | Yes | 'C12H18O2' | | |
| 31 | V36 | adapalene | Yes | Yes | 'C28H28O3' | 205.64274 | 'adrenergic agonist (opthalmic)' |
| 32 | V37 | finasteride | No | No | 'C23H36N2O2' | 2262.58982 | 'antiulcer' |
| 33 | V38 | Procainamide hydrochloride | Yes | Yes | 'C13H22ClN3O' | 525.07426 | 'erectile dysfunction, PD5 inhibitor' |
| 34 | V40 | cefadroxil | No | No | 'C16H17N3O5S' | | |
| 35 | V41 | sulfameter | No | No | 'C11H12N4O3S' | 247.72401 | 'bronchodilator' |
| 36 | V42 | sulfaquinoxaline sodium | Yes | No | 'C14H11N4NaO2S' | 406.48582 | 'beta-adrenergic blocker' |
| 37 | V43 | azithromycin | Yes | Yes | 'C38H72N2O12' | 354.10282 | 'antiviral' |
| 38 | V44 | imipenem | Yes | Yes | 'C12H19N3O5S' | 749.00374 | 'antibacterial' |
| 39 | V45 | colistin sulfate | No | No | 'C52H102N16O21S2' | 336.26431 | 'antiemetic' |
| 40 | V46 | cefoxitin sodium | Yes | Yes | 'C16H16N3NaO7S2' | 207.1116 | 'beta-lactamase inhibitor' |
| 41 | V47 | oxyphencyclimine hydrochloride | No | No | 'C20H29ClN2O3' | 293.37448 | 'antineoplastic' |
| 42 | V48 | oxybutynin chloride | No | Yes | 'C22H32ClNO3' | 201.25139 | 'anthelmintic' |
| 43 | V49 | clidinium bromide | No | Yes | 'C22H26BrNO3' | 317.36633 | 'antibacterial' |
| 44 | V50 | Fluoxetine hydrochloride | Yes | No | 'C17H19ClF3NO' | 229.25917 | 'antiviral' |

FIG. 11 Cont'd

| # | ID | Name | | | Formula | MW | Category |
|---|---|---|---|---|---|---|---|
| 45 | V51 | Tolazamide | No | No | 'C14H21N3O3S' | 432.36142 | 'anticholinergic' |
| 46 | V52 | trimethobenzamide hydrochloride | Yes | Yes | 'C21H29ClN2O5' | 291.73673 | 'analgesic, antiinflammatory' |
| 47 | V53 | Metoclopramide hydrochloride | Yes | Yes | 'C14H23Cl2N3O2' | | |
| 48 | V54 | tolnaftate | No | No | 'C19H17NOS' | 627.83133 | 'sunscreen' |
| 49 | V58 | chlorpheniramine maleate | No | No | 'C20H23ClN2O4' | 227.088 | 'vasodilator (coronary)' |
| 50 | V59 | phenylbutyric acid | Yes | Yes | 'C10H11NaO2' | 514.63265 | 'antihypertensive, angiotensin II blocker' |
| 51 | V60 | colesevalam hydrochloride (high mol wt copolymer @10mg/ml) | Yes | Yes | 'C31H72ClN4O' | 491.07588 | 'adrenegic blocker, Ca channel blocker, coronary vasodilator, antiarrhythmic' |
| 52 | V61 | Pargyline hydrochloride | Yes | Yes | 'C11H14ClN' | 197.19232 | 'antiparkinsonian' |
| 53 | V62 | telmisartan | Yes | Yes | 'C33H30N4O2' | 124.14061 | 'expectorant' |
| 54 | V63 | troclosene potassium | No | No | 'C3Cl2KN3O3' | 322.32317 | 'antibacterial' |
| 55 | V66 | bleomycin (bleomycin b2 shown) | No | No | 'C58H94N20O26S4' | 82.10582 | 'alcohol dehydrogenase inhibitor, antidote' |
| 56 | V67 | dasatinib | Yes | No | 'C22H28ClN7O3S' | 329.44309 | 'adrenocortical suppressant, antineoplastic, steroid biosynthesis inhibitor' |
| 57 | V68 | anastrozole | Yes | Yes | 'C17H19N5' | | |
| 58 | V69 | busulfan | No | No | 'C6H14O6S2' | 201.69812 | 'bronchodilator, decongestant' |
| 59 | V71 | carboplatin | Yes | Yes | 'C6H12N2O4Pt' | 381.4322 | 'gastric acid secretion inhibitor' |
| 60 | V74 | pemetrexed | Yes | Yes | 'C20H19N5Na2O6' | 320.34535 | 'immune suppressant, antineoplastic, antiviral' |
| 61 | V76 | hydroquinone | No | No | 'C6H6O2' | 433.93916 | 'analgesic, anesthetic' |
| 62 | V77 | selamectin | No | Yes | 'C43H63NO11' | 380.91873 | 'anticholinergic' |
| 63 | V78 | levodopa | No | Yes | 'C9H11NO4' | 236.05975 | 'antiinfective' |
| 64 | V79 | sucralfate | Yes | Yes | 'C12H46Al16Na8O75S8' | 372.55557 | 'anti-androgen, alpha-reductase inhibitor' |
| 65 | V80 | valganciclovir hydrochloride | Yes | Yes | 'C14H23ClN6O5' | | |
| 66 | V81 | lamivudine | Yes | Yes | 'C8H11N3O3S' | 246.30288 | 'antineoplastic, alkylating agent' |
| 67 | V82 | idoxuridine | Yes | Yes | 'C9H11IN2O5' | 390.87031 | 'antihistaminic' |

FIG. 11 Cont'd

| | | | | | |
|---|---|---|---|---|---|
| 68 | V83 | sotalol hydrochloride | Yes | Yes | 'C12H21ClN2O3S' | 110.11352 | 'antioxidant' |
| 69 | V84 | carvedilol | Yes | Yes | 'C24H26N2O4' | 345.79528 | 'antidepressant' |
| 70 | V85 | clavulanate lithium | Yes | Yes | 'C8H10LiNO5' | | |
| 71 | V86 | (Â±)-Isoproterenol hydrochloride | Yes | Yes | 'C11H18ClNO3' | 363.39499 | 'antibacterial' |
| 72 | V87 | racephedrine hydrochloride | Yes | No | 'C10H16ClNO' | 205.25608 | 'cholinergic' |
| 73 | V89 | sodium monofluorophosphate | No | No | 'FNa2O3P' | 1615.77028 | 'antineoplastic' |
| 74 | V90 | dexpanthenol | No | No | 'C9H19NO4' | 280.30729 | 'antibacterial' |
| 75 | V91 | vardenafil hydrochloride | Yes | Yes | 'C23H33ClN6O4S' | 422.49832 | 'mineralocorticoid' |
| 76 | V92 | guaiacol | Yes | No | 'C7H8O2' | 143.95 | 'carries prophylactic' |
| 77 | V93 | rabeprazole sodium | Yes | No | 'C18H20N3NaO3S' | 1351.61534 | 'antibacterial' |
| 78 | V94 | clobetasol propionate | Yes | Yes | 'C25H32ClFO5' | 307.41744 | 'antifungal' |
| 79 | V95 | mycophenolic acid | Yes | No | 'C17H20O6' | 311.40577 | 'antidiabetic' |
| 80 | V96 | fludrocortisone acetate | No | No | 'C23H31FO6' | 220.33872 | 'analgesic' |
| 81 | V97 | zaleplon | Yes | Yes | 'C17H15N5O' | | |
| 82 | V98 | bemotrizinol | Yes | Yes | 'C38H49N3O5' | | |
| 83 | V99 | parachlorophenol | Yes | Yes | 'C6H5ClO' | | |
| 84 | V100 | nitroglycerin | Yes | Yes | 'C3H5N3O9' | | |
| 85 | V102 | acetrizoic acid | Yes | Yes | 'C9H6I3NO3' | 506.03056 | 'antineoplastic' |

FIG. 11 Cont'd

| # | Overall Compound # in Screen | Alias | # of -Σ in $CV^2$ of $d_2$GFP | # of -Σ in $CV^2$ of mcherry |
|---|---|---|---|---|
| 1 | 1202 | manidipine hydrochloride | 2 | 0 |
| 2 | 1532 | phenothiazine | 2 | 0 |
| 3 | 1435 | dichlorvos | 2 | 0 |
| 4 | 1505 | fipronil | 2 | 0 |
| 5 | 1511 | trichlorfon | 2 | 0 |
| 6 | 1162 | benzydamine hydrochloride | 3 | 0 |
| 7 | 1365 | maprotiline hydrochloride | 2 | 2 |
| 8 | 1329 | Papaverine hydrochloride | 3 | 1 |
| 9 | 1514 | arsenic trioxide | 2 | 0 |
| 10 | 1310 | phenformin hydrochloride | 3 | 0 |
| 11 | 1167 | itraconazole | 2 | 0 |
| 12 | 1490 | cycloheximide | 2 | 0 |
| 13 | 1377 | hydroxyprogesterone caproate | 2 | 2 |
| 14 | 1468 | pyrithione zinc | 2 | 0 |
| 15 | 1290 | meclocycline sulfosalicylate | 5 | 3 |
| 16 | 1402 | ergotamine tartrate | 2 | 5 |
| 17 | 714 | adenosine phosphate | 2 | 2 |
| 18 | 1555 | broxaldine | 2 | 2 |

FIG. 12

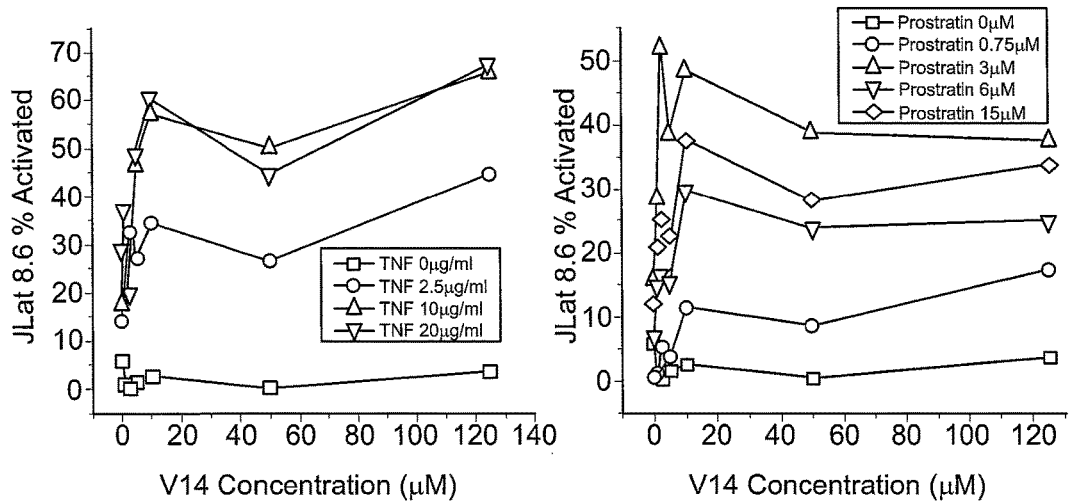
FIG. 14A
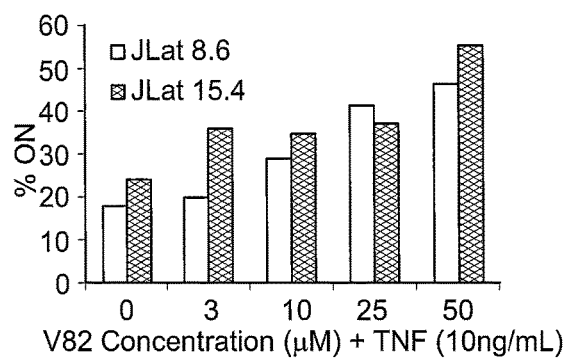
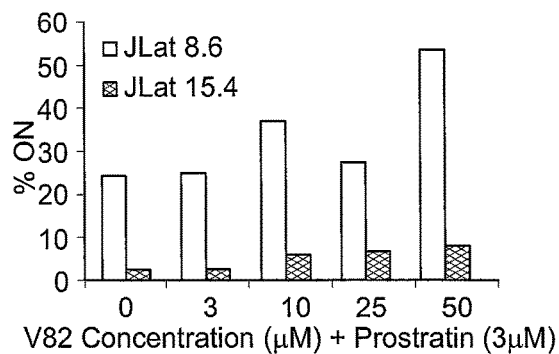
FIG. 14B

| ID # | Compound | Description |
|---|---|---|
| V1 | docetaxel | Anti-mitotic chemotherapy drug, microtubule inhibitor |
| V2 | ethinyl estradiol | Evidence for Inhibition, Activation, and Binding of Estrogen Receptor |
| V3 | estramustine | Microtubule Depolarization via binding of tubulin and associated proteins |
| V4 | felbinac | Antiinflammatory |
| V6 | bezafibrate | Antilipemic agent that lowers cholesterol and triglycerides |
| V7 | mebendazole | Microtubule Inhibitor |
| V8 | thiamylal sodium | |
| V9 | mercaptopurine | Purine nucleotide synthesis inhibitor and alters DNA/RNA synthesis |
| V10 | dutasteride | Inhibits the conversion of testosterone into dihydrotestosterone(DHT), an estrogen antagonist |
| V11 | cetirizine hydrochloride | Anti-histamine. Inhibitor of CCL11 |
| V12 | acetophenazine maleate | Inhibitor of Dopamine Receptor D1 and D2 |
| V13 | oxytetracycline | Antibiotic, binds ribosomes and modulator of translational inhibitor of CCL5 |
| V14 | artemisinin | Antimalarial. Inhibitor of CDK2(control of cell cycle) and SP1 |
| Literature Reported NEs | JQ1 | Bromodomain Protein Inhibitor |
| | AZA | DNA Methyltransferase Inhibitor |
| | TSA | Histone Deacytalase Inhibitor (HDACi) |
| | SAHA | Histone Deacytalase Inhibitor (HDACi) |
| | VPA | Histone Deacytalase Inhibitor (HDACi) |
| | MS-275 | Histone Deacytalase Inhibitor (HDACi) |
| Activators | TNF | Activator of NF-Kb |
| | Prostratin | PKC Agonist, Activator of NF-Kb |
| | PMA | PKC Agonist, Activator of NF-Kb |

FIG. 15

COMPOSITIONS, SYSTEMS AND METHODS FOR GENE EXPRESSION NOISE DRUG SCREENING AND USES THEREOF

CROSS-REFERENCE TO RELATED APPLICATIONS

This application is claiming priority to U.S. provisional application. Ser. No. 61/885,464, entitled "Gene Expression Noise Drug Screening For Reactivation Of Latent HIV-1," filed Oct. 1, 2013, and U.S. provisional application. Ser. No. 62/023,645, entitled "Compositions And Methods For Screening For Noise In Gene Expression To Identify Drug Synergies," filed Jul. 1, 2014, the disclosures of which are incorporated herein by reference in their entirety for all purposes.

STATEMENT REGARDING FEDERALLY SPONSORED RESEARCH

This invention was made with Government support under Grant Nos. D006677 and AI104380, awarded by the National Institutes of Health. The Government has certain rights in the invention.

FIELD OF THE INVENTION

The present invention relates to compositions, systems and methods of screening for compounds that modulate variability of expression of a target gene promoter allowing enhanced or decreased gene expression from that promoter. Small molecule compounds and other compounds identified by a subject method are useful to enhance gene expression fluctuations from any given promoter, e.g., an HIV-1 promoter. The present invention also relates to compositions, systems and methods useful for the reactivation of latent HIV-1 reservoirs that may persist despite highly active antiretroviral therapy (HAART) and subsequent elimination thereof. The present invention also provides compositions, systems and methods useful for suppressing reactivation of a latent HIV-1 reservoir.

BACKGROUND OF THE INVENTION

Human Immunodeficiency Virus Type 1 (HIV-1) is the etiologic agent that is responsible for AIDS, a syndrome characterized by depletion of $CD4^+$ T-lymphocytes and collapse of the immune system. HIV-1 infection is pandemic and HIV-associated diseases have become a world-wide health problem. Upon infection, HIV-1 integrates into the cellular genome of an infected cell. HIV-1 infection then leads to two different scenarios: productive infection and latent infection. Productive infection occurs most frequently and leads to death of the infected cell after release of progeny virus. During latent infection, which is rare, HIV-1 genes are not expressed after proviral integration, resulting in an infected cell that is characterized by transcriptionally silent HIV-1 genes. These fully replication-competent HIV-1 can persist dormant in cells for several years and then become reactivated (Chun et al, 1995, *Nature Med* 1(12): 1284-1290; Chun et al., 1997, *Proc Natl Acad Sci USA* 94(24):13193-13197; for review, see Bisgrove, 2005, *Expert Rev Anti Infect Ther* 3(5):805-814).

Current treatments of AIDS typically seek to block one or more steps involved in the production of viral particles. Treatment options involve administration of reverse transcriptase inhibitors, inhibitors of viral protease, fusion, entry, or integration inhibitors in different combinations to block multiple steps in the viral life cycle. This approach, termed highly active antiviral therapy (HAART) has greatly decreased morbidity and mortality in people infected with HIV-1 (Palella et al., 1998, *N Engl J Med* 338(13):855-860).

However, long-term follow-up studies have shown that HAART alone is not effective in completely eliminating HIV-1 in infected patients. In most cases, upon ceasing HAART, a rapid rebound in viremia occurs even after years of successful treatment with undetectable viral loads (Davey et al, 1999, *Proc Natl Acad Sci USA* 96(26):15109-15114; Cohen and Fauci, 2001, *Adv Intern Med* 46:207-246). The rebound in viremia is believed to be due at least in part to the reactivation of latent HIV-1. Latent forms of are not sensitive to HAART because these drugs (e.g., reverse transcriptase inhibitors, viral protease inhibitors) are only active against actively replicating forms of HIV-1. Although the frequency of latently-infected cells is only about 0.03-3 infectious units per million resting $CD4^+$T-cells (Siliciano et al., 2003, *Nature Med* 9(6):727-728), this latent population of HIV-1 serves as a source of virus for reseeding the infection after discontinuation of HAART. Due to the longevity of this latent HIV-1 reservoir, it is unlikely that HAART alone can ever clear it completely (Siliciano et al., ibid).

HIV-1 latency is closely tied to expression of HIV-1 genes, i.e., to HIV-1 transcription, which initiates at a promoter located in the 5' LTR driving transcription of the viral genome. The LTR comprises essentially 4 regions: a negative regulatory element (NRE), an enhancer region, a core promoter and a 5' untranslated region (UTR) (for review, see Bisgrove, 2005, *Expert Rev Anti Infect Ther* 3(5):805-814). Of particular interest for reactivation of HIV-1 expression is the enhancer region, which can be subdivided into a distal and proximal region. Several transcription factors bind to these regions. For example, Ets-1 and LEF-1 bind to the distal enhancer region, while the inducible transcription factors nuclear factor-kappa B (NF-κB) and NF-AT bind to and reactivate HIV-1 transcription from the proximal enhancer.

Select viral proteins are also involved in reactivation of HIV-1 gene transcription. For example, one of the early proteins expressed from the HIV-1 genome is Tat, a viral transactivator that binds to an RNA recognition element (TAR) present in all viral transcripts and primarily drives high level of HIV-1 expression by enhancing transcriptional elongation by RNA polymerase II after binding to the HIV-1 LTR.

Recently, several lines of evidence pointed to an inhibitory effect of chromatin on HIV-1 gene expression initiated on the integrated HIV-1 genome. With respect to histone H3, a protein component of a nucleosome (the base unit of chromatin), acetylation or methylation of amino acid residue lysine 9 has been implicated in transcriptionally active or inactive chromatin, respectively. It has been recognized that nucleosomes can negatively regulate gene expression by, e.g., preventing access to the DNA binding sites of transcription factors, thereby reducing or silencing expression of nearby genes (Owen-Hughes and Workman, 1994, *Crit Rev Eukaryot Gene Expr* 4(4):403-441; Knezeetic and Luse, 1986, *Cell* 45(1):95-104).

Prior to transcriptional reactivation, 5 nucleosomes are precisely positioned in the 5' LTR of HIV-1. Nucleosome nuc-0, encompassing part of the NRE region is separated from nucleosome nuc-1 by a 265 by nucleosome-free region, containing binding sites for transcription factors C/EBP, LEF-1, NF-κB, NF-AT, Sp1 and the TATA box (Verdin et al., 1993, *EMBO J* 12(12):4900; Jones and Peterlin, 1994, *Anna Rev Biochem* 63:717-743). Upon reactivation, nuc-1 is rapidly remodeled which may relieve a block to HIV-1 gene transcription. Reactivation of HIV-1 latency seems also to involve recruitment of acetyltransferase to the HIV-1 LTR, followed by acetylation of histones H3 and H4 (Lusic et al., 2003, *EMBO J* 22(24):6550-6561; Bisgrove, 2005, *Expert Rev Anti Infect Ther* 3(5):805-814). Thus, chromatin is an integral component of the HIV-1 transcriptional regulatory machinery and modulation thereof is expected to have a direct impact on the expression of HIV-1 genes.

Further, HIV-1 latency may also be explained by integration of the HIV-1 genome into heterochromatin, a transcriptionally repressive form of chromatin, that eventually may become reorganized leading to the reactivation of latent HIV-1 expression (Jordan et al., 2003, *EMBO J* 22(8):1868-1877). Another mechanism underlying HIV-1 latency may be transcriptional interference with a nearby gene (Han et al., 2004, *J Virol* 78(12):6122-6133).

Two strategies have been proposed to overcome the problem that current HAART is unable to completely clear the latent HIV-1 reservoir. The first one can be described as an intensified HAART aiming to prevent even a very low level of viral replication (Ramratnam et al., 2004, *J Acquir Immune Defic Syndr* 35(1):33-37). A second approach aims at eliminating the pool of latently infected cells by inducing HIV-1 replication in these cells, while maintaining the patient on HAART to prevent a spreading infection. The latently-infected cells would then be eliminated by the immune system or virus-mediated cell lysis.

In pursuing the second approach, purging the latent HIV-1 pool by reactivation of viral transcription, several clinical trials have been performed, although, with limited success so far. For example, studies using IL-2 or IL-2 and OKT3 have not shown significant reduction in the latent reservoir and viral rebound continues after cessation of HAART (Chun et al., 1999, *Nat Med* 5:651-655; van Praag et al., 2001, *J Clin Immunol* 21:218-226; Blankson et al., 2002, *Ann Rev Med* 53:557-593). Another potential drug useful for viral purging is IL-7 (Smithgall et al., 1996, *J Immunol* 156(6):2324-2330; Scripture-Adams et al., 2002, *J Virol* 76(24):13077-13082).

Recently, prostratin and the related 12-deoxyphorbol 13-phenylacetate (DPP) were described as promising inducers of latent HIV-1. Prostratin is a nontumor-promoting phorbol ester initially isolated in screens for inhibitors of HIV-1 replication (Gustafson et al., 1992, *J Med Chem* 35(11):1978-1986). However, further studies indicated that in addition to blocking HIV-1 infection, prostratin treatment also upregulated HIV-1 transcription from latent proviruses (Kulkosky et al., 2001, *Blood* 98(10:3006-15; Korin et al., 2002, *J Virol* 76(16):8118-8123; Biancotto et al., 2004, *J Virol* 78(19):10507-10515).

To be clinically useful, reactivators of latent HIV-1 expression must exhibit relatively low toxicity, permitting patients to withstand treatment with these agents (Perelson et al., 1997, *Nature* 387, 188-191). Although prostratin functions as a reactivator of latent HIV-1 expression and was observed to lack toxicity when applied for short time courses, in its current dosage regimen, prostratin may not be useful for long-term, multiround treatments in humans. Prostratin was reported to induce substantial growth arrest and cell death if administered in a concentration of >500 nM for more than 2 days (Williams et al., 2004, *J Biol Chem* 279(40):42008-42017). Thus, if prostratin is to be considered as a human therapeutic, it is unlikely that high-dose or protracted treatment will be tolerated. Consequently, either short-term and/or low-dose treatments will probably be the only alternative, since sustained administration of prostrating at a high-dose will probably result in dramatically negative side effects (Williams et at, 2004, *J Biol Chem* 279(40):42008-42017). However, no such protocols are available yet.

Histone acetylases and deacetylases play a major role in the control of gene expression. They regulate gene expression by acetylating and deacetylating lysine residues on histones as well as various transcription factors. The balance between the activities of histone acetylases, usually called acetyl transferases (HATs), and deacetylases (HDACs) determines the level of histone acetylation. Acetylated histones are associated with a relaxed, more open form of chromatin and activation of gene transcription, whereas deacetylated chromatin is associated with a more compacted form of chromatin and diminished transcription. Eleven different HDACs have been cloned from vertebrate organisms. Class I HDACs includes HDAC1, HDAC2, HDAC3, and HDAC8 (Van den Wyngaert et al., 2000, *FEBS Lett* 468:77-83). Class II HDACs includes HDAC4, HDAC5, HDAC6, HDAC7, HDAC7, HDAC9, and HDAC10 (Kao et al., 2000, *Genes Dev* 14:55-60; Grozinger et at, 1999, *Proc Natl Acad Sci USA*, 96:4868-73; Zhou et al., 2001, *Proc Natl Acad Sci USA*, 98:10572-77; Tong et al., 2002, *Nucleic Acids Res* 30:1114-23). HDAC11 has not been classified yet (Gao et al., 2002, *J Biol Chem* 277:25748-55). All share homology in their catalytic regions.

HDACs have also been implicated in the inhibition of HIV-1 gene expression and thus, may contribute to establishing or maintaining HIV-1 latency (Ylisastigui et al., 2004, AIDS 18(8):1101-1108). Further, it has been shown that NF-κB p50-HDAC1 complexes constitutively bind the latent HIV-1 LTR and induce histone deacetylation and repressive changes in chromatin structure of the HIV-1 LTR, changes that impair recruitment of RNA polymerase II and transcriptional initiation (Williams et al., 2006, *EMBO J* 25:139-149).

Thus, histone deacetylase (HDAC) inhibitors are also being considered as an adjuvant with HAART (see, Bisgrove, 2005, *Expert Rev Anti Infect Ther* 3(5):805-814). HDAC inhibitors have the ability to reactivate a range of HIV-1 subtypes in a variety of different cell types (Van Lint at al., 1996, *EMBO J* 15(5):1112-1120; Quivy et al., 2002, *J Virol* 76(21):11091-11103). Some HDAC inhibitors are already in clinical use for other purposes. For example, valproic acid is widely used to reduce epileptic seizures, and phenylbutyrate is used to treat sickle cell anemia and various forms of thalassemia, establishing their safety profile. Recently, it was suggested that the HDAC inhibitor valproic acid may have effects on the reactivation of latent HIV-1 (Ylisastigui et al., 2004, AIDS 18(8):1101-1108).

TSA, e.g., has been shown to inhibit HDAC1, leading to the recruitment of RNA polymerase to the latent HIV-1 LTR. This bound polymerase complex, however, remains nonprocessive, generating only short viral transcripts. Synthesis of full-length viral transcripts can be rescued by the expression of Tat (Williams et al, 2006, *EMBO J* 25:139-149).

Recently, Williams and Greene described compositions and methods for reactivating latent HIV-1 expression wherein they contacted a cell having an integrated HIV-1 genome with an reactivator of latent HIV-1 expression and with an inhibitor of an HDAC (U.S. Pat. No. 8,247,613).

Despite this progress cells latently infected with HIV-1 still represent an insurmountable barrier to viral eradication in infected patients. New approaches for the elimination of the latently infected HIV-1 cells are urgently needed (see Pomerantz, 2002, *Curr Opin Invest Drugs* 3:1133-1137). In view of this unfulfilled need, Applicants asked the question: "Can gene expression fluctuations, or 'noise,' be used as a drug discovery tool?" Studies to date hint that the answer might be yes. Some sources and phenotypic implications of gene expression noise have been investigated (Kaern et al., 2005, *Nat Rev Genet* 6:451-464; Balazsi and van Oudenaarden, 2011, *Cell* 144:910-925). On one hand, noise has been exploited as a probe to elucidate underlying structure-function relationships of genetic circuitry (Blake et al., 2003, *Nature* 422:633-637; Rosenfeld et al., 2005, *Science* 307:1962-1965; Austin et al., 2006, *Nature* 439:608-611; Ozbudak et al., 2002, *Nature Genet* 31:69-73), and on the other to play a fate determining role in systems as diverse as the sporulation-competence circuitry in *B. subtilis* (Suel et al., 2007, *Science* 315:1716-1919), mating pheromone response in yeast (Colman-Lerner et al., 2005, *Nature* 437:699-706), and HIV-1 latency (Weinberger et al., 2008, *Nature Genet* 40:466-470; Weinberger et al., 2005 *Cell* 122:169-182).

As discussed above, HIV-1 latency, a quiescently integrated viral state, has been identified as the leading barrier to completely eradicate the virus from infected individuals (Siliciano and Greene, 2011, *Cold Spring Harb Perspect Med* 1:a007096; Richman et al., 2009, *Science* 323:1304-1307). Upon infection of a cell, viral gene expression leads to either an active replication fate where the cell is hijacked of its resources to generate hundreds of viral progeny and ultimate cell death, or in rare instances, an inactive latent state where the provirus transcribes at undetectably low levels thereby evading anti-retroviral therapy. The HIV-1 promoter has high nucleosome occupancy including the stalling of RNA polymerase II after a nucleosome positioned at the transcriptional start site. This high nucleosome occupancy along with pol II stalling has been associated with higher gene expression noise in comparison to housekeeping promoters and generates diverse episodic transcriptional activity across the genome capable of modulation by signaling molecules (Singh et al., 2010, *Biophys J* 98:L32-L34; Dar et al., 2012, *Proc Natl Acad Sci USA* 109:17454-17459). Knockdown of the BAF nucleosome remodeling complex of the HIV-1 promoter was recently shown to increase latent reactivation into an actively replicating state (Rafati et al., 2011, *Plos Biology* 9:e1001206, 1-20). Together these observations support HIV-1 latency as a strong and clinically relevant phenotypic candidate for noise drug screening.

Applicants herewith provide compositions and methods useful for the elimination of latent HIV-1 reservoirs that persist despite HAART. The present invention is based, in part, on the Applicants' unexpected and surprising finding that noise modulating compounds identified by Applicants herein can synergize with an activator of latent HIV-1 expression, such as prostratin, to reactivate a latent HIV-1 reservoir.

BRIEF SUMMARY OF THE INVENTION

HIV-1's ability to enter a transcriptionally dormant state and establish a reservoir of latently infected cells is considered the major barrier to eradicating the virus from infected patients. Multiple molecular mechanisms have been proposed to drive establishment of latency and significant trials are underway to activate HIV-1 gene-expression, and reactivate the latent reservoir to clear it. Stochastic noise (i.e. fluctuations) in an HIV-1 transcriptional positive-feedback loop is known to be one mechanism that enables HIV-1 to establish latency. Here, Applicants demonstrate that small-molecule modulation of noise in HIV-1 gene expression radically perturbs HIV-1 latency. By screening a library of small-molecule drug compounds Applicants identified a subset of over 50 compounds that modulate noise in the HIV-1 LTR promoter without changing the promoter's mean expression level. Strikingly, some of these noise-modulating compounds (also referred to as variability enhancers) synergize with conventional transcriptional activators and surpass current best-in-class reactivation cocktails, while maintaining greater cell viability. Thus, noise-modulating compounds present an approach to perturb the stability of the HIV-1 latent state. In general, expression noise may represent a new unexplored axis for drug discovery that allows enhanced control over cell-fate specification decisions, such as establishing or maintaining cell-fate specification of a stem cell, establishing or maintaining viral latency, establishing or maintaining tumor metastasis, and establishing or maintaining pathogen persistence phenotypes, such as fungal or bacterial persistence.

More specifically, Applicants investigated whether tunable gene expression variability can be exploited for diseases whose phenotypes are strongly biased by individual single cells. Herein Applicants describe their surprising and unexpected findings of a noise drug screening approach on the HIV-1 LTR promoter in human T-cells in response to 1,600 FDA approved drug compounds. Using high-throughput flow cytometry Applicants identified compounds that modulate variability of gene expression without changing the mean expression level of the promoter and which would otherwise be overlooked by conventional drug screening. More specifically, Applicants herein report over 50 variability modulators (VMs) some of which, referred to as variability enhancers, (VEs) synergized reactivation of HIV-1 latency when combined with NF-$K_B$ activators. In addition to synergizing in Jurkat cells, a subset of VMs showed synergy in two leading primary cell models of latency. Other VMs were identified as variability suppressors (VSs) and suppressed latentHIV-1 reactivation when combined with a variety of activators. Compounds previously reported in the literature, such as HDAC inhibitors, azacitidine, JQ1, and cytarabine, also were found to be VEs. The unexplored variability axis of drug screening benefits systems whose phenotypic dynamics are biased at the single-cell level such as viral latency, in particular, HIV-1 latency, tumor metastasis, and fungal or bacterial persistence. Thus, the present invention relates to novel compositions and kits comprising noise-modulating compounds and activators of latent HIV-1 expression in addition to uses thereof in methods for reactivating latent HIV-1 expression, methods for eliminating a latent HIV-1 reservoir, methods for rendering latent HIV-1 sensitive to killing by an immunotoxin, and methods for treating patients infected with latent HIV-1.

The following sets forth aspects of Applicants' invention. In a first aspect, the present invention provides methods of screening for a variability modulator (VM) that modulates variability of expression of a gene promoter. In some embodiments of the present invention, this method comprises the step of contacting a first compound to a cell wherein the cell comprises a first reporter gene which comprises a gene promoter. In this embodiment, the gene promoter controls expression of the reporter gene. The first compound, when compared to a control compound, modulates variability of expression of the gene promoter without substantially changing the mean expression level of the gene promoter. A control compound does not substantially alter variability in gene expression of a gene promoter.

In some embodiments, a method of screening for a variability modulator comprises the step of determining a first variability in gene expression of the gene promoter after contacting the cell with the first compound. In some embodiments, the method of screening for a variability modulator comprises the step of determining a second variability in gene expression of the gene promoter after contacting the cell with a control compound.

In some embodiments, a method of screening for a variability modulator comprises the step of identifying the first compound as a variability modulator when the first variability in gene expression of the gene promoter is substantially different from the second variability in gene expression of the gene promoter.

In some embodiments, the method of screening for a variability modulator comprises the step of identifying the variability modulator as a variability suppressor (VS) when the first variability in gene expression of the gene promoter is lower (i.e., smaller) when compared to the second variability in gene expression of the gene promoter, i.e., when the variability in gene expression of the gene promoter in the presence of the first compound is lower (i.e., smaller) when compared to the variability in gene expression of the gene promoter in the presence of a control compound.

In some embodiments, the method of screening for a variability modulator comprises the step of identifying the variability modulator as a variability enhancer (VE) when the first variability in gene expression of the gene promoter is higher (i.e., greater) when compared to the second variability in gene expression of the gene promoter, i.e., when the variability in gene expression of the gene promoter in the presence of the first compound is higher (i.e., greater) when compared to the variability in gene expression of the gene promoter in the presence of a control compound.

In some embodiments, a method of screening for a variability modulator modulating variability of expression of a gene promoter comprises the step of contacting a second compound with the cell. In some embodiments, the method of screening for a variability modulator modulating variability of expression of a gene promoter comprises the step of determining the mean gene expression level of the reporter gene after contacting the cell with the second compound.

In some embodiments, a method of screening for a variability modulator modulating variability of expression of a gene promoter comprises the step of identifying the first compound as a synergistic variability enhancer when the first compound and the second compound synergistically activate gene expression from the gene promoter, i.e., when the first compound and the second compound synergistically increase the mean expression level of gene expression from the gene promoter.

In some embodiments, a method of screening for a variability modulator modulating variability of expression of a gene promoter comprises the step of identifying the first compound as a variability suppressor when the first compound and the second compound reduce the mean gene expression level of the reporter gene as determined either after contacting only the first compound to the cell or after contacting only the second compound to the cell.

One of skill in the art will appreciate that a wide variety of gene promoters can be used in a method of screening for a variability modulator. In some embodiments of the present invention, the gene promoter is a promoter involved in establishing or maintaining cell-fate specification of a stem cell, viral latency, tumor metastasis, fungal persistence, or bacterial persistence. A preferred gene promoter is a gene promoter involved in establishing or maintaining Human Immunodeficiency Virus Type 1 latency. A preferred gene promoter is an HIV-1 long terminal repeat (LTR) promoter.

A method of screening for a variability modulator can be used with individual compounds or in a high-throughput screening method. Preferred is a high-throughput screening method.

A method of screening for a variability modulator is not limited by a detection or measuring method. In fact several detection or measuring methods can be used. In some embodiments the detection method comprises fluorescence microscopy, FISH, detection of a fluorescent protein, single-cell RNA sequencing or flow cytometry. A preferred detection or measuring method is or comprises flow cytometry.

A method of screening for a variability modulator can be practiced in vitro and in vivo. In some embodiments of the present invention, a cell is contacted according to the invention in vitro. In some embodiments of the present invention, a cell is contacted according to the invention in vivo.

One of skill in the art will appreciate that a wide variety of cells can be used in a method of screening for a variability modulator. In some embodiments of the present invention, the cell is selected from the group consisting of a prokaryotic cell, a eukaryotic cell, a fungal cell, and a mammalian cell. In some embodiments of the present invention, the cell is a mammalian cell. In some embodiments, the mammalian cell is a human cell. Preferred human cells include, but are not limited to, T-cells. A preferred T-cell is, a Jurkat cell, a MT-4 cell, a CEM cell, a SupT1 cell, or a primary T-cell.

One of skill in the art will appreciate that a variety of second compounds can be used in a method of screening for a variability modulator, in particular for identifying VMs that synergistically activate expression from a gene promoter when both the VM (or a compound to be identified as a VM) and the second compound are used to contact a cell. In some embodiments, the second compound is an activator of gene expression selected from the group consisting of a prokaryotic activator of gene expression, a viral activator of gene expression and a eukaryotic activator of gene expression. In some embodiments, the second compound is an activator of HIV-1 gene expression (or an activator of latent HIV-1 gene expression).

Several activators of HIV-1 gene expression (or latent HIV-1 gene expression) can be used to practice a method of screening for a variability modulator. The activator of HIV-1 gene expression can be a protein kinase C (PKC) agonist, an inhibitor of histone deacetylase, an inhibitor of methylation, an inhibitor of a bromodomain protein, or an anticancer drug. A protein kinase C (PKC) agonist, an inhibitor of histone deacetylase, an inhibitor of methylation, an inhibitor of a bromodomain protein, or an anticancer drug can also be used in combination with each other to function as activators of HIV-1 gene expression In some embodiments of the present invention, an activator of HIV-1 gene expression (or latent HIV-1 gene expression) is a histone deacetylase (HDAC) inhibitor. Several HDAC inhibitors can be used to practice a method of screening for a variability modulator. In some embodiments of the methods, an HDAC inhibitor is selected from the group consisting of 12-deoxyphorbol 13-phenylacetate (DPP), Suberoylannilide Hydroxamic Acid (SAHA), MS-275, valproic acid (VPA), and trichostatin A (TSA). Also useful for practicing the methods are single stereoisomers, mixtures of stereoisomers, pharmaceutically acceptable salts, prodrugs and functional derivatives of those HDAC inhibitors.

In some embodiments of a method of screening for a variability modulator, an activator of HIV-1 gene expression (or latent HIV-1 gene expression) is a Protein Kinase C (PKC) agonist. Several PKC agonists can be used to practice the methods. In some embodiments of the present invention, a PKC agonist is selected from the group consisting of tumor necrosis factor alpha (TNFα), prostratin, PMA, and bryostatin. Also useful for practicing the methods are single stereoisomers, mixtures of stereoisomers, pharmaceutically acceptable salts, prodrugs and functional derivatives of those PKC agonists.

In some embodiments of a method of screening for a variability modulator, an activator of HIV-1 gene expression (or latent HIV-1 gene expression) is a methylation inhibitor. Several methylation inhibitors can be used to practice the methods. In some embodiments, a methylation inhibitor is azacytidine, fludarabine or adenosine. Also useful for practicing the methods are single stereoisomers, mixtures of stereoisomers, pharmaceutically acceptable salts, prodrugs and functional derivatives of azacytidine, fluradabine or adenosine.

In some embodiments of a method of screening for a variability modulator, an activator of HIV-1 gene expression (or latent HIV-1 gene expression) is a bromodomain inhibitor. Several bromodomain inhibitors can be used to practice the methods. In some embodiments, a bromodomain inhibitor is JQ1, GSK1210151A or PFI-1. Also useful for practicing the methods are single stereoisomers, mixtures of stereoisomers, pharmaceutically acceptable salts, prodrugs and functional derivatives of JQ1, GSK1210151A or PFI-1.

In some embodiments of a method of screening for a variability modulator, an activator of HIV-1 gene expression (or latent HIV-1 gene expression) is an anticancer drug. Several anticancer drugs can be used to practice the methods. In some embodiments, an anticancer drug is cytarabine. Also useful for practicing the methods are single stereoisomers, mixtures of stereoisomers, pharmaceutically acceptable salts, prodrugs and functional derivatives of cytarabine.

The first compound and/or second compound contacting the cell can be members of a library. One of skill in the art will appreciate that a wide variety of libraries can be used in the methods of screening for a variability modulator. In some embodiments of the present invention, the library is selected from the group consisting of a small molecule library, a fragment library, a peptide library, an RNAi library, an shRNA library, and an miRNA Library. In some embodiments of the present invention, the library is the Pharmakon 1600 library.

Methods of the present invention are not limited by the use of a specific reporter gene. Several first reporter genes can be used in the methods of screening for a variability modulator. In some embodiments of the present invention, the first reporter gene is selected from the group consisting of green fluorescent protein (GFP), red fluorescent protein (RFP or mCherry), cyan fluorescent protein (CFP) and yellow fluorescent protein (YFP). A preferred reporter gene is Green Fluorescent Protein (GFP).

In some embodiments of a method of screening for a variability modulator it is desirable to use a reporter gene producing a reporter protein product having a reduced or diminished half-life. Preferred reduced or diminished half-lives can be from 0.1-40 hours, from 0.1-10 hours, from 0.2-8 hours, from 0.5-7 hours, from 0.7-6 hours, from 1-5 hours, or from 2-3 hours. Other preferred reduced or diminished half-lives are less than 5 minutes, less than 10 minutes, less than 15 minutes, less than 20 minutes and less than 30 minutes.

In some embodiments of a method of screening for a variability modulator, a cell comprises a second reporter gene under control of the gene promoter. Preferably, the second reporter gene produces a reporter protein product that has a different stability than the first reporter protein product. In some embodiments, the stability of the second reporter protein product is more stable than the first reporter protein product.

In some embodiments of the present invention, the first and second compounds combined increase burst frequency and burst size of the first reporter gene.

In another aspect, the present invention provides a method for reactivating a latent HIV-1 reservoir in a mammalian cell having an integrated HIV-1 genome. In a preferred embodiment of the present invention, this method comprises the steps of (a) contacting the mammalian cell with an amount of a variability modulator sufficient to modulate variability of expression of a gene promoter without substantially changing the mean expression level of the gene promoter and (b) contacting the mammalian cell with an amount of an activator of latent HIV-1 gene expression effective to activate latent HIV-1 gene expression. Thereupon, the latent HIV-1 reservoir is reactivated.

Several variability modulators identified herein and identified by a method described herein can be used to practice the method of reactivating a latent HIV-1 reservoir. Preferred are variability enhancers (VEs).

In some embodiments of the present invention, a variability modulator is selected from the group consisting of thiamylal sodium, Estramustine, griseofulvin, telmisartan, docetaxel, riboflavin, pantothenic acid(d) na salt, mercaptopurine, pemetrexed, ethinyl estradiol, irinotecan hydrochloride, dutasteride, felbinac, vincristine sulfate, thiram, bezafibrate, Indomethacin, mebendazole, ouabain, sulfaquinoxaline sodium, oxybutynin chloride, oxyphencyclimine hydrochloride, saxagliptin, phenylmercuric acetate, troclosene potassium, artemisinin, cytarabine, thioguanine, hydroquinone, acetophenazine maleate, hexylresorcinol, oxytetracycline, cefadroxil, tolnaftate, phenylbutyric acid, atorvastatin calcium, carboplatin, 5-azacytidine, levodopa, lamivudine, sotalol hydrochloride, clavulanate lithium, digoxin, sodium monofluorophosphate, dexpanthenol, rabeprazole sodium, cetirizine hydrochloride, trilostane, modafinil, thiabendazole, adapalene, sulfameter, Fluoxetine hydrochloride, trimethobenzamide hydrochloride, Metoclopramide hydrochloride, guanethidine sulfate, trichlormethine, sucralfate, valganciclovir hydrochloride, bemotrizinol, parachlorophenol, (Â±)-Verapamil hydrochloride, oxidopamine hydrochloride, fomepizole hydrochloride, Xylazine hydrochloride, diperodon hydrochloride, zomepirac sodium, closantel, fenbendazole, finasteride, Procainamide hydrochloride, celecoxib, colistin sulfate, imipenem, cefoxitin sodium, azithromycin, clidinium bromide, Tolazamide, chlorpheniramine maleate, colesevalam hydrochloride, Pargyline hydrochloride, hydralazine hydrochloride, anastrozole, vinorelbine, bleomycin, dasatinib, busulfan, vorinostat, selamectin, idoxuridine, carvedilol, (Â±)-Isoproterenol hydrochloride, racephedrine hydrochloride, vardenafil hydrochloride, guaiacol, clobetasol propionate, mycophenolic acid, fludrocortisone acetate, zaleplon, nitroglycerin, riboflavin 5-phosphate sodium, acetriazoic acid, digitoxin, carnitine hydrochloride, albendazole, taurine, Taxol, mitomycin c, clofarabine, arginine hydrochloride, tetramizole hydrochloride, thiostrepton, lonidamine, melphalan, fludarabine phosphate, methotrexate(+/−), rifaximin, Arecoline hydrobromide, zalcitabine, erythrosine sodium, nikethamide, oxfendazole, editol, doxapram hydrochloride, aminacrine, dobutamine hydrochloride, and rutin. Also useful for practicing the methods of the present invention are single stereoisomers, mixtures of stereoisomers, pharmaceutically acceptable salts, prodrugs and functional derivatives of those variability modulators.

In some embodiments, a variability modulator is selected from the group consisting of docetaxel, ethinyl estradiol, estramustine, felbinac, bezafibrate, mebendazole, thiamylal sodium, mercaptopurine, dutasteride, cetirizine hydrochloride, acetophenazine maleate, oxytetracycline, artemisinin, hydralazine hydrochloride, Indomethacin, atorvastatin calcium, guanethidine sulfate, pantothenic acid(d) na salt, saxagliptin, (Â±)-Verapamil hydrochloride, oxidopamine hydrochloride, trilostane, fomepizole hydrochloride, modafinil, Xylazine hydrochloride, diperodon hydrochloride, zomepirac sodium, thiabendazole, closantel, hexylresorcinol, adapalene, finasteride, Procainamide hydrochloride, cefadroxil, sulfameter, sulfaquinoxaline sodium, azithromycin, imipenem, colistin sulfate, cefoxitin sodium, oxyphencyclimine hydrochloride, oxybutynin chloride, clidinium bromide, Fluoxetine hydrochloride, Tolazamide, trimethobenzamide hydrochloride, Metoclopramide hydrochloride, tolnaftate, chlorpheniramine maleate, phenylbutyric acid, colesevalam hydrochloride, Pargyline hydrochloride, telmisartan, troclosene potassium, bleomycin, dasatinib, anastrozole, busulfan, carboplatin, pemetrexed, hydroquinone, selamectin, levodopa, sucralfate, valganciclovir hydrochloride, lamivudine, idoxuridine, sotalol hydrochloride, carvedilol, clavulanate lithium, (Â±)-Isoproterenol hydrochloride, racephedrine hydrochloride, sodium monofluorophosphate, dexpanthenol, vardenafil hydrochloride, guaiacol, rabeprazole sodium, clobetasol propionate, mycophenolic acid, fludrocortisone acetate, zaleplon, bemotrizinol, parachlorophenol, nitroglycerin, and acetriazoic acid. Also useful for practicing the methods of the present invention are single stereoisomers, mixtures of stereoisomers, pharmaceutically acceptable salts, prodrugs and functional derivatives of those variability modulators.

In some embodiments, a variability modulator is selected from the group consisting of docetaxel, ethinyl estradiol, estramustine, felbinac, bezafibrate, mebendazole, mercaptopurine, dutasteride, cetirizine hydrochloride, acetophenazine maleate, oxytetracycline, and artemisinin. Also useful for practicing the methods of the present invention are single stereoisomers, mixtures of stereoisomers, pharmaceutically acceptable salts, prodrugs and functional derivatives of those variability modulators.

In some embodiments, a variability modulator is selected from the group consisting of manidipine hydrochloride, phenothiazine, dichlorvos, fipronil, trichlorfon, benzydamine hydrochloride, maprotiline hydrochloride, Papaverine hydrochloride, arsenic trioxide, phenformin hydrochloride, itraconazole, cycloheximide, hydroxyprogesterone caproate, pyrithione zinc, meclocycline sulfosalicyclate, ergotamine tartrate, adenosine phosphate, and broxaldine. Also useful for practicing the methods of the present invention are single stereoisomers, mixtures of stereoisomers, pharmaceutically acceptable salts, prodrugs and functional derivatives of those variability modulators.

Several activators of latent HIV-1 gene expression can be used to practice the method of reactivating a latent HIV-1 reservoir.

In some embodiments of the present invention, an activator of latent HIV-1 gene expression is a histone deacetylase (HDAC) inhibitor. Several HDAC inhibitors can be used to practice a method of reactivating a latent HIV-1 reservoir. In some embodiments of the present invention, an HDAC inhibitor is selected from the group consisting of 12-deoxyphorbol 13-phenylacetate (DPP), Suberoylannilide Hydroxamic Acid (SAHA), MS-275, valproic acid (VPA), and trichostatin A (TSA). Also useful for practicing the methods of the present invention are single stereoisomers, mixtures of stereoisomers, pharmaceutically acceptable salts, prodrugs and functional derivatives of those HDAC inhibitors.

In some embodiments of a method for reactivating a latent HIV-1 reservoir, an activator of latent HIV-1 gene expression is a Protein Kinase C (PKC) agonist. Several PKC agonists can be used to practice a method of the present invention. In some embodiments of the present invention, a PKC agonist is selected from the group consisting of tumor necrosis factor alpha (TNFα), prostratin, PMA, and bryostatin. Also useful for practicing methods of the present invention are single stereoisomers, mixtures of stereoisomers, pharmaceutically acceptable salts, prodrugs and functional derivatives of those PKC agonists.

In some embodiments of a method for reactivating a latent HIV-1 reservoir, an activator of latent HIV-1 gene expression is a methylation inhibitor. Several methylation inhibitors can be used to practice a method of the present invention. In some embodiments of the present invention, a methylation inhibitor is azacytidine. Also useful for practicing methods of the present invention are single stereoisomers, mixtures of stereoisomers, pharmaceutically acceptable salts, prodrugs and functional derivatives of azacytidine.

In some embodiments of a method for reactivating a latent HIV-1 reservoir, an activator of latent HIV-1 gene expression is a bromodomain inhibitor. Several bromodomain inhibitors can be used to practice a method of the present invention. In some embodiments of the present invention, a bromodomain inhibitor is JQ1, GSK1210151A or PFI-1. Also useful for practicing methods of the present invention are single stereoisomers, mixtures of stereoisomers, pharmaceutically acceptable salts, prodrugs and functional derivatives of JQ1, GSK1210151A and PFI-1.

In some embodiments of a method for reactivating a latent HIV-1 reservoir, an activator of latent HIV-1 gene expression is an anticancer drug. Several anticancer drugs can be used to practice a method of the present invention. In some embodiments of the present invention, an anticancer drug is cytarabine. Also useful for practicing methods of the present invention are single stereoisomers, mixtures of stereoisomers, pharmaceutically acceptable salts, prodrugs and functional derivatives of cytarabine.

A method of reactivating a latent HIV-1 reservoir can be practiced in vitro and in vivo. In some embodiments of the present invention, a cell is contacted according to the invention in vitro. In some embodiments of the present invention, a cell is contacted according to the invention in vivo.

Various mammalian cells can be used to practice a method reactivating a latent HIV-1 reservoir. In some embodiments of the present invention, the mammalian cell is a human cell, preferably, a human T cell.

The human cell may be contacted with a variability modulator and an activator of latent HIV-1 gene expression in vitro and in vivo. In some embodiments of the present invention, the method of activating a latent HIV-1 reservoir in a human cell, particular a human cell in a human subject, comprises the step of contacting the cell with a HAART compound. Alternatively, the method may comprise the step of contacting the cell with an immunotoxin.

In another aspect, the present invention provides a method for suppressing reactivation of a latent HIV-1 reservoir in a mammalian cell having an integrated HIV-1 genome. In some embodiments of a method for suppressing reactivation of a latent HIV-1 reservoir in a mammalian cell, the method comprises the step of contacting the mammalian cell with an amount of a variability suppressor sufficient to reduce or suppress variability of expression of a gene promoter without substantially changing the mean expression level of the gene promoter; whereby reactivation of the latent HIV-1 reservoir is suppressed.

Various variability suppressors described herein or variability suppressors isolated by a subject method described herein can be used in a method to suppress reactivation of a latent HIV-1 reservoir. In some embodiments, a variability suppressor for use in a method to suppress reactivation of a latent HIV-1 reservoir is selected from the group consisting of manidipine hydrochloride, phenothiazine, dichlorvos, fipronil, trichlorfon, benzydamine hydrochloride, maprotiline hydrochloride, Papaverine hydrochloride, arsenic trioxide, phenformin hydrochloride, itraconazole, cycloheximide, hydroxyprogesterone caproate, pyrithione zinc, meclocycline sulfosalicylate, ergotamine tartrate, adenosine phosphate, and broxaldine. Also useful for practicing a method of suppressing reactivation of a latent HIV-1 reservoir are single stereoisomers, mixtures of stereoisomers, pharmaceutically acceptable salts, prodrugs and functional derivatives of those variability suppressors.

The present invention also provides pharmaceutical compositions for practicing methods of the present invention, including, but not limited to, reactivating a latent HIV-1 reservoir in a mammalian cell. Generally, the pharmaceutical compositions comprise compositions described herein for practicing a method of the present invention. In some embodiments of the present invention, a pharmaceutical composition comprises (i) a variability enhancer in an amount sufficient to modulate variability of expression of a gene promoter without substantially changing the mean expression level of the gene promoter, (ii) an activator of latent HIV-1 gene expression in an amount effective to activate latent HIV-1 gene expression, and (iii) a pharmaceutically acceptable carrier.

The present invention also provides a pharmaceutical composition for suppressing reactivation of a latent HIV-1 reservoir in a mammalian cell. In some embodiments, such pharmaceutical composition comprises (i) a variability suppressor in an amount sufficient to modulate variability of expression of a gene promoter without substantially changing the mean expression level of the gene promoter; and (ii) a pharmaceutically acceptable carrier.

Further, the present invention provides kits for practicing methods of the present invention, including, but not limited to, reactivating, a latent HIV-1 reservoir in a mammalian cell. Generally, the kits comprise compositions described herein for practicing a method of the present invention. In some embodiments of the present invention, a kit comprises (i) a first container containing a variability modulator in an amount sufficient to modulate variability of expression of a gene promoter without substantially changing the mean expression level of the gene promoter, (ii) a second container containing an activator of latent HIV-1 gene expression in an amount effective to activate latent HIV-1 gene expression, and (iii) an instruction for using (i) and (ii) for practicing methods of the present invention, including, but not limited to, reactivating a latent HIV-1 reservoir in a mammalian cell.

The present invention also provides a kit for practicing a method for suppressing reactivation of a latent HIV-1 reservoir in a mammalian cell. In some embodiments such a kit comprises (i) a first container containing a variability suppressor in an amount sufficient to modulate variability of expression of a gene promoter without substantially changing the mean expression level of the gene promoter and (ii) an instruction for using (i) for suppressing reactivation of a latent HIV-1 reservoir in the mammalian cell.

Some embodiments of a method of screening for a variability modulator are set forth in claim format below:

Claim 1. A method of screening for a variability modulator modulating variability of expression of a gene promoter, the method comprising the step of contacting a first compound to a cell comprising a first reporter gene comprising a gene promoter; wherein the gene promoter controls expression of the reporter gene; and wherein the first compound, when compared to a control compound, modulates variability of expression of the gene promoter without substantially changing the mean expression level of the gene promoter.

Claim 2. The method according to claim 1, further comprising the step of determining a first variability in gene expression of the gene promoter after contacting the first compound to a cell.

Claim 3. The method according to any one of claims 1-2, further comprising the step of determining a second variability in gene expression of the gene promoter after contacting the cell with the control compound.

Claim 4. The method according to claim 3, further comprising the step of identifying the first compound as a variability modulator when the first variability in gene expression of the gene promoter is substantially different from the second variability in gene expression of the gene promoter.

Claim 5. The method according to claim 4, further comprising the step of identifying the variability modulator as a variability suppressor when the first variability in gene expression of the gene promoter is lower when compared to the second variability in gene expression of the gene promoter or as a variability enhancer when the first variability in gene expression of the gene promoter is higher when compared to the second variability in gene expression of the gene promoter.

Claim 6. The method according to any one of claims 1-5, further comprising the step of contacting a second compound to the cell.

Claim 7. The method according to claim 6, further comprising the step of determining the mean expression level of the gene promoter after contacting the second compound to the cell.

Claim 8. The method according to claim 6, further comprising the step of identifying the first compound as a synergistic variability enhancer when the first compound and the second compound synergistically activate gene expression from the gene promoter.

Claim 9. The method according to claim 6, further comprising the step of identifying the first compound as a variability suppressor when the first compound and the second compound reduce the mean, expression level of the gene promoter as determined either after contacting only the first compound to the cell or after contacting only the second compound to the cell.

Claim 10. The method according to any one of claims 6-8, further comprising the step of determining a level of synergism by which the first and second compounds activate the gene promoter.

Claim 11. The method according to any one of claims 1-10, wherein the gene promoter is a promoter involved in establishing or maintaining cell-fate specification of a stem cell, establishing or maintaining viral latency, establishing or maintaining Human Immunodeficiency Virus Type 1 (HIV-1) latency, establishing or maintaining tumor metastasis, establishing or maintaining fungal persistence, or establishing or maintaining bacterial persistence.

Claim 12. The method according to any one of claims 1-11, wherein the gene promoter is an HIV-1 long terminal repeat (LTR) promoter.

Claim 13. The method according to any one of claims 1-12, wherein the method is a high-throughput screening method.

Claim 14. The method according to any one of claims 1-13, wherein the method comprises fluorescence microscopy, FISH, detection of a fluorescent protein, single-cell RNA sequencing, or flow cytometry.

Claim 15. The method according to any one of claims 1-14 wherein the cell is selected from the group consisting of:
(i) a prokaryotic cell;
(ii) a eukaryotic cell;
(iii) a mammalian cell;
(iv) a human cell;
(v) a human T cell;
(vi) a Jurkat cell, a MT-4 cell, a CEM cell, a SupT1 cell, or a primary T-cell.

Claim 16. The method according to any one of claims 1-15, wherein the cell is a mammalian cell.

Claim 17. The method according to any one of claims 1-16, wherein the cell is a human cell.

Claim 18. The method according to any one of claims 1-17, wherein the cell is a human T cell.

Claim 19. The method according to any one of claims 1-18, wherein the cell is selected from the group consisting of a Jurkat cell, a MT-4 cell, a CEM cell, a SupT1 cell, and a primary T-cell.

Claim 20. The method according to any one of claims 6-19, wherein the second compound is an activator of gene expression selected from the group consisting of a prokaryotic activator of gene expression, a viral activator of gene expression, a eukaryotic activator of gene expression, and an activator of HIV-1 gene expression.

Claim 21. The method according to claim 20, wherein the activator of HIV-1 gene expression is selected from the group consisting of a protein kinase C (PKC) agonist, an inhibitor of histone deacetylase, an inhibitor of methylation, an inhibitor of a bromodomain protein, and an anticancer drug.

Claim 22. The method according to claim 21, wherein the PKC agonist is selected from the group consisting of tumor necrosis factor α, prostratin, PMA and bryostatin.

Claim 23. The method according to claim 21, wherein the inhibitor of histone deacetylase is selected from the group consisting of DPP, Suberoylannilide Hydroxamic Acid (SAHA), MS-275, valproic acid A), and trichostatin A (TSA).

Claim 24. The method according to claim 21, wherein the inhibitor of methylation is selected from the group consisting of azacitidine, fludarabine, and adenosine.

Claim 25. The method according to claim 21, wherein the inhibitor of the bromodomain protein is selected from the group consisting of JQ1, GSK1210151A, and PH-1.

Claim 26. The method according to claim 21, wherein the anticancer drug is cytarabine, single stereoisomers, mixtures of stereoisomers, pharmaceutically acceptable salts or prodrugs thereof.

Claim 27. The method according to any one of claims 1-26, wherein the first compound is a member of a library.

Claim 28. The method according to claim 27, wherein the library is selected from the group consisting of a small molecule library, a fragment library, a peptide library, an RNAi library, an shRNA library, and an miRNA library.

Claim 29. The method according to any one of claims 1-28, wherein the first reporter gene is a gene selected from the group consisting of a gene encoding a green fluorescent protein (GFP), a gene encoding a red fluorescent protein (RFP or mCherry), a gene encoding a cyan fluorescent protein (CFP), and a gene encoding a yellow fluorescent protein (YFP).

Claim 30. The method according to any one of claims 1-29, wherein the first reporter gene is a gene encoding GFP.

Claim 31. The method according to any one of claims 1-30, wherein the first reporter gene produces a reporter protein product having a half-life of between 0.1-40 hours.

Claim 32. The method according to any one of claims 1-31, wherein the cell comprises a second reporter gene under control of the gene promoter and wherein the second reporter gene produces a reporter protein product having a different stability than the first reporter protein product.

Claim 33. The method according to any one of claims 6-32, wherein the first and second compounds combined increase burst frequency and burst size of the first reporter gene.

Some embodiments of a method for modulating gene expression of a latent HIV-1 reservoir in a mammalian cell having an integrated HIV-1 genome are set forth in claim format below:

Claim 1. A method for modulating variability in expression of a latent Human Immunodeficiency Virus Type 1 ("HIV-1") reservoir in a mammalian cell having an integrated HIV-1 genome, the method comprising the step of:
contacting the mammalian cell with an amount of a variability modulator sufficient to modulate variability of expression of a gene promoter without substantially changing the mean expression level of the gene promoter;
wherein variability in expression of the latent HIV-1 reservoir is modulated.

Claim 2. The method according to claim 1, wherein the method further comprises the step of contacting the mammalian cell with an amount of an activator of latent HIV-1 gene expression effective to activate latent HIV-1 gene expression.

Claim 3. The method according to any one of claims 1-2, wherein the variability modulator is selected from the group consisting of thiamylal sodium, Estramustine, griseofulvin, telmisartan, docetaxel, riboflavin, pantothenic acid(d) na salt, mercaptopurine, pemetrexed, ethinyl estradiol, irinotecan hydrochloride, dutasteride, felbinac, vincristine sulfate, thiram, bezafibrate, Indomethacin, mebendazole, ouabain, sulfaquinoxaline sodium, oxybutynin chloride, oxyphencyclimine hydrochloride, saxagliptin, phenylmercuric acetate, troclosene potassium, artemisinin, cytarabine, thioguanine, hydroquinone, acetophenazine maleate, hexylresorcinol, oxytetracycline, cefadroxil, tolnaftate, phenylbutyric acid, atorvastatin calcium, carboplatin, 5-azacytidine, levodopa, lamivudine, sotalol hydrochloride, clavulanate lithium, digoxin, sodium monofluorophosphate, dexpanthenol, rabeprazole sodium, cetirizine hydrochloride, trilostane, modafinil, thiabendazole, adapalene, sulfameter, Fluoxetine hydrochloride, trimethobenzamide hydrochloride, Metoclopramide hydrochloride, guanethidine sulfate, trichlormethine, sucralfate, valganciclovir hydrochloride, bemotrizinol, parachlorophenol, (Â±)-Verapamil hydrochloride, oxidopamine hydrochloride, fomepizole hydrochloride, Xylazine hydrochloride, diperodon hydrochloride, zomepirac sodium, closantel, fenbendazole, finasteride, Procainamide hydrochloride, celecoxib, colistin sulfate, imipenem, cefoxitin sodium, azithromycin, clidinium bromide, Tolazamide, chlorpheniramine maleate, colesevalam hydrochloride, Pargyline hydrochloride, hydralazine hydrochloride, anastrozole, vinorelbine, bleomycin, dasatinib, busulfan, vorinostat, selamectin, idoxuridine, carvedilol, (Â±)-Isoproterenol hydrochloride, racephedrine hydrochloride, vardenafil hydrochloride, guaiacol, clobetasol propionate, mycophenolic acid, fludrocortisone acetate, zaleplon, nitroglycerin, riboflavin 5-phosphate sodium, acetriazoic acid, digitoxin, carnitine hydrochloride, albendazole, taurine, Taxol, mitomycin c, clofarabine, arginine hydrochloride, tetramizole hydrochloride, thiostrepton, lonidamine, melphalan, fludarabine phosphate, methotrexate(+/−), rifaximin, Arecoline hydrobromide, zalcitabine, erythrosine sodium, nikethamide, oxfendazole, editol, doxapram hydrochloride, aminacrine, dobutamine hydrochloride, rutin, manidipine hydrochloride, phenothiazine, dichlorvos, fipronil, trichlorfon, benzydamine hydrochloride, maprotiline hydrochloride, Papaverine hydrochloride, arsenic trioxide, phenformin hydrochloride, itraconazole, cycloheximide, hydroxyprogesterone caproate, pyrithione zinc, meclocycline sulfosalicylate, ergotamine tartrate, adenosine phosphate, broxaldine, single stereoisomers, mixtures of stereoisomers, pharmaceutically acceptable salts, prodrugs and functional derivatives thereof.

Claim 4. The method according to any one of claims 1-3, wherein the variability modulator is selected from the group consisting of docetaxel, ethinyl estradiol, estramustine, felbinac, bezafibrate, mebendazole, thiamylal sodium, mercaptopurine, dutasteride, cetirizine hydrochloride, acetophenazine maleate, oxytetracycline, artemisinin, hydralazine hydrochloride, Indomethacin, atorvastatin calcium, guanethidine sulfate, pantothenic acid(d) na salt, saxagliptin, (Â±)-Verapamil hydrochloride, oxidopamine hydrochloride, trilostane, fomepizole hydrochloride, modafinil, Xylazine hydrochloride, diperodon hydrochloride, zomepirac sodium, thiabendazole, closantel, hexylresorcinol, adapalene, finasteride, Procainamide hydrochloride, cefadroxil, sulfameter, sulfaquinoxaline sodium, azithromycin, imipenem, colistin sulfate, cefoxitin sodium, oxyphencyclimine hydrochloride, oxybutynin chloride, clidinium bromide, Fluoxetine hydrochloride, Tolazamide, trimethobenzamide hydrochloride, Metoclopramide hydrochloride, tolnaftate, chlorpheniramine maleate, phenylbutyric acid, colesevalam hydrochloride, Pargyline hydrochloride, telmisartan, troclosene potassium, bleomycin, dasatinib, anastrozole, busulfan, carboplatin, pemetrexed, hydroquinone, selamectin, levodopa, sucralfate, valganciclovir hydrochloride, lamivudine, idoxuridine, sotalol hydrochloride, carvedilol, clavulanate lithium, (Â±)-Isoproterenol hydrochloride, racephedrine hydrochloride, sodium monofluorophosphate, dexpanthenol, vardenafil hydrochloride, guaiacol, rabeprazole sodium, clobetasol propionate, mycophenolic acid, fludrocortisone acetate, zaleplon, bemotrizinol, parachlorophenol, nitroglycerin, and acetriazoic acid, single stereoisomers, mixtures of stereoisomers, pharmaceutically acceptable salts, prodrugs and functional derivatives thereof.

Claim 5. The method according to any one of claims 1-4, wherein the variability modulator is selected from the group consisting of docetaxel, ethinyl estradiol, estramustine, felbinac, bezafibrate, mebendazole, mercaptopurine, dutasteride, cetirizine hydrochloride; acetophenazine maleate, oxytetracycline, artemisinin, single stereoisomers, mixtures of stereoisomers, pharmaceutically acceptable salts, prodrugs and functional derivatives thereof.

Claim 6. The method according to any one of claims 1-3, wherein the variability modulator is selected from the group consisting of manidipine hydrochloride, phenothiazine, dichlorvos, fipronil, trichlorfon, benzydamine hydrochloride, maprotiline hydrochloride, Papaverine hydrochloride, arsenic trioxide, phenformin hydrochloride, itraconazole, cycloheximide, hydroxyprogesterone caproate, pyrithione zinc, meclocycline sulfosalicylate, ergotamine tartrate, adenosine phosphate, broxaldine, single stereoisomers, mixtures of stereoisomers, pharmaceutically acceptable salts, prodrugs and functional derivatives thereof Claim 7. The method according to claims 2-6, wherein the activator of latent HIV-1 gene expression is selected from the group consisting of a histone deacetylase (HDAC) inhibitor, a protein kinase C (PKC) agonist, an inhibitor of methylation, an inhibitor of a bromodomain protein, and an anticancer drug.

Claim 8. The method according to any one of claims 2-7, wherein the activator of latent HIV-1 gene expression is a histone deacetylase (HDAC) inhibitor.

Claim 9. The method according to any one of claims 7-8, wherein the HDAC inhibitor is selected from the group consisting of 12-deoxyphorbol 13-phenylacetate (DPP), Suberoylannilide Hydroxamic Acid (SAHA), MS-275, valproic acid (VPA), trichostatin A (TSA), single stereoisomers, mixtures of stereoisomers, pharmaceutically acceptable salts or prodrugs thereof.

Claim 10. The method according to any one of claims 2-7, wherein the activator of latent HIV-1 gene expression is a Protein Kinase C (PKC) agonist.

Claim 11. The method according to any of claims 7 and 10, wherein the PKC agonist is selected from the group consisting of tumor necrosis factor alpha (TNFα), prostratin, PMA, bryostatin, single stereoisomers, mixtures of stereoisomers, pharmaceutically acceptable salts or prodrugs thereof.

Claim 12. The method according to any one of claims 2-7, wherein the activator of latent HIV-1 gene expression is an inhibitor of methylation.

Claim 13. The method according to any one of claims 7 and 12, wherein the inhibitor of methylation is azacytidine, single stereoisomers, mixtures of stereoisomers, pharmaceutically acceptable salts or prodrugs thereof.

Claim 14. The method according to any one of claims 2-7, wherein the activator of latent HIV-1 gene expression is a bromodomain inhibitor.

Claim 15. The method according to any one of claims 7 and 14, wherein the bromodomain inhibitor is JQ1, GSK1210151A, or PFI-1, single stereoisomers, mixtures of stereoisomers, pharmaceutically acceptable salts or prodrugs thereof.

Claim 16. The method according to any one of claims 1-15, wherein the mammalian cell is in vitro.

Claim 17. The method according to any one of claims 1-15, wherein the mammalian cell is in vivo.

Claim 18. The method according to any one of claims 1-17 wherein the mammalian cell is selected from the group consisting of a human cell, a human T cell, a SupT1 cell, and a primary T-cell.

Claim 19. The method according to any one of claims 1-18, further comprising the step of contacting the mammalian cell with a HAART compound.

Some embodiments of a method for reactivating a latent HIV-1 reservoir in a mammalian cell having an integrated HIV-1 genome are set forth in claim format below:

Claim 1. A method for reactivating a latent Human Immunodeficiency Virus Type 1 ("HIV-1") reservoir in a mammalian cell having an integrated HIV-1 genome, the method comprising the steps of:
contacting the mammalian cell with an amount of a variability modulator sufficient to modulate variability of expression of a gene promoter without substantially changing the mean expression level of the gene promoter; and
contacting the mammalian cell with an amount of an activator of latent HIV-1 gene expression effective to activate latent HIV-1 gene expression;
wherein the latent HIV-1 reservoir is reactivated.

Claim 2. The method according to claim 1, wherein the variability modulator is selected from the group consisting of thiamylal sodium, Estramustine, griseofulvin, telmisartan, docetaxel, riboflavin, pantothenic acid(d) na salt, mercaptopurine, pemetrexed, ethinyl estradiol, irinotecan hydrochloride, dutasteride, felbinac, vincristine sulfate, thiram, bezafibrate, Indomethacin, mebendazole, ouabain, sulfaquinoxaline sodium, oxybutynin chloride, oxyphencyclimine hydrochloride, saxagliptin, phenylmercuric acetate, troclosene potassium, artemisinin, cytarabine, thioguanine, hydroquinone, acetophenazine maleate, hexylresorcinol, oxytetracycline, cefadroxil, tolnaftate, phenylbutyric acid, atorvastatin calcium, carboplatin, 5-azacytidine, levodopa, lamivudine, sotalol hydrochloride, clavulanate lithium, digoxin, sodium monofluorophosphate, dexpanthenol, rabeprazole sodium, cetirizine hydrochloride, trilostane, modafinil, thiabendazole, adapalene, sulfameter, Fluoxetine hydrochloride, trimethobenzamide hydrochloride, Metoclopramide hydrochloride, guanethidine sulfate, trichlormethine, sucralfate, valganciclovir hydrochloride, bemotrizinol, parachlorophenol, (Â±)-Verapamil hydrochloride, oxidopamine hydrochloride, fomepizole hydrochloride, Xylazine hydrochloride, diperodon hydrochloride, zomepirac sodium, closantel, fenbendazole, finasteride, Procainamide hydrochloride, celecoxib, colistin sulfate, imipenem, cefoxitin sodium, azithromycin, clidinium bromide, Tolazamide, chlorpheniramine maleate, colesevalam hydrochloride, Pargyline hydrochloride, hydralazine hydrochloride, anastrozole, vinorelbine, bleomycin, dasatinib, busulfan, vorinostat, selamectin, idoxuridine, carvedilol, (Â±)-Isoproterenol hydrochloride, racephedrine hydrochloride, vardenafil hydrochloride, guaiacol, clobetasol propionate, mycophenolic acid, fludrocortisone acetate, zaleplon, nitroglycerin, riboflavin 5-phosphate sodium, acetriazoic acid, digitoxin, carnitine hydrochloride, albendazole, taurine, Taxol, mitomycin c, clofarabine, arginine hydrochloride, tetramizole hydrochloride, thiostrepton, lonidamine, melphalan, fludarabine phosphate, methotrexate(+/−), rifaximin, Arecoline hydrobromide, zalcitabine, erythrosine sodium, nikethamide, oxfendazole, editol, doxapram hydrochloride, aminacrine, dobutamine hydrochloride, rutin, single stereoisomers, mixtures of stereoisomers, pharmaceutically acceptable salts, prodrugs and functional derivatives thereof.

Claim 3. The method according to any one of claims 1-2, wherein the variability modulator is selected from the group consisting of docetaxel, ethinyl estradiol, estramustine, felbinac, bezafibrate, mebendazole, thiamylal sodium, mercaptopurine, dutasteride, cetirizine hydrochloride, acetophenazine maleate, oxytetracycline, artemisinin, hydralazine hydrochloride, Indomethacin, atorvastatin calcium, guanethidine sulfate, pantothenic acid(d) na salt, saxagliptin, (Â±)-Verapamil hydrochloride, oxidopamine hydrochloride, trilostane, fomepizole hydrochloride, modafinil, Xylazine hydrochloride, diperodon hydrochloride, zomepirac sodium, thiabendazole, closantel, hexylresorcinol, adapalene, finasteride, Procainamide hydrochloride, cefadroxil, sulfameter, sulfaquinoxaline sodium, azithromycin, imipenem, colistin sulfate, cefoxitin sodium, oxyphencyclimine hydrochloride, oxybutynin chloride, clidinium bromide, Fluoxetine hydrochloride, Tolazamide, trimethobenzamide hydrochloride, Metoclopramide hydrochloride, tolnaftate, chlorpheniramine maleate, phenylbutyric acid, colesevalam hydrochloride, Pargyline hydrochloride, telmisartan, troclosene potassium, bleomycin, dasatinib, anastrozole, busulfan, carboplatin, pemetrexed, hydroquinone, selamectin, levodopa, sucralfate, valganciclovir hydrochloride, lamivudine, idoxuridine, sotalol hydrochloride, carvedilol, clavulanate lithium, (Â±)-Isoproterenol hydrochloride, racephedrine hydrochloride, sodium monofluorophosphate, dexpanthenol, vardenafil hydrochloride, guaiacol, rabeprazole sodium, clobetasol propionate, mycophenolic acid, fludrocortisone acetate, zaleplon, bemotrizinol, parachlorophenol, nitroglycerin, and acetriazoic acid, single stereoisomers, mixtures of stereoisomers, pharmaceutically acceptable salts, prodrugs and functional derivatives thereof.

Claim 4. The method according to any one of claims 1-3, wherein the variability modulator is selected from the group consisting of docetaxel, ethinyl estradiol, estramustine, felbinac, bezafibrate, mebendazole, mercaptopurine, dutasteride, cetirizine hydrochloride, acetophenazine maleate, oxytetracycline, artemisinin, single stereoisomers, mixtures of stereoisomers, pharmaceutically acceptable salts, prodrugs and functional derivatives thereof.

Claim 5. The method according to any of claims 1-4, wherein the activator of latent HIV-1 gene expression is selected from the group consisting of a histone deacetylase (HDAC) inhibitor, a protein kinase C (PKC) agonist, an inhibitor of methylation, an inhibitor of a bromodomain protein, and an anticancer drug.

Claim 6. The method according to any one of claims 1-5, wherein the activator of latent HIV-1 gene expression is a histone deacetylase (HDAC) inhibitor.

Claim 7. The method according to any one of claims 5-6, wherein the HDAC inhibitor is selected from the group consisting of 12-deoxyphorbol 13-phenylacetate (DPP), Suberoylannilide Hydroxamic Acid (SAHA), MS-275, valproic acid (VPA), trichostatin A (TSA), single stereoisomers, mixtures of stereoisomers, pharmaceutically acceptable salts or prodrugs thereof.

Claim 8. The method according to any one of claims 1-5, wherein the activator of latent HIV-1 gene expression is a Protein Kinase C (PKC) agonist.

Claim 9. The method according to any of claims 5 and 8, wherein the PKC agonist is selected from the group consisting of tumor necrosis factor alpha (TNFα), prostratin, PMA, bryostatin, single stereoisomers, mixtures of stereoisomers, pharmaceutically acceptable salts or prodrugs thereof.

Claim 10. The method according to any one of claims 1-5, wherein the activator of latent HIV-1 gene expression is an inhibitor of methylation.

Claim 11. The method according to any one of claims 5 and 10, wherein the inhibitor of methylation is azacytidine, single stereoisomers, mixtures of stereoisomers, pharmaceutically acceptable salts or prodrugs thereof.

Claim 12. The method according to any one of claims 1-5, wherein the activator of latent HIV-1 gene expression is a bromodomain inhibitor.

Claim 13. The method according to any one of claims 5 and 12, wherein the bromodomain inhibitor is JQ1, GSK1210151A, or PFI-1, single stereoisomers, mixtures of stereoisomers, pharmaceutically acceptable salts or prodrugs thereof.

Claim 14. The method according to any one of claims 1-5, wherein the activator of latent HIV-1 gene expression is an anticancer drug.

Claim 15. The method according to any one of claims 5 and 14, wherein the anticancer drug is cytarabine, single stereoisomers, mixtures of stereoisomers, pharmaceutically acceptable salts or prodrugs thereof.

Claim 16. The method according to any one of claims 1-15, wherein the mammalian cell is in vitro.

Claim 17. The method according to any one of claims 1-15, wherein the mammalian cell is in vivo.

Claim 18. The method according to any one of claims 1-17 wherein the mammalian cell is selected from the group consisting of a human cell, a human T cell, a SupT1 cell, and a primary T-cell.

Claim 19. The method according to any one of claims 1-18, further comprising the step of contacting the cell with a HAART compound.

Some embodiments of a method for suppressing reactivation of a latent HIV-1 reservoir in a mammalian cell having an integrated HIV-1 genome are set forth in claim format below:

Claim 1. A method for suppressing reactivation of a latent Human Immunodeficiency Virus Type 1 (HIV-1) reservoir in a mammalian cell having an integrated HIV-1 genome, the method comprising the step of contacting the mammalian cell with an amount of a variability suppressor sufficient to modulate variability of expression of a gene promoter without substantially changing the mean expression level of the gene promoter; whereby reactivation of the latent HIV-1 reservoir is suppressed.

Claim 2. The method according to claim 1, wherein the variability suppressor is selected from the group consisting of manidipine hydrochloride, phenothiazine, dichlorvos, fipronil, trichlorfon, benzydamine hydrochloride, maprotiline hydrochloride, Papaverine hydrochloride, arsenic trioxide, phenformin hydrochloride, itraconazole, cycloheximide, hydroxyprogesterone caproate, pyrithione zinc, meclocycline sulfosalicylate, ergotamine tartrate, adenosine phosphate, broxaldine, single stereoisomers, mixtures of stereoisomers, pharmaceutically acceptable salts, prodrugs and functional derivatives thereof.

Claim 3. The method according to any one of claims 1-2, wherein the mammalian cell is in vitro.

Claim 4. The method according to any one of claims 1-2, wherein the mammalian cell is in vivo.

Claim 5. The method according to any one of claims 1-4 wherein the mammalian cell is selected from the group consisting of a human cell, a human T cell, a SupT1 cell, and a primary T-cell.

Some embodiments of a pharmaceutical composition for modulating variability of expression of a latent HIV-1 reservoir in a mammalian cell having an integrated HIV-1 genome are set forth in claim format below:

Claim 1. A pharmaceutical composition for modulating variability of expression of a latent HIV-1 reservoir in a mammalian cell having an integrated HIV-1 genome, the composition comprising:

(i) a variability modulator in an amount sufficient to modulate variability of expression of a gene promoter without substantially changing the mean expression level of the gene promoter; and (ii) a pharmaceutically acceptable carrier.

Claim 2. The pharmaceutical composition according to claim 1, further comprising:

(iii) an activator of latent HIV-1 gene expression in an amount effective to activate latent HIV-1 gene expression.

Claim 3. The pharmaceutical composition according to any one of claims 1-2, wherein the variability modulator is selected from the group consisting of thiamylal sodium, Estramustine, griseofulvin, telmisartan, docetaxel, riboflavin, pantothenic acid(d) na salt, mercaptopurine, pemetrexed, ethinyl estradiol, irinotecan hydrochloride, dutasteride, felbinac, vincristine sulfate, thiram, bezafibrate, Indomethacin, mebendazole, ouabain, sulfaquinoxaline sodium, oxybutynin chloride, oxyphencyclimine hydrochloride, saxagliptin, phenylmercuric acetate, troclosene potassium, artemisinin, cytarabine, thioguanine, hydroquinone, acetophenazine maleate, hexylresorcinol, oxytetracycline, cefadroxil, tolnaftate, phenylbutyric acid, atorvastatin calcium, carboplatin, 5-azacytidine, levodopa, lamivudine, sotalol hydrochloride, clavulanate lithium, digoxin, sodium monofluorophosphate, dexpanthenol, rabeprazole sodium, cetirizine hydrochloride, trilostane, modafinil, thiabendazole, adapalene, sulfameter, Fluoxetine hydrochloride, trimethobenzamide hydrochloride, Metoclopramide hydrochloride, guanethidine sulfate, trichlormethine, sucralfate, valganciclovir hydrochloride, bemotrizinol, parachlorophenol, (Â±)-Verapamil hydrochloride, oxidopamine hydrochloride, fomepizole hydrochloride, Xylazine hydrochloride, diperodon hydrochloride, zomepirac sodium, closantel, fenbendazole, finasteride, Procainamide hydrochloride, celecoxib, colistin sulfate, imipenem, cefoxitin sodium, azithromycin, clidinium bromide, Tolazamide, chlorpheniramine maleate, colesevalam hydrochloride, Pargyline hydrochloride, hydralazine hydrochloride, anastrozole, vinorelbine, bleomycin, dasatinib, busulfan, vorinostat, selamectin, idoxuridine, carvedilol, (Â±)-Isoproterenol hydrochloride, racephedrine hydrochloride, vardenafil hydrochloride, guaiacol, clobetasol propionate, mycophenolic acid, fludrocortisone acetate, zaleplon, nitroglycerin, riboflavin 5-phosphate sodium, acetriazoic acid, digitoxin, carnitine hydrochloride, albendazole, taurine, Taxol, mitomycin c, clofarabine, arginine hydrochloride, tetramizole hydrochloride, thiostrepton, lonidamine, melphalan, fludarabine phosphate, methotrexate(+/−), rifaximin, Arecoline hydrobromide, zalcitabine, erythrosine sodium, nikethamide, oxfendazole, editol, doxapram hydrochloride, aminacrine, dobutamine hydrochloride, rutin, manidipine hydrochloride, phenothiazine, dichlorvos, fipronil, trichlorfon, benzydamine hydrochloride, maprotiline hydrochloride, Papaverine hydrochloride, arsenic trioxide, phenformin hydrochloride, itraconazole, cycloheximide, hydroxyprogesterone caproate, pyrithione zinc, meclocycline sulfosalicylate, ergotamine tartrate, adenosine phosphate, broxaldine, single stereoisomers, mixtures of stereoisomers, pharmaceutically acceptable salts, prodrugs and functional derivatives thereof.

Claim 4. The pharmaceutical composition according to any one of claims 1-3, wherein the variability modulator is selected from the group consisting of docetaxel, ethinyl estradiol, estramustine, felbinac, bezafibrate, mebendazole, thiamylal sodium, mercaptopurine, dutasteride, cetirizine hydrochloride, acetophenazine maleate, oxytetracycline, artemisinin, hydralazine hydrochloride, Indomethacin, atorvastatin calcium, guanethidine sulfate, pantothenic acid(d) na salt, saxagliptin, (Â±)-Verapamil hydrochloride, oxidopamine hydrochloride, trilostane, fomepizole hydrochloride, modafinil, Xylazine hydrochloride, diperodon hydrochloride, zomepirac sodium, thiabendazole, closantel, hexylresorcinol, adapalene, finasteride, Procainamide hydrochloride, cefadroxil, sulfameter, sulfaquinoxaline sodium, azithromycin, imipenem, colistin sulfate, cefoxitin sodium, oxyphencyclimine hydrochloride, oxybutynin chloride, clidinium bromide, Fluoxetine hydrochloride, Tolazamide, trimethobenzamide hydrochloride, Metoclopramide hydrochloride, tolnaftate, chlorpheniramine maleate, phenylbutyric acid, colesevalam hydrochloride, Pargyline hydrochloride, telmisartan, troclosene potassium, bleomycin, dasatinib, anastrozole, busulfan, carboplatin, pemetrexed, hydroquinone, selamectin, levodopa, sucralfate, valganciclovir hydrochloride, lamivudine, idoxuridine, sotalol hydrochloride, carvedilol, clavulanate lithium, (Â±)-Isoproterenol hydrochloride, racephedrine hydrochloride, sodium monofluorophosphate, dexpanthenol, vardenafil hydrochloride, guaiacol, rabeprazole sodium, clobetasol propionate, mycophenolic acid, fludrocortisone acetate, zaleplon, bemotrizinol, parachlorophenol, nitroglycerin, and acetriazoic acid, single stereoisomers, mixtures of stereoisomers, pharmaceutically acceptable salts, prodrugs and functional derivatives thereof.

Claim 5. The pharmaceutical composition according to any one of claims 1-4, wherein the variability modulator is selected from the group consisting of docetaxel, ethinyl estradiol, estramustine, felbinac, bezafibrate, mebendazole, mercaptopurine, dutasteride, cetirizine hydrochloride, acetophenazine maleate, oxytetracycline, artemisinin, single stereoisomers, mixtures of stereoisomers, pharmaceutically acceptable salts, prodrugs and functional derivatives thereof.

Claim 6. The pharmaceutical composition according to any one of claims 1-3, wherein the variability modulator is selected from the group consisting of manidipine hydrochloride, phenothiazine, dichlorvos, fipronil, trichlorfon, benzydamine hydrochloride, maprotiline hydrochloride, Papaverine hydrochloride, arsenic trioxide, phenformin hydrochloride, itraconazole, cycloheximide, hydroxyprogesterone caproate, pyrithione zinc, meclocycline sulfosalicylate, ergotamine tartrate, adenosine phosphate, broxaldine, single stereoisomers, mixtures of stereoisomers, pharmaceutically acceptable salts, prodrugs and functional derivatives thereof Claim 7. The pharmaceutical composition according to claims 2-6, wherein the activator of latent HIV-1 gene expression is selected from the group consisting of a histone deacetylase (HDAC) inhibitor, a protein kinase C (PKC) agonist, an inhibitor of methylation, an inhibitor of a bromodomain protein, and an anticancer drug.

Claim 8. The pharmaceutical composition according to any one of claims 2-7, wherein the activator of latent HIV-1 gene expression is a histone deacetylase (HDAC) inhibitor.

Claim 9. The pharmaceutical composition according to any one of claims 7-8, wherein the HDAC inhibitor is selected from the group consisting of 12-deoxyphorbol 13-phenylacetate (DPP), Suberoylannilide Hydroxamic Acid (SAHA), MS-275, valproic acid (VPA), trichostatin A (TSA), single stereoisomers, mixtures of stereoisomers, pharmaceutically acceptable salts or prodrugs thereof.

Claim 10. The pharmaceutical composition according to any one of claims 2-7, wherein the activator of latent HIV-1 gene expression is a Protein Kinase C (PKC) agonist.

Claim 11. The pharmaceutical composition according to any of claims 7 and 10, wherein the PKC agonist is selected from the group consisting of tumor necrosis factor alpha (TNFα), prostratin, PMA, bryostatin, single stereoisomers, mixtures of stereoisomers, pharmaceutically acceptable salts or prodrugs thereof.

Claim 12. The pharmaceutical composition according to any one of claims 2-7, wherein the activator of latent HIV-1 gene expression is an inhibitor of methylation.

Claim 13. The pharmaceutical composition according to any one of claims 7 and 12, wherein the inhibitor of methylation is azacytidine, single stereoisomers, mixtures of stereoisomers, pharmaceutically acceptable salts or prodrugs thereof.

Claim 14. The pharmaceutical composition according to any one of claims 2-7, wherein the activator of latent HIV-1 gene expression is a bromodomain inhibitor.

Claim 15. The pharmaceutical composition according to any one of claims 7 and 14, wherein the bromodomain inhibitor is JQ1, GSK1210151A, or PFI-1, single stereoisomers, mixtures of stereoisomers, pharmaceutically acceptable salts or prodrugs thereof.

Claim 16 The pharmaceutical composition according to any one of claims 2-7, wherein the activator of latent HIV-1 gene expression is an anticancer drug.

Claim 17. The pharmaceutical composition according to any one of claims 7 and 16, wherein the anticancer drug is cytarabine, single stereoisomers, mixtures of stereoisomers, pharmaceutically acceptable salts or prodrugs thereof.

Claim 18. The pharmaceutical composition according to any one of claims 1-17, wherein the mammalian cell is in vitro.

Claim 19. The pharmaceutical composition according to any one of claims 1-17, wherein the mammalian cell is in vivo.

Claim 20. The pharmaceutical composition according to any one of claims 1-19 wherein the mammalian cell is selected from the group consisting of a human cell, a human T cell, a SupT1 cell, and a primary T-cell.

Claim 21. The pharmaceutical composition according to any one of claims 1-20, further comprising (iv) a HAART compound.

Some embodiments of a pharmaceutical composition for reactivating a latent HIV-1 reservoir in a mammalian cell having an integrated HIV-1 genome are set forth in claim format below:

Claim 1. A pharmaceutical composition for reactivating a latent HIV-1 reservoir in a mammalian cell having an integrated HIV-1 genome, the composition comprising:
  (i) a variability modulator in an amount sufficient to modulate variability of expression of a gene promoter without substantially changing the mean expression level of the gene promoter;
  (ii) an activator of latent HIV-1 gene expression in an amount effective to activate latent HIV-1 gene expression; and
  (iii) a pharmaceutically acceptable carrier.

Claim 2. The pharmaceutical composition according to claim 1, wherein the variability modulator is selected from the group consisting of thiamylal sodium, Estramustine, griseofulvin, telmisartan, docetaxel, riboflavin, pantothenic acid(d) na salt, mercaptopurine, pemetrexed, ethinyl estradiol, irinotecan hydrochloride, dutasteride, felbinac, vincristine sulfate, thiram, bezafibrate, Indomethacin, mebendazole, ouabain, sulfaquinoxaline sodium, oxybutynin chloride, oxyphencyclimine hydrochloride, saxagliptin, phenylmercuric acetate, troclosene potassium, artemisinin, cytarabine, thioguanine, hydroquinone, acetophenazine maleate, hexylresorcinol, oxytetracycline, cefadroxil, tolnaftate, phenylbutyric acid, atorvastatin calcium, carboplatin, 5-azacytidine, levodopa, lamivudine, sotalol hydrochloride, clavulanate lithium, digoxin, sodium monofluorophosphate, dexpanthenol, rabeprazole sodium, cetirizine hydrochloride, trilostane, modafinil, thiabendazole, adapalene, sulfameter, Fluoxetine hydrochloride, trimethobenzamide hydrochloride, Metoclopramide hydrochloride, guanethidine sulfate, trichlormethine, sucralfate, valganciclovir hydrochloride, bemotrizinol, parachlorophenol, (±)-Verapamil hydrochloride, oxidopamine hydrochloride, fomepizole hydrochloride, Xylazine hydrochloride, diperodon hydrochloride, zomepirac sodium, closantel, fenbendazole, finasteride, Procainamide hydrochloride, celecoxib, colistin sulfate, imipenem, cefoxitin sodium, azithromycin, clidinium bromide, Tolazamide, chlorpheniramine maleate, colesevalam hydrochloride, Pargyline hydrochloride, hydralazine hydrochloride, anastrozole, vinorelbine, bleomycin, dasatinib, busulfan, vorinostat, selamectin, idoxuridine, carvedilol, (±)-Isoproterenol hydrochloride, racephedrine hydrochloride, vardenafil hydrochloride, guaiacol, clobetasol propionate, mycophenolic acid, fludrocortisone acetate, zaleplon, nitroglycerin, riboflavin 5-phosphate sodium, acetriazoic acid, digitoxin, carnitine hydrochloride, albendazole, taurine, Taxol, mitomycin c, clofarabine, arginine hydrochloride, tetramizole hydrochloride, thiostrepton, lonidamine, melphalan, fludarabine phosphate, methotrexate(+/−), rifaximin, Arecoline hydrobromide, zalcitabine, erythrosine sodium, nikethamide, oxfendazole, editol, doxapram hydrochloride, aminacrine, dobutamine hydrochloride, rutin, single stereoisomers, mixtures of stereoisomers, pharmaceutically acceptable salts, prodrugs and functional derivatives thereof.

Claim 3. The pharmaceutical composition according to any one of claims 1-2, wherein the variability modulator is selected from the group consisting of docetaxel, ethinyl estradiol, estramustine, felbinac, bezafibrate, mebendazole, thiamylal sodium, mercaptopurine, dutasteride, cetirizine hydrochloride, acetophenazine maleate, oxytetracycline, artemisinin, hydralazine hydrochloride, Indomethacin, atorvastatin calcium, guanethidine sulfate, pantothenic acid(d) na salt, saxagliptin, (±)-Verapamil hydrochloride, oxidopamine hydrochloride, trilostane, fomepizole hydrochloride, modafinil, Xylazine hydrochloride, diperodon hydrochloride, zomepirac sodium, thiabendazole, closantel, hexylresorcinol, adapalene, finasteride, Procainamide hydrochloride, cefadroxil, sulfameter, sulfaquinoxaline sodium, azithromycin, imipenem, colistin sulfate, cefoxitin sodium, oxyphencyclimine hydrochloride, oxybutynin chloride, clidinium bromide, Fluoxetine hydrochloride, Tolazamide, trimethobenzamide hydrochloride, Metoclopramide hydrochloride, tolnaftate, chlorpheniramine maleate, phenylbutyric acid, colesevalam hydrochloride, Pargyline hydrochloride, telmisartan, troclosene potassium, bleomycin, dasatinib, anastrozole, busulfan, carboplatin, pemetrexed, hydroquinone, selamectin, levodopa, sucralfate, valganciclovir hydrochloride, lamivudine, idoxuridine, sotalol hydrochloride, carvedilol, clavulanate lithium, (±)-Isoproterenol hydrochloride, racephedrine hydrochloride, sodium monofluorophosphate, dexpanthenol, vardenafil hydrochloride, guaiacol, rabeprazole sodium, clobetasol propionate, mycophenolic acid, fludrocortisone acetate, zaleplon, bemotrizinol, parachlorophenol, nitroglycerin, and acetriazoic acid, single stereoisomers, mixtures of stereoisomers, pharmaceutically acceptable salts, prodrugs and functional derivatives thereof.

Claim 4. The pharmaceutical composition according to any one of claims 1-3, wherein the variability modulator is selected from the group consisting of docetaxel, ethinyl estradiol, estramustine, felbinac, bezafibrate, mebendazole, mercaptopurine, dutasteride, cetirizine hydrochloride, acetophenazine maleate, oxytetracycline, artemisinin, single stereoisomers, mixtures of stereoisomers, pharmaceutically acceptable salts, prodrugs and functional derivatives thereof.

Claim 5. The pharmaceutical composition according to any of claims 1-4, wherein the activator of latent HIV-1 gene expression is selected from the group consisting of a histone deacetylase (HDAC) inhibitor, a protein kinase C (PKC) agonist, an inhibitor of methylation, an inhibitor of a bromodomain protein, and an anticancer drug.

Claim 6. The pharmaceutical composition according to any one of claims 1-5, wherein the activator of latent HIV-1 gene expression is a histone deacetylase (HDAC) inhibitor.

Claim 7. The pharmaceutical composition according to any one of claims 5 and 6, wherein the HDAC inhibitor is selected from the group consisting of 12-deoxyphorbol 13-phenylacetate (DPP), Suberoylannilide Hydroxamic Acid (SAHA), MS-275, valproic acid (VPA), trichostatin A (TSA), single stereoisomers, mixtures of stereoisomers, pharmaceutically acceptable salts or prodrugs thereof.

Claim 8. The pharmaceutical composition according to any one of claims 1-5, wherein the activator of latent HIV-1 gene expression is a Protein Kinase C (PKC) agonist.

Claim 9. The pharmaceutical composition according to any one of claims 5 and 8, wherein the PKC agonist is selected from the group consisting of tumor necrosis factor alpha (TNFα), prostratin, PMA, bryostatin, single stereoisomers, mixtures of stereoisomers, pharmaceutically acceptable salts or prodrugs thereof.

Claim 10. The pharmaceutical composition according to any one of claims 1-5, wherein the activator of latent HIV-1 gene expression is an inhibitor of methylation.

Claim 11. The pharmaceutical composition according to any one of claims 5 and 10, wherein the inhibitor of methylation is azacytidine, single stereoisomers, mixtures of stereoisomers, pharmaceutically acceptable salts or prodrugs thereof.

Claim 12. The pharmaceutical composition according to any one of claims 1-5, wherein the activator of latent HIV-1 gene expression is a bromodomain inhibitor.

Claim 13. The pharmaceutical composition according to any one of claims 5 and 12, wherein the bromodomain inhibitor is JQ1, GSK1210151A, or PFI-1, single stereoisomers, mixtures of stereoisomers, pharmaceutically acceptable salts or prodrugs thereof.

Claim 14. The pharmaceutical composition according to any one of claims 1-5, wherein the activator of latent HIV-1 gene expression is an anticancer drug.

Claim 15. The pharmaceutical composition according to any one of claims 5 and 14, wherein the anticancer drug is cytarabine, single stereoisomers, mixtures of stereoisomers, pharmaceutically acceptable salts or prodrugs thereof.

Claim 16. The pharmaceutical composition according to any one of claims 1-15, wherein the mammalian cell is in vitro.

Claim 17. The pharmaceutical composition according to any one of claims 1-15, wherein the mammalian cell is in vivo.

Claim 18. The pharmaceutical composition according to any one of claims 1-17 wherein the mammalian cell is selected from the group consisting of a human cell, a human T cell, a SupT1 cell, and a primary T-cell.

Claim 19. The pharmaceutical composition according to any one of claims 1-18, further comprising (iv) a HAART compound.

Some embodiments of a pharmaceutical composition for suppressing reactivation of a latent HIV-1 reservoir in a mammalian cell having an integrated HIV-1 genome are set forth in claim format below:

Claim 1. A pharmaceutical composition for suppressing reactivation of a latent Human Immunodeficiency Virus Type 1 ("HIV-1") reservoir in a mammalian cell having an integrated HIV-1 genome, the composition comprising:
(i) a variability suppressor in an amount sufficient to modulate variability of expression of a gene promoter without substantially changing the mean expression level of the gene promoter; and
(ii) a pharmaceutically acceptable carrier.

Claim 2. The pharmaceutical composition according to claim 1, wherein the variability suppressor is selected from the group consisting of manidipine hydrochloride, phenothiazine, dichlorvos, fipronil, trichlorfon, benzydamine hydrochloride, maprotiline hydrochloride, Papaverine hydrochloride, arsenic trioxide, phenformin hydrochloride, itraconazole, cycloheximide, hydroxyprogesterone caproate, pyrithione zinc, meclocycline sulfosalicylate, ergotamine tartrate, adenosine phosphate, broxaldine, single stereoisomers, mixtures of stereoisomers, pharmaceutically acceptable salts, prodrugs and functional derivatives thereof.

Some embodiments of a kit for modulating gene expression of a gene promoter in a cell are set forth in claim format below:

Claim 1. A kit for modulating gene expression of a gene promoter in a cell, the kit comprising:
(i) a first container containing a variability modulator in an amount sufficient to modulate variability of expression of a gene promoter without substantially changing the mean expression level of the gene promoter; and
(ii) an instruction for using (i) for modulating gene expression in the cell.

Claim 2. The kit according to claim 1, further comprising:
(iii) a second container containing an activator of gene expression in an amount effective to activate gene expression.

Claim 3. The kit according to any one of claims 1-2, wherein the variability modulator is selected from the group consisting of thiamylal sodium, Estramustine, griseofulvin, telmisartan, docetaxel, riboflavin, pantothenic acid(d) na salt, mercaptopurine, pemetrexed, ethinyl estradiol, irinotecan hydrochloride, dutasteride, felbinac, vincristine sulfate, thiram, bezafibrate, Indomethacin, mebendazole, ouabain, sulfaquinoxaline sodium, oxybutynin chloride, oxyphencyclimine hydrochloride, saxagliptin, phenylmercuric acetate, troclosene potassium, artemisinin, cytarabine, thioguanine, hydroquinone, acetophenazine maleate, hexylresorcinol, oxytetracycline, cefadroxil, tolnaftate, phenylbutyric acid, atorvastatin calcium, carboplatin, 5-azacytidine, levodopa, lamivudine, sotalol hydrochloride, clavulanate lithium, digoxin, sodium monofluorophosphate, dexpanthenol, rabeprazole sodium, cetirizine hydrochloride, trilostane, modafinil, thiabendazole, adapalene, sulfameter, Fluoxetine hydrochloride, trimethobenzamide hydrochloride, Metoclopramide hydrochloride, guanethidine sulfate, trichlormethine, sucralfate, valganciclovir hydrochloride, bemotrizinol, parachlorophenol, (±)-Verapamil hydrochloride, oxidopamine hydrochloride, fomepizole hydrochloride, Xylazine hydrochloride, diperodon hydrochloride, zomepirac sodium, closantel, fenbendazole, finasteride, Procainamide hydrochloride, celecoxib, colistin sulfate, imipenem, cefoxitin sodium, azithromycin, clidinium bromide, Tolazamide, chlorpheniramine maleate, colesevalam hydrochloride, Pargyline hydrochloride, hydralazine hydrochloride, anastrozole, vinorelbine, bleomycin, dasatinib, busulfan, vorinostat, selamectin, idoxuridine, carvedilol, (±)-Isoproterenol hydrochloride, racephedrine hydrochloride, vardenafil hydrochloride, guaiacol, clobetasol propionate, mycophenolic acid, fludrocortisone acetate, zaleplon, nitroglycerin, riboflavin 5-phosphate sodium, acetriazoic acid, digitoxin, carnitine hydrochloride, albendazole, taurine, Taxol, mitomycin c, clofarabine, arginine hydrochloride, tetramizole hydrochloride, thiostrepton, lonidamine, melphalan, fludarabine phosphate, methotrexate(+/−), rifaximin, Arecoline hydrobromide, zalcitabine, erythrosine sodium, nikethamide, oxfendazole, editol, doxapram hydrochloride, aminacrine, dobutamine hydrochloride, rutin, manidipine hydrochloride, phenothiazine, dichlorvos, fipronil, trichlorfon, benzydamine hydrochloride, maprotiline hydrochloride, Papaverine hydrochloride, arsenic trioxide, phenformin hydrochloride, itraconazole, cycloheximide, hydroxyprogesterone caproate, pyrithione zinc, meclocycline sulfosalicylate, ergotamine tartrate, adenosine phosphate, broxaldine, single stereoisomers, mixtures of stereoisomers, pharmaceutically acceptable salts, prodrugs and functional derivatives thereof.

Claim 4. The kit according to any one of claims 1-3, wherein the variability modulator is selected from the group consisting of docetaxel, ethinyl estradiol, estramustine, felbinac, bezafibrate, mebendazole, thiamylal sodium, mercaptopurine, dutasteride, cetirizine hydrochloride, acetophenazine maleate, oxytetracycline, artemisinin, hydralazine hydrochloride, Indomethacin, atorvastatin calcium, guanethidine sulfate, pantothenic acid(d) na salt, saxagliptin, (±)-Verapamil hydrochloride, oxidopamine hydrochloride, trilostane, fomepizole hydrochloride, modafinil, Xylazine hydrochloride, diperodon hydrochloride, zomepirac sodium, thiabendazole, closantel, hexylresorcinol, adapalene, finasteride, Procainamide hydrochloride, cefadroxil, sulfameter, sulfaquinoxaline sodium, azithromycin, imipenem, colistin sulfate, cefoxitin sodium, oxyphencyclimine hydrochloride, oxybutynin chloride, clidinium bromide, Fluoxetine hydrochloride, Tolazamide, trimethobenzamide hydrochloride, Metoclopramide hydrochloride, tolnaftate, chlorpheniramine maleate, phenylbutyric acid, colesevalam hydrochloride, Pargyline hydrochloride, telmisartan, troclosene potassium, bleomycin, dasatinib, anastrozole, busulfan, carboplatin, pemetrexed, hydroquinone, selamectin, levodopa, sucralfate, valganciclovir hydrochloride, lamivudine, idoxuridine, sotalol hydrochloride, carvedilol, clavulanate lithium, (±)-Isoproterenol hydrochloride, racephedrine hydrochloride, sodium monofluorophosphate, dexpanthenol, vardenafil hydrochloride, guaiacol, rabeprazole sodium, clobetasol propionate, mycophenolic acid, fludrocortisone acetate, zaleplon, bemotrizinol, parachlorophenol, nitroglycerin, and acetriazoic acid, single stereoisomers, mixtures of stereoisomers, pharmaceutically acceptable salts, prodrugs and functional derivatives thereof.

Claim 5. The kit according to any one of claims 1-4, wherein the variability modulator is selected from the group consisting of docetaxel, ethinyl estradiol, estramustine, felbinac, bezafibrate, mebendazole, mercaptopurine, dutasteride, cetirizine hydrochloride, acetophenazine maleate, oxytetracycline, artemisinin, single stereoisomers, mixtures of stereoisomers, pharmaceutically acceptable salts, prodrugs and functional derivatives thereof.

Claim 6. The kit according to any one of claims 1-3, wherein the variability modulator is selected from the group consisting of manidipine hydrochloride, phenothiazine, dichlorvos, fipronil, trichlorfon, benzydamine hydrochloride, maprotiline hydrochloride, Papaverine hydrochloride, arsenic trioxide, phenformin hydrochloride, itraconazole, cycloheximide, hydroxyprogesterone caproate, pyrithione zinc, meclocycline sulfosalicylate, ergotamine tartrate, adenosine phosphate, broxaldine, single stereoisomers, mixtures of stereoisomers, pharmaceutically acceptable salts, prodrugs and functional derivatives thereof.

Claim 7. The kit according to any one of claims 2-6, wherein the activator of gene expression is selected from the group consisting of a prokaryotic activator of gene expression, a viral activator of gene expression, a eukaryotic activator of gene expression, and a activator of Human Immunodeficiency Virus Type 1 (HIV-1) gene expression.

Claim 8. The kit according to any one of claims 2-7, wherein the activator of gene expression is selected from the group consisting of a histone deacetylase (HDAC) inhibitor, a protein kinase C (PKC) agonist, an inhibitor of methylation, an inhibitor of a bromodomain protein, and an anticancer drug.

Claim 9. The kit according to any one of claims 2-8, wherein the activator of gene expression is a histone deacetylase (HDAC) inhibitor.

Claim 10. The kit according to any one of claims 2-9, wherein the HDAC inhibitor is selected from the group consisting of 12-deoxyphorbol 13-phenylacetate (DPP), Suberoylannilide Hydroxamic Acid (SAHA), MS-275, valproic acid (VPA), trichostatin A (TSA), single stereoisomers, mixtures of stereoisomers, pharmaceutically acceptable salts or prodrugs thereof.

Claim 11. The kit according to any one of claims 2-8, wherein the activator of gene expression is a Protein Kinase C (PKC) agonist.

Claim 12. The kit according to any of claims 2-8 and 11, wherein the PKC agonist is selected from the group consisting of tumor necrosis factor alpha (TNFα), prostratin, PMA, bryostatin, single stereoisomers, mixtures of stereoisomers, pharmaceutically acceptable salts or prodrugs thereof.

Claim 13. The kit according to any one of claims 2-8, wherein the activator of gene expression is an inhibitor of methylation.

Claim 14. The kit according to any one of claims 2-8 and 13, wherein the inhibitor of methylation is azacytidine, single stereoisomers, mixtures of stereoisomers, pharmaceutically acceptable salts or prodrugs thereof.

Claim 15. The kit according to any one of claims 2-8, wherein the activator of gene expression is a bromodomain inhibitor.

Claim 16. The kit according to any one of claims 2-8 and 15, wherein the bromodomain inhibitor is JQ1, GSK1210151A, or PFI-1, single stereoisomers, mixtures of stereoisomers, pharmaceutically acceptable salts or prodrugs thereof.

Claim 17. The kit according to any one of claims 2-8, wherein the activator of gene expression is an anticancer drug.

Claim 18. The kit according to any one of claims 2-8 and 17, wherein the anticancer drug is cytarabine, single stereoisomers, mixtures of stereoisomers, pharmaceutically acceptable salts or prodrugs thereof.

Claim 19. The kit according to any one of claims 1-18, further comprising a container containing the cell.

Claim 20. The kit according to any one of claims 1-19 wherein the cell is selected from the group consisting of a prokaryotic cell, a eukaryotic cell, a mammalian cell, a human cell, a human T cell, a SupT1 cell, and a primary T-cell.

Claim 21. The kit according to any one of claims 1-20, further comprising a container containing a HAART compound.

Some embodiments of a kit for reactivating a latent HIV-1 reservoir in a mammalian cell having an integrated HIV-1 genome are set forth in claim format below:

Claim 1. A kit for reactivating a latent HIV-1 reservoir in a mammalian cell having an integrated HIV-1 genome, the kit comprising:
(i) a first container containing a variability modulator in an amount sufficient to modulate variability of expression of a gene promoter without substantially changing the mean expression level of the gene promoter;
(ii) a second container containing an activator of latent HIV-1 gene expression in an amount effective to activate latent HIV-1 gene expression; and
(iii) an instruction for using (i) and (ii) for reactivating the latent HIV-1 reservoir in the mammalian cell.

Claim 2. The kit according to claim 1, wherein the variability modulator is selected from the group consisting of thiamylal sodium, Estramustine, griseofulvin, telmisartan, docetaxel, riboflavin, pantothenic acid(d) na salt, mercaptopurine, pemetrexed, ethinyl estradiol, irinotecan hydrochloride, dutasteride, felbinac, vincristine sulfate, thiram, bezafibrate, Indomethacin, mebendazole, ouabain, sulfaquinoxaline sodium, oxybutynin chloride, oxyphencyclimine hydrochloride, saxagliptin, phenylmercuric acetate, troclosene potassium, artemisinin, cytarabine, thioguanine, hydroquinone, acetophenazine maleate, hexylresorcinol, oxytetracycline, cefadroxil, tolnaftate, phenylbutyric acid, atorvastatin calcium, carboplatin, 5-azacytidine, levodopa, lamivudine, sotalol hydrochloride, clavulanate lithium, digoxin, sodium monofluorophosphate, dexpanthenol, rabeprazole sodium, cetirizine hydrochloride, trilostane, modafinil, thiabendazole, adapalene, sulfameter, Fluoxetine hydrochloride, trimethobenzamide hydrochloride, Metoclopramide hydrochloride, guanethidine sulfate, trichlormethine, sucralfate, valganciclovir hydrochloride, bemotrizinol, parachlorophenol, (Â±)-Verapamil hydrochloride, oxidopamine hydrochloride, fomepizole hydrochloride, Xylazine hydrochloride, diperodon hydrochloride, zomepirac sodium, closantel, fenbendazole, finasteride, Procainamide hydrochloride, celecoxib, colistin sulfate, imipenem, cefoxitin sodium, azithromycin, clidinium bromide, Tolazamide, chlorpheniramine maleate, colesevalam hydrochloride, Pargyline hydrochloride, hydralazine hydrochloride, anastrozole, vinorelbine, bleomycin, dasatinib, busulfan, vorinostat, selamectin, idoxuridine, carvedilol, (Â±)-Isoproterenol hydrochloride, racephedrine hydrochloride, vardenafil hydrochloride, guaiacol, clobetasol propionate, mycophenolic acid, fludrocortisone acetate, zaleplon, nitroglycerin, riboflavin 5-phosphate sodium, acetriazoic acid, digitoxin, carnitine hydrochloride, albendazole, taurine, Taxol, mitomycin c, clofarabine, arginine hydrochloride, tetramizole hydrochloride, thiostrepton, lonidamine, melphalan, fludarabine phosphate, methotrexate(+/−), rifaximin, Arecoline hydrobromide, zalcitabine, erythrosine sodium, nikethamide, oxfendazole, editol, doxapram hydrochloride, aminacrine, dobutamine hydrochloride, rutin, single stereoisomers, mixtures of stereoisomers, pharmaceutically acceptable salts, prodrugs and functional derivatives thereof.

Claim 3. The kit according to claim 1, wherein the variability modulator is selected from the group consisting of docetaxel, ethinyl estradiol, estramustine, felbinac, bezafibrate, mebendazole, thiamylal sodium, mercaptopurine, dutasteride, cetirizine hydrochloride, acetophenazine maleate, oxytetracycline, artemisinin, hydralazine hydrochloride, Indomethacin, atorvastatin calcium, guanethidine sulfate, pantothenic acid(d) na salt, saxagliptin, (Â±)-Verapamil hydrochloride, oxidopamine hydrochloride, trilostane, fomepizole hydrochloride, modafinil, Xylazine hydrochloride, diperodon hydrochloride, zomepirac sodium, thiabendazole, closantel, hexylresorcinol, adapalene, finasteride, Procainamide hydrochloride, cefadroxil, sulfameter, sulfaquinoxaline sodium, azithromycin, imipenem, colistin sulfate, cefoxitin sodium, oxyphencyclimine hydrochloride, oxybutynin chloride, clidinium bromide, Fluoxetine hydrochloride, Tolazamide, trimethobenzamide hydrochloride, Metoclopramide hydrochloride, tolnaftate, chlorpheniramine maleate, phenylbutyric acid, colesevalam, Pargyline hydrochloride, telmisartan, troclosene potassium, bleomycin, dasatinib, anastrozole, busulfan, carboplatin, pemetrexed, hydroquinone, selamectin, levodopa, sucralfate, valganciclovir hydrochloride, lamivudine, idoxuridine, sotalol hydrochloride, carvedilol, clavulanate lithium, (Â±)-Isoproterenol hydrochloride, racephedrine hydrochloride, sodium monofluorophosphate, dexpanthenol, vardenafil hydrochloride, guaiacol, rabeprazole sodium, clobetasol propionate, mycophenolic acid, fludrocortisone acetate, zaleplon, bemotrizinol, parachlorophenol, nitroglycerin, and acetriazoic acid, single stereoisomers, mixtures of stereoisomers, pharmaceutically acceptable salts, prodrugs and functional derivatives thereof.

Claim 4. The kit according to any one of claims 1-3, wherein the variability modulator is selected from the group consisting of docetaxel, ethinyl estradiol, estramustine, felbinac, bezafibrate, mebendazole, mercaptopurine, dutasteride, cetirizine hydrochloride, acetophenazine maleate, oxytetracycline, artemisinin, single stereoisomers, mixtures of stereoisomers, pharmaceutically acceptable salts, prodrugs and functional derivatives thereof.

Claim 5. The kit according to any of claims 1-4, wherein the activator of latent HIV-1 gene expression is selected from the group consisting of a histone deacetylase (HDAC) inhibitor, a protein kinase C (PKC) agonist, an inhibitor of methylation, an inhibitor of a bromodomain protein, and an anticancer drug.

Claim 6. The kit according to any one of claims 1-5, wherein the activator of latent HIV-1 gene expression is a histone deacetylase (HDAC) inhibitor.

Claim 7. The kit according to any one of claims 5 and 6, wherein, the HDAC inhibitor is selected from the group consisting of 12-deoxyphorbol 13-phenylacetate (DPP), Suberoylannilide Hydroxamic Acid (SAHA), MS-275, valproic acid (VPA), trichostatin A (TSA), single stereoisomers, mixtures of stereoisomers, pharmaceutically acceptable salts or prodrugs thereof.

Claim 8. The kit according to any one of claims 1-5, wherein the activator of latent HIV-1 gene expression is a Protein Kinase C (PKC) agonist.

Claim 9. The kit according to any one of claims 5 and 8, wherein the PKC agonist is selected from the group consisting of tumor necrosis factor alpha (TNFα), prostratin, PMA, bryostatin, single stereoisomers, mixtures of stereoisomers, pharmaceutically acceptable salts or prodrugs thereof.

Claim 10. The kit according to any one of claims 1-5, wherein the activator of latent HIV-1 gene expression is an inhibitor of methylation.

Claim 11. The kit according to any one of claims 5 and 10, wherein the inhibitor of methylation is azacytidine, single stereoisomers, mixtures of stereoisomers, pharmaceutically acceptable salts or prodrugs thereof.

Claim 12. The kit according to any one of claims 1-5, wherein the activator of latent HIV-1 gene expression is a bromodomain inhibitor.

Claim 13. The kit according to any one of claims 5 and 12, wherein the bromodomain inhibitor is JQ1, GSK1210151A, or PFI-1, single stereoisomers, mixtures of stereoisomers, pharmaceutically acceptable salts or prodrugs thereof.

Claim 14. The kit according to any one of claims 1-5, wherein the activator of latent HIV-1 gene expression is an anticancer drug.

Claim 15. The kit according to any one of claims 5 and 14, wherein the anticancer drug is cytarabine, single stereoisomers, mixtures of stereoisomers, pharmaceutically acceptable salts or prodrugs thereof.

Claim 16. The kit according to any one of claims 1-15, wherein the mammalian cell is in vitro.

Claim 17. The kit according to any one of claims 1-15, wherein the mammalian cell is in vivo.

Claim 18. The kit according to any one of claims 1-17 wherein the mammalian cell is selected from the group consisting of a human cell, a human T cell, a SupT1 cell, and a primary T-cell.

Claim 19. The kit according to any one of claims 1-18, further comprising (iv) a third container containing a HAART compound.

Some embodiments of a kit for suppressing reactivation of a latent HIV-1 reservoir in a mammalian cell having an integrated HIV-1 genome are set forth in claim format below:

Claim 1. A kit for suppressing reactivation of a latent Human Immunodeficiency Virus Type 1 ("HIV-1") reservoir in a mammalian cell having an integrated HIV-1 genome, the kit comprising:
  (i) a first container containing a variability suppressor in an amount sufficient to modulate variability of expression of a gene promoter without substantially changing the mean expression level of the gene promoter; and
  (ii) an instruction for using (i) for suppression of reactivation of a latent HIV-1 reservoir in the mammalian cell.

Claim 2. The kit according to claim 1, wherein the wherein the variability suppressor is selected from the group consisting of manidipine hydrochloride, phenothiazine, dichlorvos, fipronil, trichlorfon, benzydamine hydrochloride, maprotiline hydrochloride, Papaverine hydrochloride, arsenic trioxide, phenformin hydrochloride, itraconazole, cycloheximide, hydroxyprogesterone caproate, pyrithione zinc, meclocycline sulfosalicylate, ergotamine tartrate, adenosine phosphate, broxaldine, single stereoisomers, mixtures of stereoisomers, pharmaceutically acceptable salts, prodrugs and functional derivatives thereof.

Some embodiments of a use of a variability modulator for modulating variability of expression of a latent HIV-1 reservoir in a mammalian cell having an integrated HIV-1 genome are set forth in claim format below:

Claim 1. A use of a variability modulator for modulating variability in expression of a latent Human Immunodeficiency Virus Type 1 ("HIV-1") reservoir in a mammalian cell having an integrated HIV-1 genome, the use comprising the step of:
  contacting the mammalian cell with an amount of a variability modulator sufficient to modulate variability of expression of a gene promoter without substantially changing the mean expression level of the gene promoter;
  wherein variability of expression of the latent HIV-1 reservoir is modulated.

Claim 2. The use according to claim 1, wherein the use further comprises contacting the mammalian cell with an amount of an activator of latent HIV-1 gene expression effective to activate latent HIV-1 gene expression.

Claim 3. The use according to any one of claims 1-2, wherein the variability modulator is selected from the group consisting of thiamylal sodium, Estramustine, griseofulvin, telmisartan, docetaxel, riboflavin, pantothenic acid(d) na salt, mercaptopurine, pemetrexed, ethinyl estradiol, irinotecan hydrochloride, dutasteride, felbinac, vincristine sulfate, thiram, bezafibrate, Indomethacin, mebendazole, ouabain, sulfaquinoxaline sodium, oxybutynin chloride, oxyphencyclimine hydrochloride, saxagliptin, phenylmercuric acetate, troclosene potassium, artemisinin, cytarabine, thioguanine, hydroquinone, acetophenazine maleate, hexylresorcinol, oxytetracycline, cefadroxil, tolnaftate, phenylbutyric acid, atorvastatin calcium, carboplatin, 5-azacytidine, levodopa, lamivudine, sotalol hydrochloride, clavulanate lithium, digoxin, sodium monofluorophosphate, dexpanthenol, rabeprazole sodium, cetirizine hydrochloride, trilostane, modafinil, thiabendazole, adapalene, sulfameter, Fluoxetine hydrochloride, trimethobenzamide hydrochloride, Metoclopramide hydrochloride, guanethidine sulfate, trichlormethine, sucralfate, valganciclovir hydrochloride, bemotrizinol, parachlorophenol, (±)-Verapamil hydrochloride, oxidopamine hydrochloride, fomepizole hydrochloride, Xylazine hydrochloride, diperodon hydrochloride, zomepirac sodium, closantel, fenbendazole, finasteride, Procainamide hydrochloride, celecoxib, colistin sulfate, imipenem, cefoxitin sodium, azithromycin, clidinium bromide, Tolazamide, chlorpheniramine maleate, colesevalam hydrochloride, Pargyline hydrochloride, hydralazine hydrochloride, anastrozole, vinorelbine, bleomycin, dasatinib, busulfan, vorinostat, selamectin, idoxuridine, carvedilol, (±)-Isoproterenol hydrochloride, racephedrine hydrochloride, vardenafil hydrochloride, guaiacol, clobetasol propionate, mycophenolic acid, fludrocortisone acetate, zaleplon, nitroglycerin, riboflavin 5-phosphate sodium, acetriazoic acid, digitoxin, carnitine hydrochloride, albendazole, taurine, Taxol, mitomycin c, clofarabine, arginine hydrochloride, tetramizole hydrochloride, thiostrepton, lonidamine, melphalan, fludarabine phosphate, methotrexate(+/−), rifaximin, Arecoline hydrobromide, zalcitabine, erythrosine sodium, nikethamide, oxfendazole, editol, doxapram hydrochloride, aminacrine, dobutamine hydrochloride, rutin, manidipine hydrochloride, phenothiazine, dichlorvos, fipronil, trichlorfon, benzydamine hydrochloride, maprotiline hydrochloride, Papaverine hydrochloride, arsenic trioxide, phenformin hydrochloride, itraconazole, cycloheximide, hydroxyprogesterone caproate, pyrithione zinc, meclocycline sulfosalicylate, ergotamine tartrate, adenosine phosphate, broxaldine, single stereoisomers, mixtures of stereoisomers, pharmaceutically acceptable salts, prodrugs and functional derivatives thereof.

Claim 4. The use according to any one of claims 1-3, wherein the variability modulator is selected from the group consisting of docetaxel, ethinyl estradiol, estramustine, felbinac, bezafibrate, mebendazole, thiamylal sodium, mercaptopurine, dutasteride, cetirizine hydrochloride, acetophenazine maleate, oxytetracycline, artemisinin, hydralazine hydrochloride, Indomethacin, atorvastatin calcium, guanethidine sulfate, pantothenic acid(d) na salt, saxagliptin, (±)-Verapamil hydrochloride, oxidopamine hydrochloride, trilostane, fomepizole hydrochloride, modafinil, Xylazine hydrochloride, diperodon hydrochloride, zomepirac sodium, thiabendazole, closantel, hexylresorcinol, adapalene, finasteride, Procainamide hydrochloride, cefadroxil, sulfameter, sulfaquinoxaline sodium, azithromycin, imipenem, colistin sulfate, cefoxitin sodium, oxyphencyclimine hydrochloride, oxybutynin chloride, clidinium bromide, Fluoxetine hydrochloride, Tolazamide, trimethobenzamide hydrochloride, Metoclopramide hydrochloride, tolnaftate, chlorpheniramine maleate, phenylbutyric acid, colesevalam hydrochloride, Pargyline hydrochloride, telmisartan, troclosene potassium, bleomycin, dasatinib, anastrozole, busulfan, carboplatin, pemetrexed, hydroquinone, selamectin, levodopa, sucralfate, valganciclovir hydrochloride, lamivudine, idoxuridine, sotalol hydrochloride, carvedilol, clavulanate lithium, (±)-Isoproterenol hydrochloride, racephedrine hydrochloride, sodium monofluorophosphate, dexpanthenol, vardenafil hydrochloride, guaiacol, rabeprazole sodium, clobetasol propionate, mycophenolic acid, fludrocortisone acetate, zaleplon, bemotrizinol, parachlorophenol, nitroglycerin, and acetriazoic acid, single stereoisomers, mixtures of stereoisomers, pharmaceutically acceptable salts, prodrugs and functional derivatives thereof.

Claim 5. The use according to any one of claims 1-4, wherein the variability modulator is selected from the group consisting of docetaxel, ethinyl estradiol, estramustine, felbinac, bezafibrate, mebendazole, mercaptopurine, dutasteride, cetirizine hydrochloride, acetophenazine maleate, oxytetracycline, artemisinin, single stereoisomers, mixtures of stereoisomers, pharmaceutically acceptable salts, prodrugs and functional derivatives thereof.

Claim 6. The use according to any one of claims 1-3, wherein the variability modulator is selected from the group consisting of manidipine hydrochloride, phenothiazine, dichlorvos, fipronil, trichlorfon, benzydamine hydrochloride, maprotiline hydrochloride, Papaverine hydrochloride, arsenic trioxide, phenformin hydrochloride, itraconazole, cycloheximide, hydroxyprogesterone caproate, pyrithione zinc, meclocycline sulfosalicylate, ergotamine tartrate, adenosine phosphate, broxaldine, single stereoisomers, mixtures of stereoisomers, pharmaceutically acceptable salts, prodrugs and functional derivatives thereof Claim 7. The use according to claims 2-6, wherein the activator of latent HIV-1 gene expression is selected from the group consisting of a histone deacetylase (HDAC) inhibitor, a protein kinase C (PKC) agonist, an inhibitor of methylation, an inhibitor of a bromodomain protein, and an anticancer drug.

Claim 8. The use according to any one of claims 2-7, wherein the activator of latent HIV-1 gene expression is a histone deacetylase (HDAC) inhibitor.

Claim 9. The use according to any one of claims 7-8, wherein the HDAC inhibitor is selected from the group consisting of 12-deoxyphorbol 13-phenylacetate (DPP), Suberoylannilide Hydroxamic Acid (SAHA), MS-275, valproic acid (VPA), trichostatin A (TSA), single stereoisomers, mixtures of stereoisomers, pharmaceutically acceptable salts or prodrugs thereof.

Claim 10. The use according to any one of claims 2-7, wherein the activator of latent HIV-1 gene expression is a Protein Kinase C (PKC) agonist.

Claim 11. The use according to any of claims 7 and 10, wherein the PKC agonist is selected from the group consisting of tumor necrosis factor alpha (TNFα), prostratin, PMA, bryostatin, single stereoisomers, mixtures of stereoisomers, pharmaceutically acceptable salts or prodrugs thereof.

Claim 12. The use according to any one of claims 2-7, wherein the activator of latent HIV-1 gene expression is an inhibitor of methylation.

Claim 13. The use according to any one of claims 7 and 12, wherein the inhibitor of methylation is azacytidine, single stereoisomers, mixtures of stereoisomers, pharmaceutically acceptable salts or prodrugs thereof.

Claim 14. The use according to any one of claims 2-7, wherein the activator of latent HIV-1 gene expression is a bromodomain inhibitor.

Claim 15. The use according to any one of claims 7 and 14, wherein the bromodomain inhibitor is JQ1, GSK1210151A, or PFI-1, single stereoisomers, mixtures of stereoisomers, pharmaceutically acceptable salts or prodrugs thereof.

Claim 16. The use according to any one of claims 2-7, wherein the activator of latent HIV-1 gene expression is an anticancer drug.

Claim 17. The method according to any one of claims 7 and 16, wherein the anticancer drug is cytarabine, single stereoisomers, mixtures of stereoisomers, pharmaceutically acceptable salts or prodrugs thereof.

Claim 18. The use according to any one of claims 1-17, wherein the mammalian cell is in vitro.

Claim 19. The use according to any one of claims 1-17, wherein the mammalian cell is in vivo.

Claim 20. The use according to any one of claims 1-19, wherein the mammalian cell is selected from the group consisting of a human cell, a human T cell, a SupT1 cell, and a primary T-cell.

Claim 21. The use according to any one of claims 1-20, further comprising the step of contacting the mammalian cell with a HAART compound.

Some embodiments of a use of a variability modulator for reactivating a latent HIV-1 reservoir in a mammalian cell having an integrated HIV-1 genome are set forth in claim format below:

Claim 1. A use of a variability modulator for reactivating a latent Human Immunodeficiency Virus Type 1 ("HIV-1") reservoir in a mammalian cell having an integrated HIV-1 genome, the use comprising the steps of:
  contacting the mammalian cell with an amount of a variability modulator sufficient to modulate variability of expression of a gene promoter without substantially changing the mean expression level of the gene promoter; and contacting the mammalian cell with an amount of an activator of latent HIV-1 gene expression effective to activate latent gene expression;
wherein the latent HIV-1 reservoir is reactivated.

Claim 2. The use according to claim 1, wherein the variability modulator is selected from the group consisting of thiamylal sodium, Estramustine, griseofulvin, telmisartan, docetaxel, riboflavin, pantothenic acid(d) na salt, mercaptopurine, pemetrexed, ethinyl estradiol, irinotecan hydrochloride, dutasteride, felbinac, vincristine sulfate, thiram, bezafibrate, Indomethacin, mebendazole, ouabain, sulfaquinoxaline sodium, oxybutynin chloride, oxyphencyclimine hydrochloride, saxagliptin, phenylmercuric acetate, troclosene potassium, artemisinin, cytarabine, thioguanine, hydroquinone, acetophenazine maleate, hexylresorcinol, oxytetracycline, cefadroxil, tolnaftate, phenylbutyric acid, atorvastatin calcium, carboplatin, 5-azacytidine, levodopa, lamivudine, sotalol hydrochloride, clavulanate lithium, digoxin, sodium monofluorophosphate, dexpanthenol, rabeprazole sodium, cetirizine hydrochloride, trilostane, modafinil, thiabendazole, adapalene, sulfameter, Fluoxetine hydrochloride, trimethobenzamide hydrochloride, Metoclopramide hydrochloride, guanethidine sulfate, trichlormethine, sucralfate, valganciclovir hydrochloride, bemotrizinol, parachlorophenol, (±)-Verapamil hydrochloride, oxidopamine hydrochloride, fomepizole hydrochloride, Xylazine hydrochloride, diperodon hydrochloride, zomepirac sodium, closantel, fenbendazole, finasteride, Procainamide hydrochloride, celecoxib, colistin sulfate, imipenem, cefoxitin sodium, azithromycin, clidinium bromide, Tolazamide, chlorpheniramine maleate, colesevalam hydrochloride, Pargyline hydrochloride, hydralazine hydrochloride, anastrozole, vinorelbine, bleomycin, dasatinib, busulfan, vorinostat, selamectin, idoxuridine, carvedilol, (±)-Isoproterenol hydrochloride, racephedrine hydrochloride, vardenafil hydrochloride, guaiacol, clobetasol propionate, mycophenolic acid, fludrocortisone acetate, zaleplon, nitroglycerin, riboflavin 5-phosphate sodium, acetriazoic acid, digitoxin, carnitine hydrochloride, albendazole, taurine, Taxol, mitomycin c, clofarabine, arginine hydrochloride, tetramizole hydrochloride, thiostrepton, lonidamine, melphalan, fludarabine phosphate, methotrexate(+/−), rifaximin, Arecoline hydrobromide, zalcitabine, erythrosine sodium, nikethamide, oxfendazole, editol, doxapram hydrochloride, aminacrine, dobutamine hydrochloride, rutin, single stereoisomers, mixtures of stereoisomers, pharmaceutically acceptable salts, prodrugs and functional derivatives thereof.

Claim 3. The use according to claim 1, wherein the variability modulator is selected from the group consisting of docetaxel, ethinyl estradiol, estramustine, felbinac, bezafibrate, mebendazole, thiamylal sodium, mercaptopurine, dutasteride, cetirizine hydrochloride, acetophenazine maleate, oxytetracycline, artemisinin, hydralazine hydrochloride, Indomethacin, atorvastatin calcium, guanethidine sulfate, pantothenic acid(d) na salt, saxagliptin, (±)-Verapamil hydrochloride, oxidopamine hydrochloride, trilostane, fomepizole hydrochloride, modafinil, Xylazine hydrochloride, diperodon hydrochloride, zomepirac sodium, thiabendazole, closantel, hexylresorcinol, adapalene, finasteride, Procainamide hydrochloride, cefadroxil, sulfameter, sulfaquinoxaline sodium, azithromycin, imipenem, colistin sulfate, cefoxitin sodium, oxyphencyclimine hydrochloride, oxybutynin chloride, clidinium bromide, Fluoxetine hydrochloride, Tolazamide, trimethobenzamide hydrochloride, Metoclopramide hydrochloride, tolnaftate, chlorpheniramine maleate, phenylbutyric acid, colesevalam hydrochloride, Pargyline hydrochloride, telmisartan, troclosene potassium, bleomycin, dasatinib, anastrozole, busulfan, carboplatin, pemetrexed, hydroquinone, selamectin, levodopa, sucralfate, valganciclovir hydrochloride, lamivudine, idoxuridine, sotalol hydrochloride, carvedilol, clavulanate lithium, (±)-Isoproterenol hydrochloride, racephedrine hydrochloride, sodium monofluorophosphate, dexpanthenol, vardenafil hydrochloride, guaiacol, rabeprazole sodium, clobetasol propionate, mycophenolic acid, fludrocortisone acetate, zaleplon, bemotrizinol, parachlorophenol, nitroglycerin, and acetriazoic acid, single stereoisomers, mixtures of stereoisomers, pharmaceutically acceptable salts, prodrugs and functional derivatives thereof.

Claim 4. The use according to any one of claims 1-3, wherein the variability modulator is selected from the group consisting of docetaxel, ethinyl estradiol, estramustine, felbinac, bezafibrate, mebendazole, mercaptopurine, dutasteride, cetirizine hydrochloride, acetophenazine maleate, oxytetracycline, artemisinin, single stereoisomers, mixtures of stereoisomers, pharmaceutically acceptable salts, prodrugs and functional derivatives thereof.

Claim 5. The use according to any of claims 1-4, wherein the activator of latent HIV-1 gene expression is selected from the group consisting of a histone deacetylase (HDAC)

inhibitor, a protein kinase C (PKC) agonist, an inhibitor of methylation, an inhibitor of a bromodomain protein, and an anticancer drug.

Claim 6. The use according to any one of claims 1-5, wherein the activator of latent HIV-1 gene expression is a histone deacetylase (HDAC) inhibitor.

Claim 7. The use according to any one of claims 5-6, wherein the HDAC inhibitor is selected from the group consisting of 12-deoxyphorbol 13-phenylacetate (DPP), Suberoylannilide Hydroxamic Acid (SAHA), MS-275, valproic acid (VPA), trichostatin A (TSA), single stereoisomers, mixtures of stereoisomers, pharmaceutically acceptable salts or prodrugs thereof.

Claim 8. The use according to any one of claims 1-5, wherein the activator of latent HIV-1 gene expression is a Protein Kinase C (PKC) agonist.

Claim 9. The use according to any of claims 5 and 8, wherein the PKC agonist is selected from the group consisting of tumor necrosis factor alpha (TNFα), prostratin, PMA, bryostatin, single stereoisomers, mixtures of stereoisomers, pharmaceutically acceptable salts or prodrugs thereof.

Claim 10. The use according to any one of claims 1-5, wherein the activator of latent HIV-1 gene expression is an inhibitor of methylation.

Claim 11. The use according to any one of claims 5 and 10, wherein the inhibitor of methylation is azacytidine, single stereoisomers, mixtures of stereoisomers, pharmaceutically acceptable salts or prodrugs thereof.

Claim 12. The use according to any one of claims 1-5, wherein the activator of latent HIV-1 gene expression is a bromodomain inhibitor.

Claim 13. The use according to any one of claims 5 and 12, wherein the bromodomain inhibitor is JQ1, GSK1210151A, or PFI-1, single stereoisomers, mixtures of stereoisomers, pharmaceutically acceptable salts or prodrugs thereof.

Claim 14. The use according to any one of claims 1-5, wherein the activator of latent HIV-1 gene expression is an anticancer drug.

Claim 15. The use according to any one of claims 5 and 14, wherein the anticancer drug is cytarabine, single stereoisomers, mixtures of stereoisomers, pharmaceutically acceptable salts or prodrugs thereof.

Claim 16. The use according to any one of claims 1-15, wherein the mammalian cell is in vitro.

Claim 17. The use according to any one of claims 1-15, wherein the mammalian cell is in vivo.

Claim 18. The use according to any one of claims 1-17 wherein the mammalian cell is selected from the group consisting of a human cell, a human T cell, a SupT1 cell, and a primary T-cell.

Claim 19. The use according to any one of claims 1-18, further comprising the step of contacting the mammalian cell with a HAART compound.

Some embodiments of a use of a variability suppressor for suppressing reactivation of a latent HIV-1 reservoir in a mammalian cell having an integrated HIV-1 genome are set forth in claim format below:

Claim 1. A use of a variability suppressor for suppressing reactivation of a latent Human Immunodeficiency Virus Type 1 (HIV-1) reservoir in a mammalian cell having an integrated HIV-1 genome, the use comprising the step of contacting the mammalian cell with an amount of a variability suppressor sufficient to modulate variability of expression of a gene promoter without substantially changing the mean expression level of the gene promoter; whereby reactivation of the latent HIV-1 reservoir is suppressed.

Claim 2. The use according to claim 1, wherein the variability suppressor is selected from the group consisting of manidipine hydrochloride, phenothiazine, dichlorvos, fipronil, trichlorfon, benzydamine hydrochloride, maprotiline hydrochloride, Papaverine hydrochloride, arsenic trioxide, phenformin hydrochloride, itraconazole, cycloheximide, hydroxyprogesterone caproate, pyrithione zinc, meclocycline sulfosalicylate, ergotamine tartrate, adenosine phosphate, broxaldine, single stereoisomers, mixtures of stereoisomers, pharmaceutically acceptable salts, prodrugs and functional derivatives thereof.

Claim 3. The use according to any one of claims 1-2, wherein the mammalian cell is in vitro.

Claim 4. The use according to any one of claims 1-2, wherein the mammalian cell is in vivo.

Claim 5. The use according to any one of claims 1-4 wherein the mammalian cell is selected from the group consisting of a human cell, a human T cell, a SupT1 cell, and a primary T-cell.

Some embodiments of a use of a variability modulator for producing a medicament for modulating variability of expression of a latent HIV-1 reservoir in a mammalian cell having an integrated HIV-1 genome are set forth in claim format below:

Claim 1. A use of a variability modulator for producing a medicament for modulating variability of expression of a latent HIV-1 reservoir in a mammalian cell having an integrated HIV-1 genome, the medicament comprising:
 (i) a variability modulator in an amount sufficient to modulate variability of expression of a gene promoter without substantially changing the mean expression level of the gene promoter; and
 (ii) a pharmaceutically acceptable carrier.

Claim 2. The use according to claim 1, wherein the medicament further comprises an activator of latent HIV-1 gene expression in an amount effective to activate latent HIV-1 gene expression.

Claim 3. The use according to any one of claims 1-2, wherein the variability modulator is selected from the group consisting of thiamylal sodium, Estramustine, griseofulvin, telmisartan, docetaxel, riboflavin, pantothenic acid(d) na salt, mercaptopurine, pemetrexed, ethinyl estradiol, irinotecan hydrochloride, dutasteride, felbinac, vincristine sulfate, thiram, bezafibrate, Indomethacin, mebendazole, ouabain, sulfaquinoxaline sodium, oxybutynin chloride, oxyphencyclimine hydrochloride, saxagliptin, phenylmercuric acetate, troclosene potassium, artemisinin, cytarabine, thioguanine, hydroquinone, acetophenazine maleate, hexylresorcinol, oxytetracycline, cefadroxil, tolnaftate, phenylbutyric acid, atorvastatin calcium, carboplatin, 5-azacytidine, levodopa, lamivudine, sotalol hydrochloride, clavulanate lithium, digoxin, sodium monofluorophosphate, dexpanthenol, rabeprazole sodium, cetirizine hydrochloride, trilostane, modafinil, thiabendazole, adapalene, sulfameter, Fluoxetine hydrochloride, trimethobenzamide hydrochloride, Metoclopramide hydrochloride, guanethidine sulfate, trichlormethine, sucralfate, valganciclovir hydrochloride, bemotrizinol, parachlorophenol, (Â±)-Verapamil hydrochloride, oxidopamine hydrochloride, fomepizole hydrochloride, Xylazine hydrochloride, diperodon hydrochloride, zomepirac sodium, closantel, fenbendazole, finasteride, Procainamide hydrochloride, celecoxib, colistin sulfate, imipenem, cefoxitin sodium, azithromycin, clidinium bromide, Tolazamide, chlorpheniramine maleate, colesevalam hydrochloride, Pargyline hydrochloride, hydralazine hydrochloride, anastrozole, vinorelbine, bleomycin, dasatinib, busulfan, vorinostat, selamectin, idoxuridine, carvedilol, (Â±)-Isoproterenol hydrochloride, racephedrine hydrochloride, vardenafil hydrochloride, guaiacol, clobetasol propionate, mycophenolic acid, fludrocortisone acetate, zaleplon, nitroglycerin, riboflavin 5-phosphate sodium, acetriazoic acid, digitoxin, carnitine hydrochloride, albendazole, taurine, Taxol, mitomycin c, clofarabine, arginine hydrochloride, tetramizole hydrochloride, thiostrepton, lonidamine, melphalan, fludarabine phosphate, methotrexate(+/−), rifaximin, Arecoline hydrobromide, zalcitabine, erythrosine sodium, nikethamide, oxfendazole, editol, doxapram hydrochloride, aminacrine, dobutamine hydrochloride, rutin, manidipine hydrochloride, phenothiazine, dichlorvos, fipronil, trichlorfon, benzydamine hydrochloride, maprotiline hydrochloride, Papaverine hydrochloride, arsenic trioxide, phenformin hydrochloride, itraconazole, cycloheximide, hydroxyprogesterone caproate, pyrithione zinc, meclocycline sulfosalicylate, ergotamine tartrate, adenosine phosphate, broxaldine, single stereoisomers, mixtures of stereoisomers, pharmaceutically acceptable salts, prodrugs and functional derivatives thereof.

Claim 4. The use according to any one of claims 1-3, wherein the variability modulator is selected from the group consisting of docetaxel, ethinyl estradiol, estramustine, felbinac, bezafibrate, mebendazole, thiamylal sodium, mercaptopurine, dutasteride, cetirizine hydrochloride, acetophenazine maleate, oxytetracycline, artemisinin, hydralazine hydrochloride, Indomethacin, atorvastatin calcium, guanethidine sulfate, pantothenic acid(d) na salt, saxagliptin, (Â±)-Verapamil hydrochloride, oxidopamine hydrochloride, trilostane, fomepizole hydrochloride, modafinil, Xylazine hydrochloride, diperodon hydrochloride, zomepirac sodium, thiabendazole, closantel, hexylresorcinol, adapalene, finasteride, Procainamide hydrochloride, cefadroxil, sulfameter, sulfaquinoxaline sodium, azithromycin, imipenem, colistin sulfate, cefoxitin sodium, oxyphencyclimine hydrochloride, oxybutynin chloride, clidinium bromide, Fluoxetine hydrochloride, Tolazamide, trimethobenzamide hydrochloride, Metoclopramide hydrochloride, tolnaftate, chlorpheniramine maleate, phenylbutyric acid, colesevalam hydrochloride, Pargyline hydrochloride, telmisartan, troclosene potassium, bleomycin, dasatinib, anastrozole, busulfan, carboplatin, pemetrexed, hydroquinone, selamectin, levodopa, sucralfate, valganciclovir hydrochloride, lamivudine, idoxuridine, sotalol hydrochloride, carvedilol, clavulanate lithium, (Â±)-Isoproterenol hydrochloride, racephedrine hydrochloride, sodium monofluorophosphate, dexpanthenol, vardenafil hydrochloride, guaiacol, rabeprazole sodium, clobetasol propionate, mycophenolic acid, fludrocortisone acetate, zaleplon, bemotrizinol, parachlorophenol, nitroglycerin, and acetriazoic acid, single stereoisomers, mixtures of stereoisomers, pharmaceutically acceptable salts, prodrugs and functional derivatives thereof.

Claim 5. The use according to any one of claims 1-4, wherein the variability modulator is selected from the group consisting of docetaxel, ethinyl estradiol, estramustine, felbinac, bezafibrate, mebendazole, mercaptopurine, dutasteride, cetirizine hydrochloride, acetophenazine maleate, oxytetracycline, artemisinin, single stereoisomers, mixtures of stereoisomers, pharmaceutically acceptable salts, prodrugs and functional derivatives thereof.

Claim 6. The use according to any one of claims 1-3, wherein the variability modulator is selected from the group consisting of manidipine hydrochloride, phenothiazine, dichlorvos, fipronil, trichlorfon, benzydamine hydrochloride, maprotiline hydrochloride, Papaverine hydrochloride, arsenic trioxide, phenformin hydrochloride, itraconazole, cycloheximide, hydroxyprogesterone caproate, pyrithione zinc, meclocycline sulfosalicylate, ergotamine tartrate, adenosine phosphate, broxaldine, single stereoisomers, mixtures of stereoisomers, pharmaceutically acceptable salts, prodrugs and functional derivatives thereof Claim 7. The use according to claims 2-6, wherein the activator of latent HIV-1 gene expression is selected from the group consisting of a histone deacetylase (HDAC) inhibitor, a protein kinase C (PKC) agonist, an inhibitor of methylation, an inhibitor of a bromodomain protein, and an anticancer drug.

Claim 8. The use according to any one of claims 2-7, wherein the activator of latent HIV-1 gene expression is a histone deacetylase (HDAC) inhibitor.

Claim 9. The use according to any one of claims 7-8, wherein the HDAC inhibitor is selected from the group consisting of 12-deoxyphorbol 13-phenylacetate (DPP), Suberoylannilide Hydroxamic Acid (SAHA), MS-275, valproic acid (VPA), trichostatin A (TSA), single stereoisomers, mixtures of stereoisomers, pharmaceutically acceptable salts or prodrugs thereof.

Claim 10. The use according to any one of claims 2-7, wherein the activator of latent HIV-1 gene expression is a Protein Kinase C (PKC) agonist.

Claim 11. The use according to any of claims 7 and 10, wherein the PKC agonist is selected from the group consisting of tumor necrosis factor alpha (TNFα), prostratin, PMA, bryostatin, single stereoisomers, mixtures of stereoisomers, pharmaceutically acceptable salts or prodrugs thereof.

Claim 12. The use according to any one of claims 2-7, wherein the activator of latent HIV-1 gene expression is an inhibitor of methylation.

Claim 13. The use according to any one of claims 7 and 12, wherein the inhibitor of methylation is azacytidine, single stereoisomers, mixtures of stereoisomers, pharmaceutically acceptable salts or prodrugs thereof.

Claim 14. The use according to any one of claims 2-7, wherein the activator of latent HIV-1 gene expression is a bromodomain inhibitor.

Claim 15. The use according to any one of claims 7 and 14, wherein the bromodomain inhibitor is JQ1, GSK1210151A, or PFI-1, single stereoisomers, mixtures of stereoisomers, pharmaceutically acceptable salts or prodrugs thereof.

Claim 16. The use according to any one of claims 2-7, wherein the activator of latent HIV-1 gene expression is an anticancer drug.

Claim 17. The use according to any one of claims 7 and 16, wherein the anticancer drug is cytarabine, single stereoisomers, mixtures of stereoisomers, pharmaceutically acceptable salts or prodrugs thereof.

Claim 18. The use according to any one of claims 1-17, wherein the mammalian cell is in vitro.

Claim 19. The use according to any one of claims 1-17, wherein the mammalian cell is in vivo.

Claim 20. The use according to any one of claims 1-19 wherein the mammalian cell is selected from the group consisting of a human cell, a human T cell, a SupT1 cell, and a primary T-cell.

Claim 21. The use according to any one of claims 1-20, wherein the medicament further comprises a HAART compound.

Some embodiments of a use of a variability modulator for producing a medicament for reactivating a latent HIV-1 reservoir in a mammalian cell having an integrated HIV-1 genome are set forth in claim format below:

Claim 1. A use of a variability modulator for producing a medicament for reactivating a latent HIV-1 reservoir in a mammalian cell having an integrated HIV-1 genome, the medicament comprising:
(i) a variability modulator in an amount sufficient to modulate variability of expression of a gene promoter without substantially changing the mean expression level of the gene promoter;
(ii) an activator of latent HIV-1 gene expression in an amount effective to activate latent HIV-1 gene expression; and
(iii) a pharmaceutically acceptable carrier.

Claim 2. The use according to claim 1, wherein the variability modulator is selected from the group consisting of thiamylal sodium, Estramustine, griseofulvin, telmisartan, docetaxel, riboflavin, pantothenic acid(d) na salt, mercaptopurine, pemetrexed, ethinyl estradiol, irinotecan hydrochloride, dutasteride, felbinac, vincristine sulfate, thiram, bezafibrate, Indomethacin, mebendazole, ouabain, sulfaquinoxaline sodium, oxybutynin chloride, oxyphencyclimine hydrochloride, saxagliptin, phenylmercuric acetate, troclosene potassium, artemisinin, cytarabine, thioguanine, hydroquinone, acetophenazine maleate, hexylresorcinol, oxytetracycline, cefadroxil, tolnaftate, phenylbutyric acid, atorvastatin calcium, carboplatin, 5-azacytidine, levodopa, lamivudine, sotalol hydrochloride, clavulanate lithium, digoxin, sodium monofluorophosphate, dexpanthenol, rabeprazole sodium, cetirizine hydrochloride, trilostane, modafinil, thiabendazole, adapalene, sulfameter, Fluoxetine hydrochloride, trimethobenzamide hydrochloride, Metoclopramide hydrochloride, guanethidine sulfate, trichlormethine, sucralfate, valganciclovir hydrochloride, bemotrizinol, parachlorophenol, (Â±)-Verapamil hydrochloride, oxidopamine hydrochloride, fomepizole hydrochloride, Xylazine hydrochloride, diperodon hydrochloride, zomepirac sodium, closantel, fenbendazole, finasteride, Procainamide hydrochloride, celecoxib, colistin sulfate, imipenem, cefoxitin sodium, azithromycin, clidinium bromide, Tolazamide, chlorpheniramine maleate, colesevalam hydrochloride, Pargyline hydrochloride, hydralazine hydrochloride, anastrozole, vinorelbine, bleomycin, dasatinib, busulfan, vorinostat, selamectin, idoxuridine, carvedilol, (Â±)-Isoproterenol hydrochloride, racephedrine hydrochloride, vardenafil hydrochloride, guaiacol, clobetasol propionate, mycophenolic acid, fludrocortisone acetate, zaleplon, nitroglycerin, riboflavin 5-phosphate sodium, acetriazoic acid, digitoxin, carnitine hydrochloride, albendazole, taurine, Taxol, mitomycin c, clofarabine, arginine hydrochloride, tetramizole hydrochloride, thiostrepton, lonidamine, melphalan, fludarabine phosphate, methotrexate(+/−), rifaximin, Arecoline hydrobromide, zalcitabine, erythrosine sodium, nikethamide, oxfendazole, editol, doxapram hydrochloride, aminacrine, dobutamine hydrochloride, rutin, single stereoisomers, mixtures of stereoisomers, pharmaceutically acceptable salts, prodrugs and functional derivatives thereof.

Claim 3. The use according to any one of claims 1-2, wherein the variability modulator is selected from the group consisting of docetaxel, ethinyl estradiol, estramustine, felbinac, bezafibrate, mebendazole, thiamylal sodium, mercaptopurine, dutasteride, cetirizine hydrochloride, acetophenazine maleate, oxytetracycline, artemisinin, hydralazine hydrochloride, Indomethacin, atorvastatin calcium, guanethidine sulfate, pantothenic acid(d) na salt, saxagliptin, (Â±)-Verapamil hydrochloride, oxidopamine hydrochloride, trilostane, fomepizole hydrochloride, modafinil, Xylazine hydrochloride, diperodon hydrochloride, zomepirac sodium, thiabendazole, closantel, hexylresorcinol, adapalene, finasteride, Procainamide hydrochloride, cefadroxil, sulfameter, sulfaquinoxaline sodium, azithromycin, imipenem, colistin sulfate, cefoxitin sodium, oxyphencyclimine hydrochloride, oxybutynin chloride, clidinium bromide, Fluoxetine hydrochloride, Tolazamide, trimethobenzamide hydrochloride, Metoclopramide hydrochloride, tolnaftate, chlorpheniramine maleate, phenylbutyric acid, colesevalam hydrochloride, Pargyline hydrochloride, telmisartan, troclosene potassium, bleomycin, dasatinib, anastrozole, busulfan, carboplatin, pemetrexed, hydroquinone, selamectin, levodopa, sucralfate, valganciclovir hydrochloride, lamivudine, idoxuridine, sotalol hydrochloride, carvedilol, clavulanate lithium, (Â±)-Isoproterenol hydrochloride, racephedrine hydrochloride, sodium monofluorophosphate, dexpanthenol, vardenafil hydrochloride, guaiacol, rabeprazole sodium, clobetasol propionate, mycophenolic acid, fludrocortisone acetate, zaleplon, bemotrizinol, parachlorophenol, nitroglycerin, and acetriazoic acid, single stereoisomers, mixtures of stereoisomers, pharmaceutically acceptable salts, prodrugs and functional derivatives thereof.

Claim 4. The use according to any one of claims 1-3, wherein the variability modulator is selected from the group consisting of docetaxel, ethinyl estradiol, estramustine, felbinac, bezafibrate, mebendazole, mercaptopurine, dutasteride, cetirizine hydrochloride; acetophenazine maleate, oxytetracycline, artemisinin, single stereoisomers, mixtures of stereoisomers, pharmaceutically acceptable salts, prodrugs and functional derivatives thereof.

Claim 5. The use according to any of claims 1-4, wherein the activator of latent HIV-1 gene expression is selected from the group consisting of a histone deacetylase (HDAC) inhibitor, a protein kinase C (PKC) agonist, an inhibitor of methylation, an inhibitor of a bromodomain protein, and an anticancer drug, Claim 6. The use according to any one of claims 1-5, wherein the activator of latent HIV-1 gene expression is a histone deacetylase (HDAC) inhibitor.

Claim 7. The use according to any one of claims 5 and 6, wherein the HDAC inhibitor is selected from the group consisting of 12-deoxyphorbol 13-phenylacetate (DPP), Suberoylannilide Hydroxamic Acid (SAHA), MS-275, valproic acid (VPA), trichostatin A (TSA), single stereoisomers, mixtures of stereoisomers, pharmaceutically acceptable salts or prodrugs thereof.

Claim 8. The use according to any one of claims 1-5, wherein the activator of latent HIV-1 gene expression is a Protein Kinase C (PKC) agonist.

Claim 9. The use according to any one of claims 5 and 8, wherein the PKC agonist is selected from the group consisting of tumor necrosis factor alpha (TNFα), prostratin, PMA, bryostatin, single stereoisomers, mixtures of stereoisomers, pharmaceutically acceptable salts or prodrugs thereof.

Claim 10. The use according to any one of claims 1-5, wherein the activator of latent HIV-1 gene expression is an inhibitor of methylation.

Claim 11. The use according to any one of claims 5 and 10, wherein the inhibitor of methylation is azacytidine, single stereoisomers, mixtures of stereoisomers, pharmaceutically acceptable salts or prodrugs thereof.

Claim 12. The use according to any one of claims 1-5, wherein the activator of latent HIV-1 gene expression is a bromodomain inhibitor.

Claim 13. The use according to any one of claims 5 and 12, wherein the bromodomain inhibitor is JQ1, GSK1210151A, or PFI-1, single stereoisomers, mixtures of stereoisomers, pharmaceutically acceptable salts or prodrugs thereof.

Claim 14. The use according to any one of claims 1-5, wherein the activator of latent HIV-1 gene expression is an anticancer drug.

Claim 15. The use according to any one of claims 5 and 14, wherein the anticancer drug is cytarabine, single stereoisomers, mixtures of stereoisomers, pharmaceutically acceptable salts or prodrugs thereof.

Claim 16. The use according to any one of claims 1-15, wherein the mammalian cell is in vitro.

Claim 17. The use according to any one of claims 1-15, wherein the mammalian cell is in vivo.

Claim 18. The use according to any one of claims 1-17 wherein the mammalian cell is selected from the group consisting of a human cell, a human T cell, a SupT1 cell, and a primary T-cell.

Claim 19. The use according to any one of claims 1-18, wherein the medicament further comprises a HAART compound.

Some embodiments of a use of a variability suppressor for producing a medicament for suppressing reactivation of a latent HIV-1 reservoir in a mammalian cell having an integrated HIV-1 genome are set forth in claim format below:

Claim 1. A use of a variability suppressor for producing a medicament for suppressing reactivation of a latent Human Immunodeficiency Virus Type 1 ("HIV-1") reservoir in a mammalian cell having an integrated HIV-1 genome, the medicament comprising:
(i) a variability suppressor in an amount sufficient to modulate variability of expression of a gene promoter without substantially changing the mean expression level of the gene promoter; and
(ii) a pharmaceutically acceptable carrier.

Claim 2. The use according to claim 1, wherein the variability suppressor is selected from the group consisting of manidipine hydrochloride, phenothiazine, dichlorvos, fipronil, trichlorfon, benzydamine hydrochloride, maprotiline hydrochloride, Papaverine hydrochloride, arsenic trioxide, phenformin hydrochloride, itraconazole, cycloheximide, hydroxyprogesterone caproate, pyrithione zinc, meclocycline sulfosalicylate, ergotamine tartrate, adenosine phosphate, broxaldine, single stereoisomers, mixtures of stereoisomers, pharmaceutically acceptable salts, prodrugs and functional derivatives thereof.

BRIEF DESCRIPTION OF THE DRAWINGS

FIG. 1A schematically depicts that every molecular species fluctuates about a deterministic trend (dashed line) that is determined by the underlying information or regulation in expressing the molecular species. Noise is simply the subtraction of the fluctuating signal from the expected deterministic signal/trend. FIG. 1B schematically depicts two main sources of noise. One source of noise is intrinsic and occurs on a promoter by promoter basis within the cell (each promoter has its individual intrinsic noise). The other noise source, sometimes referred to as global resources, is extrinsic noise and is shared by all promoters as all gene expression in the cell relies on these components (such as RNA polymerase, ribonucleotides, ATP, amino acids, ribosomes, tRNAs, cell division, protein decay, to name a few). Details are described, e.g., in Example 2.

FIG. 3A schematically depicts a time-series of single cell gene product trajectories for a canonical promoter driving expression of gene X under different conditions: Untreated, treatment with Drug A (Activator) alone, treatment with Drug V (Variability Modulator) alone, treatment with Drug A+V in combination, treatment with Drug VE (Variability enhancer), treatment with Drug VE and Drug A in combination; treatment with Drug VS (variability suppressor) alone, and treatment with Drug VS and Drug A in combination. Activator drug A increases the mean of gene product "X" (<X>). Variability enhancer (VE) and variability suppressor (VS) increase or decrease variability ($\sigma^2$), or the "noise" coefficient of variation (CV=$\sigma$/<X>), respectively, without changing <X>. In combination, Drugs A+VE potentiate the system above the phenotypic switching threshold longer than Drug A alone, and Drugs A+VS antagonize activation by Drug A and increases the stability of the latent state. Thus, positive feedback enhances and extends gene expression fluctuations which would cause the activator and variability combination (Drug A+V) to increase expression levels into the active regime at a higher probability than the activator drug alone (Drug A). Details are described, e.g., in Example 2.

FIG. 3B schematically depicts the two-state model of episodic transcription where transcriptional initiation and termination occur at rates $k_{on}$ and $k_{off}$. Transcription occurs with transcription rate $k_m$ in the ON state. Activators primarily affect burst frequency, $k_{on}$, while the Variability Modulators (VMs) affect burst size (or the # of mRNA per activity pulse), $k_m$ and/or $k_{off}$. For enhanced variability, activator drugs A & variability enhancer drug VE in combination would cause an increase in both transcriptional burst size and frequency, producing a pulse train of large spikes which potentially increases the ability of HIV-1 positive feedback to initiate and drive HIV-1 out of latency. For suppressed variability, activator drugs A & and variability suppressor drug VS in combination would reduce stochastic fluctuations that can enable viral reactivations, i.e., lead to suppression of reactivation of a latent HIV-1 reservoir. Details are described, e.g., in Example 2.

FIG. 3C schematically depicts the effects of Activator Drug A, and Activator Drugs A+Variability Enhancer Drug (VE) on the switching between an actively transcribing and non-transcribing promoter state (on or off). More specifically, for enhanced variability, drugs A+VE in combination cause an increase in both transcriptional burst size and frequency producing a pulse train of large spikes which increases the ability of HIV-1 positive feedback to initiate and drive HIV-1 out of latency. Drug A alone initiates promoter activity state at a higher frequency than the untreated promoter state switching, while Drug VE alone transcriptionally increases expression noise by larger bursts in promoter activity state. Details are described, e.g., in Example 2.

FIG. 3D schematically depicts movement in noise (defined as the variance divided by the mean squared, or $CV^2$) versus transcript abundance for drug treatments using VE alone, A alone and in combination (left) and VS alone, A alone and in combination (right). VE drug treatment moves transcription to a higher burst size model line which then in addition to A can surpass mean abundance levels caused by A alone. Details are described, e.g., in Example 2.

FIG. 3E schematically depicts variability modulation of gene expression in a population of cells to synergistically enhance or suppress gene expression and alter phenotypic diversity. The x-axis shows gene product expression levels ("Transcript Level"). Variability modulators fall into two categories, variability enhancers (VE; upper panel) and variability suppressors (VS; lower panel). FIG. 3E, upper, schematically depicts that the noise drug screen identifies compounds that enhance gene expression variability of a treated cell population (Variability Enhancer Drug VE) without substantially changing their mean expression level. Those VEs are then used in combination with known drugs that activate a gene of interest (Activator Drug A) for a combined variable activation (Drug A+VE in combination). For HIV-1, the desired reactivation of the total latent population past a phenotypic threshold into an active replicating state may be potentially reached by widening the distribution tail through variable activation. In cases where the variability modulator is not antagonistic to an activator drug A, synergistic activation of the Drug A+V combination may occur. FIG. 3E lower, schematically depicts that an alternate therapeutic strategy for the latent reservoir is stabilizing it in a secured latent state. Here, the variability suppressor VS decreases variability in gene expression which can result in suppressed activation also when combined with either an exogenous or endogenous activator. In a case where it is desired to keep the untreated disease model/target population in an inactivated state below the phenotypic threshold (vertical dashed line) the variability suppressor drug can reduce activation when used in combination with drug A. Details are described, e.g., in Example 2.

FIG. 3F schematically depicts stochastic simulations of a two-state model for 200 untreated single-cells (trajectories, upper-left). Increasing $k_{on}$ (i.e. by adding an "activator") increases mean expression levels (trajectories, lower-left). Reducing $k_{off}$, with decreased $k_{on}$ (i.e. adding a "noise enhancer"), only changes the noise (trajectories, upper-right). Combining a noise enhancer with an activator generates synergy with more trajectories entering into active replication (trajectories, lower-right). Lowered insets: Promoter activity versus time without treatment, after treatment with an activator, after treatment with a noise enhancer, and after treatment using a combination of activator and noise enhancer. Details are described, e.g., in Example 2.

FIG. 5 schematically depicts a two-step noise drug screening process. As shown, Step 1 screens for compounds that modulate variability of gene expression without changing the mean expression level of a gene promoter. Cells are infected with an expression construct wherein, e.g., an LTR drives expression of a reporter gene, such as a gene encoding a green fluorescent protein ($d_2$GFP; see examples for further details). A single isoclone is then used as an "LTR Isoclone Target" having a predetermined expression of GFP to identify variability modulator compounds (VMs), some of which will ultimately be characterized as Variability Suppressors (VSs, indicated as Down-regulated Stabilizers, thin arrows), while others will be characterized as Variability Enhancers (VEs, indicated as Up-regulated Reactivators, thick arrows). In Step 2, known or suspected transcriptional activators of latent HIV-1, such as TNF, SAHA, or prostratin, are used in combination with a VM, preferably a VE, to synergistically reactivate latent HIV-1. Details are described, e.g., in Example 2.

FIG. 6A schematically depicts the result of exposing an isoclonal population of cells containing an HIV-1 LTR driving a 2.5-hour half-life $d_2$GFP to 1,600 Food & Drug Administration (FDA)-approved drugs as measured using high throughput flow cytometry. Green Fluorescent Protein (GFP) noise magnitude ($CV^2$) and mean fluorescence (<GFP FL>(a.u.)) were quantified for the untreated target (open squares) and drug treatments using the 1,600 compounds ("Treated"; open circles). TNF was used as a positive control (open diamond). Variability modulator (VM) hit regions were defined using ±2σ in noise from a constant burst size model line based on the two-state model of episodic transcription which lands through the noise scatter around the untreated measurements (solid line). The lower dashed diagonal line corresponds to −2σ and the upper dashed diagonal line corresponds to +2σ. As shown, variability enhancers were distinguished from variability suppressors by either scoring above or below the constant burst size model line (Two-State Model Line"), respectively. (a.u.), arbitrary units. Details are described, e.g., in Example 3.

FIG. 6B schematically depicts the result of selecting 85 variability enhancers (open hexagons) having minimal mean fluorescence changes from the noise drug screen of FIG. 6A for a secondary combination drug screen of latent HIV-1. Here, the relative noise coordinates are in relation to each VEs corresponding untreated noise coordinate from a plate set. Essentially the panel shows the origin of the noise versus abundance (FL) plot to where the untreated samples are and looks at those compounds that moved relative to them Δ<GFP FL>(a.u.), difference between the <GFP FL> determined without treatment for a specific set of plates. TNF) open diamond) was used as a control. Untreated, open square. Details are described, e.g., in Example 3.

FIG. 6C schematically depicts a result demonstrating that VMs can enhance variability in gene expression across hundreds of integration sites using three different treatments of an LTR $d_2$GFP polyclonal cell population and a shotgun single-cell time-lapse fluorescence microscopy approach (Dar et al., 2012, Proc Natl Acad Sci USA 109:17454-17459). Each data point represents a subcluster of ~90 unique single cells. Each cell was tracked and quantified for GFP fluorescence for 12 hours after a 24 hour pretreatment with the compound. Fluorescent trajectories represent high-frequency noise processed by detrending their general deterministic behavior (based on all cells in the population) in addition to mean suppression of individual cell trajectories to focus on the intrinsic noise fluctuations (Dar et al., 2012, *Proc Natl Acad Sci USA* 109:17454-17459; Weinberger et al., (2008) *Nat Genet* 40:466-470). Similar to a previous report showing that JQ1 enhances variability across ~1,000 integration sites (Boehm et al, 2013, *Cell Cycle* 12:452-462), here the three VEs tested, V1, V11 and V13, have increased high frequency noise magnitude (HF-CV$^2$) across a clustering of ~500 polyclonal single cells compared to the untreated polyclonal population suggesting that the detected VE hits are not unique to the isoclone cell line used in the drug screen. Details are described, e.g., in Example 3.

FIG. 6D schematically depicts the application of noise coordinates of leading transcriptional modulators of an LTR promoter to the isoclone target. Protein Kinase C (PKC) agonists known to activate the promoter via NF-K$_B$ (TNFα, prostratin, and PMA) increase mean expression level and decrease variability in gene expression. Global inhibitors of histone deacetylation (SAHA, TSA, VPA, MS-275), Methylation inhibitor (AZA), and Bromodomain inhibitor (JQ1) increase variability in gene expression with and without effecting mean expression level. Some combinations of these known variability enhancers with PKC agonist activators have been reported to synergistically reactivate latency strongly supporting the V+A drug reactivation theory. Bryostatin, which has also been described in some systems to down-regulate PKC also scored lower in the isoclone target used. Details are described, e.g., in Example 3.

FIG. 6E schematically depicts a result of screening a cell line in which an additional LTR promoter driving expression of a stable mCherry reporter was expressed in the same LTR-d$_2$GFP cell line of the drug screen This two-reporter system enables the differentiation between drugs that are primarily extrinsic (global cellular resources; e.g., see, FIG. 1B) and post-transcriptional variability modulators (open diamonds) in which the noise magnitude increases in both reporters, or a mixture of extrinsic and intrinsic noise modulation that primarily acts on transcription (d$_2$GFP; open hexagons represent selected VMs used in the study). Treatment of the system with known transcriptional activators HDACi ("Chromatin Remodelers," SAHA, TSA, VPA, and MS-275, indicated by open circles), PKC agonists ("NF-K$_B$ Activators," bryostatin, prostratin, PMA, and TNF, indicated by open triangles), and AZA demonstrates how activators of NF-K$_B$ decrease both mCherry and d$_2$GFP noise (open triangles) while chromatin remodelers decrease mCherry noise and increase d$_2$GFP noise (open circles). Details are described, e.g., in Example 3.

FIGS. 7A-J schematically depict results showing that many variability modulators synergize with TNFα and Prostratin to increase latent HIV-1 reactivation in a Jurkat T-cell line. Details are described, e.g., in Examples 3 and 4.

FIG. 7A schematically depicts HIV-1 latency reactivation in JLat 8.6 cells using TNFα (upper) and Prostratin (lower) in combination with the 85 variability enhancers (VEs) from FIG. 6. Reactivation with activators TNFα (upper) and Prostratin (lower) is graphed in ascending order and the activators alone are shown as "Untreated" (column to the left). Increased reactivation of HIV-1 latency is observed for most of the combinations of activators TNFα or Prostratin) and variability enhancers (open bars) reaching, in this experiment, up to twice the reactivation of the activator without the VE (stripped bars). In other experiments (e.g., see FIG. 7D, below), a reactivation of up to 3-fold has been observed. Considering that at most 100% latent HIV-1 reservoir reactivation can be obtained, enhancing Drug A mediated latent HIV-1 reactivation from about 20-30% by 3-fold by using a VE as described herein, latent HIV-1 reactivation of up to 90% is possible, with a conservative estimate of about 70-85%. In JLat 8.6 cells after 48 hr treatment, about 70% of detected VEs synergized with TNFα and about 60% detected VEs synergized with Prostratin. For each VM (identified by "V" and a number) a pair of columns is shown. The column to the left represents VM only and the column to the right represents the VM in combination with either TNFα (upper panel) or Prostratin (lower panel). In many tests, the reactivation of HIV-1 latency by the VM only was substantially undetectable; hence the left column of the pair is barely visible for some VMs tested. Arrows point to VMs that show synergy in reactivation with TNFα and Prostratin and those that don't. The upper corner of FIG. 7A schematically depicts the latent HIV-1 expression construct in JLat 8.6 cells. Details are described, e.g., in Example 4.

FIG. 7B schematically depicts the mean activation (from FIG. 7A) versus mean noise magnitude enhancement (from FIG. 6B) plotted for the VMs that synergized activation and yields an upwards trend. Circles represent TNF addition and squares represent prostratin addition. Each of the two data points is an average for half of the compounds that synergized reactivation. "% ON" means % reactivation, i.e., the percentage of the latent population that is reactivated under a drug condition. Details are described, e.g., in Example 4.

FIG. 7C schematically depicts an increase in mean fluorescence of the activated cells with both TNFα (open diamonds; TNF alone is shown as filled diamond) and Prostratin (open triangles; Prostratin alone is shown as filled triangle) for VEs that synergize in FIG. 7A. Details are described, e.g., in Example 4.

FIG. 7D depicts dose response surfaces for V11 in combination with various concentrations of TNFα (upper) and Prostratin (lower) obtained from JLat 8.6 cells after 4-8 hr treatment. Side bar values represent the percentage of reactivated HIV-1. Black arrows represent equal reactivation levels reached with decreased activator and increased VM concentrations. The dose response surface reveals that V11 at 25 μM provides more than three times as much latent HIV-1 reactivation than TNFα or Prostratin alone. "% ON" means % reactivation, i.e., the percentage of the latent population that is reactivated under a drug condition. Details are described, e.g., in Examples 3 and 4.

FIG. 7E schematically shows a dose response bar graph for V11 in combination with various concentrations of TNFα on JLat 8.6 cells after 48 hr treatment. V11 at 25 μM when used in combination with TNFα resulted in about twice as much reactivation than TNFα alone and at 50 μM in about three times as much reactivation than TNFα alone. At the 50 μM V11 concentration about 80% of the latent HIV-1 reservoir was reactivated in combination with TNFα. Details are described, e.g., in Example 4.

FIG. 7F schematically shows a dose response bar graph for V11 in combination with various concentrations of Prostratin on JLat 8.6 cells after 48 hr treatment. V11 at 25 μM when used in combination with Prostratin resulted in about twice as much reactivation than Prostratin alone and at 50 μM in about three times as much reactivation than Prostratin alone. At the 50 μM V11 concentration about 50% of the latent HIV-1 reservoir was reactivated in combination with Prostratin. Details are described, e.g., in Example 4.

FIG. 7G schematically depicts mean activation (from FIG. 7A) versus mean noise magnitude enhancement (from FIGS. 6A and 6B) plotted for the VMs that synergized activation and which are correlated for both TNFα and Prostratin. Details are described, e.g., in Example 4.

FIG. 7H schematically depicts distributions of mean fluorescence of the activated cells for VEs that synergized with TNFα ("VEs+TNF," thin lines and open circles) versus TNFα treatment alone ("TNF ONLY," thicker line with open diamonds). Increased <GFP FL> suggests that synergistic reactivation occurs through enhanced levels of transcription. Details are described, e.g., in Example 4.

FIG. 7I schematically depicts that V11 and V14 further increase reactivation of a latent HIV-reservoir when combined with TNFα and Prostratin (▲ and ▼, respectively), a leading activation synergy pair, and further in comparison to other leading synergy pairs such as Prostratin and SAHA without significant reduction in viability. JLat 8.6 cells were treated for 48 hours. Details are described, e.g., in Example 4.

FIG. 7J (left) schematically depicts an example of a variability suppressor VS1 that reduces (suppresses) HIV-1 latency reactivation in combination with TNFα, Prostratin, TSA or SAHA (burst frequency and burst size modulators, respectively). In combination with HDAC inhibitors, VS1 reduces burst size and counter-acts the HDAC inhibitor increase of burst size resulting in decreased (suppressed) HIV-1 latency reactivation. FIG. 7J (right) schematically depicts a result demonstrating that VS1 decreases TNFα-mediated reactivation of HIV-1 latency in JLat 9.2 cells by about 40%. This results underscores the use of a VS in compositions for and in methods of suppressing reactivation of HIV-1 latency. Details are described, e.g., in Example 4.

FIGS. 8A-D schematically depict results showing that variability modulators synergistically reactivate HIV-1 latency in two primary cell models. Details are described in Example 5. FIG. 8A depicts a subset of 14 VMs out of the 85 identified variability enhancers that were chosen for both range of variability enhancement and reactivation synergy in the JLat cell line experiments (FIG. 7A). The axes represent the difference in noise and mean from the untreated cells in FIG. 6. Details are described, e.g., in Example 5.

FIG. 8B shows the identity of 12 selected VMs used in the primary cell experiment of FIG. 8A. Of the twelve VMs tested, three cause cell cycle arrest through microtubule inhibition, three are estrogen receptor (ESR1) agonists, and two are antihistamines that are associated with CCL11 and CCL5 inhibition. Details are described, e.g., in Example 5.

FIG. 8C schematically depicts results showing latency reactivation assays for the Siliciano primary cell models of latency. (Yang et al., 2009, The Journal of Clinical Investigation 119(11):3473-3486). In this model, synergistic reactivation was observed for VMs combined with PMA, Prostratin, and Bryostatin (Activator concentrations: PMA: 0.1 ng/ml Prostratin 0.3 uM, Bryostatin 0.3 nM; each activator alone shown as a solid bar and combination with VMs shown as open bars). V2, V3 and V10 synergized with either PMA, prostratin or bryostatin in the Siliciano model. Details are described, e.g., in Example 5.

FIG. 8D schematically depicts results showing latency reactivation assays for Planelles primary cell models of latency from two individual donors analyzed (Donor 190 (upper panel) and Donor GSK1 (lower panel)). Synergistic reactivation was observed for VMs combined with PMA, Prostratin, and Bryostatin (Activator concentrations: PMA: 5 ng/ml, Prostratin 3 uM, Bryostatin 1.5 nM). V4 and V14 synergized with bryostatin in the Planelles model. Details are described, e.g., in Example 5.

FIG. 10 shows a listing of 126 Variability Enhancers (VEs) identified in an initial noise screening assay as described herein. Also shown in the figure are the overall compound # in the screen, the name of the compound (Alias), the formula of the compound, the bioactivity of the respective compound, # of +Σ in $CV^2$ of $d_2GFP$, and # of +Σ in $CV^2$ of mCherry. Details are described, e.g., in Example 3.

FIG. 11 shows a listing of 85 VEs, a subset of those shown in FIG. 10, eliminating those that showed lower cell viability. Those 85 VEs have been identified as described herein. Also shown in the figure are the VE IDs in the screen, the name of the compound (Alias), whether or not the respective compound synergized with TNFα in That 8.6 cells (see also FIG. 7A), whether or not the respective compound synergized with Prostratin in Mat 8.6 cells (see also FIG. 7A), the formula of the compound, its molecular weight, and the bioactivity of the respective compound. Details are described, e.g., in Examples 3 and 5.

FIG. 12 shows a listing of 18 Variability Suppressors (VSs) identified as described herein. Also shown in the figure are the overall compound # in the screen, the name of the compound (Alias), # of −Σ in $CV^2$ of $d_2GFP$, and # of −Σ in $CV^2$ of mCherry.

FIG. 13A schematically depicts stochastic simulations showing the long-lived mCherry signal averaging out changes in underlying promoter activity with and without a noise-enhancing compound. Conversely, the $d_2GFP$ signal is capable of tracking modulations of the underlying episodic transcription. The lower panels represent the promoter activity levels for each of the simulations with and without noise-enhancing compound. FIG. 13B schematically depicts noise deviations of the two reporters from the untreated origin and shows minimal mCherry noise deviations for the 85 selected noise enhancers (hexagons). 25 compounds with deviations of >2σ in both $d_2GFP$ and mCherry noise (diamonds) were excluded from the latency reactivation assay and are made up of post-transcriptional modifiers. Treatment of the two-reporter system with known transcriptional activators (HDACi, PKC agonists, AZA) all increased mean mCherry resulting in lower mCherry noise (expected from theory and mCherry scatter analysis described herein). As expected, the activators of NF-kB decrease both mCherry and $d_2GFP$ noise (triangles) while chromatin remodelers decrease mCherry noise and increase $d_2GFP$ noise (circles). The increased $d_2GFP$ noise can be directly attributed to modulation of transcriptional bursts. Details are described, e.g., in Example 8.

FIGS. 14A and 14B schematically depict dose response curves for compounds V14 and V82 with TNF and Prostratin. FIG. 14A schematically depicts V14 dose response curves with four different concentrations of TNF (left) and five different concentrations of Prostratin (right) at 24 and 48 hours. Dose response curves show peak activation at aV14 concentration of about 10 µM. FIG. 14B schematically depicts V82 treatment for 48 hours of two JLat cell lines showing maximal reactivation at 50 µM V82 and TNF (upper) or Prostratin (lower). Details are described, e.g., in Example 9.

FIG. 15 depicts compounds commonly referenced in this application showing the compound's ID, e.g., noise enhancer ("NE") ID, compound name, and its description/biological function. Also listed are known NEs (also referred herein to as VEs) and tested activators.

FIG. 18A schematically depicts a primary T-cell model of HIV-1 latency 48 h after reactivation with PMA or a subset of noise enhancers (% reactivation percentage is calculated relative to maximal reactivation potential). Maximal increased activation was observed with PMA and V7 by ~20% or half the available range. The asterisk symbolizes that, due to large error bars, V9 does not synergize significantly. The horizontal line represents the mean calculated Bliss Independence Score (C. I. Bliss, *Ann. Appl. Biol.* 26:585-615 (1939)), a measure for strict additivity for all of the compounds. FIG. 18B schematically depicts stochastic simulations of noise suppression, which reduces noise without altering the mean expression level but limits reactivation induced by an activator. FIG. 18C schematically depicts that noise-suppressor molecule VS1 decreased TNF-induced reactivation by ~40% in two JLat cell lines (upper=JLat 15.4, lower=JLat 8.6), and decreased Prostratin-induced reactivation by ~50% in the primary T-cell model (right). Details are described, e.g., in Example 10.

FIG. 19A schematically depicts noise versus mean fluorescence for all compounds (small open diamonds) screened on the d$_2$GFP channel. Open squares represent the untreated plate sets, large open diamonds represent their corresponding TNF controls. FIG. 19B schematically depicts noise versus mean fluorescence for all compounds (small open diamonds) screened on the mCherry channel. Open squares represent the untreated plate sets, large open diamonds represent their corresponding TNF controls. Simultaneous changes in both d$_2$GFP and mCherry noise enable to identify compounds causing non-transcriptional perturbations. FIG. 19C schematically depicts the result from 5 plate sets screened, which identified 25 compounds that enhanced noise in both reporters by more than 2–σ. A compound list and classification (mode of action, "MOA") of the 25 post-transcriptional compounds filtered from the detected noise enhancer hits (CC=Cell Cycle, PTL=Post-translation, TL=Translation, NFL=Inflammation, TR=Translation; ATP=ATP metabolism) is shown. Details are described, e.g., in Example 11.

DETAILED DESCRIPTION OF THE INVENTION

I. Definitions

Figure 1A:
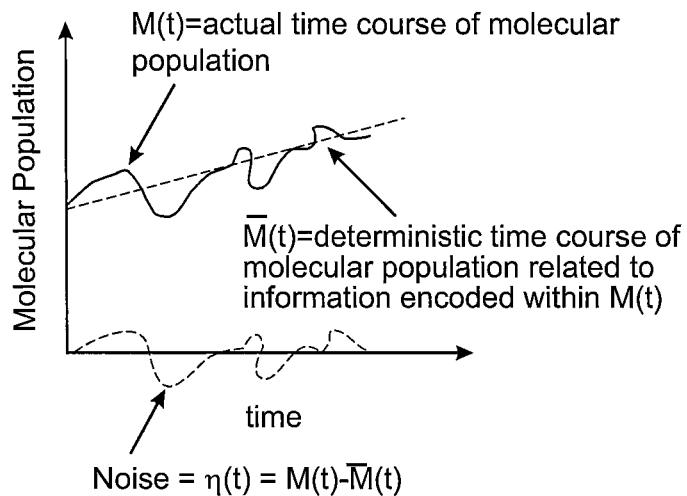
FIGS. 1A and 1B schematically depict "Noise" (Simpson et al., 2009, Wiley Interdisciplinary Reviews-Nanomedicine and Nanobiotechnology 1:214-225., Cox et al., 2006, Chaos 16, 026102 1-15).
Figure 1B:
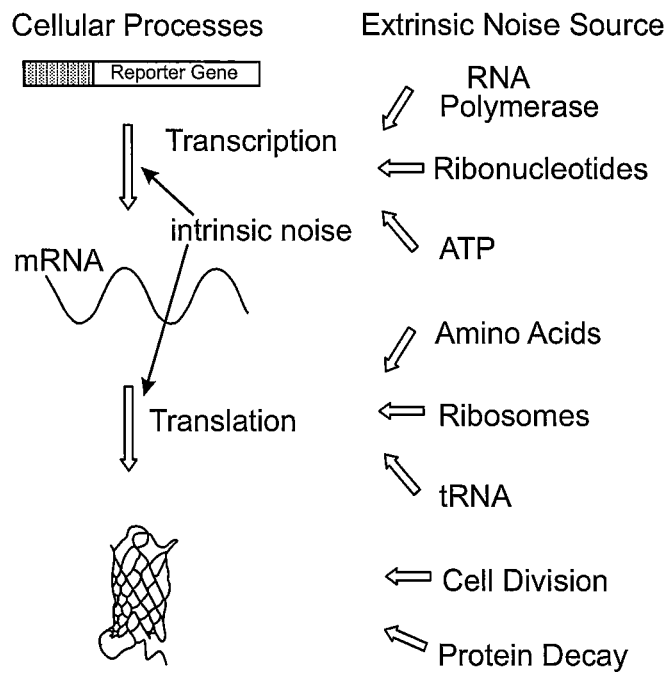
Figure 2:
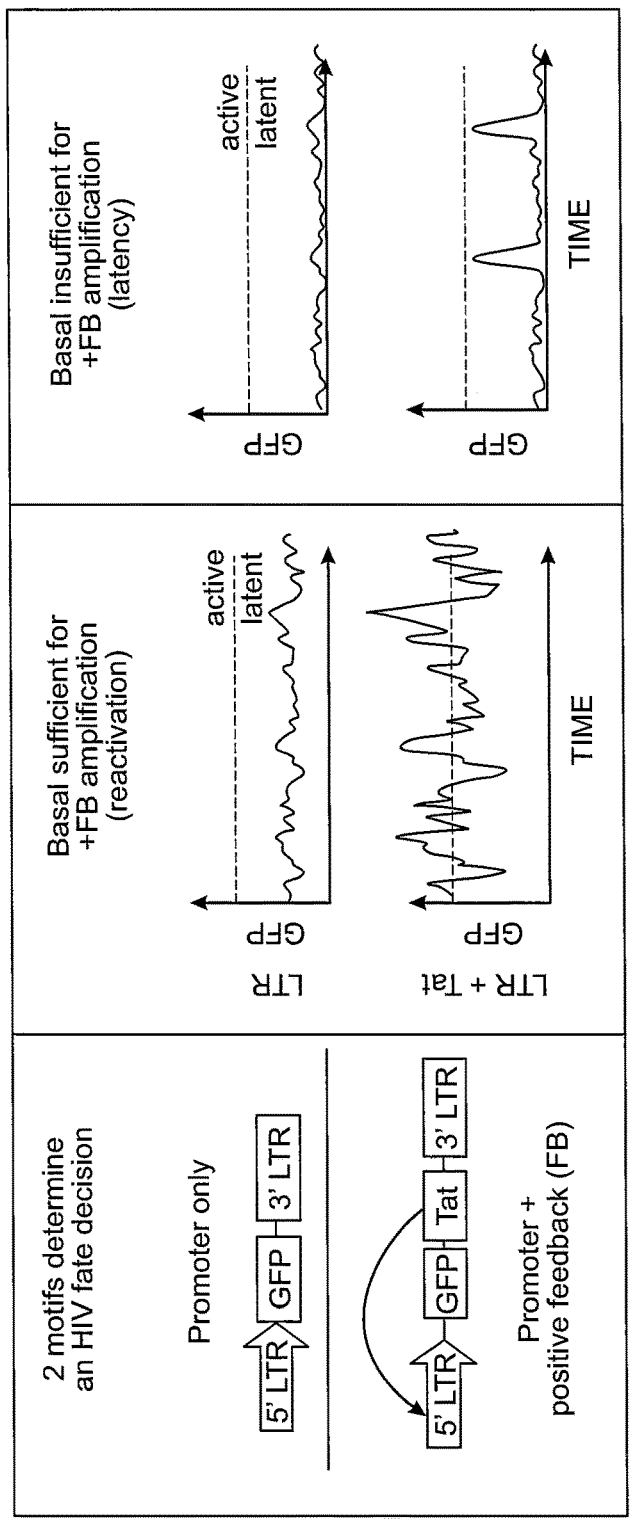
FIG. 2 schematically depicts that noise from two regulatory motifs control HIV-1 entrance into and exit from latency. HIV-1 TAT positive feedback is a transcriptional feedback loop and functions in response to underlying transcriptional pulses of the promoter. Depending on what the promoter state is, the positive feedback can help engage active replication or not. For the case where underlying transcriptional pulses are large enough, positive feedback is able to surpass a threshold into active replication of HIV (middle). For the case where transcriptional pulses are small, the feedback is unable to surpass the threshold and switch out of the latent state (right). LTR, long terminal repeat; GFP, green fluorescent protein. Details are described, e.g., in Example 2.

Throughout the present specification and the accompanying claims the words "comprise" and "include" and variations thereof such as "comprises", "comprising", "includes" and "including" are to be interpreted inclusively. That is, these words are intended to convey the possible inclusion of other elements or integers not specifically recited, where the context allows. No language in the specification should be construed as indicating any non-claimed element essential to the practice of the invention. As used herein, the term "consisting of" is intended to mean including and limited to whatever follows the phrase "consisting of". Thus the phrase "consisting of" indicates that the listed elements are required or mandatory and that no other elements may be present. The term "consisting essentially of" means that the composition, method or structure may include additional ingredients, steps and/or parts, but only if the additional ingredients, steps and/or parts do not materially alter the basic and novel characteristics of the claimed composition, method or structure.

The terms "a" and "an" and "the" and similar referents used in the context of describing the invention (especially in the context of the following claims) are to be construed to cover both the singular and the plural, unless otherwise indicated herein or clearly contradicted by context.

Recitation of ranges of values herein are merely intended to serve as a shorthand method of referring individually to each separate value falling within the range, unless otherwise indicated herein, each individual value is incorporated into the specification as if it were individually recited herein. Ranges may be expressed herein as from "about" (or "approximate") one particular value, and/or to "about" (or "approximate") another particular value. When such a range is expressed, another embodiment includes from the one particular value and/or to the other particular value. Similarly, when values are expressed as approximations, by use of the antecedent "about" or "approximate" it will be understood that the particular value forms another embodiment. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that when a value is disclosed that is "less than or equal to the value" or "greater than or equal to the value" possible ranges between these values are also disclosed, as appropriately understood by the skilled artisan. For example, if the value "10" is disclosed the "less than or equal to 10" as well as "greater than or equal to 10" is also disclosed.

All methods described herein can be performed in any suitable order unless otherwise indicated herein or otherwise clearly contradicted by context. Further, all methods described herein and having more than one step can be performed by more than one person or entity. Thus, a person or an entity can perform step (a) of a method, another person or another entity can perform step (b) of the method, and a yet another person or a yet another entity can perform step (c) of the method, etc. The use of any and all examples, or exemplary language (e.g. "such as") provided herein is intended merely to better illuminate the invention and does not pose a limitation on the scope of the invention otherwise claimed.

Units, prefixes, and symbols are denoted in their Système International de Unites (SI) accepted form. Unless otherwise indicated, nucleic acids are written left to right in 5' to 3' orientation; amino acid sequences are written left to right in amino to carboxy orientation.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is herein deemed to contain the group as modified thus fulfilling the written description of all Markush groups used in the appended claims.

The headings used herein are for organizational purposes only and are not meant to be used to limit the scope of the description or the claims, which can be had by reference to the specification as a whole. Accordingly, the terms defined immediately below are more fully defined by reference to the specification in its entirety.

Illustrations are for the purpose of describing a preferred embodiment of the invention and are not intended to limit the invention thereto.

Unless defined otherwise, all technical and scientific terms used herein have the meaning commonly understood by a person skilled in the art to which this invention belongs. The following references provide one of skill with a general definition of many of the terms used in this invention: Singleton et al., *Dictionary of Microbiology and Molecular Biology* (2nd ed. 1994); The Cambridge Dictionary of Science and Technology (Walker ed., 1988); *The Glossary of Genetics,* 5th Ed., R. Rieger et al. (eds.), Springer Verlag (1991); and Hale & Marham, *The Harper Collins Dictionary of Biology* (1991). As used herein, the following terms have the meanings ascribed to them unless specified otherwise.

As used herein, the term "about" refers to a range of values of plus or minus 10% of a specified value. For example, the phrase "about 200" includes plus or minus 10% of 200, or from 180 to 220, unless clearly contradicted by context.

As used herein, the terms "activating latent HIV-1 gene expression", "reactivating latent HIV-1 gene expression", "activating a latent HIV-1 reservoir", "reactivating a latent HIV-1 reservoir" or grammatical equivalents refer to a process that stimulates HIV-1 proviral latent DNA integrated into the genome of a host to begin transcription initiation, transcription elongation or replication and production of infectious virus and/or cell surface antigens, such as gp120 and/or gp41. "Activating latent HIV-1 gene expression", "reactivating latent HIV-1 gene expression", "activating a latent HIV-1 reservoir", "reactivating a latent HIV-1 reservoir" can be measured by methods described herein and known in the art. "Activating latent HIV-1 gene expression", "reactivating latent HIV-1 gene expression", "activating a latent HIV-1 reservoir", "reactivating a latent HIV-1 reservoir" although desirable, must not be complete, i.e., must not be 100%. It does not mean that each and every latent HIV-1 genome must be activated or reactivated. In some embodiments of the present invention, "activating latent HIV-1 gene expression", "reactivating latent HIV-1 gene expression", "activating a latent HIV-1 reservoir", or "reactivating a latent HIV-1 reservoir" means that at least about 10% of the HIV-1 proviral latent DNA integrated into the genome of a host begins transcription initiation, transcription elongation or replication and production of infectious virus and/or cell surface antigens, such as gp120 and/or gp41. In some embodiments at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about between 60% and 70%, at least about between 70% and 80%, at least about between 80% and 90%, at least about between 90% and 95%, or at least about between 95% and 100% of the HIV-1 proviral latent DNA integrated into the genome of a host begins transcription initiation, transcription elongation or replication and production of infectious virus and/or cell surface antigens, such as gp120 and/or gp41.

As used herein, the terms "activator of latent HIV-1 gene expression", "reactivator of latent HIV-1 gene expression" "activator of latent HIV-1 reservoir", "reactivator of latent HIV-1 reservoir" or grammatical equivalents thereof refer to a compound that can initiate activation of latent HIV-1 gene expression or reactivation of latent HIV-1 gene expression.

As used herein, the term "administering" means the actual physical introduction of a composition into or onto (as appropriate) a host or cell. Any and all methods of introducing the composition into or onto the host or cell are contemplated according to the invention; the method is not dependent on any particular means of introduction and is not to be so construed. Means of introduction are well-known to those skilled in the art, and also are exemplified herein.

As used herein, the term "administration in combination," "combination therapy" or similar grammatical equivalents refers to both simultaneous and sequential administration of compounds. One or more activators of HIV-1 latency and one or more noise modulators can be delivered or administered at the same site or a different site and can be administered at the same time or after a delay, preferably not exceeding 48 hours. Concurrent or combined administration, as used herein, means that one or more activator of HIV-1 latency and one or more noise modulators are administered to a subject either (a) simultaneously, or (b) at different times during the course of a common treatment schedule. In the latter case, the compounds are administered sufficiently close in time to achieve the intended effect. Concurrent or combined administration, as used herein, also means that one or more activator of HIV-1 latency and one or more noise modulators can be administered in combination with another compound useful for the treatment of HIV-1 infection and AIDS, such as HAART.

As used herein, the terms "agent" or "compound," used interchangeably herein, mean any chemical compound, for example, a macromolecule or a small molecule disclosed herein. The agent can have a formula weight of less than about 10,000 grams per mole, less than 5,000 grams per mole, less than 1,000 grams per mole, or less than about 500 grams per mole. The agent can be naturally occurring (e.g., a herb or a nature product), synthetic, or both. Examples of macromolecules are proteins, protein complexes, and glycoproteins, nucleic acids, e.g., DNA, RNA and PNA (peptide nucleic acid). Examples of small molecules are peptides, peptidomimetics (e.g., peptoids), amino acids, amino acid analogs, polynucleotides, polynucleotide analogs, nucleotides, nucleotide analogs, organic or inorganic compounds e.g., heteroorganic or organometallic compounds. An agent can be the only substance used by the method described herein. Alternatively, a collection of agents can be used either consecutively or concurrently by the methods described herein.

As used herein, the terms "antagonist" or "inhibitor" or "suppressor" (used interchangeably herein) mean a chemical substance that diminishes, abolishes or interferes with the physiological action of a nucleic acid or polypeptide. The antagonist may be, for example, a chemical antagonist, a pharmacokinetic antagonist, a non-competitive antagonist, or a physiological antagonist, such as a biomolecule, e.g., a polypeptide, a peptide antagonist or a non-peptide antagonist. A preferred antagonist diminishes, abolishes or interferes, whether fully or partially, with the reactivation or activation of a latent HIV-1 reservoir as measured by any suitable assay, including those described and referenced herein.

As used herein, the term "biologically active" when referring to an agent or compound is art-recognized and refers to a form of the agent or compound that allows for it, or a portion of the amount of the agent or compound administered, to be absorbed by, incorporated into, or otherwise be physiologically available to a subject or patient to whom it is administered.

As used herein, the term "biological sample" means a sample of biological tissue or fluid that contains nucleic acids or polypeptides. Such samples are typically from humans, but include tissues isolated from non-human primates, or rodents, e.g., mice, and rats. Biological samples may also include sections of tissues such as biopsy and autopsy samples, frozen sections taken for histological purposes, blood, plasma, serum, sputum, stool, tears, mucus, hair, skin, etc. Biological samples also include explants and primary and/or transformed cell cultures derived from patient tissues. A "biological sample" also refers to a cell or population of cells or a quantity of tissue or fluid from an animal. Most often, the biological sample has been removed from an animal, but the term "biological sample" can also refer to cells or tissue analyzed in vivo, i.e., without removal from the animal. Typically, a "biological sample" will contain cells from the animal, but the term can also refer to non-cellular biological material, such as non-cellular fractions of blood, saliva, or urine, that can be used to measure expression level of a polynucleotide or polypeptide. Numerous types of biological samples can be used in the present invention, including, but not limited to, a tissue biopsy or a blood sample. As used herein, a "tissue biopsy" refers to an amount of tissue removed from an animal, preferably a human, for diagnostic analysis. "Tissue biopsy" can refer to any type of biopsy, such as needle biopsy, fine needle biopsy, surgical biopsy, etc. A "biological sample" encompasses samples that have been manipulated in any way after their procurement, such as by treatment with reagents; washed; or enrichment for certain cell populations, such as CD4$^+$ T lymphocytes, glial cells, macrophages, tumor cells, peripheral blood mononuclear cells (PBMC), and the like. The term "biological sample" encompasses a clinical sample, and also includes cells in culture, cell supernatants, tissue samples, organs, bone marrow, and the like. As used herein, "providing a biological sample" means to obtain a biological sample for use in methods described in this invention. Most often, this will be done by removing a sample of cells from a subject, but can also be accomplished by using previously isolated cells (e.g., isolated by another person, at another time, and/or for another purpose), or by performing the methods of the invention in vivo. Archival tissues, having treatment or outcome history, will be particularly useful.

As used herein, the term "burst frequency" refers to the initiation rate of a promoter transitioning into a transcribing state.

As used herein, the term "burst size" refers to the number of mRNA molecules produced per transcriptional activity pulse. Mathematically, the research community has appropriately defined burst size as the transcription rate divided by the kinetic rate for the active promoter state to switch into the inactive state.

As used herein, the term "contacting" refers to an instance of exposure of at least one substance to another substance. For example, contacting can include contacting a substance, such as a cell or a polypeptide to an agent or compound described herein. A cell can be contacted with the agent, for example, by adding the agent to the culture medium (by continuous infusion, by bolus delivery, or by changing the medium to a medium that contains the agent) or by adding the agent to the extracellular fluid in vivo (by local delivery, systemic delivery, intravenous injection, bolus delivery, or continuous infusion). The duration of contact with a cell or group of cells is determined by the time the agent is present at physiologically effective (biologically active) levels or at presumed physiologically effective (biologically active) levels in the medium or extracellular fluid bathing the cell. In the present invention, for example, a virally infected cell (e.g., an HIV-1 infected cell) or a cell at risk for viral infection (e.g., before, at about the same time, or shortly after HIV-1 infection of the cell) is contacted with an agent. The term "contacting" is used herein interchangeably with the following: combined with, added to, mixed with, passed over, incubated with, flowed over, placed in direct physical association with another substance, etc., unless clearly contradicted by context.

As used herein, if, for example, a biological sample is obtained from a patient having a disease, the terms "control" or "control sample," refer to a biological sample from a healthy patient or a biological sample from a patient not having the disease.

As used herein, the term "carrier" in the context of "pharmaceutically acceptable carrier" refers to an inert substance used as a diluent, adjuvant, excipient or vehicle with which a drug, medicament or vaccine is administered.

As used herein, "coefficient of variation" or "CV" or "% CV" refers to the standard deviation divided by the average.

As used herein, the terms "decreased expression" or "reduced expression" or "lower expression" refer to a finding that the level of a gene expression product is lower and/or the activity of the gene expression product is lower, relative to a control or reference. Preferably, the decrease is at least 20%, more preferably, the decrease is at least 30%, at least 40%, at least 50%, at least 60%, at least 70%, at least 80%, or at least 90% and most preferably, the decrease is at least 100%, relative to a control. A gene expression product can be an mRNA transcribed from a gene or a polypeptide encoded by a gene.

As used herein, the term "derivative" refers to a compound that is derived from a similar compound or a compound that can be imagined to arise from another compound, if one atom is replaced with another atom or group of atoms. For example, a hydrogen atom of a compound may be substituted by alkyl, acyl, amino, hydroxyl, halo, haloalkyl, etc. to produce a derivative of that compound or a derivatized compound. A "functional derivative" refers to a derivative of a compound that substantially functions as the compound from which it was derived.

As used herein, the term "different" means not the same, not of the same identity.

As used herein, the terms "disorder", "disease" or "pathological condition" are used inclusively and refer to any deviation from the normal structure or function of any part, organ or system of the body (or any combination thereof). A specific disease is manifested by characteristic symptoms and signs, including biological, chemical and physical changes, and is often associated with a variety of other factors including, but not limited to, demographic, environmental, employment, genetic and medically historical factors. Certain characteristic signs, symptoms, and related factors can be quantitated through a variety of methods to yield important diagnostic information. Disease specifically includes HIV-1 infection, HIV-1 latency, AIDS and pathological conditions associated with or developing in a subject as a consequence of HIV-1 infection, HIV-1 latency, and AIDS.

As used herein, the terms "dosage unit," or simply "dose" or "dosage" refer to discrete, predetermined quantities of a compound that can be administered as unitary dosages to a subject. A predetermined quantity of active compound can be selected to produce a desired therapeutic effect and can be administered with a pharmaceutically acceptable carrier. The predetermined quantity in each unit dosage can depend on factors that include, but are not limited to, (a) the unique characteristics of the active compound and the particular therapeutic effect to be achieved, and (b) the limitations inherent in the art of creating and administering such dosage units.

As used herein, the terms "effective amount", "effective dose", "sufficient amount", "amount effective to", "therapeutically effective amount" or grammatical equivalents thereof mean a dosage sufficient to produce a desired result, to ameliorate, or in some manner, reduce a symptom or stop or reverse progression of a condition. In some embodiments, the desired result is an increase in latent HIV-1 gene expression. In other embodiments, the desired result is the complete eradication of a latent HIV-1 reservoir. Amelioration of a symptom of a particular condition by administration of a pharmaceutical composition described herein refers to any lessening, whether permanent or temporary, lasting or transit that can be associated with the administration of the pharmaceutical composition. An "effective amount" can be administered in vivo and in vitro.

The terms "eliminating", "eradicating" or "purging" are used interchangeably.

As used herein, the term "excipient" refers to an inert substance used as a diluent or vehicle for a drug.

As used herein, the term "gene promoter" is defined as an array of nucleic acid control sequences that direct transcription of a nucleic acid. As used herein, a gene promoter includes necessary nucleic acid sequences near the start site of transcription, such as, in the case of a polymerase II type promoter, a TATA element. A gene promoter also optionally includes distal enhancer or repressor elements, which can be located as much as several thousand base pairs from the start site of transcription. An exemplary gene promoter is an HIV-1 LTR gene promoter.

As used herein, the term "HAART" refers to a treatment for HIV-1 infection which is a cocktail of anti-viral drugs known as Highly Active Anti-Retroviral Therapy. HAART includes two reverse transcriptase inhibitors and a protease inhibitor. HAART reduces the viral load in many patients to levels below the current limits of detection, but the rapid mutation rate of this virus limits the efficacy of this therapy (Perrin and Telenti, 1998, *Science* 280:1871-1873). In addition, HAART is substantially ineffective in treating latent HIV-1 infection.

As used herein the abbreviation "HDAC" means histone deacetylase.

As used herein, the terms "HDAC inhibitor" or "inhibitor of HDAC" mean any compound that (i) inhibits the activity of a histone deacetylase (HDAC) and (ii) has an effect on the activation of latent HIV-1 gene expression.

As used herein, the term "HIV-1" is used herein to refer to the Human Immunodeficiency Virus Type 1. It is recognized that the HIV-1 virus is an example of a hyper-mutable retrovirus, having diverged into many subtypes. However, methods and compounds of the present invention can activate the LTR promoters from all HIV-1 and other retroviruses, which are similar to HIV-1 in the LTR region. Thus, the term "HIV-1" used herein, unless otherwise indicated, refers to any retrovirus which is regulated by an LTR promoter.

As used herein, the term "HIV-1 infection" refers to indications of the presence of the Human Immunodeficiency Virus Type 1 (HIV-1) in an individual and includes asymptomatic seropositivity, aids-related complex (arc), HIV-1 latency, and acquired immunodeficiency syndrome (AIDS).

As used herein, the term "HIV-1 viral load" refers to the number of HIV-1 viral particles in a sample of blood plasma. HIV-1 viral load is increasingly employed as a surrogate marker for disease progression. It can be measured by PCR and bDNA tests and is expressed in number of HIV-1 copies or equivalents per milliliter.

As used herein, the terms "individual," "host," "subject," and "patient," used interchangeably herein, refer to a mammal, including, but not limited to, murines, felines, simians, humans, mammalian farm animals, mammalian sport animals, and mammalian pets. The term includes mammals that are susceptible to infection by an immunodeficiency virus, in particular HIV-1. A preferred subject is a human.

As used herein, the terms "individual," "host," "subject," or "patient" to be treated for a condition or disease by a subject method means either a human or non-human animal in need of treatment for a condition or disease. A preferred condition is HIV-1 infection, HIV-1 latency, or AIDS or a condition affected by or caused by HIV-1 infection, HIV-1 latency, or AIDS.

As used herein, the terms "inhibition" or "inhibits" or "suppression" or "suppresses" mean to reduce an activity as compared to a control (e.g. an activity in the absence of such inhibition or suppression). It is understood that inhibition or suppression can mean from a slight reduction in activity to the complete ablation of all activity. An "inhibitor" or "suppressor" can be anything that reduces an activity. For example, an inhibition of reactivation of HIV-1 latency by a disclosed composition can be determined by assaying the amount of an HIV-1 mRNA or HIV-1 polypeptide associated with reactivation of HIV-1 gene expression (i.e., the level or activity value) in the presence of the composition and comparing that to the amount of that HIV-1 mRNA (or HIV-1 polypeptide) in the absence of the composition. In this example, if the amount of the HIV-mRNA (or HIV-1 polypeptide) is reduced in the presence of the composition as compared to the amount of the HIV-1 mRNA (or HIV-1 polypeptide) in the absence of the composition, the composition can be said to inhibit the reactivation of HIV-1 latency. Inhibition of HIV-1 latency is achieved when the level or activity value (i.e., measured HIV-1 mRNA or HIV-1 polypeptide) relative to a control is reduced by about 10%, preferably about 20%, preferably about 30%, preferably about 40%, preferably about 50%, preferably about 60%, preferably about 70%, preferably about 80%, preferably about 90%, or preferably about 90-100%.

As used herein, the term "in vitro" means outside the body of the organism from which a cell or cells is obtained or from which a cell line is isolated.

As used herein, the term "in vivo" means within the body of the organism from which a cell or cells is obtained or from which a cell line is isolated.

Compounds that have the same molecular formula but differ in the nature or sequence of bonding of their atoms or the arrangement of their atoms in space are termed "isomers." Isomers that differ in the arrangement of their atoms in space are termed "stereoisomers." "Stereoisomer" and "stereoisomers" refer to compounds that exist in different stereoisomeric forms if they possess one or more asymmetric centers or a double bond with asymmetric substitution and, therefore, can be produced as individual stereoisomers or as mixtures. Stereoisomers include enantiomers and diastereomers. Stereoisomers that are not mirror images of one another are termed "diastereomers" and those that are non-superimposable mirror images of each other are termed "enantiomers." When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture." Unless otherwise indicated, the description is intended to include individual stereoisomers as well as mixtures. The methods for the determination of stereochemistry and the separation of stereoisomers are well-known in the art (see discussion in Chapter 4 of *Advanced Organic Chemistry*, 4th edition J. March, John Wiley and Sons, New York, 1992) differ in the chirality of one or more stereocenters.

As used herein, the terms "latency", "latent", "latently infected reservoir" or grammatical equivalents thereof refer to the integration of a viral genome or integration of a partial viral genome within a host cell genome further characterized by (i) the substantially undetectable level of non-spliced viral RNA (<500 copies RNA/ml by a commonly used PCR assay; Chun et al., 1997, *Proc Natl Acad Sci USA*, 94:13193-13197); (ii) substantial absence of detectable viral production; or (iii) only about $10^5$ to $10^6$ latently infected CD4 memory T cells in a subject (Williams et al., 2004, *J Biol Chem* 279(40):42008-42017). "Latency" also means a concept describing (i) an asymptomatic clinical condition; (ii) the state of viral activity within a population of cells, or (iii) the down-regulation or absence of gene expression within an infected cell.

As used herein, the term "level of gene expression" refers to the detectable "level of an mRNA" produced by transcription of a gene and/or detectable "level of a polypeptide" produced by translation of an mRNA coding for the polypeptide.

As used herein, the term "level of an mRNA" in a biological sample refers to the amount of mRNA transcribed from a gene that is present in a cell or a biological sample. The mRNA generally encodes a functional protein, although mutations may be present that alter or eliminate the function of the encoded protein. A "level of mRNA" need not be quantified, but can simply be detected, e.g., a subjective, visual detection by a human, with or without comparison to a level from a control sample or a level expected of a control sample. A preferred mRNA is an HIV-1 mRNA.

As used herein, the term "level of a polypeptide" in a biological sample refers to the amount of polypeptide translated from an mRNA that is present in a cell or biological sample. The polypeptide may or may not have protein activity. A "level of a polypeptide" need not be quantified, but can simply be detected, e.g., a subjective, visual detection by a human, with or without comparison to a level from a control sample or a level expected of a control sample. A preferred polypeptide is an HIV-1 polypeptide, such as $GP_{120}$, reverse transcriptase, Gag polypeptide or its protease-processed products.

As used herein, the abbreviation "LTR" means Long Terminal Repeat, and refers to a sequence repeated at the 5' and 3' ends of an HIV-1 genome, which consists of an enhancer and a promoter region for gene expression, an RNA transcription start site, and an untranslated RNA sequence.

As used herein, "mammal" or "mammalian" means or relates to the class mammalia including, but not limited to the orders carnivore (e.g., dogs and cats), rodentia (e.g., mice, guinea pigs, and rats), and primates (e.g., humans, chimpanzees, and monkeys).

As used herein, the term "mammalian cell" includes reference to a cell derived from a mammal including, but not limited to, human, rat, mouse, guinea pig, chimpanzee, or macaque. The cell may be cultured in vivo or in vitro.

As used herein, the term "mean expression level" refers to an average mRNA or protein abundance of a gene product during steady state of expression from a promoter. Mean expression level may be quantified as described herein and as known in the art on both the single cell level and on a plurality of cell level.

The terms "modulate," "modulation," or "modulating" are art-recognized and refer to up-regulation (i.e., activation, stimulation, increase), or down regulation (i.e., inhibition, suppression, reduction, or decrease) of a response, or the two in combination or apart. Thus, the term "modulate" encompasses "increase," "stimulate," or "activate" and "decrease," "inhibit," "suppress," "reduce," or "decrease." In some embodiments, of particular interest are agents which inhibit reactivation of latent HIV-1 gene expression, and/or which reduce a level of an HIV-1 polypeptide in a cell, and/or which reduce a level of an HIV-1 mRNA in a cell. In other embodiments, of particular interest are agents which increase reactivation of latent HIV-1 expression, and/or which increase a level of an HIV-1 polypeptide in a cell, and/or which increase a level of an HIV-1 mRNA in a cell.

As used herein, the terms "noise" or "variance" or "variability" refer to stochastic fluctuations in gene expression. Noise or variability in gene expression is attributed to the random timing of molecular interactions that occur during transcription, translation and degradation. Noise can be observed in a population of cells or in a single cell, e.g., the expression of a gene of interest may fluctuate in time within a single cell when measured for a prolonged period of time. Likewise, when expression of a target gene is determined in individual cells within a population of cells, at a given time, the expression of the target gene in individual cells may fluctuate. The terms variability enhancer ("VE") and noise enhancer ("NE") are used interchangeably herein.

As used herein, the term "noise magnitude" refers to the variance in gene expression divided by the mean squared, or otherwise known as the coefficient of variation squared ("CV$^2$").

As used herein, the terms "noise modulator" or "variability modulator" refers to a compound that modulates the noise or variability in gene expression. This is also referred to herein as modulation of expression of a gene promoter and modulation of expression of a gene promoter without substantially changing the mean expression level of the gene promoter. The terms include variability enhancer and variability suppressor.

As used herein, the term "operably linked" refers to a functional linkage between a nucleic acid expression control sequence (such as a promoter, or array of transcription factor binding sites) and a second nucleic acid sequence, wherein the expression control sequence directs transcription of the nucleic acid corresponding to the second sequence. For example an LTR promoter can be operably linked to a reporter gene such that expression of the reporter gene product depends on the activity of the LTR promoter.

The terms "optional" or "optionally" as used throughout the specification means that the subsequently described event or circumstance may but need not occur, and that the description includes instances where the event or circumstance occurs and instances in which it does not. The terms also refer to a subsequently described composition that may but need not be present, and that the description includes instances where the composition is present and instances in which the composition is not present.

As used herein, the term "non-processive transcription" means initiation with inefficient elongation (transcription complexes pause and drop off the DNA) leading to an abundance of short, non-polyadenylated RNA and only rarely in elongated full length mRNAs. "Processive transcription" means efficient elongation of transcripts leading to high levels of poly-adenylated mRNA.

As used herein, the term "pharmaceutically acceptable" refers to a composition that is physiologically tolerable and does not typically produce an allergic or similar untoward reaction when administered to a subject, preferably a human subject. Preferably, as used herein, the term "pharmaceutically acceptable" means approved by a regulatory agency of a Federal or state government or listed in the U.S. Pharmacopeia or other generally recognized pharmacopeia for use in animals, and more particularly in humans.

As used herein, the term "physiologically functional derivative" refers to any pharmaceutically acceptable derivative of a compound of the present invention, for example an ester or an amide thereof, and includes any pharmaceutically acceptable salt, ester, or salt of such ester of a compound of the present invention which, upon administration to a mammal, such as a human, is capable of providing (directly or indirectly) a compound of the present invention or an active metabolite or residue thereof. It will be appreciated by those skilled in the art that the compounds of the present invention may be modified to provide physiologically functional derivatives thereof at any of the functional groups in the compounds, and that the compounds of the present invention may be so modified at more than one position.

As used herein, the terms "polypeptide" and "protein" (used interchangeably herein) refer to a polymer of amino acid residues.

As used herein, the term "population of cells" refers to cells, preferably mammalian cells, more preferably human cells, grown in vitro or in vivo. The term also refers to cells within a host and may comprise a mixture of cells, such as virally infected cells and uninfected cells. Preferred populations of cells, without limitation, include, a population of CD4 T-cells, a population of CD4 T-cells within a host, a population of CD4 T-cells comprising HIV-1 infected CD4 T-cells, a population of CD4 T-cells within a host comprising HIV-1 infected CD4 T-cells, a population of CD4 T-cells comprising a latent HIV-1 genome, and a population of CD4 T-cells within a host comprising a latent HIV-1 genome.

As used herein, the term "prodrug" refers to a compound, which is a drug precursor and which, following administration and absorption, releases the drug in vivo via some metabolic process. (See, e.g., Wihnan, "Prodrugs in Cancer Chemotherapy" *Biochemical Society Transactions,* 14, pp. 375-382, 615th Meeting Belfast (1986) and Stella et al., "Prodrugs: A Chemical Approach to Targeted Drug Delivery," *Directed Drug Delivery,* Borchardt et al, (ed.), pp. 247-267, Humana Press (1985). Prodrugs of this invention include, but are not limited to, phosphate-containing prodrugs, thiophosphate-containing prodrugs, sulfate-containing prodrugs, peptide-containing prodrugs, D-amino acid-modified prodrugs, glycosylated prodrugs, 3-lactam-containing prodrugs, optionally substituted phenoxyacetamide-containing prodrugs or optionally substituted phenylacetamide-containing prodrugs, 5 fluorocytosine and other 5-fluorouridine prodrugs.

As used herein, the terms "reactivated," or "activated" or grammatical equivalents thereof, in the context of in vivo reactivated or activated HIV-1, refers to an HIV-1 that, after a period of latency, becomes transcriptionally active, and in many instances forms infectious viral particles. The terms "reactivated" or "activated" or grammatical equivalents thereof, as used herein in the context of in vitro reactivated HIV-1 in a subject cell, refers to an HIV-1 (e.g., a recombinant HIV-1) that, after a period of latency, becomes transcriptionally active, i.e., a functional Tat protein mediates transcription from a functional HIV-1 promoter (e.g., a long terminal repeat promoter).

As used herein, the term "salt" refers to a salt of a compound which is prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge et al., 1977, "Pharmaceutical Salts", *Journal of Pharmaceuti-*

*cal Science*, 66:1-19). Certain specific compounds of the present invention contain both basic and acidic functionalities that allow the compounds to be converted into either base or acid addition salts.

As used herein, the term "small molecule" refers to a molecule having a molecular weight of less than 5, 2, 1, or 0.5 kDa. In many embodiments, such small molecules do not include a peptide bond or a phosphodiester bond. For example, they can be non-polymeric. In some embodiments, the molecule has a molecular weight of at least 50, 100, 200, or 400 Dalton.

As used herein, the term "substantially not changing" and grammatical equivalents thereof refer to a level, amount, or concentration of a parameter, such as a chemical compound, a metabolite, a nucleic acid, a polypeptide or a physical parameter (absorption, half-life, pH, temperature, viscosity, etc.) measured in a sample, such as a biological sample, that has an increase or decrease of less than 30%, preferably less than 25%, more preferable less than 20%, even more preferable less than 15% and still more preferably an increase or decrease of less than 10% and most preferably an increase or decrease of less than 5% when compared to the level, amount, or concentration of the same chemical compound, metabolite, nucleic acid, polypeptide or physical parameter in a control sample.

As used herein, the term "suppression of reactivation of a latent HIV-1 reservoir" or grammatical equivalents refer to a process that inhibits or suppresses transcriptional initiation, transcription elongation or replication, production of infectious virus and/or cell surface antigens, such as gp120 and/or gp41. "Suppression of reactivation of a latent HIV-1 reservoir" can be measured by methods described herein and methods known in the art. "Suppression of reactivation of a latent HIV-1 reservoir," although desirable, must not be complete, i.e., must not be 100%. It does not mean that each and every latent HIV-1 genome must be kept in its latent state. In some embodiments of the present invention, "suppression of reactivation of a latent HIV-1 reservoir" means that at least about 10% of the HIV-1 proviral latent DNA integrated into the genome of a host does not begin transcription initiation, transcription elongation or replication and production of infectious virus and/or cell surface antigens, such as gp120 and/or gp41. In some embodiments "suppression of reactivation of a latent HIV-1 reservoir" by a compound, such as VS, is at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about between 60% and 70%, at least about between 70% and 80%, at least about between 80% and 90%, at least about between 90% and 95%, or at least about between 95% and 100% when compared to a control compound or a reference.

As used herein, the terms "synergism", "synergistic," "synergy," "synergizing," "synergistically" or grammatical equivalents thereof mean an interaction of two or more agents such that the effect when combined is greater than the predicted effect based on the response of each agent applied separately. A therapeutic synergism means a therapeutic effect achieved with a tolerated regimen of the combined agents that exceeds the optimal effect achieved at any tolerated dose of monotherapy. A synergistic effect can be about two-fold, about three-fold, about five-fold, about ten-fold or more when compared to the additive effect of the individual agents. Synergy, synergism or synergistic effects of a combination of agents can be determined as described in Ting-Chao Chou, *Theoretical Basis, Experimental Design, and Computerized Simulation of Synergism and Antagonism in Drug Combination Studies, Pharmacol Rev* 58:621-681 (2006), which is incorporated by reference in its entirety. A determination of a synergistic interaction between a compound or a pharmaceutically acceptable salt thereof and one or more agents may be based on the results obtained from the assays described herein. The results of these assays can be analyzed using the Chou and Talalay combination method and Dose-Effect Analysis with CalcuSyn software in order to obtain a Combination Index (Chou and Talalay, *Adv Enzyme Regul* (1984) 22:27-55). The combinations provided by this invention can be evaluated in several assay systems, and the data can be analyzed utilizing a standard program for quantifying synergism, additivism, and antagonism among agents. A preferred program is that described by Chou and Talalay, in "New Avenues in Developmental Cancer Chemotherapy," Academic Press, 1987, Chapter 2. A combination therapy may provide "synergy" and prove "synergistic", i.e., the effect achieved when the active ingredients used together is greater than the sum of the effects that results from using the compounds separately. A synergistic effect may be attained when the active ingredients are: (i) co-formulated and administered or delivered simultaneously in a combined, unit dosage formulation; (ii) delivered by alternation or in parallel as separate formulations; or (iii) by some other regimen. When delivered in alternation therapy, a synergistic effect may be attained when the compounds are administered or delivered sequentially, e.g., by different injections in separate syringes. In general, during alternation therapy, an effective dosage of each active ingredient is administered sequentially, i.e., serially, whereas in combination therapy, effective dosages of two or more active ingredients are administered together.

As used herein, the abbreviation "TAR" means the Trans-Activating Response element which is the target for Tat binding. The TAR region is the first 59-61 nt of the nascent RNA, the leader sequence positioned immediately 3' of the transcription start site. It forms a stem-loop structure.

As used herein, the terms "Tat" or "Tat polypeptide" mean the virally encoded trans-activating protein which functions as an elongation factor. Tat is essential for viral replication as the key viral element for increasing HIV-1 gene expression.

As used herein, the term "transcription competent" in the context of transcription-competent latent HIV-1, refers to a latent HIV-1 (including latent HIV-1-based retroviral vectors) that encodes functional Tat and has a functional TAR site in the LTR.

As used herein, the terms "treatment", "treating" or grammatical equivalents thereof refer to both therapeutic treatment and prophylactic or preventative measures. Those in need of treatment include subjects already afflicted with the disease or disorder as well as those in which the disease or disorder is to be prevented. Hence, a subject may have been diagnosed as having the disease or disorder or may be predisposed or susceptible to the disease. As such, the terms include: (1) preventing a pathological condition, disorder, or disease, i.e. causing the clinical symptoms of a pathological condition, disorder, or disease not to develop in a subject that may be predisposed to the pathological condition, disorder, or disease but does not yet experience any symptoms of the pathological condition, disorder, or disease; (2) inhibiting the pathological condition, disorder, or disease, i.e. arresting or reducing the development of the pathological condition, disorder, or disease or its clinical symptoms; or (3) relieving the pathological condition, disorder, or disease, i.e. causing regression of the pathological condition, disorder, or disease or its clinical symptoms. These terms encompass also prophylaxis, therapy and cure. Treatment means any manner in which the symptoms of a pathological condition, disorder, or disease are ameliorated or otherwise beneficially altered. Preferably, the subject in need of such treatment is a mammal, more preferable a human.

As used herein, the term "variability" in the context of gene expression of a gene promoter refers to noise magnitude.

As used herein the abbreviation "VE" means variability enhancer. Within a population of cells a variability enhancer keeps the mean expression level of a gene promoter the same and increases the variability (noise magnitude) of the expression of the gene promoter.

As used herein the abbreviation "VM" means variability modulator. Within a population of cells a variability modulator keeps the mean expression level of a gene promoter the same and modulates (decreases or increases) the variability (noise magnitude) of expression of the gene promoter.

As used herein the abbreviation "VS" means variability suppressor. Within a population of cells a variability suppressor keeps the mean expression level of a gene promoter the same and decreases the variability (noise magnitude) of expression of the gene promoter.

Applicants investigated whether tunable gene expression variability can be exploited for diseases whose phenotypes are strongly biased by individual single cells, such as HIV-1 latency. Described herein are methods and cell lines to screen for small molecule compounds that enhance expression fluctuations from an HIV-1 promoter. Applicants describe their surprising and unexpected findings of such noise drug screening approach on the HIV-1 LTR promoter in human T-cells in response to 1600 FDA approved drug compounds. Using high-throughput flow cytometry Applicants identified compounds that modulated variability (variability enhancers and variability suppressors) without changing the mean expression level of the promoter and which otherwise would be overlooked by conventional drug screening. Based on quantifying transcriptional fluctuations in the LTR promoter, Applicants demonstrated that some small molecule compounds identified synergize with known activators of HIV-1 latency activators (such as TNFα or prostratin, and others) to allow for enhanced activation of gene expression and reactivation of latent HIV-1 virus in several model systems. Applicants' approach presents an easy and rapid metric to efficiently parse compound libraries and identify potential synergistic activators, in addition to suppressor compounds. Further described are compositions and methods for reactivation of a latent HIV-1 reservoir.

II. Compounds and Compositions

The present invention describes a variety of compounds useful for practicing the compositions, systems and methods of the invention. Applicants describe herein novel approaches for eliminating a latent HIV-1 reservoir, wherein expression of the latent HIV-1 is activated by contacting a cell with a variability modulator and an activator of latent HIV-1 gene expression. As described herein, it is an objective of the present invention to provide variability modulators (VMs), in particular variability enhancers (VEs) for reactivating a latent HIV-1 reservoir in combination with an activator of latent HIV-1 gene expression. It is also an objective of the present invention to provide variability modulators, in particular variability suppressors (VSs) for inhibiting reactivation of a latent HIV-1. VEs and VSs are useful to practice the methods of the present invention. Thus, the present invention provides compositions and methods that are useful in a wide range of methods. These methods include, but are not limited to, a method for screening for a variability modulator, a method for reactivating a latent HIV-1 reservoir, a method for reactivation of latent HIV-1 gene expression, a method for eliminating a latent HIV-1 reservoir, a method for increasing latent HIV-1 gene expression, a method for rendering a latent HIV-1 sensitive to killing by an immunotoxin or HAART, a method for suppressing or inhibiting activation of a latent HIV-1 reservoir, a method for treating HIV-1 latency in a subject in need thereof; and a method for increasing the activity of an LTR promoter in a cell.

Applicants' invention also provides for a use of a variability modulator for modulating gene expression of a gene in a prokaryotic cell, a use of a variability modulator for modulating gene expression of a gene in a eukaryotic cell, a use of a variability modulator for modulating gene expression of a gene in a fungal cell, a use of a variability modulator for modulating gene expression of a gene in a mammalian cell, a use of a variability modulator for modulating a latent HIV-1 reservoir in a mammalian cell, a use of a variability modulator for reactivating a latent HIV-1 reservoir in a mammalian cell, and a use of a variability modulator for suppressing reactivation of a latent HIV-1 reservoir in a mammalian cell.

Variability modulators, in particular variability enhancers (VEs) and variability suppressors (VSs) are also useful for producing pharmaceutical compositions, medicaments, and kits, as described herein, for practicing a method of the present invention. Pharmaceutical compositions, medicaments and kits can be used, preferably, in methods for modulating gene expression of a gene in a prokaryotic cell, in methods for modulating gene expression of a gene in a eukaryotic cell, in methods for modulating gene expression of a gene in a fungal cell, in methods of modulating gene expression of a gene in a mammalian cell, in methods for modulating latency of an HIV-1 reservoir in a mammalian cell, in methods for reactivating a latent HIV-1 reservoir in a mammalian cell and in methods for suppressing reactivation of a latent HIV-1 reservoir in a mammalian cell.

This invention discloses the surprising finding that VEs synergize with activators of gene expression, such as with an activator of latent HIV-1 gene expression. The compounds and compositions disclosed herein can be used in either the compositions, systems, methods, pharmaceutical compositions, medicaments, and kits described herein.

The following provides further support for claims set forth herein.

A. Variability Modulators (VMs)

As described herein, Applicants have screened a small molecule compound library of 1,600 FDA-approved compounds and identified 144 variability modulators. Those variability modulators include thiamylal sodium, Estramustine, griseofulvin, telmisartan, docetaxel, riboflavin, pantothenic acid(d) na salt, mercaptopurine, pemetrexed, ethinyl estradiol, irinotecan hydrochloride, dutasteride, felbinac, vincristine sulfate, thiram, bezafibrate, Indomethacin, mebendazole, ouabain, sulfaquinoxaline sodium, oxybutynin chloride, oxyphencyclimine hydrochloride, saxagliptin, phenylmercuric acetate, troclosene potassium, artemisinin, cytarabine, thioguanine, hydroquinone, acetophenazine maleate, exylresorcinol, oxytetracycline, cefadroxil, tolnaftate, phenylbutyric acid, atorvastatin calcium, carboplatin, 5-azacytidine, levodopa, lamivudine, sotalol hydrochloride, clavulanate lithium, digoxin, sodium monofluorophosphate, dexpanthenol, rabeprazole sodium, cetirizine hydrochloride, trilostane, modafinil, thiabendazole, adapalene, sulfameter, Fluoxetine hydrochloride, trimethobenzamide hydrochloride, Metoclopramide hydrochloride, guanethidine sulfate, trichlormethine, sucralfate, valganciclovir hydrochloride, bemotrizinol, parachlorophenol, (±)-Verapamil hydrochloride, oxidopamine hydrochloride, fomepizole hydrochloride, Xylazine hydrochloride, diperodon hydrochloride, zomepirac sodium, closantel, fenbendazole, finasteride, Procainamide hydrochloride, celecoxib, colistin sulfate, imipenem, cefoxitin sodium, azithromycin, clidinium bromide, Tolazamide, chlorpheniramine maleate, colesevalam hydrochloride, Pargyline hydrochloride, hydralazine hydrochloride, anastrozole, vinorelbine, bleomycin, dasatinib, busulfan, vorinostat, selamectin, idoxuridine, carvediloi, (±)-Isoproterenol hydrochloride, racephedrine hydrochloride, vardenafil hydrochloride, guaiacol, clobetasol propionate, mycophenolic acid, fludrocortisone acetate, zaleplon, nitroglycerin, riboflavin 5-phosphate sodium, acetriazoic acid, Digitoxin, carnitine hydrochloride, lonidamine, Taxol, mitomycin c, clofarabine, arginine hydrochloride, melphalan, fludarabine phosphate, methotrexate(+/−), taurine, albendazole, rifaximin, tetramizole hydrochloride, thiostrepton, Arecoline hydrobromide, zalcitabine, erythrosine sodium, nikethamide, oxfendazole, editol, doxapram hydrochloride, aminacrine, dobutamine hydrochloride, rutin, manidipine hydrochloride, phenothiazine, dichlorvos, fipronil, trichlorfon, benzydamine hydrochloride, maprotiline hydrochloride, Papaverine hydrochloride, arsenic trioxide, phenformin hydrochloride, itraconazole, cycloheximide, hydroxyprogesterone caproate, pyrithione zinc, meclocycline sulfosalicylate, ergotamine tartrate, adenosine phosphate, and broxaldine.

Thus, in some embodiments of the present invention, compositions, systems and methods comprise a variability modulator selected from the group consisting of thiamylal sodium, Estramustine, griseofulvin, telmisartan, docetaxel, riboflavin, pantothenic acid(d) na salt, mercaptopurine, pemetrexed, ethinyl estradiol, irinotecan hydrochloride, dutasteride, felbinac, vincristine sulfate, thiram, bezafibrate, Indomethacin, mebendazole, ouabain, sulfaquinoxaline sodium, oxybutynin chloride, oxyphencyclimine hydrochloride, saxagliptin, phenylmercuric acetate, troclosene potassium, artemisinin, cytarabine, thioguanine, hydroquinone, acetophenazine maleate, exylresorcinol, oxytetracycline, cefadroxil, tolnaftate, phenylbutyric acid, atorvastatin calcium, carboplatin, 5-azacytidine, levodopa, lamivudine, sotalol hydrochloride, clavulanate lithium, digoxin, sodium monofluorophosphate, dexpanthenol, rabeprazole sodium, cetirizine hydrochloride, trilostane, modafinil, thiabendazole, adapalene, sulfameter, Fluoxetine hydrochloride, trimethobenzamide hydrochloride, Metoclopramide hydrochloride, guanethidine sulfate, trichlormethine, sucralfate, valganciclovir hydrochloride, bemotrizinol, parachlorophenol, (±)-Verapamil hydrochloride, oxidopamine hydrochloride, fomepizole hydrochloride, Xylazine hydrochloride, diperodon hydrochloride, zomepirac sodium, closantel, fenbendazole, finasteride, Procainamide hydrochloride, celecoxib, colistin sulfate, imipenem, cefoxitin sodium, azithromycin, clidinium bromide, Tolazamide, chlorpheniramine maleate, colesevalam hydrochloride, Pargyline hydrochloride, hydralazine hydrochloride, anastrozole, vinorelbine, bleomycin, dasatinib, busulfan, vorinostat, selamectin, idoxuridine, carvedilol, (±)-Isoproterenol hydrochloride, racephedrine hydrochloride, vardenafil hydrochloride, guaiacol, clobetasol propionate, mycophenolic acid, fludrocortisone acetate, zaleplon, nitroglycerin, riboflavin 5-phosphate sodium, acetriazoic acid, Digitoxin, carnitine hydrochloride, lonidamine, Taxol, mitomycin c, clofarabine, arginine hydrochloride, melphalan, fludarabine phosphate, methotrexate(+/−), taurine, albendazole, rifaximin, tetramizole hydrochloride, thiostrepton, Arecoline hydrobromide, zalcitabine, erythrosine sodium, nikethamide, oxfendazole, editol, doxapram hydrochloride, aminacrine, dobutamine hydrochloride, rutin, manidipine hydrochloride, phenothiazine, dichlorvos, fipronil, trichlorfon, benzydamine hydrochloride, maprotiline hydrochloride, Papaverine hydrochloride, arsenic trioxide, phenformin hydrochloride, itraconazole, cycloheximide, hydroxyprogesterone caproate, pyrithione zinc, meclocycline sulfosalicylate, ergotamine tartrate, adenosine phosphate, and broxaldine. Also useful for practicing the methods of the present invention are single stereoisomers, mixtures of stereoisomers, pharmaceutically acceptable salts, prodrugs and functional derivatives of those variability modulators.

1. Screening for Variability Modulators

Compositions, systems, and methods described herein (see, Examples) can be used to identify additional VMs from, e.g., any compound library comprising agents that are expected to function as a variability modulator.

i. Libraries for Screening

One of skill in the art will appreciate that a wide variety of compound libraries can be used in the methods of the present invention, e.g., in a method of screening for a VM. In some embodiments of the present invention, the library is a small molecule library. In other embodiments, the compound library is a peptide library.

Thus, in some embodiments of the present invention, a compound library is selected from the group consisting of a small molecule library, and a peptide library.

In some embodiments of the present invention, a compound library is a library of diverse and bioactive small molecules. In some embodiments of the present invention, a diverse and bioactive small molecule library comprise small molecules that are FDA approved. A preferred library of diverse and bioactive small molecules is the Pharmakon 1600 library. This library can be obtained from Microsource Discovery Systems, Inc. (USA).

2. Testing of Variability Modulators

Any variability modulator can be tested by a method described herein.

3. Variability Enhancers (VEs)

Among the VMs identified herein, some are characterized as variability enhancers (VEs) in various assay systems. Screening the Pharmakon 1600 library, 126 VEs were identified (FIG. 10). Those 126 VEs include thiamylal sodium, Estramustine, griseofulvin, telmisartan, docetaxel, riboflavin, pantothenic acid(d) na salt, mercaptopurine, pemetrexed, ethinyl estradiol, irinotecan hydrochloride, dutasteride, felbinac, vincristine sulfate, thiram, bezafibrate, Indomethacin, mebendazole, ouabain, sulfaquinoxaline sodium, oxybutynin chloride, oxyphencyclimine hydrochloride, saxagliptin, phenylmercuric acetate, troclosene potassium, artemisinin, cytarabine, thioguanine, hydroquinone, acetophenazine maleate, hexylresorcinol, oxytetracycline, cefadroxil, tolnaftate, phenylbutyric acid, atorvastatin calcium, carboplatin, 5-azacytidine, levodopa, lamivudine, sotalol hydrochloride, clavulanate lithium, digoxin, sodium monofluorophosphate, dexpanthenol, rabeprazole sodium, cetirizine hydrochloride, trilostane, modafinil, thiabendazole, adapalene, sulfameter, Fluoxetine hydrochloride, trimethobenzamide hydrochloride, Metoclopramide hydrochloride, guanethidine sulfate, trichlormethine, sucralfate, valganciclovir hydrochloride, bemotrizinol, parachlorophenol, (±)-Verapamil hydrochloride, oxidopamine hydrochloride, fomepizole hydrochloride, Xylazine hydrochloride, diperodon hydrochloride, zomepirac sodium, closantel, fenbendazole, finasteride, Procainamide hydrochloride, celecoxib, colistin sulfate, imipenem, cefoxitin sodium, azithromycin, clidinium bromide, Tolazamide, chlorpheniramine maleate, colesevalam hydrochloride, Pargyline hydrochloride, hydralazine hydrochloride, anastrozole, vinorelbine, bleomycin, dasatinib, busulfan, vorinostat, selamectin, idoxuridine, carvedilol, (±)-Isoproterenol hydrochloride, racephedrine hydrochloride, vardenafil hydrochloride, guaiacol, clobetasol propionate, mycophenolic acid, fludrocortisone acetate, zaleplon, nitroglycerin, riboflavin 5-phosphate sodium, acetriazoic acid, digitoxin, carnitine hydrochloride, albendazole, taurine, Taxol, mitomycin c, clofarabine, arginine hydrochloride, tetramizole hydrochloride, thiostrepton, lonidamine, melphalan, fludarabine phosphate, methotrexate(+/−), rifaximin, Arecoline hydrobromide, zalcitabine, erythrosine sodium, nikethamide, oxfendazole, editol, doxapram hydrochloride, aminacrine, dobutamine hydrochloride, and rutin.

Thus, in some embodiments of the present invention, a VE is selected from the group consisting of thiamylal sodium, Estramustine, griseofulvin, telmisartan, docetaxel, riboflavin, pantothenic acid(d) na salt, mercaptopurine, pemetrexed, ethinyl estradiol, irinotecan hydrochloride, dutasteride, felbinac, vincristine sulfate, thiram, bezafibrate, Indomethacin, mebendazole, ouabain, sulfaquinoxaline sodium, oxybutynin chloride, oxyphencyclimine hydrochloride, saxagliptin, phenylmercuric acetate, troclosene potassium, artemisinin, cytarabine, thioguanine, hydroquinone, acetophenazine maleate, hexylresorcinol, oxytetracycline, cefadroxil, tolnaftate, phenylbutyric acid, atorvastatin calcium, carboplatin, 5-azacytidine, levodopa, lamivudine, sotalol hydrochloride, clavulanate lithium, digoxin, sodium monofluorophosphate, dexpanthenol, rabeprazole sodium, cetirizine hydrochloride, trilostane, modafinil, thiabendazole, adapalene, sulfameter, Fluoxetine hydrochloride, trimethobenzamide hydrochloride, Metoclopramide hydrochloride, guanethidine sulfate, trichlormethine, sucralfate, valganciclovir hydrochloride, bemotrizinol, parachlorophenol, (±)-Verapamil hydrochloride, oxidopamine hydrochloride, fomepizole hydrochloride, Xylazine hydrochloride, diperodon hydrochloride, zomepirac sodium, closantel, fenbendazole, finasteride, Procainamide hydrochloride, celecoxib, colistin sulfate, imipenem, cefoxitin sodium, azithromycin, clidinium bromide, Tolazamide, chlorpheniramine maleate, colesevalam hydrochloride, Pargyline hydrochloride, hydralazine hydrochloride, anastrozole, vinorelbine, bleomycin, dasatinib, busulfan, vorinostat, selamectin, idoxuridine, carvedilol, (±)-Isoproterenol hydrochloride, racephedrine hydrochloride, vardenafil hydrochloride, guaiacol, clobetasol propionate, mycophenolic acid, fludrocortisone acetate, zaleplon, nitroglycerin, riboflavin 5-phosphate sodium, acetriazoic acid, digitoxin, carnitine hydrochloride, albendazole, taurine, Taxol, mitomycin c, clofarabine, arginine hydrochloride, tetramizole hydrochloride, thiostrepton, lonidamine, melphalan, fludarabine phosphate, methotrexate(+/−), rifaximin, Arecoline hydrobromide, zalcitabine, erythrosine sodium, nikethamide, oxfendazole, editol, doxapram hydrochloride, aminacrine, dobutamine hydrochloride, rutin, single stereoisomers, mixtures of stereoisomers, pharmaceutically acceptable salts, prodrugs and functional derivatives thereof.

As described herein, some of the 126 VEs initially identified in the Pharmakon 1600 library synergize with an activator drug for latent HIV-1 gene expression tested herein. As one of ordinary skill in the art will appreciate, HIV-1 latency is just one expression system to which VMs may be applied and studied in great detail by Applicants herein. VMs, however, can be used to modulate gene expression of any gene in a mammalian cell. Applicants' compositions, systems and methods provided primarily in the context of HIV-1 latency, are also useful for analyzing gene expression of other genes in a mammalian cell.

In the context of HIV-1 latency, 85 VEs were identified herein that synergized with one or more of PMA, prostratin, TNFα, and bryostatin. Those 85 VEs are shown in FIG. 11 and include docetaxel (V1), ethinyl estradiol (V2), estramustine (V3), felbinac (V4), bezafibrate (V6), mebendazole (V7), thiamylal sodium (V8), mercaptopurine (V9), dutasteride (V10), cetirizine hydrochloride (V11), acetophenazine maleate (V12), oxytetracycline (V13), artemisinin (V14), hydralazine hydrochloride (V17), Indomethacin (V18), atorvastatin calcium (V20), guanethidine sulfate (V21), pantothenic acid(d) na salt (V22), saxagliptin (V23), (±)-Verapamil hydrochloride (V24), oxidopamine hydrochloride (V25), trilostane (V26), fomepizole hydrochloride (V27), modafinil (V28), Xylazine hydrochloride (V29), diperodon hydrochloride (V30), zomepirac sodium (V31), thiabendazole (V33), closantel (V34), hexylresorcinol (V35), adapalene (V36), finasteride (V37), Procainamide hydrochloride (V38), cefadroxil (V40), sulfameter (V41), sulfaquinoxaline sodium (V42), azithromycin (V43), imipenem (V44), colistin sulfate (V45), cefoxitin sodium (V46), oxyphencyclimine hydrochloride (V47), oxybutynin chloride (V48), clidinium bromide (V49), Fluoxetine hydrochloride (V50), Tolazamide (V51), trimethobenzamide hydrochloride (V52), Metoclopramide hydrochloride (V53), tolnaftate (V54), chlorpheniramine maleate (V58), phenylbutyric acid (V59), colesevalam hydrochloride (V60), Pargyline hydrochloride (V61), telmisartan (V62), troclosene potassium (V63), bleomycin (V66), dasatinib (V67), anastrozole (V68), busulfan (V69), carboplatin (V71), pemetrexed (V74), hydroquinone (V76), selamectin (V77), levodopa (V78), sucralfate (V79), valganciclovir hydrochloride (V80), lamivudine (V81), idoxuridine (V82), sotalol hydrochloride (V83), carvedilol (V84), clavulanate lithium (V85), (±)-Isoproterenol hydrochloride (V86), racephedrine hydrochloride (V87), sodium monofluorophosphate (V89), dexpanthenol (V90), vardenafil hydrochloride (V91), guaiacol (V92), rabeprazole sodium (V93), clobetasol propionate (V94), mycophenolic acid (V95), fludrocortisone acetate (V96), zaleplon (V97), bemotrizinol (V98), parachlorophenol (V99), nitroglycerin (V100), and acetriazoic acid (V102). The numbers V1 through V102 following the compound identified refer to the identification number of the compound in the screens and figures described herein.

Thus, in some embodiments of the present invention, a VE is selected from the group consisting of docetaxel, ethinyl estradiol, estramustine, felbinac, bezafibrate, mebendazole, thiamylal sodium, mercaptopurine, dutasteride, cetirizine hydrochloride, acetophenazine maleate, oxytetracycline, artemisinin, hydralazine hydrochloride, Indomethacin, atorvastatin calcium, guanethidine sulfate, pantothenic acid(d) na salt, saxagliptin, (±)-Verapamil hydrochloride, oxidopamine hydrochloride, trilostane, fomepizole hydrochloride, modafinil, Xylazine hydrochloride, diperodon hydrochloride, zomepirac sodium, thiabendazole, closantel, hexylresorcinol, adapalene, finasteride, Procainamide hydrochloride, cefadroxil, sulfameter, sulfaquinoxaline sodium, azithromycin, imipenem, colistin sulfate, cefoxitin sodium, oxyphencyclimine hydrochloride, oxybutynin chloride, clidinium bromide, Fluoxetine hydrochloride, Tolazamide, trimethobenzamide hydrochloride, Metoclopramide hydrochloride, tolnaftate, chlorpheniramine maleate, phenylbutyric acid, colesevalam hydrochloride, Pargyline hydrochloride, telmisartan, troclosene potassium, bleomycin, dasatinib, anastrozole, busulfan, carboplatin, pemetrexed, hydroquinone, selamectin, levodopa, sucralfate, valganciclovir hydrochloride, lamivudine, idoxuridine, sotalol hydrochloride, carvedilol, clavulanate lithium, (Â±)-Isoproterenol hydrochloride, racephedrine hydrochloride, sodium monofluorophosphate, dexpanthenol, vardenafil hydrochloride, guaiacol, rabeprazole sodium, clobetasol propionate, mycophenolic acid, fludrocortisone acetate, zaleplon, bemotrizinol, parachlorophenol, nitroglycerin, and acetriazoic acid, single stereoisomers, mixtures of stereoisomers, pharmaceutically acceptable salts, prodrugs and functional derivatives thereof.

In some embodiments, a variability modulator is selected from the group consisting of docetaxel, ethinyl estradiol, estramustine, felbinac, bezafibrate, mebendazole, mercaptopurine, dutasteride, cetirizine hydrochloride, acetophenazine maleate, oxytetracycline, and artemisinin. Also useful for practicing the methods of the present invention are single stereoisomers, mixtures of stereoisomers, pharmaceutically acceptable salts, prodrugs and functional derivatives of those variability modulators.

4. Variability Suppressors (VSs)

Among the VMs identified herein, some are characterized as variability suppressors (VSs) in various assay systems. VSs identified within the Pharmakon 1600 library include manidipine hydrochloride, phenothiazine, dichlorvos, fipmnil, trichlorfon, benzydamine hydrochloride, maprotiline hydrochloride, Papaverine hydrochloride, arsenic trioxide, phenformin hydrochloride, itraconazole, cycloheximide, hydroxyprogesterone caproate, pyrithione zinc, meclocycline sulfosalicylate, ergotamine tartrate, adenosine phosphate, and broxaldine. Other VSs can be identified by one of ordinary skill in the art using compositions, systems, and methods described by Applicants herein.

Thus, in some embodiments of the present invention, a VS is selected from the group consisting of include manidipine hydrochloride, phenothiazine, dichlorvos, fipronil, trichlorfon, benzydamine hydrochloride, maprotiline hydrochloride, Papaverine hydrochloride, arsenic trioxide, phenformin hydrochloride, itraconazole, cycloheximide, hydroxyprogesterone caproate, pyrithione zinc, meclocycline sulfosalicylate, ergotamine tartrate, adenosine phosphate, broxaldine, single stereoisomers, mixtures of stereoisomers, pharmaceutically acceptable salts, prodrugs and functional derivatives thereof.

B. Drugs for Modulating and Activating Gene Expression

As described herein several classes of drugs can be used in combination with a Variability Modulator (VM) to practice a method of the present invention, e.g., a method for modulating gene expression of a gene in a prokaryotic cell, a method for modulating gene expression of a gene in a eukaryotic cell, a method for modulating gene expression of a gene in a fungal cell, a method for modulating gene expression of a gene in a mammalian cell, a method for modulating variability of a latent HIV-1 reservoir in a mammalian cell, a method for reactivating a latent HIV-1 reservoir or a method for preventing (or suppression) of the reactivation of a latent HIV-1 reservoir.

As described herein, a preferred use of a variability modulator is for modulating variability of gene expression in a cell. As further described herein, in some embodiments, modulation of variability in gene expression by a variability modulator comprises contacting the cell with an activator of gene expression. As one of ordinary skill in the art will appreciate, numerous activators of gene expression are known in the art. Without being bound by theory, Applicants believe that in view of their surprising and unexpected findings, any activator of gene expression can be used in combination with a variability modulator. Thus, in methods, wherein the cell is a prokaryotic cell (or wherein the gene promoter is a prokaryotic gene promoter), a variability modulator may be combined, as described herein, with a prokaryotic activator of gene activation. Similarly, in methods, wherein the cell is a eukaryotic cell (or wherein the gene promoter is a eukaryotic gene promoter), a variability modulator may be combined, as described herein, with a eukaryotic activator of gene activation. In methods, wherein the cell is a prokaryotic cell and wherein the gene promoter is a prokaryotic viral gene promoter, a variability modulator may be combined, as described herein, with a prokaryotic viral activator of gene activation. Similarly, in methods, wherein the cell is a eukaryotic cell and wherein the gene promoter is a eukaryotic viral gene promoter, a variability modulator may be combined, as described herein, with a eukaryotic viral activator of gene activation. In methods, wherein the cell is a eukaryotic cell and wherein the gene promoter is a fungal gene promoter, a variability modulator may be combined, as described herein, with a fungal activator of gene activation.

In methods, wherein the cell is a eukaryotic cell and wherein the gene promoter is an HIV-1 gene promoter (e.g., an LTR gene promoter), a variability modulator may be combined, as described herein, with a activator of HIV-1 gene activation. As described herein, a preferred model of using a variability modulator for modulating variability in gene expression of a gene in a mammalian cell is modulating HIV-1 latency. As further described herein, in some embodiments, modulation of HIV-1 latency by a variability modulator further comprises an activator drug of HIV-1 latency. Those classes of activator drugs include, but are not limited to, HDAC inhibitors, PKC agonists, methylation inhibitors, bromodomain inhibitors, and anticancer drugs. Broadly, those activator drugs activate a latent HIV-1 reservoir to a certain level, however, not to 100%. In many instances, activator drugs activate latent HIV-1 gene expression to not more than 10-30%, which means that about 70-90% latent HIV-1 genomes in a cell are not activated. As demonstrated herein, adding a variability modulator, preferably a variability enhancer, to an activator drug for HIV-1 latency, significantly increases reactivation of HIV-1 latency.

1. HDAC Inhibitors

Several HDAC inhibitors can be used to practice methods of the present invention. An HDAC inhibitor may be any molecule that effects a reduction in the activity of a histone deacetylase. This includes proteins, peptides, DNA molecules (including antisense), RNA molecules (including RNAi and antisense) and small molecules.

Small molecule HDAC inhibitors include, but are not limited to, trichostatin A, butyric acid, phenylbutyrate, phenylacetate, trapoxin B (porphrin derivative, $C_{33}H_{30}N_4O_6$, Kijima et at, 1993, *J Biol Chem* 268(30):22429-35), MS 275-27 (benzamide derivative, $C_{21}H_{20}N_4O_3$), hydroximates (e.g., suberoylanilide hydroxamic acid (SAHA, hydroxamic acid, $C_{14}H_{20}N_2O_3$, Butler et at, 2000, *Cancer Res* 60:5165-5170; Marks et al., *Clin Cancer Res* 7:759-760; Richon et al., 1998, *Proc Natl Acad Sci USA*, 95(6):3003-7); azelaic bishydroxamic acid (ABHA, Parsons et al., 2002, *Biochem Pharmacol* 53:1719-1724); suberic bishydroxamic acid (SBHA); m-carboxycinnamic acid bis-hydroxamide (CBHA, hydroxamic acid, $C_{14}H_{20}N_2O_3$, Coffey et al., 2001, *Cancer Res* 61:3591-3594), depudecin (fungal metabolite, $C_{31}H_{16}O_4$), oxamflatin (aromatic sulfonamide, $C_{18}H_{34}N_2O_4S_1$), apicidin (cyclo(N—O-methyl-L-tryptophanyl-L-isoleucine-D-pipecolinyl-1-2-amino-8-oxodecanoyl, cyclopeptide $C_{29}H_{38}N_5O_6$), Scriptaid (hydroxamic acid, $C_{38}H_{12}N_2O_4$), pyroxamide (suberoyl-3-aminopyridineamide hydroxyamic acid, $C_{13}H_{20}N_3O_3$, Butler et al., 2001, *Clin Cancer Res* 7:962-970)., 2-amino-8-oxo-9,10-epoxy-decanoyl (AEO, ketone, $C_{10}H_{17}NO_3$), 3-(4-aroyl-1H-pyrrol-2-yl)-N-hydroxy-2-propenamide (propenamide, $C_{14}H_{12}N_2O_3$), CI-994 (N-acetyldinaline; Kraker et al., 2003, *Mol Cancer Ther* 2(4):401-8; el-Beltagi et al., 1993, *Cancer Res* 53:3008-14; commercially available from Pfizer), CHAP1 (trichostatin A+trapoxinB, hydroxamic/porphyrin derivatives), CHAP31 (Furumai et al., 2001, *Proc Natl Acad Sci USA* 98:97-92; Komatsu et al., 2001, *Cancer Res* 61(11):4459-66; commercially available from Japan Energy Corporation); CHAP50 (Furumai et al., 2001, *Proc Natl Acad Sci USA* 98:97-92; Komatsu et al., 2001, *Cancer Res* 61(11):4459-66; commercially available from Japan Energy Corporation), MS-275 (Suzuki et at, 1999, *J Med Chem* 42:3001-3; commercially available from Mitsui Pharmaceuticals, Inc.), M344 (Jung et al., 1999, *J Med Chem* 42:4669-4679), LAQ-824 (Catley et al., 2003, *Blood* 102 (7):2615-22), FR901228 (cyclopeptide, $C_{24}H_{36}N_4O_6S_2$), FK228 (depsipeptide, Darkin-Rattray et al, 1996, *Proc Natl Acad Sci USA* 93(23):13143-7) and HC-toxin (Brosch et at, 1995, *Plant Cell* (11):1941-50). Additionally, the following references describe histone deacetylase inhibitors which may be selected for use in the current invention: AU 9,013,101; AU 9,013,201; AU 9,013,401; AU 6,794,700; EP 1,233,958; EP 1,208,086; EP 1,174,438; EP 1,173,562; EP 1,170,008; EP 1,123,111; JP 2001/348340; U.S. 2002/103192; U.S. 2002/65282; U.S. 2002/61860; WO 02/51842; WO 02/50285; WO 02/46144; WO 02/46129; WO 02/30879; WO 02/26703; WO 02/26696; WO 01/70675; WO 01/42437; WO 01/38322; WO 01/18045; WO 01/14581; Furumai et al. 2002, *Cancer Res* 62:4916-21; Hinnebusch et al., 2002, *J Nutr* 132:1012-7; Mai et at, 2002, *J Med Chem* 45:1778-1784; Vigushin et al., 2002, *Anticancer Drugs* 13:1-13; Gottlicher et at, 2001, *EMBO J* 20:6969-78; Jung, 2001, *Curr Med Chem* 8:1505-11; Komatsu et at, 2001, *Cancer Res* 61:4459-66; Su et al., 2000, 60:3137-3142.

In some embodiments of the present invention, an HDAC inhibitor is selected from the group consisting of 12-deoxyphorbol 13-phenylacetate (DPP), Suberoylannilide Hydroxamic Acid (SAHA), MS-275, valproic acid (VPA), and trichostatin A (TSA). Also useful for practicing compositions, systems, and methods of the present invention are single stereoisomers, mixtures of stereoisomers, pharmaceutically acceptable salts, prodrugs and functional derivatives of those HDAC inhibitors.

i. 12-Deoxyphorbol 13-Phenylacetate (DPP)

In some embodiments of the present invention, an HDAC inhibitor is 12-deoxyphorbol 13-phenylacetate (DPP; Bocklandt at al., 2003, *Antiviral Res* 59(2):89-98; Kulkjosky et al., 2004, *AIDS Res Hum Retroviruses* 20(5):497-505). DPP has been reported to be 20-40 fold more potent than prostratin, probably due to its more lipophilic side chain structure (Bocklandt et al., 2003, *Antiviral Res* 59(2):89-98).

Also useful for practicing compositions, systems, and methods of the present invention are single stereoisomers, mixtures of stereoisomers, pharmaceutically acceptable salts, prodrugs and functional derivatives of DPP. DPP can be obtained, e.g., through Enzo Life Sciences (Farmingdale, N.Y., USA).

ii. Suberoylannilide Hydroxamic Acid (SAHA)

In some embodiments of the present invention, an HDAC inhibitor is Suberoylannilide Hydroxamic Acid (SAHA). Also useful for practicing compositions and methods of the present invention are single stereoisomers, mixtures of stereoisomers, pharmaceutically acceptable salts, prodrugs and functional derivatives of SAHA. SAHA also is known as N-hydroxy-N'-phenyl-octanediamide, Suberoylanilide hydroxamic acid, or Vorin and can be obtained, e.g., through Sigma-Aldrich (St. Louis, Mo., USA).

iii. Valproic Acid (VPA)

In some embodiments of the present invention, an HDAC inhibitor is valproic acid (VPA). Valproic acid, valproate sodium, and divalproex belong to a group of medicines called anticonvulsants that are currently marketed to control certain types of seizures in the treatment of epilepsy. Valproic acid is marketed as "Depakene" (Abbott Laboratories). Divalproex is marketed as "Depakote" (Sanofi-Aventis for UK; Abbott Laboratories for U.S.) and as "Epival" (Abbott Laboratories for Canada). Valproate sodium is marketed as "Depacxon." Divalproex and valproate sodium form valproic acid in the body. Divalproex is available for oral administration as delayed-release capsules (U.S.) and delayed-release tablets (U.S. and Canada). VpA is also available for oral administration as capsules (U.S.) and as syrup (U.S. and Canada). Valproate sodium is used for parenteral administration (injection) in the U.S.

Also useful for practicing compositions, systems, and methods of the present invention are single stereoisomers, mixtures of stereoisomers, pharmaceutically acceptable salts, prodrugs and functional derivatives of VPA. VPA also is known as 2-propylpentanoic acid and can be obtained, e.g., through Sigma-Aldrich (St. Louis, Mo., USA).

VPA is rapidly absorbed after oral administration. Peak serum levels occur approximately 1 to 4 hours after a single oral dose. The serum half-life of VPA is typically in the range of 6-16 hours.

iv. MS-275

In some embodiments of the present invention, an HDAC inhibitor is MS-275. Also useful for practicing compositions and methods of the present invention are single stereoisomers, mixtures of stereoisomers, pharmaceutically acceptable salts, prodrugs and functional derivatives of MS-275. MS-275 also is known as 3-pyridinylmethyl [[4-[[(2-aminophenyl)amino]carbonyl]phenyl]methyl]carbamate, N-(2-Aminophenyl)-4-[N-(pyridine-3ylmethoxycarbonyl)aminomethyl]benzamide and can be obtained, e.g., through Sigma-Aldrich (St. Louis, Mo., USA).

v. Trichostatin A (TSA)

In some embodiments of the present invention, an HDAC inhibitor is trichostatin A (TSA). Also useful for practicing compositions, systems, and methods of the present invention are single stereoisomers, mixtures of stereoisomers, pharmaceutically acceptable salts, prodrugs and functional derivatives of TSA. TSA also is known as [R-(E,E)]-7-[4-(Dimethylamino)phenyl]-N-hydroxy-4,6-dimethyl-7-oxo-2,4-heptadienamide and can be obtained, e.g., through Sigma-Aldrich (St. Louis, Mo., USA).

2. Protein Kinase C Agonists and NF-$K_B$ Inducers

Several Protein Kinase C (PKC) agonists and NF-$K_B$ inducers can be used to practice compositions, systems, and methods of the present invention. In some embodiments of the present invention, a PKC agonist or NF-$K_B$ inducer is selected from the group consisting of tumor necrosis factor alpha (TNFα), prostratin, PMA, and bryostatin. Also useful for practicing compositions, systems, and methods of the present invention are single stereoisomers, mixtures of stereoisomers, pharmaceutically acceptable salts, prodrugs and functional derivatives of those PKC agonists and NF-$K_B$ inducers.

i. Tumor Necrosis Factor-Alpha (TNFα)

In some embodiments of the present invention, a PKC agonist/NF-$K_B$ inducer is tumor necrosis factor-alpha (TNFα). Also useful for practicing compositions, systems, and methods of the present invention are single stereoisomers, mixtures of stereoisomers, pharmaceutically acceptable salts, prodrugs and functional derivatives of TNFα. TNFα can be obtained, e.g., through R&D Systems.

ii. Prostratin

In some embodiments of the present invention, a PKC agonist/NF-$K_B$ inducer is prostratin (12-deoxyphorbol 13-acetate). Prostratin is a relatively polar, non-tumorigenic phorbol ester, identified in extracts of *Homalanthus nutans*, a tropical plant used in Samoan herbal medicine primarily for the treatment of jaundice and stimulates protein kinase C (PKC; Gustafson et al., 1992, *J Med Chem* 35(11):1978-86).

Also useful for practicing compositions, systems, and methods of the present invention are single stereoisomers, mixtures of stereoisomers, pharmaceutically acceptable salts, prodrugs and functional derivatives of prostratin. Prostratin can be obtained, e.g., through Sigma-Aldrich (St. Louis, Mo., USA).

iii. Phorbol 12-Myristate 13-Acetate (PMA)

In some embodiments of the present invention, a PKC agonist/NF-$K_B$ inducer is phorbol 12-myristate 13-acetate (PMA). Also useful for practicing compositions, systems, and methods of the present invention are single stereoisomers, mixtures of stereoisomers, pharmaceutically acceptable salts, prodrugs and functional derivatives of PMA. PMA also is known as 12-O-Tetradecanoylphorbol 13-acetate, 4β,9α,12β,13α,20-Pentahydroxytiglia-1,6-dien-3-one 12-tetradecanoate 13-acetate, PMA, or TPA and can be obtained, e.g., through Sigma-Aldrich (St. Louis, Mo., USA).

iv. Bryostatin

In some embodiments of the present invention, a PKC agonist/NF-$K_B$ inducer is bryostatin. Also useful for practicing compositions, systems, and methods of the present invention are single stereoisomers, mixtures of stereoisomers, pharmaceutically acceptable salts, prodrugs and functional derivatives of bryostatin. Bryostatin can be obtained, e.g., through Sigma-Aldrich (St. Louis, Mo., USA).

v. Other PKC Agonists and NF-$K_B$ Inducers

Several other PKC agonists/NF-$K_B$ inducers can be used to practice compositions and methods of the present invention. Those include, but are not limited to TNF-beta (Messer et al., 1990, *Cytokine* 2(6):389-97); IL-1beta (Osborn at al., 1989 *Proc Natl Acad Sci* USA 86(7):2336-40); lipopolysaccharide (Sen et al., 1986 *Cell* 47(6):921-8); UV-light (Stein et al., 1989, *Mol Cell Biol* 9(11):5169-81); CD3 antibodies (Tong-Starkesen et al., 1989, *J Immunol* 142(2):702-7); CD3/CD28 antibodies in conjunction (Tong-Starkesen et al., 1989 *J Immunol* 142(2):702-7); Etopiside (Bessho et al., 1999, *Anticancer Res* 19(1B):693-8); Daunorubicin (Wang et al., 1996, *Science* 274(5288):784-7); hydrogen peroxide (Shreck at al., 1991, *EMBO J* 10(8):2247-58); Nocodazole (Rosette et al., 1995, *J Cell Biol* 128(6):1111-9); LIGHT (Zou et al., 2005, *J Cell Physiol* 205(3):437-43); bleomycin (Ishii et al., 2002, *Toxicol Appl Pharmicol* 184(2):88-97); camptothecin (Piret et at, 1996 *Nucleic Acids Res* 24(20:4242-8); cisplatin (Nie at al., 1998, *Mol Pharmacol* 53(4):663-9); celecoxib (Kim et al., 2004, *J Cancer Res Clin Oncol* 130(9):551-60); ciprofibrate (Li et al., 1996, *Carcinogenesis* 17(11):2305-9); cyclopordigiosin (Teshima et al., 2004, *Nitric Oxide* 11(1):9-16); dacarbazine (Lev et at, 2003, *Mol Cancer Ther* 2(8):753-63); Daio-Orengedeokuto (Cho et al., 2004, *Can J Physiol Pharmacal* 82(6):380-6); daunomycin (Das et al., 1997, *J Biol Chem* 272(23):14914-20); diazoxide (Eliseev et al., 2004, *J Biol Chem* 279(45):46748-54); diclofenac (Cho et al., 2005, *FEBS Lett* 579(20):4213-8); 5,6-dimethylxanthenone-4-acetic acid (Ching et al., 1999, *Biochem Pharmacol* 58(7):1173-81); flavone-8-acetic acid (Ching et al., 1999, *Biochem Pharmacol* 58(7):1173-81); haloperidol (Post et al., 1998, *J Neurosci* 18(20):8236-46); imiquimod (Schon et al., 2006, *Expert Opin Ther Targets* 10(1):69-76); isochamaejasmin (Tian et al., 2005, *Mol Pharmacol* 68(6):1534-42); Kunbi-Boshin-Hangam-Tang (Koo et al., 2001, *Immunopharmacol Immunotoxicol* 23(2):175-86); lithium (Nemeth et al., 2002, *J Biol Chem* 277(10):7713-9); mitoxantrone (Boland et al., 2000, *J Biol Chem* 275(33):25231-8); morphine (Yin et al., *J Neuroimmunol* 2006 Mar. 7 [Epub ahead of print]); nipradilol (Ando et al., 2005, *Exp Eye Res* 80(4):501-7); norepinephrine (Minneman et al., 2000, *J Neurochem* 74(6):2392-400); nystatin (Ogawa et al., 2006, *J Invest Dermatol* 126(2):349-53); oltipraz (Nho et al., 2004, *J Biol Chem* 279(25):26019-27); protocatechuic acid (Zhou-Stache et al., 2002, *Med Biol Eng Comput* 40(6):698-703); SN38 (metabolite of CPT-11; Kishida et al., 2005, *Cancer Chemother Pharmacol* 55(4):393-403); tamoxifen (Ferline et al., 1999, *Br J Cancer* 79(2):257-63); Taxol (Paclitaxel; Hwang et al., 1995, *Cancer Biochem Biophys* 14(4):265-72); vinblastine (Rosette et al., 1995, *J Cell Biol* 128(6):1111-9); vincristine (Das et al., 1997, *J Biol Chem* 272(23):14914-20); and WR1065 (Grdina et al., 2002, *Mil Med* 167(2 Suppl):51-3).

3. Methylation Inhibitors

Several methylation inhibitors can be used to practice compositions and methods of the present invention. In some embodiments of the present invention, a methylation inhibitor is azacytidine. Also useful for practicing compositions, systems, and methods of the present invention are single stereoisomers, mixtures of stereoisomers, pharmaceutically acceptable salts, prodrugs and functional derivatives of azacytidine. Azacytidine also is known as 4-Amino-1-(β-D-ribofuranosyl)1,3,5-triazin-2(1H)-one, 5-azacitidine, or Ladakamycin and can be obtained, e.g., through Sigma-Aldrich (St. Louis, Mo., USA).

4. Bromodomain Inhibitors

Several bromodomain inhibitors can be used to practice compositions and methods of the present invention. In some embodiments of the present invention, a bromodomain inhibitor is JQ1, GSK1210151A or PFI-1. Also useful for practicing compositions, systems, and methods of the present invention are single stereoisomers, mixtures of stereoisomers, pharmaceutically acceptable salts, prodrugs and functional derivatives of JQ1, GSK1210151A and PH-1. JQ1 also is known as t-Butyl-2-((6S)-4-(4-chlorophenyl)-2,3,9-trimethyl-6H-thieno[3,2-f][1,2,4]triazolo[4,3-a][1,4]diazepin-6-yl)acetate and can be obtained, e.g., through Bio Vision, Inc. Milpitas, Calif., USA). PFI-1 and GSK1210151A, also known as I-BET151, can be obtained, e.g., from Selleckchem (Houston, Tex.).

5. Anticancer Drugs

Several anticancer drugs can be used to practice compositions and methods of the present invention. In some embodiments of the present invention, an anticancer drug is cytarabine. Also useful for practicing compositions, systems, and methods of the present invention are single stereoisomers, mixtures of stereoisomers, pharmaceutically acceptable salts, prodrugs and functional derivatives of cytarabine. Cytarabine also is known as (β-D-arabinofuranosyl)cytosine, Ara-C, arabinocytidine, arabinosylcytosine, or Cytosine arabinoside and can be obtained, e.g., through Sigma-Aldrich (St. Louis, Mo., USA).

III. Methods

The present invention describes a variety of methods using compounds, compositions, and systems of the invention.

A. Methods of Screening for a Variability Modulator

The present invention provides methods of screening for a variability modulator, such as a variability enhancer (VE) or a variability suppressor (VS). The present invention also provides methods of screening for a VE that synergistically activates a gene promoter in combination with a second compound, such as an activator of gene expression, i.e., methods of screening for a VE that when combined with the second compound synergistically increases the mean expression level of gene expression from the gene promoter.

In some embodiments of the present invention, a method of screening for a variability modulator modulating variability of expression of a gene promoter comprises the step of (a) contacting a first compound to a cell wherein the cell comprises a first reporter gene. The gene promoter desirably controls expression of the reporter gene and the first compound, when compared to a control, modulates variability of expression of the gene promoter without substantially changing the mean expression level of the gene promoter. As described herein, the first compound can be a member of a library, more specifically, a library comprising a plurality of compounds.

In some embodiments of the present invention, the method of screening for a variability modulator comprises the step of determining a first variability in gene expression of the gene promoter after contacting the cell with the first compound.

In some embodiments of the present invention, the method of screening for a variability modulator comprises the step of determining a second variability in gene expression of the gene promoter after contacting the cell with the control compound. As it will be apparent to one of skill in the art, the description of determining a first, a second, a third, etc., variability in gene expression does not mean that the first determination needs to be made prior to the second determination or that the second determination needs to be made prior to a third determination, etc. First, second, third, etc. merely refer to different determinations. A control compound does not alter expression variability.

In some embodiments of the present invention, the method of screening for a variability modulator comprises the step of identifying the first compound as a variability modulator when the first variability in gene expression of the gene promoter (determined after contacting the cell with the first compound) is substantially different when compared to the second variability in gene expression of the gene promoter (determined after contacting the cell with a control compound in the absence of the first compound).

In some embodiments of the present invention, the method of screening for a variability modulator comprises the step of identifying the first compound as a variability suppressor when the first variability in gene expression of the gene promoter (determined after contacting the cell with the first compound) is substantially lower (i.e., smaller) when compared to the second variability in gene expression of the gene promoter (determined after contacting the cell with a control compound in the absence of the first compound). In some embodiments of the present invention, the method of screening for a variability modulator comprises the step of identifying the first compound as a variability suppressor when the first compound either reduces the ability of a cell to transition into a new cellular state compared to a control compound, or the first and the second compound together reduce the mean-expression level of the gene promoter either as compared after contacting only the first compound to the cell (which generates no change in mean-expression level) or after contacting only the second compound to the cell.

In some embodiments of the present invention, the method of screening for a variability modulator comprises the step of identifying the first compound as a variability enhancer when the first variability in gene expression of the first reporter gene (determined after contacting the cell with the first compound) is substantially higher (i.e., greater) when compared to the second variability in gene expression of the first reporter gene (determined after contacting the cell with a control compound in the absence of the first compound). A control compound does not alter expression variability.

In some embodiments of the present invention, the method of screening for a variability modulator comprises the step of contacting a second compound to the cell.

In some embodiments of the present invention, the method of screening for a variability modulator comprises the step of determining the mean expression level of the reporter gene (i.e., determining a level of mRNA transcribed from the reporter gene and/or determining a level of a polypeptide encoded by the reporter gene) after contacting the cell with the second compound.

In some embodiments of the present invention, the method of screening for a variability modulator comprises the step of determining the level of synergism by which the first and second compounds activate the gene promoter.

In some embodiments of the present invention, the method of screening for a variability modulator comprises the step of identifying the first compound as a variability suppressor when the first compound and the second compound combined reduce the mean expression level of the gene promoter as determined either after contacting the cell only with the first compound or contacting the cell only with the second compound.

In some embodiments of the present invention, the method of screening for a variability modulator comprises the step of identifying the first compound as a synergistic variability enhancer when the first compound and the second compound combined synergistically activate the level of gene expression from the gene promoter, i.e., when the first compound and the second compound synergistically increase the mean expression level of gene expression from the gene promoter.

1. Gene Promoters

One of skill in the art will appreciate that a wide variety of gene promoters can be used in the methods of screening for a variability modulator (VM), in particular for a variability enhancer (VE), for a variability enhancer (VE) that synergistically activates a gene promoter or for a variability suppressor (VS) that inhibits activation of a gene promoter. Essentially any gene promoter driving expression of a detectable reporter gene can be analyzed according to a method of the present invention, wherein variability in expression of the reporter gene or changes in the mean expression level of the gene promoter are detectable either by detecting an mRNA level or by detecting a polypeptide encoded by that gene. In some embodiments of the present invention, the gene promoter is a gene promoter involved in establishing or maintaining cell-fate specification of a stem cell, establishing or maintaining viral latency, establishing or maintaining Human Immunodeficiency Virus-Type 1 (HIV-1) latency, establishing or maintaining tumor metastasis, establishing or maintaining fungal persistence or establishing or maintaining bacterial persistence. A preferred gene promoter is a gene promoter involved in establishing or maintaining HIV-1 latency. A preferred gene promoter is a HIV-1 long terminal repeat (LTR) promoter.

2. High Throughput Screening

Methods of screening for a VM, in particular for a variability enhancer (VE), for a VE that synergistically activates a gene promoter or for a VS that inhibits activation of a gene promoter can be used with individual compounds or in a high-throughput screening method. A preferred method is a high-throughput screening method. High-throughput methods that can be combined with the specifics of a screening method described herein, are known in the art.

3. Detection Methods

Methods of screening for a VM, in particular for a variability enhancer (VE), for a VE that synergistically activates a gene promoter or for a VS that inhibits activation of a gene promoter are not limited by a detection or measuring method of the protein product encoded by the reporter gene or the mRNA transcribed from the reporter gene. In fact several detection or measuring methods can be used (See also below, D. General Methods). In some embodiments, the method comprises fluorescence microscopy, FISH, detection of a fluorescent protein, flow cytometry, single-cell RNA sequencing, or a polymerase Chain reaction (PCR) method. A preferred detection or measuring method is or comprises flow cytometry. These methods are known in the art.

4. In Vitro and In Vivo Screening for VMs

Methods of screening for a VM, in particular for a variability enhancer (VE), for a VE that synergistically activates a gene promoter or for a VS that inhibits activation of a gene promoter can be practiced in vitro and in vivo. In some embodiments of the present invention, a cell is contacted according to the invention in vitro. In some embodiments of the present invention, a cell is contacted according to the invention in vivo.

In some embodiments where the screening for a compound is performed in vivo, the method comprises the step of administering a compound according to the present invention to a non-human animal, for example, by an intradermal, intravenous, subcutaneous, oral, aerosol, intramuscular and intraperitoneal route of administration. Screening methods of the present invention can also be practiced in vitro, for example, by transfection, electroporation, microinjection, lipofection, adsorption, protoplast fusion, use of protein carrying agents, use of ion carrying agents, and use of detergents for cell permeabilization.

5. Cells

One of skill in the art will appreciate that a wide variety of cells can be used in the methods of screening for a VM, in particular screening for a variability enhancer (VE), for a VE that synergistically activates a gene promoter or for a VS that inhibits activation of a gene promoter. In some embodiments of the present invention, a cell is a prokaryotic cell, e.g., an *E. coli* cell or a *Bacillus* cell. In some embodiments of a method of the present invention, a prokaryotic cell is selected from the group consisting of *Eubacterium* sp, *Barnesiella* sp, *Acetanaerobacterium* sp, *Acetanaerobacterium* sp, *Butyrivibrio* sp, *Butyricimonas* sp, *Lachnospiraceae* sp, *Porphyromonas* sp, *Prevotella* sp, *Rumen bacterium* sp, *Filifactor* sp, *Cyanobacterium* sp, *Alistipes* sp, *Candida, Kloeckera, Hanseniaspora, Zygosaccharomyces, Schizosaccharomyces, Torulaspora, Brettanomyces, Saccharomycodes, Pichia, Williopsis, Pediococcus, Lactobacillus,* and *Oenococcus*. In some embodiments of the present invention, the cell is a eukaryotic cell. In some embodiments of the present invention, the cell is a fungal cell, e.g., a yeast cell. In some embodiments of the present invention, the cell is a mammalian cell. In some embodiments, the mammalian cell is a human cell. Preferred human cells include, but are not limited to, a T-cell. A preferred T-cell includes, but is not limited to, a Jurkat cell, a MT-4 cell, a CEM cell, a SupT1 cell or a primary T-cell. Preferred are also JLat cells as described herein.

6. Second Compounds

One of skill in the art will appreciate that a wide variety of second compounds can be used in the methods of screening for a VM, in particular screening for a variability enhancer (VE), for a VE that synergistically activates a gene promoter or for a VS that inhibits activation of a gene promoter.

In some embodiments, the second compound is an activator of gene expression. Numerous activators of gene expression are known in the art. In some embodiments, an activator of gene expression is a viral activator of a gene expression. In some embodiments, an activator of gene expression is a prokaryotic activator of a gene expression. In some embodiments, an activator of gene expression is a eukaryotic activator of a gene expression. In some embodiments, an activator of gene expression is a mammalian activator of a gene expression. In some embodiments, an activator of gene expression is a human activator of a gene expression. Such activators of gene expression are known in the art.

In some embodiments, the second compound contacting the cell is an activator of HIV-1 gene expression. In some embodiments, the second compound contacting the cell is an activator of latent HIV-1 gene expression as described herein.

In some embodiments, the second compound is a member of a library, preferably a library comprising a plurality of compounds.

7. Compounds as Members of a Library

One of skill in the art will appreciate that a wide variety of first and second compounds can be used in the methods of screening for a VM, in particular for a VE that synergistically activates a gene promoter or for a VS that inhibits activation of a gene promoter. In some embodiments of the present invention, the first compound and/or second compound contacting the cell are members of a library. One of skill in the art will appreciate that a wide variety of libraries can be used in the methods of screening for a compound that synergistically activates a gene promoter. In some embodiments of the present invention, the library is selected from the group consisting of a small molecule library, a fragment library, a peptide library, an RNAi library, an shRNA library, and an miRNA library. The preparation of those libraries is known in the art and numerous libraries have been described in the art. A preferred library is the Pharmakon 1600 compound library, which can be obtained, e.g., from Microsource Discovery Systems, Inc. (USA).

In some embodiments of the present invention, the first and second compounds combined increase burst frequency and burst size of a reporter gene, e.g., increase burst frequency and burst size of the first reporter gene.

8. Reporter Genes

One of skill in the art will appreciate that a wide variety of reporter genes can be used in the methods of screening for a VM, in particular for a VE that synergistically activates a gene promoter or for a VS that inhibits activation of a gene promoter.

Several first reporter genes can be used in the screening methods described herein. In some embodiments of the present invention, the first reporter gene is a gene encoding a fluorescent protein. In some embodiments of the present invention, the first reporter gene is a gene encoding a fluorescent protein product. In some embodiments of the present invention, the first reporter gene is selected from the group of genes consisting of a gene encoding a green fluorescent protein (GFP), a gene encoding a red fluorescent protein (RFP or mCherry), a gene encoding a cyan fluorescent protein (CFP), and a gene encoding a yellow fluorescent protein (YFP). A preferred reporter gene is a gene encoding a green fluorescent protein (GFP).

In some embodiments of the screening methods described herein it is desirable to use a reporter gene producing a reporter protein product having a reduced or diminished half-life. Preferred reduced or diminished half-lives can be from 0.1-40 hours, from 0.1-10 hours, from 0.2-8 hours, from 0.5-7 hours, from 0.7-6 hours, from 1-5 hours, or from 2-3 hours. Other preferred reduced or diminished half-lives are less than 5 minutes, less than 10 minutes, less than 15 minutes, less than 20 minutes, and less than 30 minutes. A preferred reporter gene is Green Fluorescent Protein (GFP) having a reduced or diminished half-life. A particularly preferred reporter gene is GFP having a half-life of about 2-3 hours. An exemplary GFP having a reduced or diminished half-life of about 2.5 hours, $d_2$GPF, is described herein (see, Examples). Other preferred reporter genes are genes encoding for GFPs having a half-life of less than 5 minutes, less than 10 minutes, less than 15 minutes, less than 20 minutes, and less than 30 minutes.

In some embodiments of the screening methods described herein, the cell may comprise a second reporter gene under control of a gene promoter and wherein the second reporter gene produces a reporter protein product which has a different stability than the first reporter protein product. Preferably, the second reporter protein product is more stable than the first reporter protein product. In some embodiments, expression of the first and second reporter genes is driven (controlled) by the same gene promoter. In other embodiments, expression of the first and second reporter genes is driven (controlled) by different gene promoters.

In some embodiments, a second reporter gene encoding the second reporter protein product is a red fluorescent protein (RFP or mCherry). mCherry expression constructs are described herein.

B. Methods of Modulating Variability in Gene Expression in a Cell

The present invention provides a method for modulating variability in gene expression in a cell. In a preferred embodiment of the present invention, this method comprises the steps of contacting the cell with an amount of a variability modulator sufficient to modulate variability of expression of a gene promoter without substantially changing the mean expression level of the gene promoter. Thereupon, gene expression in the cell is modulated. In some embodiments, the method of modulating variability in gene expression in a mammalian cell comprises the step of contacting the cell with an amount of an activator of gene expression effective to activate gene expression from the gene promoter. As described, herein the method of modulating variability in gene expression in a cell is not limited to a particular cell.

Variability modulators that can be used to practice the method of modulating variability in gene expression in a cell are set forth herein. Preferred are variability enhancers (VEs) and variability suppressors (VSs). Other components useful for use in methods of modulating variability in gene expression in a cell, such as cells, reporter genes, methods of detections, etc., are set forth herein as well. While the below describes in great detail methods of modulating a latent HIV-1 reservoir, methods of reactivation of a latent HIV-1 reservoir, and methods of suppressing reactivation of a latent HIV-1 reservoir, the skilled artisan will appreciate that aspects of those methods can be applied to the modulation of variability of any gene expression in any cell and will be able to practice methods of modulating variability in gene expression of any gene in a cell using Applicants' detailed description as guidance.

C. Methods of Reactivating a Latent HIV-1 Reservoir

The present invention provides a method for reactivating a latent HIV-1 reservoir in a mammalian cell having an integrated HIV-1 genome. In a preferred embodiment of the present invention, this method comprises the steps of (a) contacting the mammalian cell with an amount of a variability modulator sufficient to modulate variability of expression of a gene promoter without substantially changing the mean expression level of the gene promoter and (b) contacting the mammalian cell with an amount of an activator of latent HIV-1 gene expression effective to activate latent HIV-1 gene expression. Thereupon, the latent HIV-1 reservoir is reactivated.

Several variability modulators can be used to practice the method of reactivating a latent HIV-1 reservoir. Preferred are variability enhancers (VEs). Useful VEs, e.g., are listed in FIGS. 10 and 11. Other VEs for use in this method can be isolated using the guidance provided by Applicants herein.

In some embodiments of the present invention, a variability modulator is selected from the group consisting of thiamylal sodium, Estramustine, griseofulvin, telmisartan, docetaxel, riboflavin, pantothenic acid(d) na salt, mercaptopurine, pemetrexed, ethinyl estradiol, irinotecan hydrochloride, dutasteride, felbinac, vincristine sulfate, thiram, bezafibrate, Indomethacin, mebendazole, ouabain, sulfaquinoxaline sodium, oxybutynin chloride, oxyphencyclimine hydrochloride, saxagliptin, phenylmercuric acetate, troclosene potassium, artemisinin, cytarabine, thioguanine, hydroquinone, acetophenazine maleate, hexylresorcinol, oxytetracycline, cefadroxil, tolnaftate, phenylbutyric acid, atorvastatin calcium, carboplatin, 5-azacytidine, levodopa, lamivudine, sotalol hydrochloride, clavulanate lithium, digoxin, sodium monofluorophosphate, dexpanthenol, rabeprazole sodium, cetirizine hydrochloride, trilostane, modafinil, thiabendazole, adapalene, sulfameter, Fluoxetine hydrochloride, trimethobenzamide hydrochloride, Metoclopramide hydrochloride, guanethidine sulfate, trichlormethine, sucralfate, valganciclovir hydrochloride, bemotrizinol, parachlorophenol, (±)-Verapamil hydrochloride, oxidopamine hydrochloride, fomepizole hydrochloride, Xylazine hydrochloride, diperodon hydrochloride, zomepirac sodium, closantel, fenbendazole, finasteride, Procainamide hydrochloride, celecoxib, colistin sulfate, imipenem, cefoxitin sodium, azithromycin, clidinium bromide, Tolazamide, chlorpheniramine maleate, colesevalam hydrochloride, Pargyline hydrochloride, hydralazine hydrochloride, anastrozole, vinorelbine, bleomycin, dasatinib, busulfan, vorinostat, selamectin, idoxuridine, carvedilol, (±)-Isoproterenol hydrochloride, racephedrine hydrochloride, vardenafil hydrochloride, guaiacol, clobetasol propionate, mycophenolic acid, fludrocortisone acetate, zaleplon, nitroglycerin, riboflavin 5-phosphate sodium, acetriazoic acid, digitoxin, carnitine hydrochloride, albendazole, taurine, Taxol, mitomycin c, clofarabine, arginine hydrochloride, tetramizole hydrochloride, thiostrepton, lonidamine, melphalan, fludarabine phosphate, methotrexate(+/−), rifaximin, Arecoline hydrobromide, zalcitabine, erythrosine sodium, nikethamide, oxfendazole, editol, doxapram hydrochloride, aminacrine, dobutamine hydrochloride, rutin, single stereoisomers, mixtures of stereoisomers, pharmaceutically acceptable salts, prodrugs and functional derivatives thereof.

In some embodiments, the variability modulator is selected from the group consisting of docetaxel, ethinyl estradiol, estramustine, felbinac, bezafibrate, mebendazole, thiamylal sodium, mercaptopurine, dutasteride, cetirizine hydrochloride, acetophenazine maleate, oxytetracycline, artemisinin, hydralazine hydrochloride, Indomethacin, atorvastatin calcium, guanethidine sulfate, pantothenic acid(d) na salt, saxagliptin, (±)-Verapamil hydrochloride, oxidopamine hydrochloride, trilostane, fomepizole hydrochloride, modafinil, Xylazine hydrochloride, diperodon hydrochloride, zomepirac sodium, thiabendazole, closantel, hexylresorcinol, adapalene, finasteride, Procainamide hydrochloride, cefadroxil, sulfameter, sulfaquinoxaline sodium, azithromycin, imipenem, colistin sulfate, cefoxitin sodium, oxyphencyclimine hydrochloride, oxybutynin chloride, clidinium bromide, Fluoxetine hydrochloride, Tolazamide, trimethobenzamide hydrochloride, Metoclopramide hydrochloride, tolnaftate, chlorpheniramine maleate, phenylbutyric acid, colesevalam hydrochloride, Pargyline hydrochloride, telmisartan, troclosene potassium, bleomycin, dasatinib, anastrozole, busulfan, carboplatin, pemetrexed, hydroquinone, selamectin, levodopa, sucralfate, valganciclovir hydrochloride, lamivudine, idoxuridine, sotalol hydrochloride, carvedilol, clavulanate lithium, (±)-Isoproterenol hydrochloride, racephedrine hydrochloride, sodium monofluorophosphate, dexpanthenol, vardenafil hydrochloride, guaiacol, rabeprazole sodium, clobetasol propionate, mycophenolic acid, fludrocortisone acetate, zaleplon, bemotrizinol, parachlorophenol, nitroglycerin, and acetriazoic acid, single stereoisomers, mixtures of stereoisomers, pharmaceutically acceptable salts, prodrugs and functional derivatives thereof.

Several activators of latent HIV-1 gene expression can be used to practice the method of reactivating a latent HIV-1 reservoir. In some embodiments of the present invention, an activator of latent HIV-1 gene expression is a histone deacetylase (HDAC) inhibitor as described herein. In some embodiments of the present invention, an HDAC inhibitor is selected from the group consisting of 12-deoxyphorbol 13-phenylacetate (DPP), Suberoylannilide Hydroxamic Acid (SAHA), MS-275, valproic acid (VPA), and trichostatin A (TSA). Also useful for practicing the methods of the present invention are single stereoisomers, mixtures of stereoisomers, pharmaceutically acceptable salts, prodrugs and functional derivatives of those HDAC inhibitors.

In some embodiments of the present invention, an activator of latent HIV-1 gene expression is a Protein Kinase C (PKC) agonist as described herein. In some embodiments of the present invention, a PKC agonist is selected from the group consisting of tumor necrosis factor alpha (TNFα), prostratin, PMA, and bryostatin. Also useful for practicing the methods of the present invention are single stereoisomers, mixtures of stereoisomers, pharmaceutically acceptable salts, prodrugs and functional derivatives of those PKC agonists.

In some embodiments of the present invention, an activator of latent HIV-1 gene expression is a methylation inhibitor as described herein. In some embodiments of the present invention, a methylation inhibitor is azacytidine. Also useful for practicing the methods of the present invention are single stereoisomers, mixtures of stereoisomers, pharmaceutically acceptable salts, prodrugs and functional derivatives of azacytidine.

In some embodiments of the present invention, an activator of latent HIV-1 gene expression is a bromodomain inhibitor as described herein. In some embodiments of the present invention, a bromodomain inhibitor is JQ1. Also useful for practicing the methods of the present invention are single stereoisomers, mixtures of stereoisomers, pharmaceutically acceptable salts, prodrugs and functional derivatives of JQ1.

In some embodiments of the present invention, an activator of latent HIV-1 gene expression is an anticancer drug as described herein. In some embodiments of the present invention, an anticancer drug is cytarabine. Also useful for practicing the methods of the present invention are single stereoisomers, mixtures of stereoisomers, pharmaceutically acceptable salts, prodrugs and functional derivatives of cytarabine.

The method of reactivating a latent HIV-1 reservoir in a mammalian cell having an integrated HIV-1 genome of the present invention can be practiced in vitro and in vivo.

Various mammalian cells can be used to practice the method of reactivating a latent HIV-1 reservoir in a mammalian cell having an integrated HIV-1 genome, as long as the cell comprises at least one copy of an integrated HIV-1 genome. In some embodiments of the present invention, the mammalian cell is a human cell. The methods of the present invention can be applied to any cell wherein an HIV-1 genome is integrated into the cellular DNA, preferably a mammalian cell and even more preferred a human cell. Cells include, but are not limited to, e.g., a resting lymphoid mononuclear cell obtained from a mammal including e.g., lymphocytes, such as T cells (CD4, CD8, cytolytic, helper), B cells, natural killer cells; mononuclear phagocytes, such as monocytes, macrophages, epitheloid cells, giant cells, microglia, Kupffer cells, alveolar macrophages; dentritic cells, such as interdigitating dendrite cells, Langerhans cells, or follicular dendritic cells; granulocytes; etc. Preferred is a CD4+ T cell. Also preferred is a myeloid mononuclear cell, preferably, a peripheral blood mononuclear cell or tissue macrophage.

The human cell may be contacted with a variability modulator and an activator of latent HIV-1 gene expression in vitro and in vivo. In some embodiments of the present invention, the method of activating a latent HIV-1 reservoir in a human cell, particular a human cell in a human subject, comprises the step of contacting the cell with a HAART compound. Alternatively, the method may comprise the step of contacting the cell with an immunotoxin.

In a preferred embodiment, the step of contacting a compound or composition of the invention with a mammalian cell is performed by administering the compound or composition to a mammalian cell in a human, preferably a human having a latent HIV-1 infection.

In some embodiments of the present invention, a variability modulator and an activator of latent HIV-1 gene expression are used simultaneously for the contacting of the mammalian cell. This can be done by contacting the mammalian cell with a composition comprising both compounds as further described herein. In other embodiments, the variability modulator and the activator of latent HIV-1 gene expression are used sequentially.

It is understood, that when practicing the method of reactivating a latent HIV-1 reservoir according to the present invention, it results in an increase of the activity of an LTR promoter in the mammalian cell leading to an increased expression of HIV-1 mRNA and HIV-1 polypeptides, each of which can be measured by routine methods known in the art.

As described herein, some VEs (the VEs described herein are all FDA-approved and hence, have been tested for their low, if any, toxicity) synergistically interact with an activator of latent HIV-1 gene expression to increase reactivation of HIV-1 latency and to increase reactivation of latent HIV-1 gene expression. Because of this synergistic effect, an activator of latent HIV-1 gene expression, and in particular prostratin, can be used in a lower dose to essentially achieve the same or greater effect on activation of latent HIV-1 gene expression than would be obtained when using the activator of latent HIV-1 gene expression alone. Thus in some embodiments, the amount of an activator of latent HIV-1 gene expression, e.g., prostratin, contacting the mammalian cell is less than 50% of an amount of an activator of latent HIV-1 gene expression, e.g., prostratin, that is required to obtain the same expression level in the absence of a VE. In another embodiment the amount of an activator of latent HIV-1 gene expression, e.g., prostratin, contacting the mammalian cell is less than 25%, preferably less than 20%, preferably less than 10%, more preferably less than 5% and even more preferably less than 2% of an amount an activator of latent HIV-1 gene expression, e.g., prostratin, that is required to obtain the same expression level in the absence of a VE.

D. Methods of Treating HIV-1 Latency

In a preferred embodiment of the present invention, compositions of the invention are used in a method for treating HIV-1 latency. This method can be practiced in vitro. Preferably, this method is practiced in vivo. Preferably, this method is practiced in a host latently infected with HIV-1, e.g., a human latently infected with HIV-1. In some embodiments, this method seeks to completely eradicate a latent HIV-1 reservoir in a latently HIV-1 infected subject. In this context "completely eradicate" means that either no detectable HIV-1 can be determined in a sample obtained from such a host or the host is relieved of all of the symptoms of having an HIV-1 infection and/or having AIDS. In some embodiments, this method seeks to increase reactivation of a latent HIV-1 reservoir in a latently HIV-1 infected subject to a level that is higher than what is obtained by using a known activator of latent HIV-1 gene expression. In other embodiments, this method seeks to decrease reactivation of a latent HIV-1 reservoir in a latently HIV-1 infected subject to a level that is lower than what is obtained by using a known activator of latent HIV-1 gene expression. In other embodiments, this method seeks to decrease reactivation of a latent HIV-1 reservoir in a latently HIV-1 infected subject to a level that is lower than what is obtained by using a combination HAART therapy.

1. Treating HIV-1 Latency with a Variability Enhancer and an Activator Drug

In some embodiments, a method of treating HIV-1 latency comprises the step of administering to a latently HIV-1-infected host a therapeutically effective amount of a composition comprising a VE and an activator of latent HIV-1 gene expression.

In some embodiments of the present invention, this method comprises the steps of (a) contacting a mammalian cell with an amount of a variability modulator sufficient to modulate variability of expression of a gene promoter without substantially changing the mean expression level of the gene promoter and (b) contacting the mammalian cell with an amount of an activator of latent HIV-1 gene expression effective to treat latent HIV-1 latency. Thereupon, the latent HIV-1 latency is treated. VMs, VEs and activators for latent HIV-1 gene expression useful to practice this method have been described herein. Useful VEs are described in FIGS. 10 and 11.

When practiced in vivo, the method, optionally comprises the step of administering HAART. Thus, in yet another embodiment of the present invention, a method of treating a latently HIV-1-infected host comprises the step of administering highly active antiretroviral therapy (HAART).

According to this embodiment, a composition comprising a VE and an activator of latent HIV-1 gene expression may be coadministered with any HAART regimen. The current standard of care using HAART is usually a combination of at least three nucleoside reverse transcriptase inhibitors and frequently includes a protease inhibitor, or alternatively a non-nucleoside reverse transcriptase inhibitor. Patients who have low $CD4^+$ cell counts or high plasma RNA levels may require more aggressive HAART. For patients with relatively normal $CD4^+$ cell counts and low to non-measurable levels of plasma HIV-1 RNA over prolonged periods (i.e. slow or non-progressors) may require less aggressive HAART. For antiretroviral-naive patients who are treated with initial antiretroviral regimen, different combinations (or cocktails) of antiretroviral drugs can be used.

Preferably, a composition comprising a VE and an activator of latent HIV-1 expression may be coadministered with a "cocktail" of nucleoside reverse transcriptase inhibitors, non-nucleoside HIV-1 reverse transcriptase inhibitors, and protease inhibitors. For example, a composition comprising a VE and an activator of latent HIV-1 gene expression may be coadministered with a cocktail of two nucleoside reverse transcriptase inhibitors (e.g. ZIDOVUDINE® (AZT) and LAMIVUDINE® (3TC)), and one protease inhibitor (e.g. INDINAVIR® (MK-639)). A composition comprising a VE and an activator of latent HIV-1 gene expression may also be coadministered with a cocktail of one nucleoside reverse transcriptase inhibitor (e.g. STAVUDINE® (d4T)), one non-nucleoside reverse transcriptase inhibitor (e.g. NEVIRAPINE® (BI-RG-587)), and one protease inhibitor (e.g. NELFINAVIR® (AG-1343)). Alternatively, a composition comprising an activator of latent HIV-1 expression and an HDAC inhibitor may be coadministered with a cocktail of one nucleoside reverse transcriptase inhibitor (e.g. ZIDOVUDINE® (AZT)), and two protease inhibitors (e.g. NELFINAVIR® (AG-1343) and SAQINAVIR® (Ro-31-8959)).

Coadministration in the context of this invention is defined to mean the administration of more than one therapeutic in the course of a coordinated treatment to achieve an improved clinical outcome. Such coadministration may also be coextensive, that is, occurring during overlapping periods of time. Further discussion of such conventional treatment can be found in the art (e.g., Gulick, 1997; *Qual Life Res* 6:471-474; Henry et al., 1997, *Postgrad Med* 102:100-107; Hicks, 1997, *Radiol Clin North Am* 35:995-1005; Goldschmidt, 1996, *Am Fam Physician* 54:574-580).

This regimen is continued for a period past the point when, e.g., the levels of integrated and unintegrated HIV-1 in active and memory T cells are undetectably low. At the end of the period, the patient is weaned from HAART and from the VEs and activators of latent HIV-1 gene expression. At this point, the patient is monitored for reestablishment of normal immune function and for signs of reemergence of HIV-1 infection. Additionally, any needed conjunctive immunotherapy, such as bone marrow transplants, various cytokines or vaccination, may be administered. After this, the patient is monitored on a routine basis for life to detect reemergence of HIV-1 infection, in which case repeat therapy according to the above preferred embodiment is recommended.

2. Treating HIV-1 Latency with a Variability Suppressor

As described herein, some VMs have been characterized herein as functioning as Variability Suppressors (VSs), i.e., those VSs reduce the reactivation of latent HIV-1 reservoir when used either alone or in combination with an activator of latent HIV-1 gene expression. This is another unexpected and surprising finding of the invention described herein and provides for a novel method of treating HIV-1 latency by increasing the latent stability of an HIV-1 genome integrated in a cell and thus, avoid or inhibit (i.e., suppress) reactivation of a latent reservoir and rebound of a viral load. This is of particular interest after combination HAART therapy is completed.

In some embodiments of the present invention, a method of treating HIV-1 latency comprises the step of contacting a mammalian cell with an amount of a variability suppressor sufficient to modulate variability of expression of a gene promoter without substantially changing the mean expression level of the gene promoter and to inhibit latent HIV-1 gene expression. Thereupon, the latent HIV-1 latency is treated. VSs useful to practice this method have been described herein. Useful VSs are shown, e.g., in FIG. 12. Other VSs for use in this method can be identified using the guidance provided by Applicants herein.

In some embodiments of a method of treating HIV-1 latency, a VS is selected from the group consisting of manidipine hydrochloride, phenothiazine, dichlorvos, fipronil, trichlorfon, benzydamine hydrochloride, maprotiline hydrochloride, Papaverine hydrochloride, arsenic trioxide, phenformin hydrochloride, itraconazole, cycloheximide, hydroxyprogesterone caproate, pyrithione zinc, meclocycline sulfosalicyclate, ergotamine tartrate, adenosine phosphate, broxaldine, single stereoisomers, mixtures of stereoisomers, pharmaceutically acceptable salts, prodrugs and functional derivatives thereof.

In some embodiments, a method of treating HIV-1 latency comprises the step of contacting the mammalian cell with an amount of an activator of latent HIV-1 gene expression effective to treat latent HIV-1 latency.

In some embodiments of the method of treating HIV-1 latency the step of contacting a mammalian cell with the VS is done after HAART therapy.

E. Use of a Variability Modulator to Modulate Variability in Gene Expression of a Latent HIV-1 Reservoir in a Cell Some embodiments of a use of a variability modulator for modulating variability in gene expression of a latent HIV-1 reservoir in a mammalian cell having an integrated HIV-1 genome are set forth in claim format herein (see Brief Summary Of Invention). As one of ordinary skill in the art will appreciate, variability modulators described herein and VMs that can be isolated by the guidance provided herein, are not only useful for modulating variability in gene expression of a latent HIV-1 reservoir, but also can be used to modulate variability in gene expression of any gene driving a detectable reporter gene in a cell.

F. Use of a Variability Modulator to Reactivate Gene Expression of a Latent HIV-1 Reservoir in a Mammalian Cell Some embodiments of a use of a variability modulator, preferably a variability enhancer, for reactivating gene expression of a latent HIV-1 reservoir in a mammalian cell having an integrated HIV-1 genome are set forth in claim format herein (see Brief Summary Of Invention). As one of ordinary skill in the art will appreciate, variability modulators, preferably variability enhancers, described herein and VMs, preferably VPs, that can be isolated by the guidance provided herein, are not only useful for reactivating gene expression of a latent HIV-1 reservoir, but also can be used to reactivate gene expression of any silent, dormant or inactive gene in a cell, preferably in a mammalian cell.

G. Use of a Variability Modulator to Suppress Reactivation of a Latent HIV-1 Reservoir in a Mammalian Cell Some embodiments of a use of a variability modulator, preferably a variability suppressor, for suppressing reactivation of a latent HIV-1 reservoir in a mammalian cell having an integrated HIV-1 genome are set forth in claim format herein (see Brief Summary Of Invention). As one of ordinary skill in the art will appreciate, variability modulators, preferably variability suppressors, described herein and VMs, preferably VSs, that can be isolated by the guidance provided herein, are not only useful for suppressing reactivation of a latent HIV-1 reservoir, but also can be used to suppress reactivation of any silent, dormant or inactive gene in a cell, preferably in a mammlian cell.

H. Use of a Variability Modulator for Producing a Medicament to Modulate Variability in Gene Expression of a Latent HIV-1 Reservoir in a Mammalian Cell Some embodiments of a use of a variability modulator for producing a medicament for modulating variability in gene expression of a latent HIV-1 reservoir in a mammalian cell having an integrated HIV-1 genome are set forth in claim format herein (see Brief Summary Of Invention). As one of ordinary skill in the art will appreciate, variability modulators described herein and VMs that can be isolated by the guidance provided herein, are not only useful for producing a medicament for modulating variability in gene expression of a latent HIV-1 reservoir, but also can be used to produce a medicament for modulating variability in gene expression of any gene driving a detectable reporter gene in a cell, preferably in a mammalian cell.

I. Use of a Variability Modulator to Produce a Medicament for Reactivation of a Latent HIV-1 Reservoir in a Mammalian Cell Some embodiments of a use of a variability modulator, preferably a variability enhancer, for producing a medicament for reactivating gene expression of a latent HIV-1 reservoir in a mammalian cell having an integrated HIV-1 genome are set forth in claim format herein (see Brief Summary Of Invention). As one of ordinary skill in the art will appreciate, variability modulators, preferably variability enhancers, described herein and VMs, preferably VEs, that can be isolated by the guidance provided herein, are not only useful for producing a medicament for reactivating gene expression of a latent HIV-1 reservoir, but also can be used to produce a medicament for reactivating gene expression of any silent, dormant or inactive gene in a cell, preferably in a mammalian cell.

J. Use of a Variability Modulator to Produce a Medicament for Suppressing Reactivation of a Latent HIV-1 Reservoir in a Mammalian Cell Some embodiments of a use of a variability modulator, preferably a variability suppressor, for producing a medicament for suppressing reactivation of a latent HIV-1 reservoir in a mammalian cell having an integrated HIV-1 genome are set forth in claim format herein (see Brief Summary Of Invention). As one of ordinary skill in the art will appreciate, variability modulators, preferably variability suppressors, described herein and VMs, preferably VSs, that can be isolated by the guidance provided herein, are not only useful for producing a medicament for suppressing reactivation of a latent HIV-1 reservoir, but also can be used to produce a medicament to suppress reactivation of any silent, dormant or inactive gene in a cell, preferably in a mammalian cell.

K. General Methods

Methods of activation of latent HIV-1 expression (also referred to as reactivation of latent HIV-1 gene expression) or treating HIV-1 latency as described herein, typically result in the conversion of latently HIV-1 infected cells to productively infected cells. This transition can be measured by any characteristic of active viral infection, e.g., production of infectious particles, reverse transcriptase activity, secreted antigens, cell-surface antigens, soluble antigens, HIV-1 RNA and HIV-1 DNA, etc.

The methods of the present invention described above, may optionally comprise the step of determining or detecting reactivation of latent HIV-1 gene expression. In one embodiment, such a method comprises determining or detecting an mRNA, preferably an HIV-1 mRNA. Other mRNAs, such as Tat mRNA, NF-$K_B$ mRNA, NF-AT mRNA and other mRNAs encoding polypeptides described herein can also be determined using the following methods.

1. Detection of mRNA

A preferred mRNA is an HIV-1 mRNA. Thus, expression levels of HIV-1 mRNA may be determined. Detecting an increased expression level of the HIV-1 mRNA relative to the mRNA level present in a latently infected cell indicates activation of the latent HIV-1 gene expression. In one embodiment, the step of determining the level of the HIV-1 mRNA comprises an amplification reaction. Methods of evaluating mRNA expression of a particular gene are well known to those of skill in the art, and include, inter alia, hybridization and amplification based assays.

i. Direct Hybridization-Based Assays

Methods of detecting and/or quantifying the level of a gene transcript (mRNA or cDNA made therefrom) using nucleic acid hybridization techniques are known to those of skill in the art. For example, one method for evaluating the presence, absence, or quantity of HIV-1 polynucleotides involves a Northern blot. Gene expression levels can also be analyzed by techniques known in the art, e.g., dot blotting, in situ hybridization, RNase protection, probing DNA microchip arrays, and the like (e.g., see Sambrook, J., Fritsch, E. F., and Maniatis, "Molecular Cloning A Laboratory Manual" by T. published by Cold Spring Harbor Laboratory Press, 2nd edition, 1989).

ii. Amplification-Based Assays

In another embodiment, amplification-based assays are used to measure the expression level of an HIV-1 gene. In such an assay, the HIV-1 nucleic acid sequences act as a template in an amplification reaction (e.g., Polymerase Chain Reaction, or PCR). In a quantitative amplification, the amount of amplification product will be proportional to the amount of template in the original sample. Comparison to appropriate controls provides a measure of the level of HIV-1 mRNA in the sample. Methods of quantitative amplification are well known to those of skill in the art. Detailed protocols for quantitative PCR are provided, e.g., in Innis et al. (1990) *PCR Protocols, A Guide to Methods and Applications*, Academic Press, Inc. N.Y.). Exemplary methods using HIV-1 nucleic acids as a template for PCR are described as well (E.g., see (Williams et al., 2004, *J Biol Chem* 279(40):42008-42017; Williams et al., 2006, *EMBO J* 25:139-149).

In one embodiment, a TaqMan based assay is used to quantify the HIV-1 polynucleotides. TaqMan based assays use a fluorogenic oligonucleotide probe that contains a 5' fluorescent dye and a 3' quenching agent. The probe hybridizes to a PCR product, but cannot itself be extended due to a blocking agent at the 3' end. When the PCR product is amplified in subsequent cycles, the 5' nuclease activity of the polymerase, e.g., AmpliTaq, results in the cleavage of the TaqMan probe. This cleavage separates the 5' fluorescent dye and the 3' quenching agent, thereby resulting in an increase in fluorescence as a function of amplification (see, for example, Heid et at, 1996, *Genome Res* 6(10):986-94; Morris et al., 1996, *J Clin Microbiol* 34(12):2933-6).

Other suitable amplification methods include, but are not limited to, ligase chain reaction (LCR) (see, Wu and Wallace, 1989, *Genomics* 4:560; Landegren et al., 1988, *Science* 241:1077; and Barringer et al., 1990, *Gene* 89:117), transcription amplification (Kwoh et al., 1989, *Proc Natl Acad Sci USA* 86:1173), self-sustained sequence replication (Guatelli et al., 1990, *Proc Nat Acad Sci USA* 87:1874), dot PCR, linker adapter PCR, etc.

iii. Sequencing-Based Assays

Methods of detecting and/or quantifying the level of a gene transcript (mRNA or cDNA made therefrom) using nucleic acid sequencing are known to those of skill in the art and also find use herein, in particular single-cell RNA sequencing.

2. Detection of Polypeptide

The methods of the present invention described above, may optionally comprise the step of determining or detecting activation of latent HIV-1 gene expression. In one embodiment, such a method comprises determining or detecting a polypeptide, preferably an HIV-1 polypeptide or a polypeptide for which the coding region has been inserted into the HIV-1 genome, such as the GFP polypeptide of the Mat cell lines described herein and by Jordan et al. (Jordan et al., 2003, *EMBO J* 22(8):1868-1877). Other polypeptides, such as Tat, NF-$K_B$, NF-AT and others described herein can also be determined using the following methods.

Expression levels of an HIV-1 polypeptide may be determined by several methods, including, but not limited to, affinity capture, mass spectrometry, traditional immunoassays directed to HIV-1 proteins (such as gp120 and reverse transcriptase), PAGE, Western Blotting, flow cytometry, or HPLC as further described herein or as known by one of skill in the art.

Detection paradigms that can be employed to this end include optical methods, electrochemical methods (voltametry and amperometry techniques), atomic force microscopy, and radio frequency methods, e.g., multipolar resonance spectroscopy. Illustrative of optical methods, in addition to microscopy, both confocal and non-confocal, are detection of fluorescence, luminescence, chemiluminescence, absorbance, reflectance, transmittance, and birefringence or refractive index (e.g., surface plasmon resonance, ellipsometry, a resonant mirror method, a grating coupler waveguide method or interferometry).

3. Determining Viral Load

Methods and compositions for determining viral load have been described, e.g., in U.S. Pat. Appl. Publ. 2001/0039007, published Nov. 8, 2001, incorporated herewith by reference in its entirety.

IV. Systems

A system of the present invention comprises a composition of the present invention and at least one additional component. A non-limiting system of the present invention is a cell comprising a composition of the present invention.

Another exemplary and non-limiting system of the present invention is high throughput screening apparatus comprising the use of a composition of the present invention, preferably, a high throughput screening apparatus comprising a VM, a VE, or a VS as described herein, more preferably, a high throughput screening apparatus comprising a VM, a VE or a VS in combination with an activator of gene expression as described herein.

V. Pharmaceutical Compositions

Some embodiments of pharmaceutical compositions are set forth in claim format herein (see Brief Summary Of Invention).

In one aspect the present invention provides a pharmaceutical composition or a medicament comprising a variability modulator of the present invention and optionally a pharmaceutically acceptable carrier. The present invention also provides a pharmaceutical composition or a medicament comprising at least an activator of latent HIV-1 expression and a variability modulator of the present invention and optionally a pharmaceutically acceptable carrier. A pharmaceutical composition or medicament can be administered to a subject for the treatment of, for example, a condition or disease as described herein.

A pharmaceutical composition may include any combination of activator compounds and/or variability modulators (VM, VE or VS). A pharmaceutical composition may include any combination of latent HIV-1 activator compounds, HIV-1 transcription activators and/or variability modulators (VM, VE or VS).

The present invention also provides pharmaceutical compositions for practicing methods of the present invention, including, but not limited to, reactivating a latent HIV-1 reservoir in a mammalian cell. Generally, the pharmaceutical compositions comprise compositions described herein for practicing a method of the present invention. In some embodiments of the present invention, a pharmaceutical composition comprises (i) a variability modulator in an amount sufficient to modulate variability of expression of a gene promoter without substantially changing the mean expression level of the gene promoter, and (ii) a pharmaceutically acceptable carrier. In some embodiments of the present invention, a pharmaceutical composition comprises (i) a variability modulator in an amount sufficient to modulate variability of expression of a gene promoter without substantially changing the mean expression level of the gene promoter, (ii) an activator of latent HIV-1 gene expression in an amount effective to activate latent HIV-1 gene expression; and (iii) a pharmaceutically acceptable carrier.

A. Formulation and Administration

Compounds of the present invention, such as the activators of latent HIV-1 gene expression and variability modulators described herein, are useful in the manufacture of a pharmaceutical composition or a medicament comprising an effective amount thereof in conjunction or in a mixture with excipients or carriers suitable for either enteral or parenteral application.

Pharmaceutical compositions or medicaments for use in the present invention can be formulated by standard techniques using one or more physiologically acceptable carriers or excipients. Suitable pharmaceutical carriers are described herein and in "Remington's Pharmaceutical Sciences" by E. W. Martin. The small molecule compounds of the present invention and their physiologically acceptable salts and solvates can be formulated for administration by any suitable route, including via inhalation, topically, nasally, orally, parenterally, or rectally. Thus, the administration of the pharmaceutical composition may be made by intradermal, subdermal, intravenous, intramuscular, intranasal, intracerebral, intratracheal, intraarterial, intraperitoneal, intravesical, intrapleural, intracoronary or intratumoral injection, with a syringe or other devices. Transdermal administration is also contemplated, as are inhalation or aerosol administration. Tablets and capsules can be administered orally, rectally or vaginally.

For oral administration, a pharmaceutical composition or a medicament can take the form of, for example, a tablet or a capsule prepared by conventional means with a pharmaceutically acceptable excipient. Preferred are tablets and gelatin capsules comprising the active ingredient, i.e., a small molecule compound of the present invention, a VM, a VE, a VS, an activator of latent HIV-1 gene expression, together with (a) diluents or fillers, e.g., lactose, dextrose, sucrose, mannitol, sorbitol, cellulose (e.g., ethyl cellulose, microcrystalline cellulose), glycine, pectin, polyacrylates and/or calcium hydrogen phosphate, calcium sulfate; (b) lubricants, e.g., silica, talcum, stearic acid, its magnesium or calcium salt, metallic stearates, colloidal silicon dioxide, hydrogenated vegetable oil, corn starch, sodium benzoate, sodium acetate and/or polyethyleneglycol; for tablets also (c) binders, e.g., magnesium aluminum silicate, starch paste, gelatin, tragacanth, methylcellulose, sodium carboxymethylcellulose, polyvinylpyrrolidone and/or hydroxypropyl methylcellulose; if desired (d) disintegrants, e.g., starches (e.g., potato starch or sodium starch), glycolate, agar, alginic acid or its sodium salt, or effervescent mixtures; (e) wetting agents, e.g., sodium lauryl sulphate, and/or (f) absorbents, colorants, flavors and sweeteners.

Tablets may be either film coated or enteric coated according to methods known in the art. Liquid preparations for oral administration can take the form of, for example, solutions, syrups, or suspensions, or they can be presented as a dry product for reconstitution with water or other suitable vehicle before use. Such liquid preparations can be prepared by conventional means with pharmaceutically acceptable additives, for example, suspending agents, for example, sorbitol syrup, cellulose derivatives, or hydrogenated edible fats; emulsifying agents, for example, lecithin or acacia; non-aqueous vehicles, for example, almond oil, oily esters, ethyl alcohol, or fractionated vegetable oils; and preservatives, for example, methyl or propyl-p-hydroxybenzoates or sorbic acid. The preparations can also contain buffer salts, flavoring, coloring, and/or sweetening agents as appropriate. If desired, preparations for oral administration can be suitably formulated to give controlled release of the active compound.

Compounds of the present invention can be formulated for parenteral administration by injection, for example by bolus injection or continuous infusion. Formulations for injection can be presented in unit dosage form, for example, in ampoules or in multi-dose containers, with an added preservative. Injectable compositions are preferably aqueous isotonic solutions or suspensions, and suppositories are preferably prepared from fatty emulsions or suspensions. The compositions may be sterilized and/or contain adjuvants, such as preserving, stabilizing, wetting or emulsifying agents, solution promoters, salts for regulating the osmotic pressure and/or buffers. Alternatively, the active ingredient can be in powder form for constitution with a suitable vehicle, for example, sterile pyrogen-free water, before use. In addition, they may also contain other therapeutically valuable substances. The compositions are prepared according to conventional mixing, granulating or coating methods, respectively, and contain about 0.1 to 75%, preferably about 1 to 50%, of the active ingredient.

For administration by inhalation, the compounds may be conveniently delivered in the form of an aerosol spray presentation from pressurized packs or a nebulizer, with the use of a suitable propellant, for example, dichlorodifluoromethane, trichlorofluoromethane, dichlorotetrafluoroethane, carbon dioxide, or other suitable gas. In the case of a pressurized aerosol, the dosage unit can be determined by providing a valve to deliver a metered amount. Capsules and cartridges of, for example, gelatin for use in an inhaler or insufflator can be formulated containing a powder mix of the compound and a suitable powder base, for example, lactose or starch.

Suitable formulations for transdermal application include an effective amount of a compound of the present invention with a carrier or excipient. Preferred carriers and excipients include absorbable pharmacologically acceptable solvents to assist passage through the skin of the host. For example, transdermal devices are in the form of a bandage comprising a backing member, a reservoir containing the compound optionally with carriers, optionally a rate controlling barrier to deliver the compound to the skin of the host at a controlled and predetermined rate over a prolonged period of time, and means to secure the device to the skin. Matrix transdermal formulations may also be used.

Suitable formulations for topical application, e.g., to the skin and eyes, are preferably aqueous solutions, ointments, creams or gels well-known in the art. Such may contain solubilizers, stabilizers, tonicity enhancing agents, buffers and preservatives.

Compounds of the present invention can also be formulated in rectal compositions, for example, suppositories or retention enemas, for example, containing conventional suppository bases, for example, cocoa butter or other glycerides.

Furthermore, compounds of the present invention can be formulated as a depot preparation. Such long-acting formulations can be administered by implantation (for example, subcutaneously or intramuscularly) or by intramuscular injection. Thus, for example, the compounds can be formulated with suitable polymeric or hydrophobic materials (for example as an emulsion in an acceptable oil) or ion exchange resins, or as sparingly soluble derivatives, for example, as a sparingly soluble salt.

Compositions of the present invention can, if desired, be presented in a pack or dispenser device that can contain one or more unit dosage forms containing the active ingredient. The pack can, for example, comprise metal or plastic foil, for example, a blister pack. The pack or dispenser device can be accompanied by instructions for administration.

In some embodiment of the present invention, a pharmaceutical composition or medicament comprises an effective amount of a variability modulator and an activator of latent HIV-1 gene expression as described above, and another therapeutic agent, such as a component used for HAART, as described herein. When used with compounds of the invention, such a therapeutic agent may be used individually (e.g., a component used for HAART and compounds of the present invention), sequentially (e.g., a component used for HAART and compounds of the present invention for a period of time followed by e.g., a second component used for HAART and compounds of the present invention), or in combination with One or more other such therapeutic agents (e.g., a reverse transcriptase inhibitor used for HAART, a protease inhibitor used for HAART, and compounds of the present invention). Administration may be by the same or different route of administration or together in the same pharmaceutical formulation.

Thus, in a preferred embodiment of the present invention, a pharmaceutical composition comprises (i), a variability modulator, (ii) an activator of latent HIV-1 gene expression, and (iii) a pharmaceutically acceptable carrier.

B. Therapeutic Effective Amount and Dosing

In some embodiments of the present invention, a pharmaceutical composition or medicament is administered to a subject, preferably a human, at a therapeutically effective dose to prevent, treat, or control a condition or disease as described herein, such as HIV-1 latency or reactivation of latent HIV-1 gene expression. The pharmaceutical composition or medicament is administered to a subject in an amount sufficient to elicit an effective therapeutic response in the subject. An effective therapeutic response is a response that at least partially arrests or slows the symptoms or complications of the condition or disease. An amount adequate to accomplish this is defined as "therapeutically effective dose."

The dosage of active compounds of the present invention administered is dependent on the species of warm-blooded animal (mammal), the body weight, age, individual condition, surface area of the area to be treated and on the form of administration. The size of the dose also will be determined by the existence, nature, and extent of any adverse effects that accompany the administration of a particular small molecule compound in a particular subject. A unit dosage for oral administration to a mammal of about 50 to 70 kg may contain between about 5 and 500 mg of the active ingredient. Typically, a dosage of the active compounds of the present invention, is a dosage that is sufficient to achieve the desired effect. Optimal dosing schedules can be calculated from measurements of compound accumulation in the body of a subject. In general, dosage may be given once or more daily, weekly, or monthly. Persons of ordinary skill in the art can easily determine optimum dosages, dosing methodologies and repetition rates.

In some embodiments of the present invention, a pharmaceutical composition or medicament comprising compounds of the present invention is administered in a daily dose in the range from about 0.1 mg of each compound per kg of subject weight (0.1 mg/kg) to about 1 g/kg for multiple days. In another embodiment, the daily dose is a dose in the range of about 5 mg/kg to about 500 mg/kg. In yet another embodiment, the daily dose is about 10 mg/kg to about 250 mg/kg. In another embodiment, the daily dose is about 25 mg/kg to about 150 mg/kg. A preferred dose is about 10 mg/kg. The daily dose can be administered once per day or divided into subdoses and administered in multiple doses, e.g., twice, three times, or four times per day. However, as will be appreciated by a skilled artisan, VMs, VEs, VSs, and activators of latent HIV-1 gene expression may be administered in different amounts and at different times.

A recommended initial dose for VPA, in the treatment of seizures (see above), for example, is 15 mg/kg/day orally, increasing at 1-week intervals by 5-10 mg/kg/day until seizures are controlled or side effects preclude further increases. A maximum recommended dose is 60 mg/kg/day. When the total daily dose exceeds 250 mg, it should be given in a divided regimen. A similar dosing regimen may be used for VPA in the methods of the present invention, i.e., in combination with one or more VMs, VEs or VSs.

To achieve the desired therapeutic effect, compounds of the present invention may be administered for multiple days at the therapeutically effective daily dose. Thus, therapeutically effective administration of compounds of the present invention to treat a condition or disease described herein in a subject requires periodic (e.g., daily) administration that continues for a period ranging from three days to two weeks or longer. Typically, compounds will be administered for at least three consecutive days, often for at least five consecutive days, more often for at least ten, and sometimes for 20, 30, 40 or more consecutive days. While consecutive daily doses are a preferred route to achieve a therapeutically effective dose, a therapeutically beneficial effect can be achieved even if the compounds are not administered daily, so long as the administration is repeated frequently enough to maintain a therapeutically effective concentration of the compounds in the subject. For example, one can administer the compounds every other day, every third day, or, if higher dose ranges are employed and tolerated by the subject, once a week. A preferred dosing schedule, for example, is administering daily for a week, one week off and repeating this cycle dosing schedule for 3-4 cycles.

Optimum dosages, toxicity, and therapeutic efficacy of such compounds may vary depending on the relative potency of individual compounds and can be determined by standard pharmaceutical procedures in cell cultures or experimental animals, for example, by determining the $LD_{50}$ (the dose lethal to 50% of the population) and the $ED_{50}$ (the dose therapeutically effective in 50% of the population). The dose ratio between toxic and therapeutic effects is the therapeutic index and can be expressed as the ratio, $LD_{50}/ED_{50}$. Compounds that exhibit large therapeutic indices are preferred. While compounds that exhibit toxic side effects can be used, care should be taken to design a delivery system that targets such compounds to the site of affected tissue to minimize potential damage to normal cells and, thereby, reduce side effects. As mentioned herein, the VMs, VEs, and VSs are identified within a collection of 1,600 FDA-approved compounds and thus, are expected to have low, if any toxicity or side effects.

Data obtained from, for example, cell culture assays and animal studies can be used to formulate a dosage range for use in humans. The dosage of such small molecule compounds lies preferably within a range of circulating concentrations that include the $ED_{50}$ with little or no toxicity. The dosage can vary within this range depending upon the dosage form employed and the route of administration. For any compounds used in the methods of the invention, the therapeutically effective dose can be estimated initially from cell culture assays. A dose can be formulated in animal models to achieve a circulating plasma concentration range that includes the $IC_{50}$ (the concentration of the test compound that achieves a half-maximal inhibition of symptoms) as determined in cell culture. Such information can be used to more accurately determine useful doses in humans. Levels in plasma can be measured, for example, by high performance liquid chromatography (HPLC). In general, the dose equivalent of compounds is from about 1 ng/kg to 100 mg/kg for a typical subject.

Following successful treatment, it may be desirable to have the subject undergo maintenance therapy to prevent the recurrence of the condition or disease treated.

VI. Kits

Some embodiments of kits are set forth in claim format herein (see Brief Summary Of Invention).

For use in the diagnostic, research, and therapeutic applications suggested above, kits are also provided by the invention. In the diagnostic and research applications such kits may include any or all of the following: assay reagents, buffers, a compound of the present invention, an HIV-1 polypeptide, an HIV-1 nucleic acid, an anti-HIV-1 polypeptide antibody, hybridization probes and/or primers, expression constructs for e.g., Tat, NF-$K_B$, or NF-AT, etc. A therapeutic product may include sterile saline or another pharmaceutically acceptable emulsion and suspension base.

In some embodiment of the present invention, a kit comprises one or more VMs, VEs, or VSs. In some embodiment of the present invention, a kit comprises one or more VMs, VEs, VSs and one or more activators of latent HIV-1 gene expression. Optionally, the kit includes one or more components used for HAART as described herein. Typically, these compounds are provided in a container.

In some embodiments, the present invention provides kits for practicing methods of the present invention, including, but not limited to, reactivating a latent HIV-1 reservoir in a mammalian cell. Generally, the kits comprise compositions described herein for practicing a method of the present invention. In some embodiments of the present invention, a kit comprises (i) a first container containing a variability modulator in an amount sufficient to modulate variability of expression of a gene promoter without substantially changing the mean expression level of the gene promoter, (ii) a second container containing an activator of latent HIV-1 gene expression in an amount effective to activate latent HIV-1 gene expression; and (iii) an instruction for using (i) and (ii) for practicing methods of the present invention, including, but not limited to, reactivating a latent HIV-1 reservoir in a mammalian cell.

The instructional materials may contain directions (i.e., protocols) for the practice of the methods of this invention. The instructions may be present in the subject kits in a variety of forms, one or more of which may be present in the kit. While the instructional materials typically comprise written or printed materials they are not limited to such. Any medium capable of storing such instructions and communicating them to an end user is contemplated by this invention. Such media include, but are not limited to electronic storage media (e.g., magnetic discs, tapes, cartridges, chips), optical media (e.g., CD ROM), and the like. Such media may include addresses to internet sites that provide such instructional materials.

Optionally, the instruction comprises warnings of possible side effects and drug-drug or drug-food interactions.

A wide variety of kits and components can be prepared according to the present invention, depending upon the intended user of the kit and the particular needs of the user.

In some embodiments of the present invention, the kit is a pharmaceutical kit and comprises a pharmaceutical composition comprising (i) a VM, a VE, or a VS, and (ii) a pharmaceutical acceptable carrier. In some embodiments of the present invention, the kit is a pharmaceutical kit and comprises a pharmaceutical composition comprising (i) a VM, a VE, or a VS, (ii) an activator of latent HIV-1 gene expression, and (iii) a pharmaceutical acceptable carrier. Optionally, the pharmaceutical kit comprises a component for use in HAART as described herein. Pharmaceutical kits optionally comprise an instruction stating that the pharmaceutical composition can or should be used for treating a condition or disease described herein.

Additional kit embodiments of the present invention include optional functional components that would allow one of ordinary skill in the art to perform any of the method variations described herein.

Preferred embodiments of this invention are described herein, including the best mode known to the inventors for carrying out the invention. Of course, variations, changes, modifications and substitution of equivalents on those preferred embodiments will become apparent to those of ordinary skill in the art upon reading the foregoing description. The inventors expect skilled artisans to employ such variations, changes, modifications and substitution of equivalents as appropriate, and the inventors intend for the invention to be practiced otherwise than specifically described herein. Those of skill in the art will readily recognize a variety of non-critical parameters that could be changed, altered or modified to yield essentially similar results. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

While each of the elements of the present invention is described herein as containing multiple embodiments, it should be understood that, unless indicated otherwise, each of the embodiments of a given element of the present invention is capable of being used with each of the embodiments of the other elements of the present invention and each such use is intended to form a distinct embodiment of the present invention.

The referenced patents, patent applications, and scientific literature referred to herein are hereby incorporated by reference in their entirety as if each individual publication, patent or patent application were specifically and individually indicated to be incorporated by reference. Any conflict between any reference cited herein and the specific teachings of this specification shall be resolved in favor of the latter. Likewise, any conflict between an art-understood definition of a word or phrase and a definition of the word or phrase as specifically taught in this specification shall be resolved in favor of the latter.

As can be appreciated from the disclosure above, the present invention has a wide variety of applications. The invention is further illustrated by the following examples, which are only illustrative and are not intended to limit the definition and scope of the invention in any way.

VII. Examples

The below examples are meant to illustrate specific embodiments of the methods and compositions described herein and should not be construed as limiting the scope of the invention in any way.

Example 1

General Methods

The practice of the present invention will employ, unless otherwise indicated, conventional techniques of molecular biology, microbiology, virology, recombinant DNA, and so forth which are within the skill of the art. Such techniques are explained fully in the literature. See e.g., Sambrook, Fritsch, and Maniatis, *Molecular Cloning: A Laboratory Manual*, Second Edition (1989), *Oligonucleotide Synthesis* (M. J. Gait Ed., 1984), *Animal Cell Culture* (R. I. Freshney, Ed., 1987), the series *Methods In Enzymology* (Academic Press, Inc.); *Gene Transfer Vectors For Mammalian Cells* (J. M. Miller and M. P. Calos eds. 1987), *Current Protocols In Molecular Biology* (F. M. Ausubel, R. Brent, R. E. Kingston, D. D. Moore, J. G. Siedman, J. A. Smith, and K. Struhl, eds., 1987).

A. Cell Culture

Jurkat cells were cultured in RPMI 1640 supplemented with 10% FBS and 1% penicillin-streptomycin. JLat 6.3, JLat 8.6, and JLat 9.2 cells are Jurkat T cell lines containing integrated but transcriptionally latent HIV-1 proviruses. These JLat cells contain wild-type Tat and TAR and appear to be highly representative of the latently infected cells present in vivo (Williams et al., 2004, *J Biol Chem* 279(40): 42008-42017). JLat 6.3 T cells, JLat 8.6 T-cells and JLat 9.2 T cells can be obtained from Jordan et al., (Jordan et al., 2003, *EMBO J* 22(8):1868-1877). JLat cells may also be cultured in RPMI 1640 supplemented with 10% fetal calf serum (FCS) and penicillin/streptomycin and L-glutamine as described (Williams et al., 2004, *J Biol Chem* 279(40): 42008-42017; Williams et al., 2006, *EMBO J* 25:139-149).

B. Primary T-Cell Model of HIV-1 Latency

Details on the Siliciano T-Cell model of HIV-1 latency can be found in Yang et al., 2009, *J Clin Invest* 119:3473-3486. Details on the Planelles T-Cell model of HIV-1 latency can be found in Bosque and Planelles, 2009, *Blood* 113:58-65.

C. Expression Constructs

A Jurkat isoclone of LTR-$d_2$GFP and LTR-mCherry was used for noise drug screening and chosen from a previously reported isoclone library (Singh et al., 2012, *Biophysical Journal*, 2010, 98(8):L32-L34; Dar et al., 2012, *Proc Natl Acad Sci USA* 109:17454-17459). JLat (clones 8.6, 9.2, and 10.6) were obtained and previously described (Jordan et al., 2003, *EMBO J* 22(8):1868-1877).

D. Compounds

TNFα (Sigma-Aldrich) was used at concentrations of 10 ng/ml. Prostratin (Sigma) at a concentration of 3 µM, SAHA (NCI Chemical Carcinogen Repository, Midwest Research Institute) at 2.5 µM, TSA at 400 nM, JQ1 at 1 µM, PMA at 200 ng/ml, VPA at 1 mM, Bryostatin at 20 nM, MS-275 at 10 µM, Azacitidine at 5 µM.

E. Drug Screening and Flow Cytometry Analysis

The Pharmakon1600 diverse compound library (Microsource Discovery Systems, Inc.) was used in the current screen. Drug treatments were performed for 24 hours at 10 uM final concentration in 96-well plates. Compounds were automatically added into 200 µl cultures at the final concentration of 0.1% DMSO. Automated compound addition to plates was performed using a liquid handling system (Beckman Coulter Biomek FX Laboratory Automation Workstation) at the University of California, at San Francisco (UCSF) Small Molecule Discovery Center (SMDC). Flow cytometry was performed using a high throughput sampler (HTS) module attached to a BD LSRIIflow cytometer at the J. David Gladstone Institutes Flow Cytometry Core, University of California, San Francisco. Tracking and monitoring of cytometer performance was performed daily using a standard software protocol and calibration beads. Plates were kept in the incubator until measurement and each well was automatically mixed before samples were analyzed. $5\times10^4$ of all live cells that passed a specific forward scatter (FSC)—side scatter (SSC) gate were collected from each well for noise magnitude measurements from which a conservative gating was applied for about $3\times10^3$ cells of similar FSC vs SSC to reduce extrinsic noise contributions primarily due to differences in cell volume and state. Each 96-well plate included a column of untreated control cells, cells treated with TNFα (positive control) and one well of non-' fluorescent naïve Jurkat cells. For HIV-1 reactivation experiments $1\times10^4$ live cells were collected.

F. Single Cell Analysis of Variability Modulator (VM) Drug-Treated Cells

Lentiviral vectors expressing the LTR-GFP cassette in the absence of Tat were described (Weinberger et al., 2005, *Cell*, 122(2):169-182) and used to infect $5\times10^5$ Jurkat cells at a multiplicity of infection <0.1, resulting in 25,000-50,000 infected cells each presumably with a unique integration site. Cells were then sorted by FACS to isolate green fluorescent protein-labeled (GFP+) cells and fluorescently imaged on glass-bottom dishes in RPMI 1640 with 10% fetal calf serum and 1% penicillin-streptomycin and 10 μM of VM at t=0 h for the population which was pre-treated with VM 1 day before imaging. The imaging took place in humidified conditions at 37° C. and 5% $CO_2$ for 12-24 h with a 40×(1.2 NA) oil-immersion objective on a Zeiss Observer Z1 microscope equipped with an automated linear-encoded X-Y stage, as described. (Weinberger et al., 2008, *Nature Genetics*, 40(4):466-470; Dar at al., 2012, *Proc Natl Acad Sci USA* 109:17454-17459). Image processing and cell tracking were performed in Matlab™ with an in-house algorithm (Weinberger at al., 2008, *Nature Genetics*, 40(4): 466-470; Dar et al., 2012, *Proc Natl Acad Sci USA* 109: 17454-17459). Using a multiple well sample holder up to 4 drug treatments could be imaged at once and a single 12-h experiment could generate up to 500 single-cell trajectories for analysis per treatment. For each trajectory, noise auto-correlation [Φ(t)] and magnitude ($CV^2$) were calculated using an established noise-processing algorithm (Weinberger at al., 2008, *Nature Genetics*, 40(4):466-470; Dar at al., 2012, *Proc Natl Acad Sci USA* 109:17454-17459; Boehm et al., 2013, *Cell Cycle* 12:452-462).

Example 2

Noise Drug Screening Approach—Overview

Figure 3A:
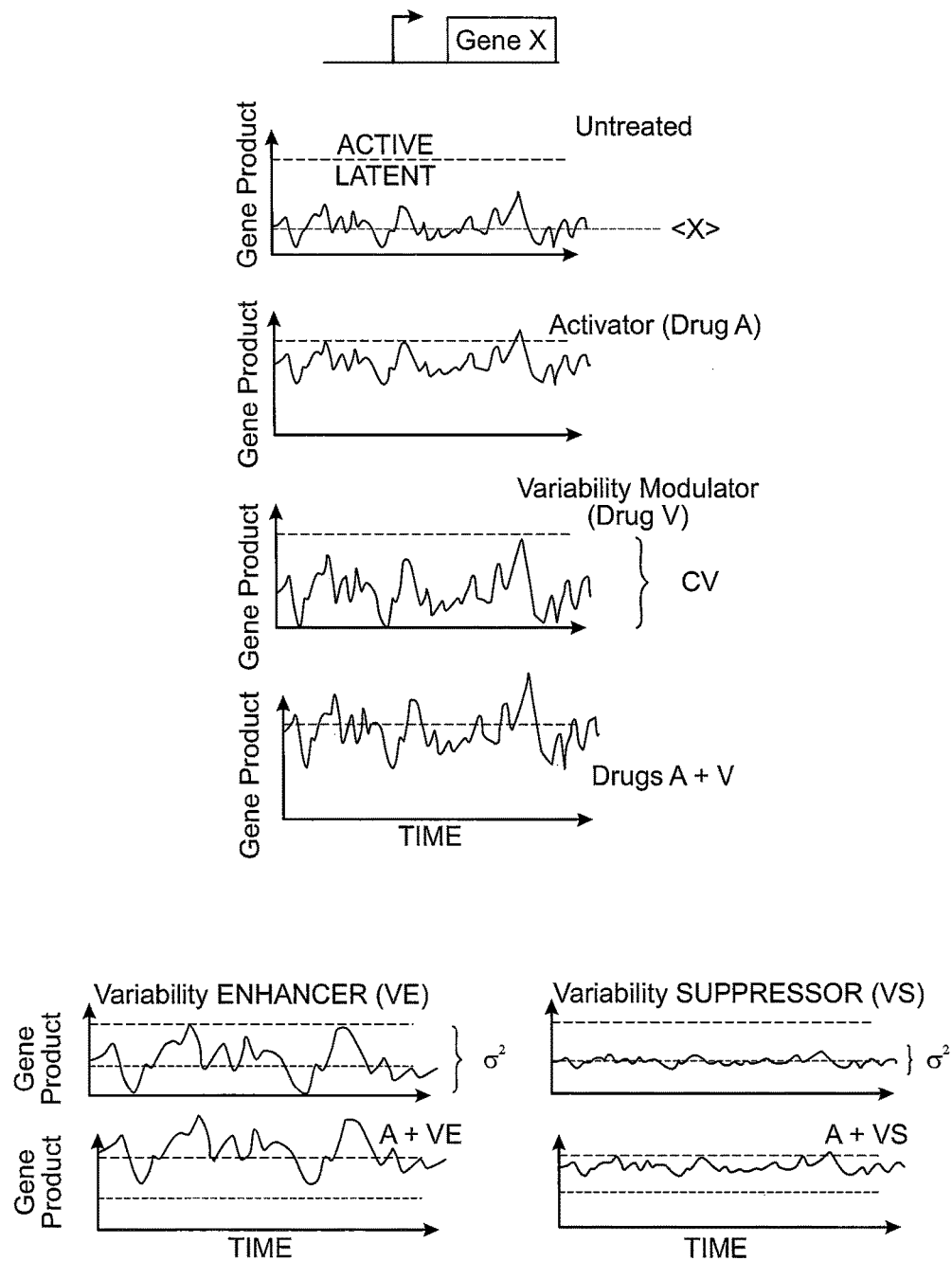
FIGS. 3A-F schematically depict variability modulation in a single cell and in a population of cells to synergistically enhance or suppress gene expression and later phenotypic diversity.
Figure 3B:
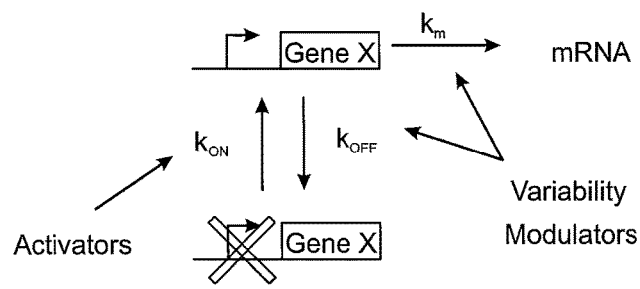
Figure 3C:
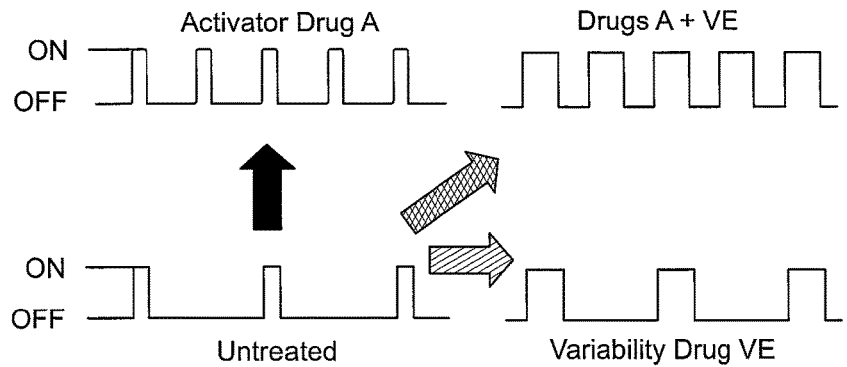
Figure 3D:
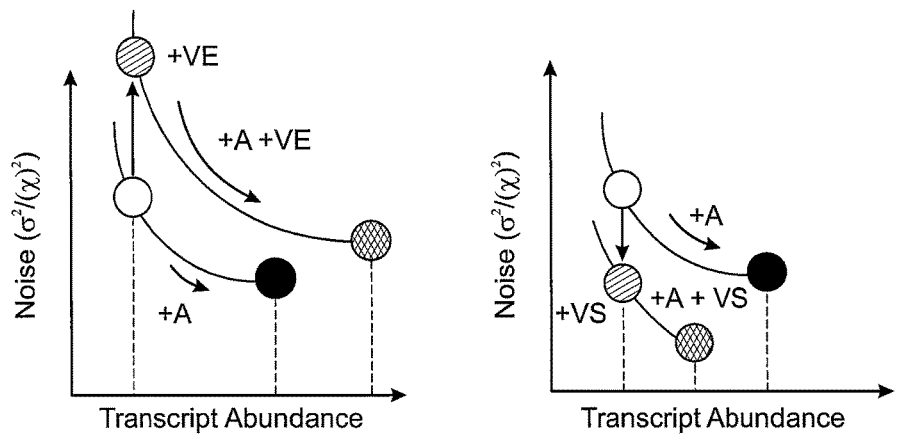
Figure 3E:
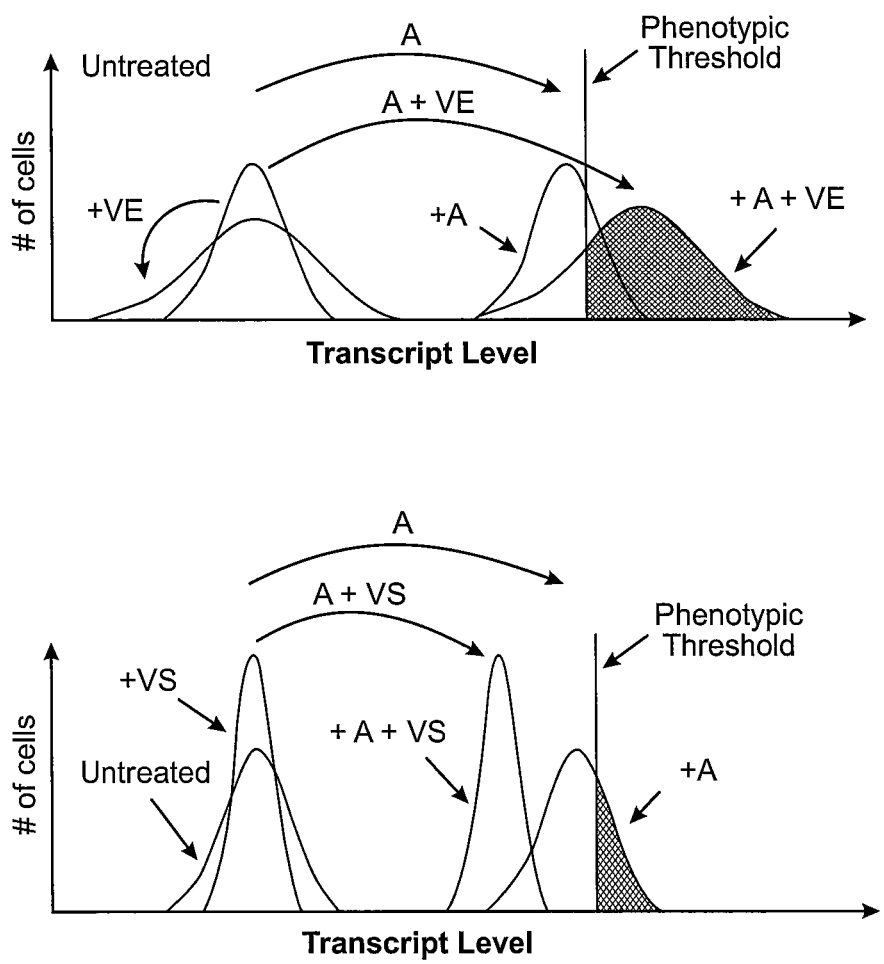
Figure 3F:
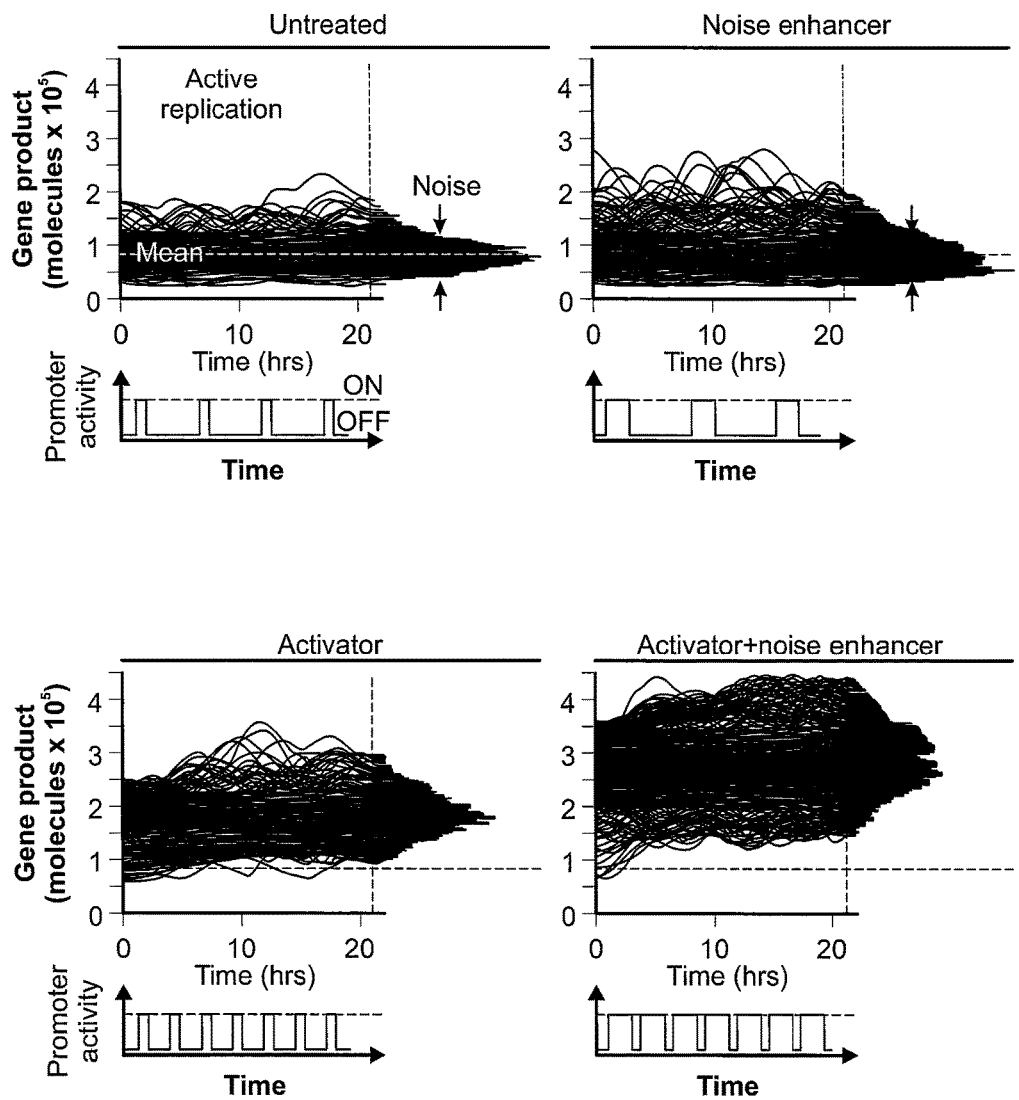
Figure 4:
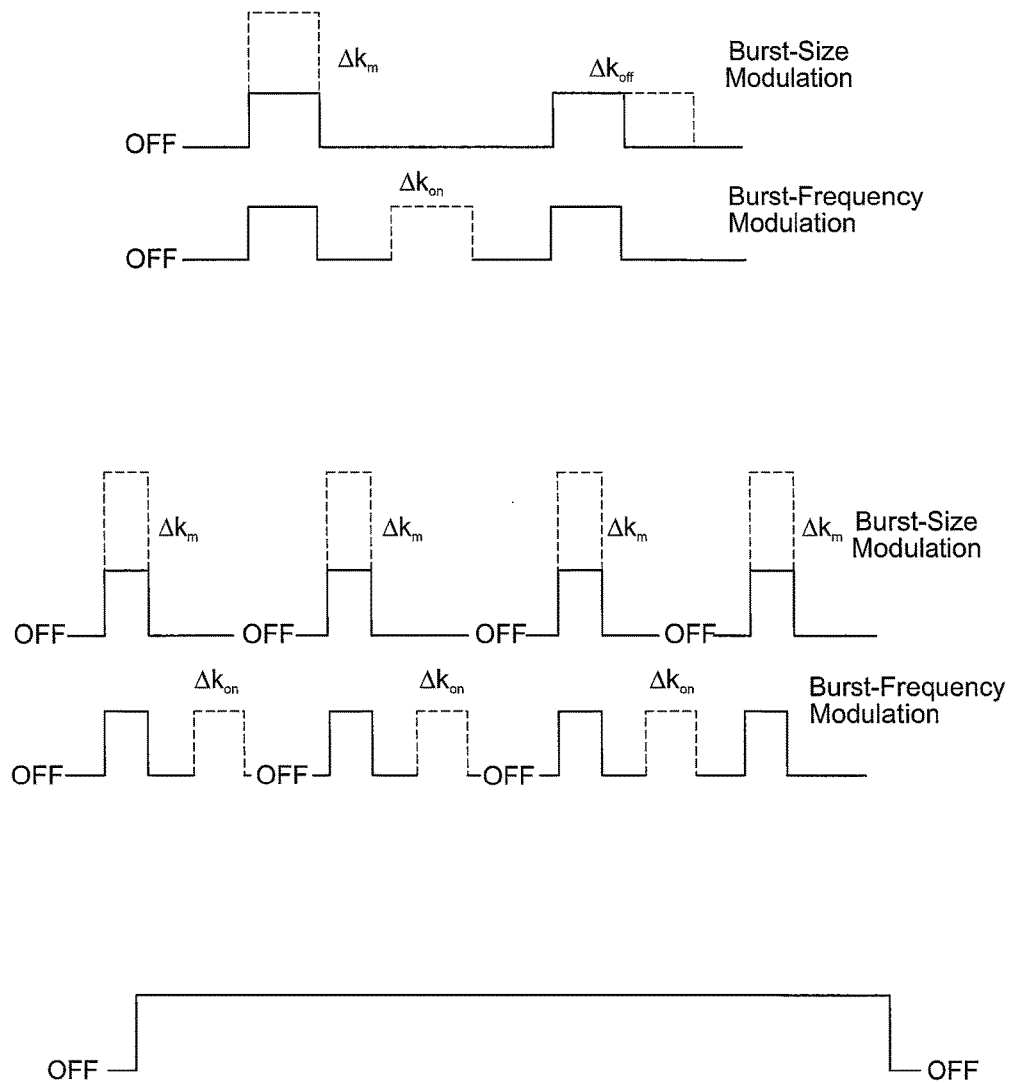
FIG. 4 schematically depicts models for transcriptional pulse train reactivation of HIV-1 latency. The upper two panels depict models employing infrequent extra-large spikes (burst-size modulation) or frequent bursts (burst-frequency modulation) in comparison to a long active period (lower panel). Details are described, e.g., in Example 2.

Basic concepts of the noise drug screening approach used and developed herein are schematically shown in FIGS. 1A, 1B, 2, 3A-3F, 4, and 5. The noise drug screen approach for latent HIV-1 reactivation began with screening for variability modulators (VMs), i.e., drugs that modulate variability in gene expression from a target promoter without significant changes in mean expression level (FIGS. 3E, 5). The VMs are then applied in combination with known activators to the full disease model (Drugs A+V, FIGS. 3E, 5). In cases where the mechanisms of action of the two drugs are non-antagonistic the combination generates variable activation and potentially extends the response distribution of an untreated cell population ("Untreated") beyond a phenotypic threshold (e.g. latency versus active replication). The threshold would not be reached by the activator drug alone (Drug A) or a combination of activator drugs. Without being bound by theory, variability suppression is believed to stabilize a phenotypic state below the threshold and suppress activation by either an exogenous drug or native cellular factors (FIG. 3E, lower). A time-dependent illustration of each drug case for the a gene X controlled by a promoter (e.g., HIV-1 long terminal repeat (LTR) promoter driving GFP) is shown in FIG. 3A. The HIV-1 trans-activator of transcription (Tat) forms a positive feedback loop through activation of the LTR that amplifies and extends fluctuations generated by the underlying promoter and can further extend transient fluctuations past the threshold into an actively replicating state (Weinberger et al., 2008, *Nature Genet* 40:466-470). Controlling the strength of Tat positive feedback has been shown to directly bias the latency decision (Weinberger et al., 2008, *Nature Genet* 40:466-470). Drugs A and V in combination provide the largest dwell time for a single cell expression level above the activation threshold (FIG. 3A, "Drug A+V"). Fluctuations above the phenotypic threshold (dashed line) increase the probability for Tat positive feedback to commence and drive active replication.

LTR promoter fluctuations become the primary focus underlying proviral latent stability and the target of drug screening for VMs. The conventional model of episodic transcription is a 2-state model where all the processes involved in transcriptional initiation and elongation are lumped into 3 parameters (FIG. 3B) (Kepler and Elston, 2001, *Biophys J* 81:3116-3136; Simpson et al., 2004, *J Theor Biol* 229:383-394). Transitions between an ON and OFF state occurs at rates $k_{on}$ and $k_{off}$ with transcription from the ON state at rate $k_m$. Theory and experiments have demonstrated that drugs that increase transcriptional burst frequency ($k_{on}$) increase protein abundance and decrease noise while amplifying burst size, or the number of mRNA produced per transcriptional pulse, ($k_m/k_{off}$), and increases both noise magnitude and protein abundance (Singh et al., 2010, *Biophys J* 98:L32-L34; Dar et al., 2012, *Proc Natl Acad Sci USA* 109:17454-17459). For variability enhancement, drugs A and V synergize by affecting the three model parameters to increase burst frequency and burst size resulting in a high frequency of large transcriptional bursts.

Example 3

Figure 6A:
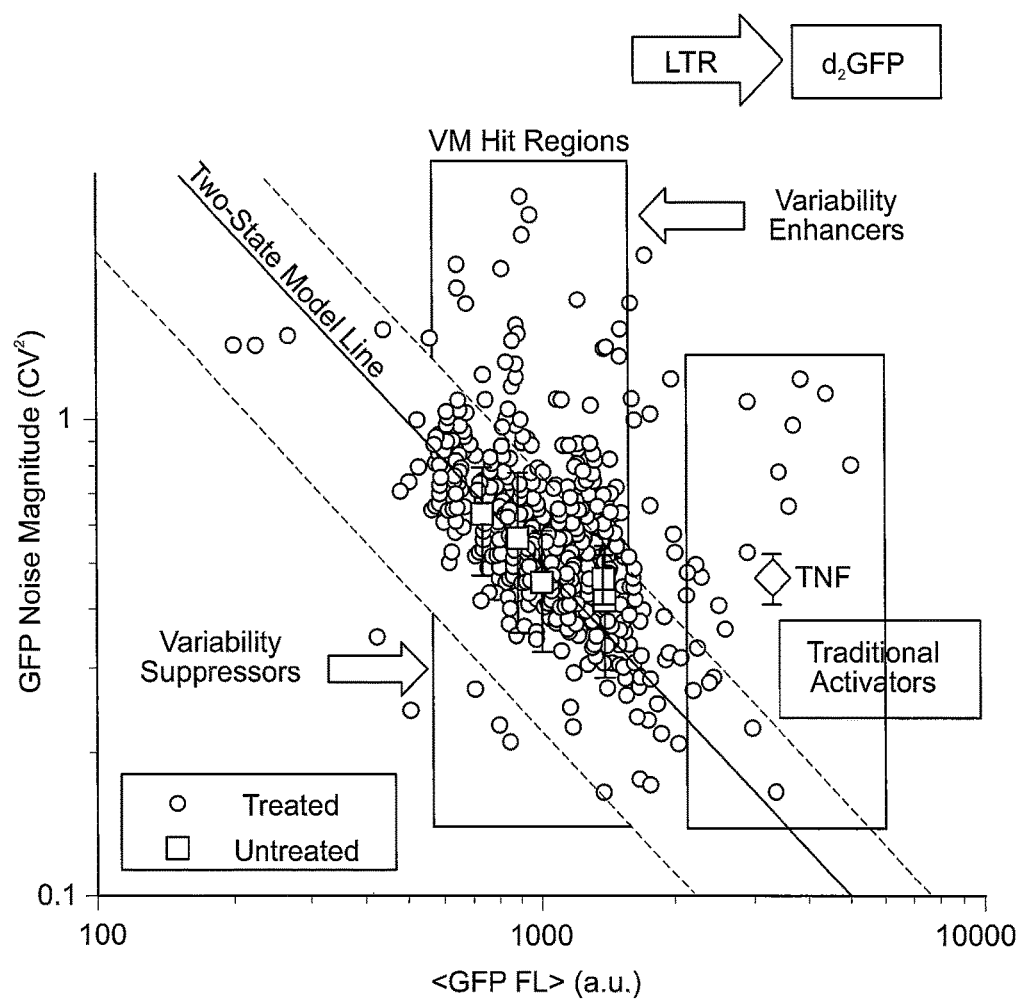
FIGS. 6A-E schematically depict results from the screening of the HIV-1 LTR promoter for drugs that modulate variability in gene expression. Details are described in Example 3.
Figure 6B:
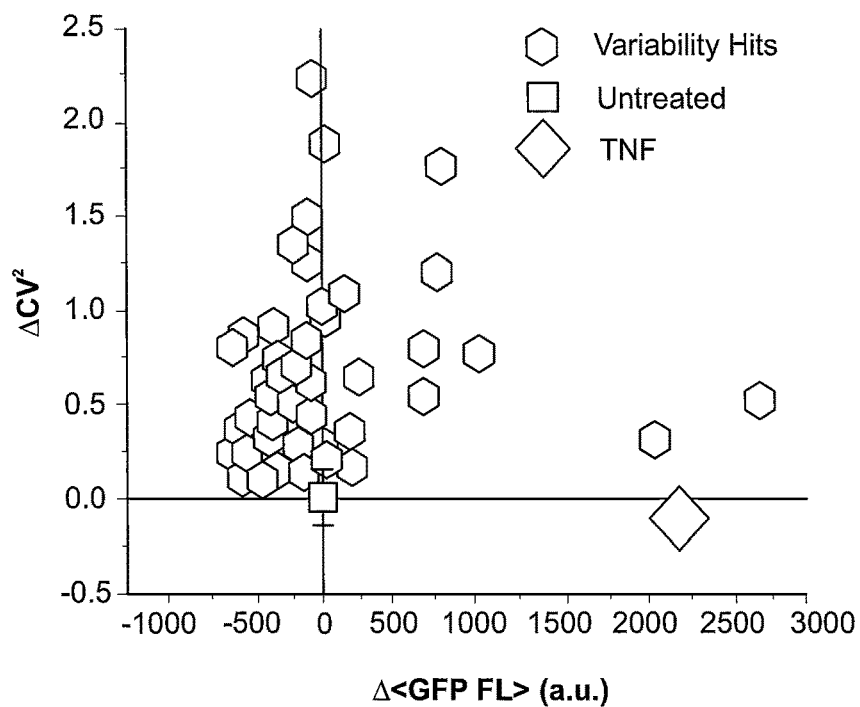
Figure 6C:
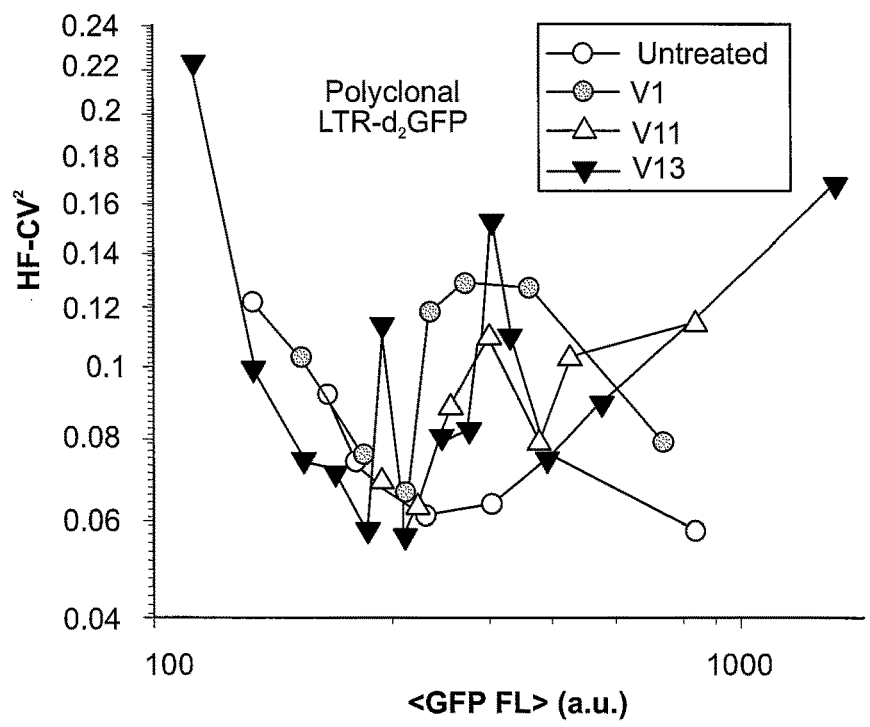
Figure 6D:
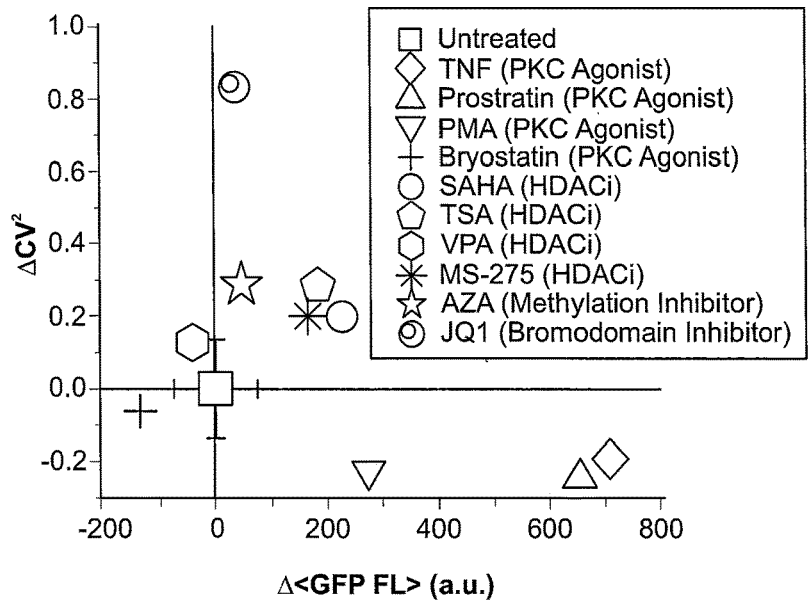
Figure 6E:
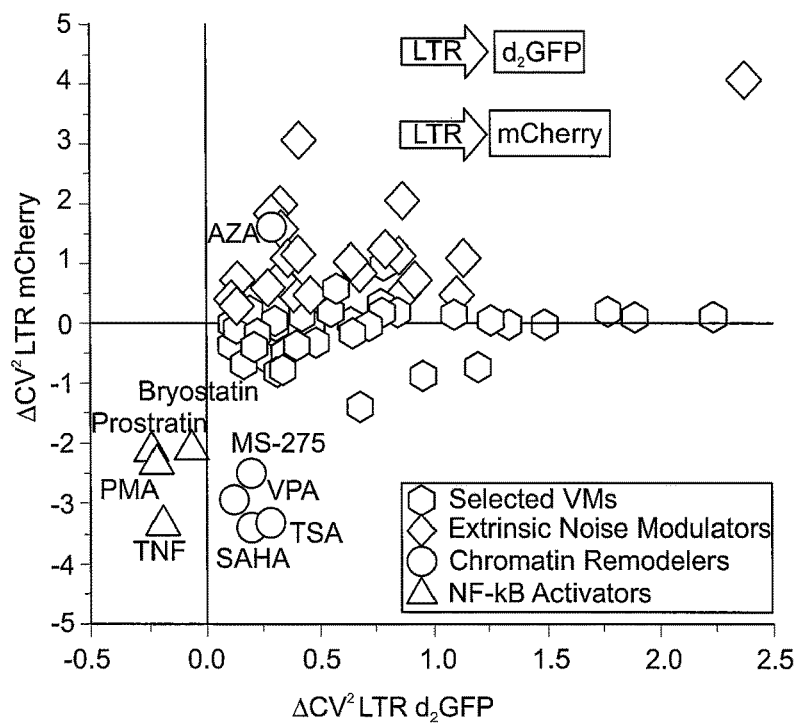

Identification of Compounds that Modulate Variability of Expression of an HIV-1 Gene Promoter To identify chemical compounds that modulate variability of expression of an HIV-1 LTR promoter, 1600 small molecule bioactive compounds (Pharmakon1600 by Microsource Discovery Systems, Inc.) were screened on an isoclonal population of human Jurkat T-cells harboring an LTR driving a destabilized 2.5-hour half-life GFP (FIG. 6A). Without being bound by theory, a destabilized reporter is required to observe transcriptional noise with shorter time scales. GFP noise magnitude (quantified by the variance over the mean fluorescence squared, $CV^2$) and mean fluorescence were measured by high-throughput flow cytometry 24 hours post 10 uM drug exposure. To control for extrinsic variability in gene expression due to cell volume and state a conservative gating on the population forward versus side scatter was applied (See General Methods). A second LTR driving a long-lived mCherry reporter was integrated and screened alongside the destabilized reporter drug target to control for fluctuations in global resources and post-transcriptional noise sources (FIG. 6E).

In total, 5 sets of 96-well plates of live isoclonal populations of Jurkat cells having the integrated LTR-$d_2$GFP and LTR-mCherry constructs were screened. Cell fixation was avoided to reduce quenching of fluorescence and additional sources of cell to cell fluorescence variability. Each plate set included untreated controls (shown as squares in FIGS. 6A, B, D, and as open circles in FIG. 6C), positive controls using tumor necrosis factor alpha (TNFα, shown as "TNF" and diamonds in FIGS. 6A, B, D), an activator of NF-$K_B$ sites in the promoter, and a non-fluorescent naïve cell population to control for background and autofluorescence (FIG. 6A). Compounds causing excessive cell death or that color tinted the sample wells were excluded from the analysis. In general, most of the drug treatments deviated from their untreated control with a slight decrease in fluorescence and increase in variability (gray "fingers" behind each untreated plate set, squares, FIG. 6A). The VM hit region (see FIG. 6A) was defined by a deviation of at least ±2−σ in noise magnitude and mean fluorescence from the untreated control (FIG. 6A).

Initially 126 variability enhancers were identified (FIG. 10). Some of those were not pursued any further herein as they impacted cell viability. 85 variability enhancers (FIG. 11) were selected for testing increased reactivation of HIV-1 latency (FIG. 6B). To assess whether identified VMs are specific to the integration site of the drug screen target, a polyclonal LTR $d_2$GFP population was treated with select VM hits and imaged using time-lapse single cell fluorescence microscopy (Dar et al., 2012, *Proc Natl Acad Sci USA* 109:17454-17459; Boehm et al., 2013, *Cell Cycle* 12:452-462) (FIG. 6C). For each treatment ~500 cells were collected and processed using a polyclonal sub-clustering method which enables the measurement of gene expression dynamics for thousands of integration sites in parallel (Dar et al., 2012, *Proc Natl Acad Sci USA* 109:17454-17459). Variability enhancers V1, V11, and V13 all displayed increased noise magnitude trends above the untreated population (FIG. 6C) in the mid-abundance regime from which the drug screen isoclone was selected. These results suggest that these variability enhancers are not local to a specific integration site, but would affect viral integration sites globally.

A variety of known transcriptional regulators of the LTR were used on the screen target to reveal that leading histone deacetylase inhibitors (HDACi) such as SAHA, TSA, VPA, and MS-275, methylation inhibitors such as azacytidine (AZA), and bromodomain protein inhibitors (JQ1) are all variability enhancers and have already been reported to synergize for latent HIV-1 reactivation with Protein Kinase C (PKC) agonists such as TNFα, Prostratin and PMA that activate the LTR via NF-K$_B$ (FIG. 7D) (Boehm et al., 2013, *Cell Cycle* 12:452-462; McDonald et al., 2008, *Phys Rev E* 77:046110). Activator drugs TNFα, Prostratin, and PMA all increase burst frequency through initiation of LTR transcription and decrease noise magnitude (FIG. 6D). In addition, Cytarabine, an anticancer drug, and +5σ VM hit in the screen, was recently reported to synergize with TNFα in reactivation of latent HIV-1 (Shishido et al., 2012, *Journal of Virology* 86:9055-9069). These results show that many of the currently known transcriptional synergies for latent reactivation include VMs and suggest that the present screening strategy which can identify compounds with diverse mechanisms of action, could produce novel synergies.

To distinguish between compounds that primarily target transcription versus post-transcriptional processes and global resources (extrinsic noise) a second reporter of the LTR promoter driving a stable mCherry gene was included in the same targeted cell population used in the drug noise screen (FIG. 6E). The stable reporter averages out and is unaffected by fluctuations due to episodic transcription. Theory predicts that the destabilized d$_2$GFP reporter can detect transcriptional bursting noise contributions ($\gamma_p$>>k$_{on}$, k$_{off}$, where $\gamma_p$ is the fluorescent reporter degradation rate) while the two reporters together will move their noise magnitudes to changes in non-transcriptional noise sources. Filtering out non-transcriptional noise signatures of VM hits increases the probability for synergistic reactivation of latency. Noise from the two reporters was compared using the same processing as the LTR-d$_2$GFP. The LTR-mCherry ΔCV$^2$ of the 85 selected VMs primarily land along the ΔCV$^2$ d$_2$GFP axis. Transcriptional modifiers SAHA, TSA, MS-275, AZA, TNFα, Prostratin, PMA, and Bryostatin increase transcriptional burst frequency (decreasing noise in mCherry) either with or without increasing burst size (positive and negative deviations in d$_2$GFP respectively, FIG. 6E). In total, the screen yielded 25 hits that significantly enhanced variability in gene expression in both channels (filled diamonds) and were excluded from the selected set of 85 VMs (gray hexagons). Of these 25 compounds 15 were identified as modifiers of cell cycle, ATP, inflammation, post-translational modifications, and translation. By filtering ~20% of the VM hits the use of a differential stability 2-reporter system demonstrates an additional application of gene expression fluctuations for drug discovery with foundations dating back from earlier studies in a bacterial 2-reporter system (Elowitz et al., 2002, *Science* 297:1183-1186).

Example 4

Figure 7A:
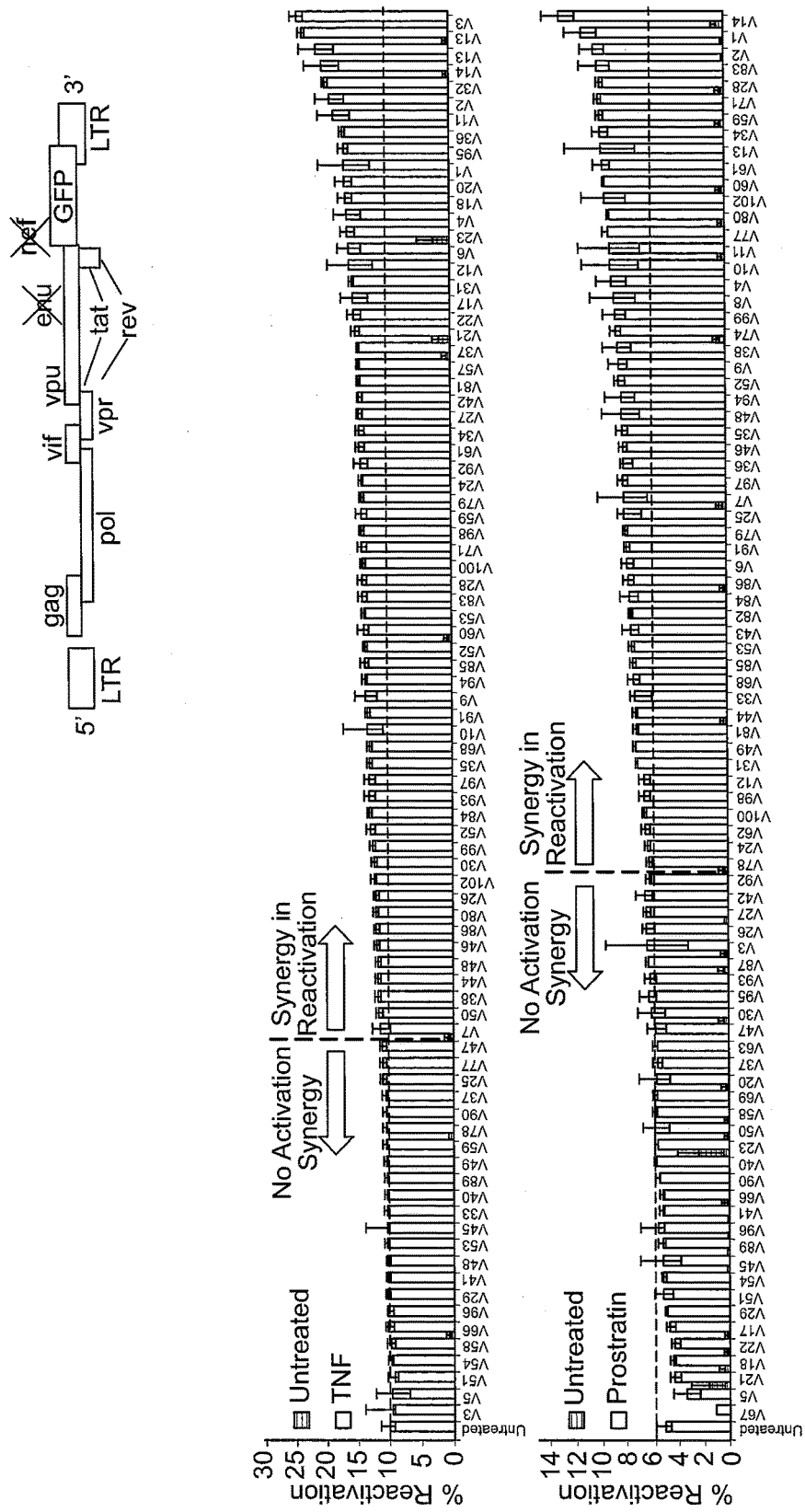
Figure 7B:
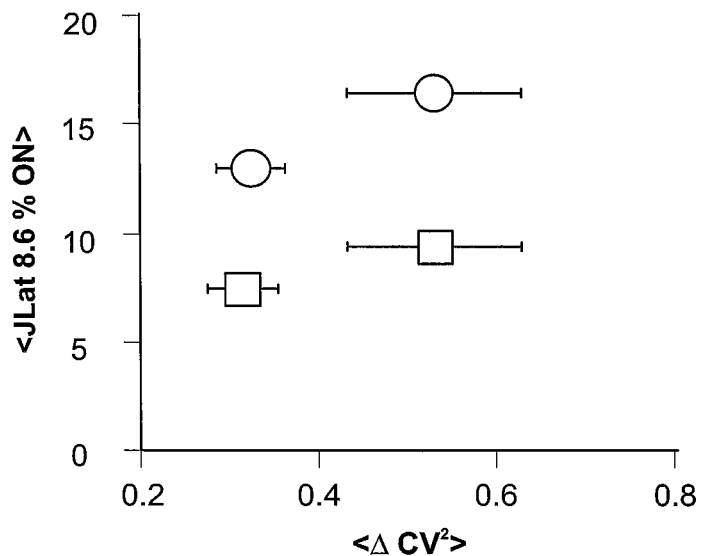
Figure 7C:
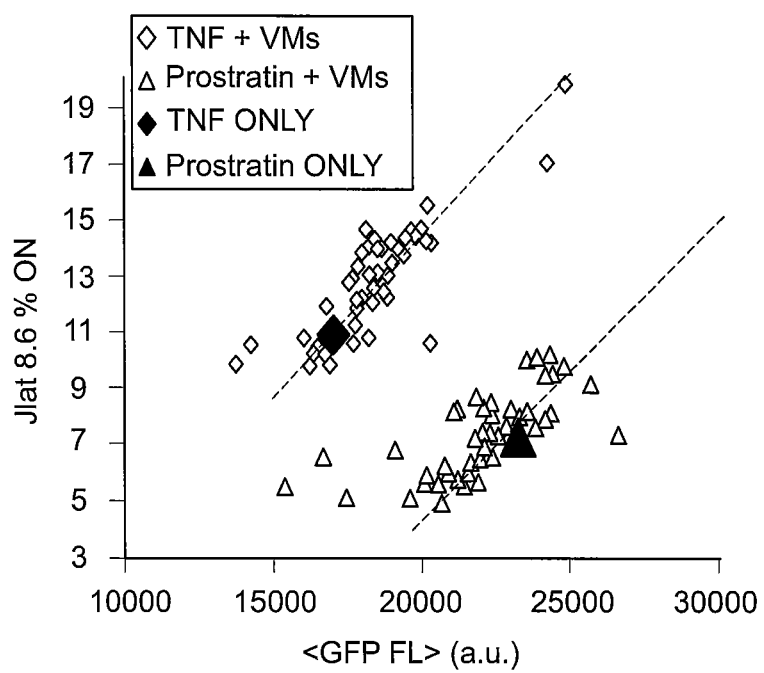

A Majority of Variability Modulators Synergize with TNFα and Prostratin to Increase Latent HIV-1 Reactivation in a Jurkat T-Cell Line To test for increased latent HIV-1 reactivation by the 85 selected VMs in combination with transcriptional activators a model system for HIV-1 latency (JLat) was used in a T-cell line (Jordan et al., 2003 *EMBO J* 22:1868-1877). In the JLat cells, full-length HIV-1 has GFP inserted in place of the gene encoding for Nef and the envelope gene (Env) has been deleted (Jordan et al., 2003 *EMBO J* 22:1868-1877). From various JLat lines differing in proviral integration site, JLat 8.6 and 9.2, two low activation cell lines were used herein, and a more activatable JLat 10.6 cell line was also tested for a subset of the VM hits. In JLat 8.6 cells VMs showed no significant reactivation on their own or synergy in combination with SAHA, TSA, or AZA, but showed increased synergy in combination with TNF, Prostratin, PMA, and Bryostatin (FIG. 7A). An increase in TNFα reactivation was observed for ~70% of the VMs with up to about twice the reactivation of TNFα alone (FIG. 7A upper, bold bars versus "untreated" black bar at left end). ~60% of the VMs synergized with Prostratin and increased reactivation by about twice the 6% reactivation of Prostratin alone (FIG. 7A lower, bold bars). The VMs that synergized the mean % ON versus the increase in noise magnitude in the drug screen isoclone were correlated with one another (FIG. 7B) suggesting the higher the variability or burst size modulation the more reactivation of HIV-1 latency occurs. VMs showed an increase in the mean fluorescence of activated cells with increasing % of activation suggesting variable activation, from FIG. 3E, where the population exposed to drugs A+V has increased its mean expression level and not just variability in gene expression in response to drug A alone (FIG. 7C).

A dose response surface with various TNFα and Prostratin concentrations for V11 yielded almost double the reactivation of HIV-1 latency in JLat 8.6 cells at a concentration of 25 uM post 48 hour treatment (FIG. 7D). Interestingly, similar reactivation levels were reached by combining increased variability modulator and decreased activator concentrations (black arrows). This result suggests a potential protective function for VM compounds in HIV-1 therapies by reducing the current intolerable concentrations of PKC agonist treatment in patients.

Figure 7E:
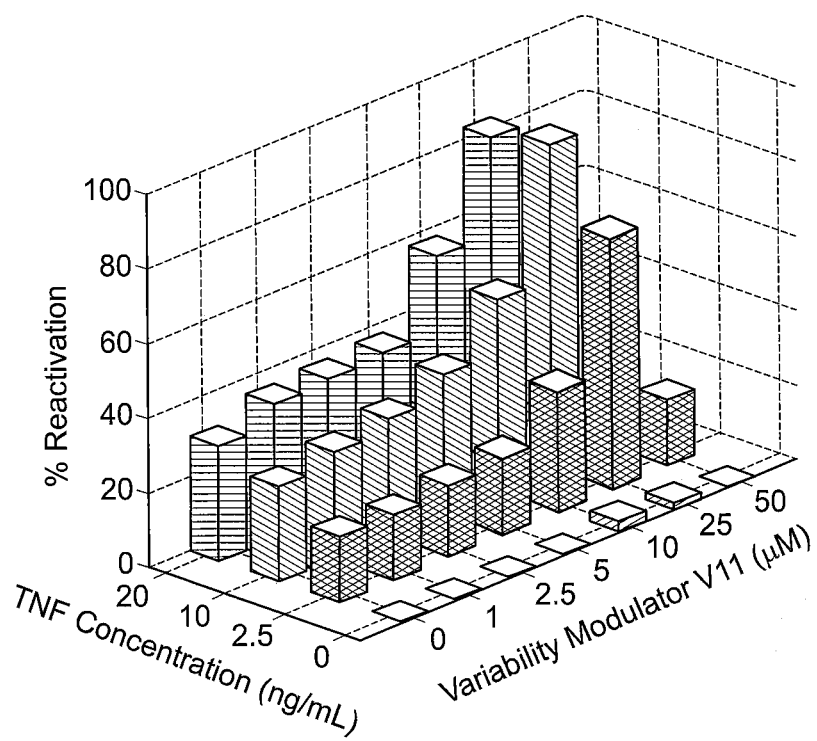
Figure 7F:
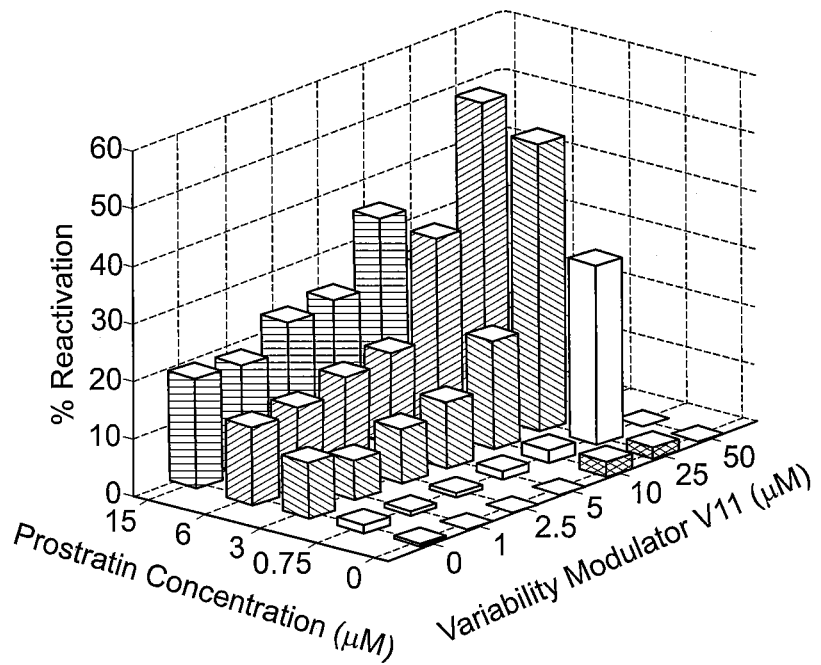
Figure 7G:
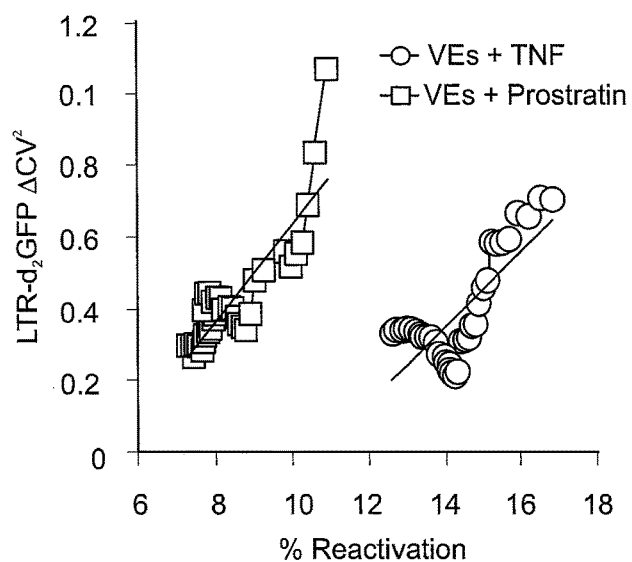
Figure 7H:
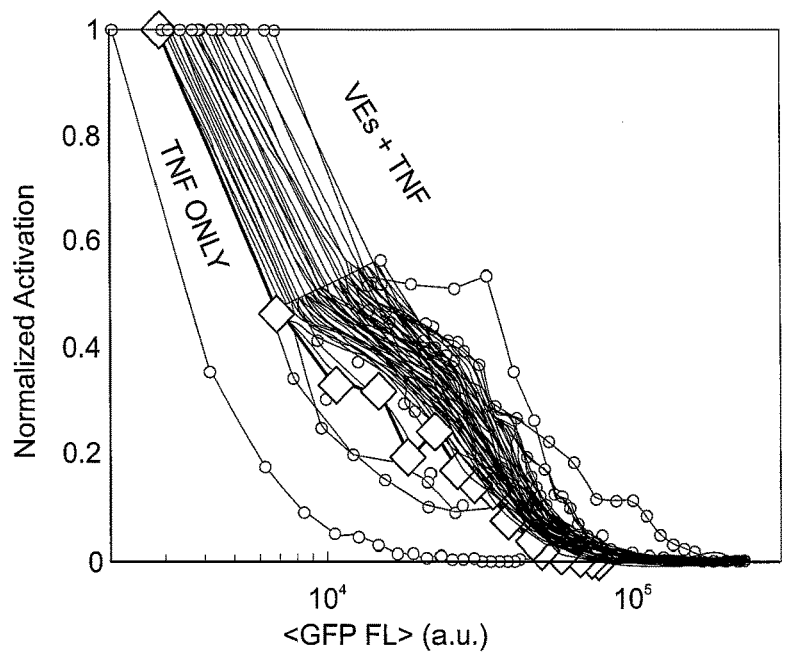
Figure 7I:
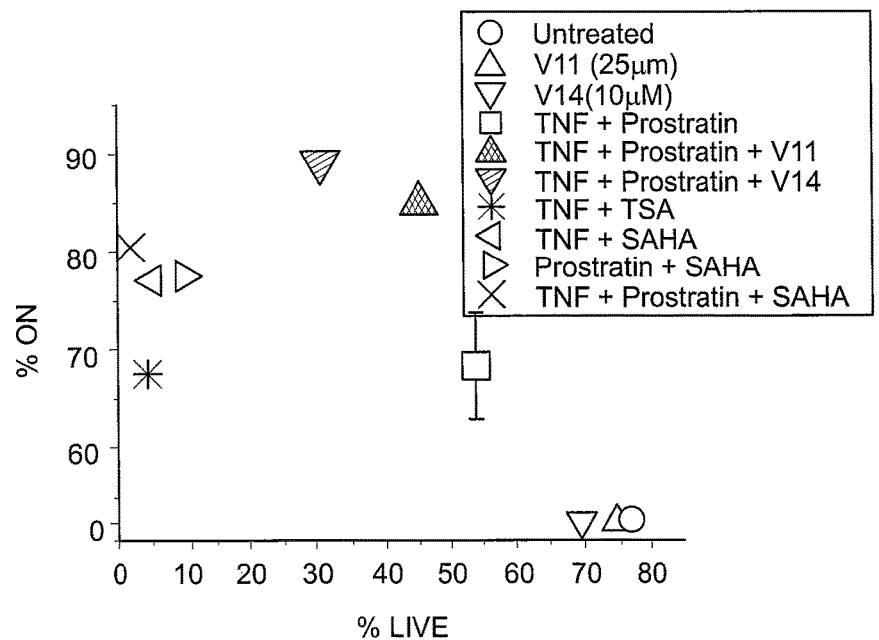
Figure 7J:
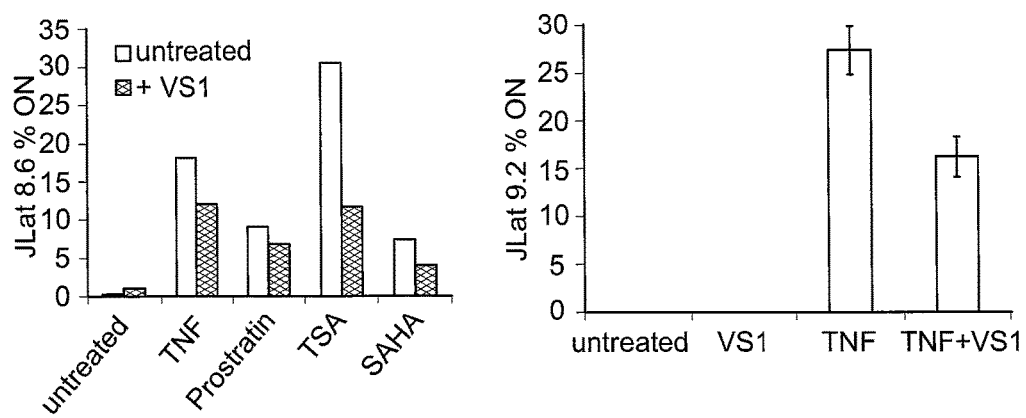

Of the variability suppressor hits that were detected, Manidipin HCl, was found to suppress reactivation in That 8.6 when combined with TNFα or Prostratin (Activator Drug A's) as well as TSA or SAHA (HDAC inhibitors that are themselves both activators and variability enhancers), (FIG. 7I, left). Manidipin decreased TNFα activation of JLat 9.2, a latent cell line harboring a different proviral integration site by about 40% (FIG. 7J, right). This demonstrates that a variability suppressor can both suppress activation by an activator as well as negate variability enhancement of drugs that are both activators and VMs (reduces burst size amplification). Manidipin is a calcium channel blocker and recently calcium flux has been associated with and shown to synergize with Prostratin for NF-K$_B$ dependent activation of HIV-1 latency (Chan et al., 2013, *PLoS ONE*, in press).

Example 5

Figure 8C:
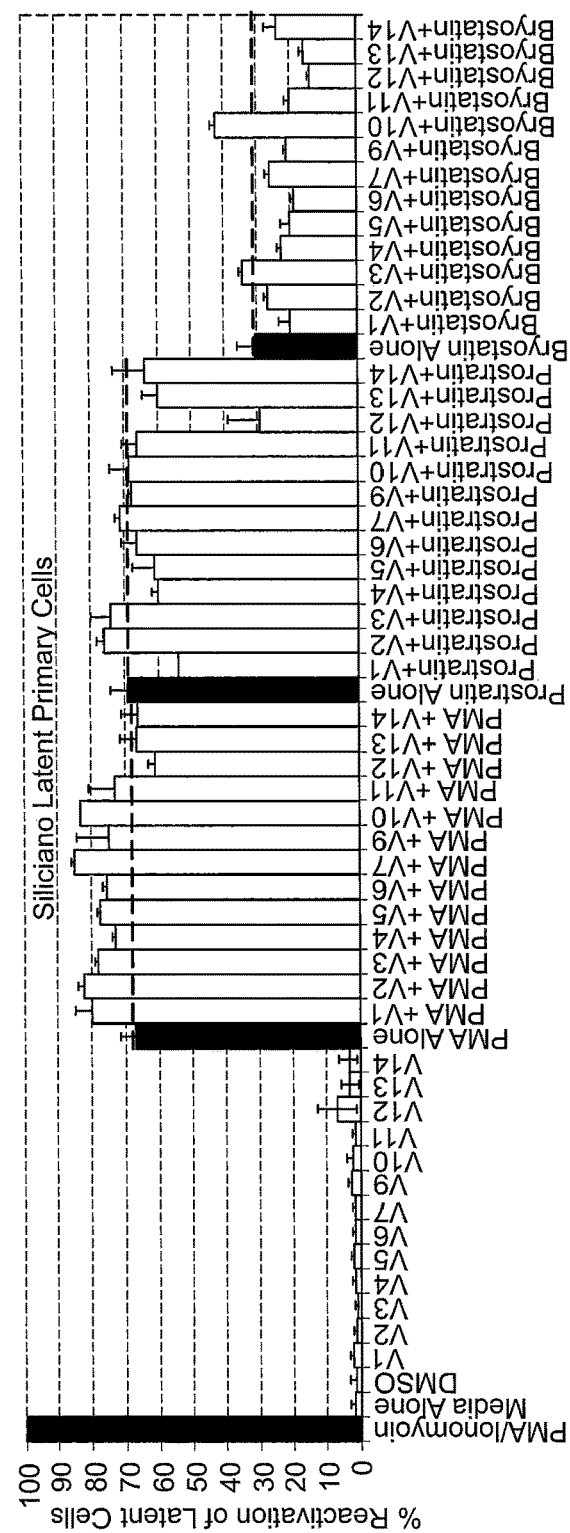
Figure 8D:
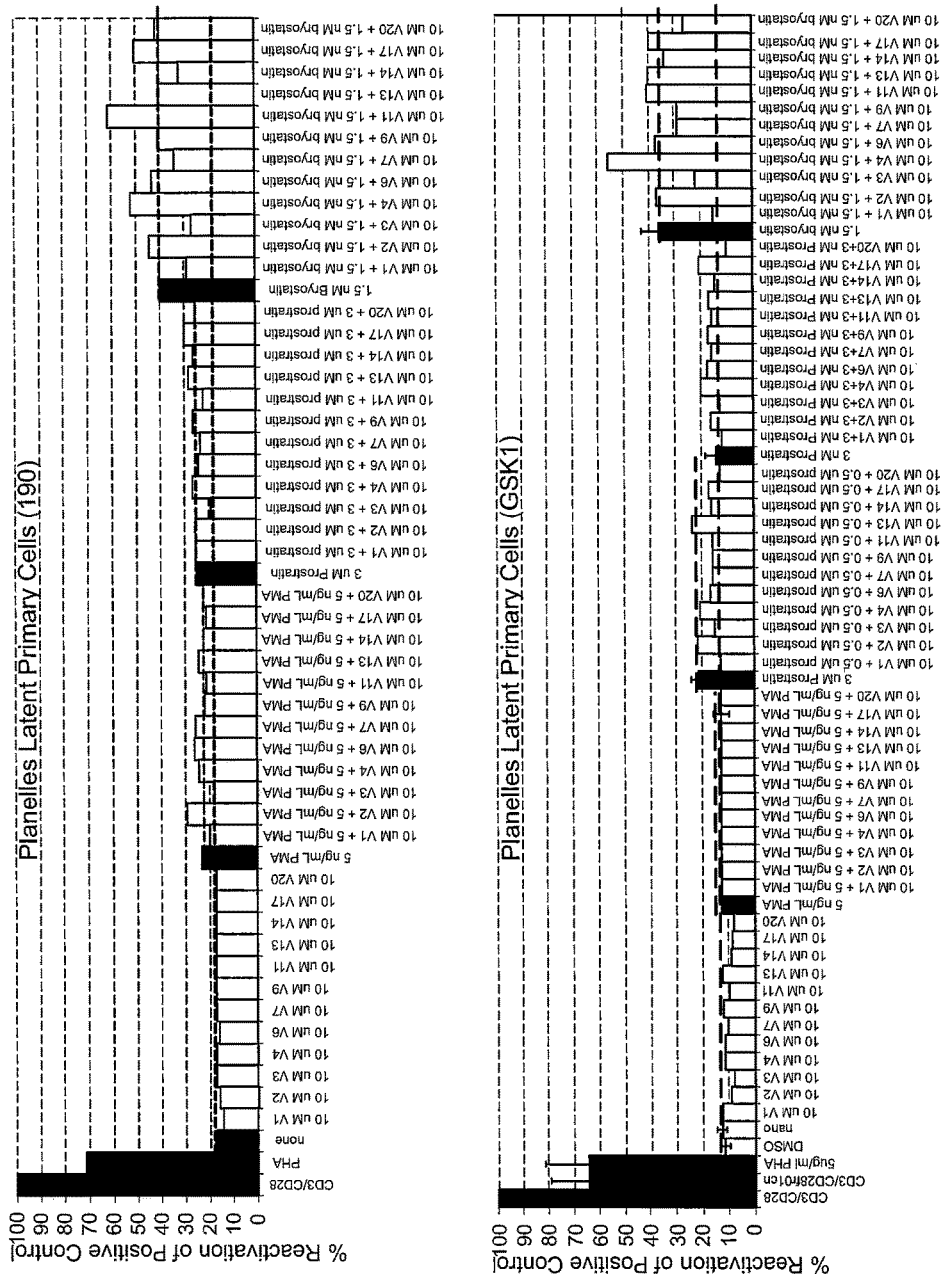

Variability Modulators Synergistically Reactivate HIV-1 Latency in Two Primary Cell Models To test if VMs enhance reactivation in a primary cell model of latency 14 VMs were selected from the 85 VMs initially screened on the JLat cell line. The VM subset spanned a range of reactivation with TNFα/Prostratin and modulations of noise (FIGS. 7A and 8A). Two separate primary cell models of latency were screened (Bosque and Planelles, 2009, *Blood* 113:58-65; Yang et al., 2009, *J Clin Invest* 119:3473-3486) The Siliciano model of latency is generated using primary human CD4+ T cells which are transduced with Bcl-2 to allow long-term in vitro survival. The Bcl-2+ cells are activated with -CD3/-CD28 antibody and infected with a GFP expressing virus. Cells remain in culture for over a month to allow transition into resting memory states and then sorted for GFP-cells after which the sorted cells are the latent pool of cells tested for reactivation. Several VMs demonstrated increased reactivation with PMA, Bryostatin, and Prostratin (FIGS. 8C, 8D). Reactivation experiments were designed with a positive control (PMA with Ionomycin or -CD3/-CD28 activation) as well as media only or VM treatment measurements. The Siliciano model displayed synergy between PMA and most of the VMs tested (FIG. 8C). Fewer VMs increased reactivation in combination with Prostratin and Bryostatin. V3 and V10 appear to synergize with all three activators. In the Planelles model synergy was observed with Bryostatin from cells of two different donors.

Overall the results suggested that variability modulators reactivate HIV-1 latency more effectively with transcriptional activators such as PKC agonists, and display antagonistic synergy with other VMs such as SAHA TSA, AZA, WA, and MS-275 (FIGS. 7-8). The VM subset applied in combination with one another did not show any activation synergy in the JLat model Interestingly TNFα and Prostratin synergize with one another even while increasing transcriptional initiation via the same NF-$K_B$ sites in the promoter (Williams et al., 2004, *J Biol Chem* 279:42008-42017) and have similar noise vectors (FIG. 6D). To test the possibility of increasing burst size and frequency with three drugs, two VMs from the screen (V11 and V14) were tested on a JLat cell line with both TNFα and Prostratin. The two activators with VM showed increased activation suggesting that combinatorial "stacking" of three or more non-antagonistic VMs with activators may prove to be an optimal strategy for maximizing latent reactivation similar to combination HAART therapy to completely impair viral replication (FIG. 7D).

Of the 85 VMs tested in the reactivation screen some include known transcriptional mechanisms of HIV-1 such as activators of p53 (known to bind CDK9 and stall transcriptional elongation), modulators of TNFα and NF-$K_B$, methylation inhibitors, and modulators of JUN-B and c-FOS (regulators of transcription at AP-1 sites in the LTR). A table summarizing 12 of the 14 VMs investigated for reactivation in the primary cell experiments is presented in FIG. 8B. Among the 12 variability modulators, three are microtubule inhibitors (V1, V3 and V7), three are estrogen receptor (ESR1) agonists (V2, V3, and V10), and two are antihistamines (V11, V13). V2, V3, and V10 are strong suspects of changing HIV-1 LTR transcription since ESR1 binds SP1, which has 3 binding sites in the LTR promoter. ESR1 also binds p300, which is involved in acetylation of Tat positive FB (Ott et al., 1999, *Curr Biol* 9(24), 1489-1493). Estrogen has been reported to directly affect the efficiency of SP1 binding to the LTR in a Tat independent manner (Katagiri et al., 2006, *Int Immunopharmacol* 6:170-181) and estradiol regulates HIV-1 replication in peripheral blood mononuclear cells (PBMCs) through transcriptional mechanisms (Asin at al., 2008, *AIDS Res Hum Retroviruses* 24:701-716). V9, a nucleotide synthesis inhibitor alters transcription. The antihistamines V11 and V13 inhibit CCL11 and CCL5. CCL11 is a ligand for CCR2, CCR3, and CCR5. CCL5 or RANTES is a beta-chemokine known to suppress HIV-1 LTR transcription and is produced by CD4+ and CD8+ T-cells.

FIG. 11 summarizes the VEs that synergized with either TNFα or prostratin in the JLat cell models described herein.

Example 6

Figure 9:
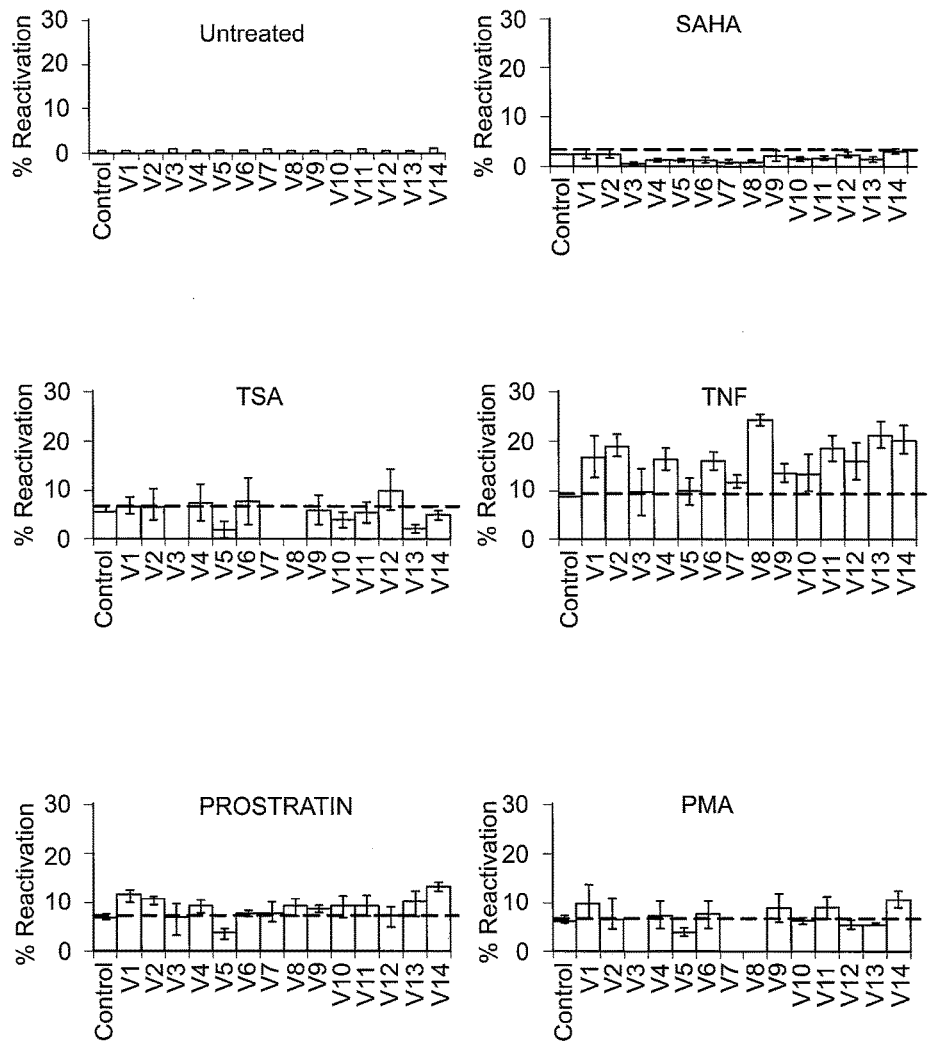
FIG. 9 schematically depicts a result obtained in Jurkat T-cells, wherein HIV-1 latency was reactivated with a set of variability enhancers V1-V14 and tested for reactivation with HDAC inhibitors SAHA (upper right) and TSA (middle left) and PKC agonists that activate the HIV-1 LTR NF-$K_B$ sites, such as TNF (middle right), Prostratin (lower left), and PMA (lower right). SAHA and TSA, known activator drugs for HIV-1 latency also were identified herein as VEs. Details are described in Example 6. "Untreated", VEs V1 through V14 only. "Control" shows activator drugs only—without addition of VE. Details are described, e.g., in Example 6.

Variability Modulators can Antagonize the Activation of Latent Gene Expression by Another Variability Enhancer, E.G., SAHA The JLat 8.6 cell line, a model of HIV-1 latency in Jurkat T-cells, was reactivated with a set of variability enhancers V1-V14 and tested for reactivation with HDAC inhibitors SAHA and TSA, and PKC agonists that activate the HIV-1 LTR NF-$K_B$ sites (TNF, Prostratin and PMA). The result of this study is shown in FIG. 9. It is noteworthy that in combination with most variability enhancers, reactivation of latent HIV-1 was suppressed by combining a variability enhancer with SAHA, which by itself is an activator and variability enhancer. This study demonstrates that variability enhancement can antagonize the activation of another variability enhancer and activator, such as SAHA, which is commonly used in the field, such that both categories of VMs can antagonize reactivation of latency and variability can be used to characterize which type of transcriptional activator the VM is antagonizing.

Example 7

Variability Modulators Change Burst Size Through Independent Mechanisms Different from SAHA In the following type of comparative reactivation it was investigated how the VMs V1 through V14 decrease or antagonize SAHA-mediated latent HIV-1 reactivation.

Example 8

Identification of Noise-Enhancer Compounds that Synergize with Activators

Figure 13A:
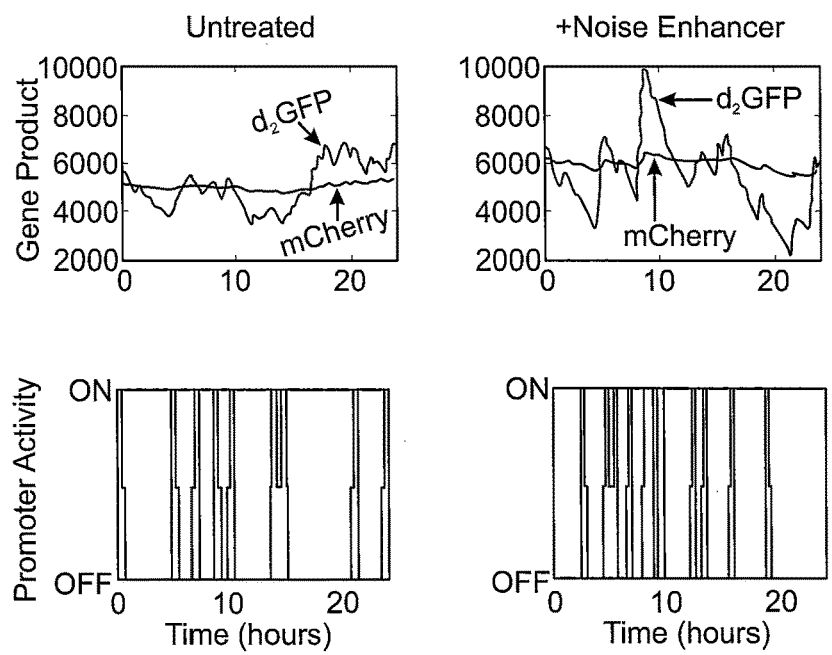
FIGS. 13A and 13B schematically depict identification of 25 post-transcriptional modulators using a two-reporter system.
Figure 13B:
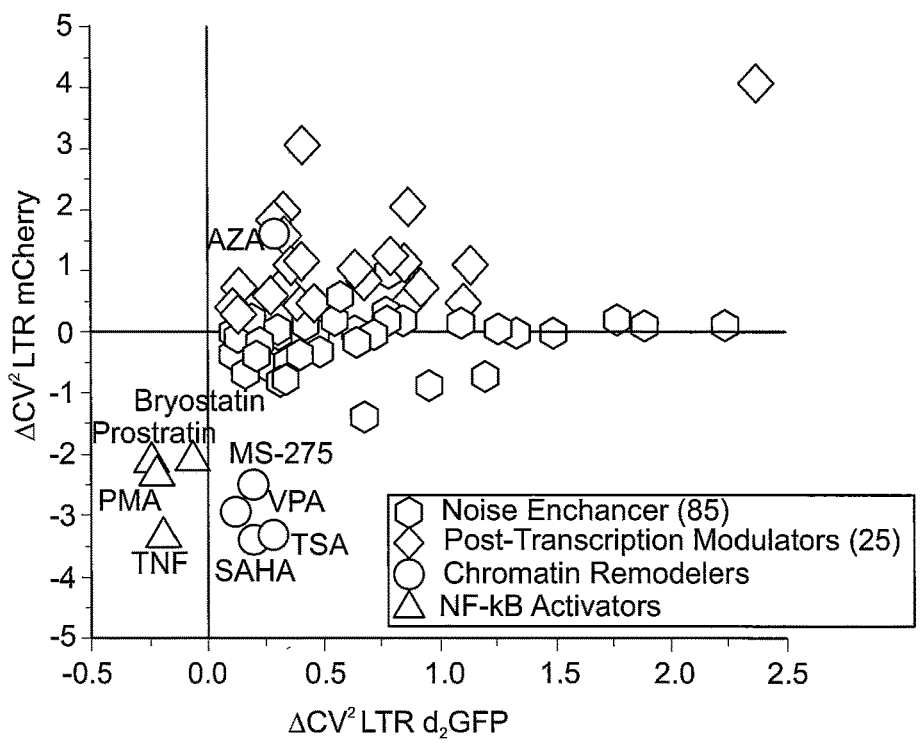

To find noise-enhancer compounds that synergize with activators (i.e., VEs), compounds that were transcriptional modulators were identified using a stable mCherry reporter driven off a second LTR integration (FIG. 13). The differential stability of mCherry and $d_2$GFP allowed the selection of compounds that enhanced transcriptional noise. This two-reporter assay filtered out 25 compounds, leaving 85 transcriptional noise-enhancer compounds (see also, FIG. 6A and FIG. 11). To ensure that the observed noise enhancement was not an artifact of a specific HIV-integration site, a single-cell microscopy approach (19) was used. Noise enhancement across a broad spectrum of HIV-1 integration sites was observed (see, FIG. 6C).

Example 9

Further Optimization of Reactivation

Figure 16:
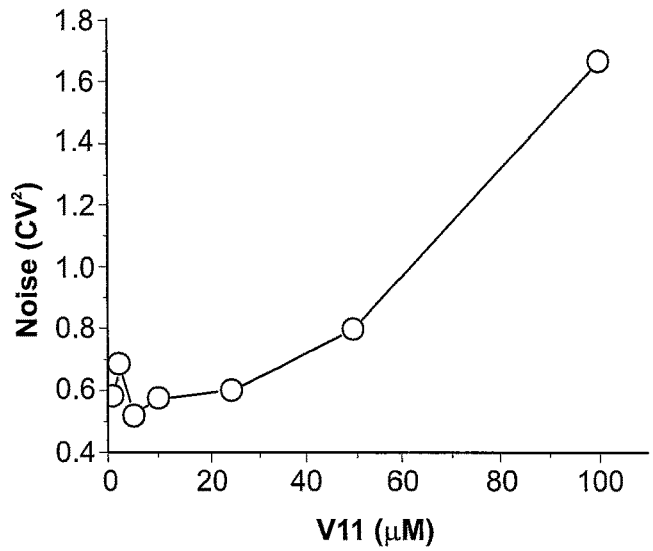
FIG. 16 schematically depicts that noise enhancement of the LTR promoter increases with V11 concentrations. Treatment of the drug screen LTR-d$_2$GFP cell line with increasing V11 concentration yields an increasing trend in gene expression noise. Details are described, e.g., in Example 9.
Figure 17:
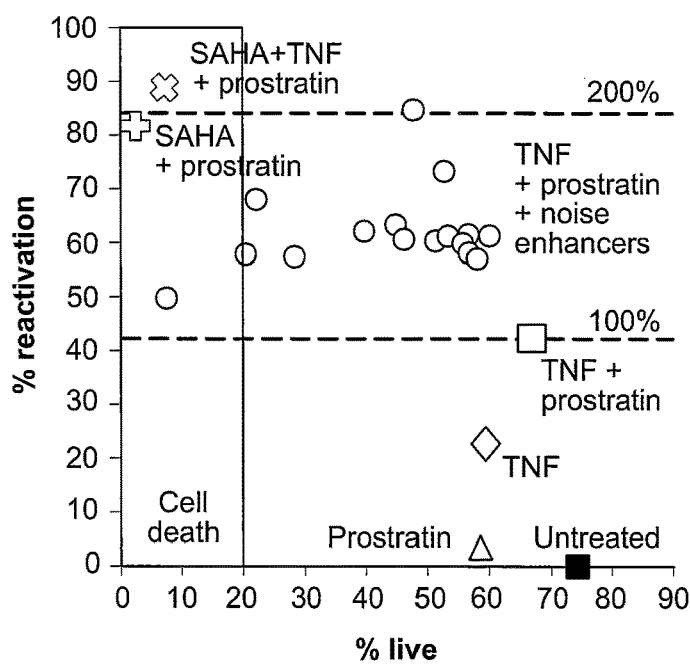
FIG. 17 schematically depicts reactivation percentage versus drug toxicity for conventional reactivation cocktails (e.g. TNF+Prostratin, SAHA+Prostratin, SAHA+TNF+ Prostratin) and 21 cocktails containing noise-enhancer compounds in combination with TNF+Prostratin. Controls: TNF alone, Prostratin alone, and Untreated, as indicated. Measurements were performed in duplicate on JLat cell line 8.6 after 48 h treatment. Viability measurements in uninfected cells indicate that reduced viability resulted from chemical cytotoxicity and not viral reactivation (data not shown and FIG. 16). % live; percentage of viable cells after treatment as indicated. Details are described, e.g., in Example 9.

To test whether reactivation could be further optimized, the doses of noise enhancers and activators were varied (FIG. 14). The dose-response matrix for TNF or Prostratin with Cetirizine Hydrochloride (noise enhancer V11) exhibited a peak in HIV-1 reactivation at 25 μM V11 (see also FIG. 15), and achieved greater reactivation than was caused by TNF or Prostratin alone (FIG. 7E and FIG. 16). Moreover, noise-enhancer cocktails exhibited substantially less off-target cytotoxicity than did other reactivation cocktails. Leading reactivation cocktails were compared to 21 combinations of a noise enhancer with TNF+Prostratin (FIG. 17).

All noise-enhancing cocktails increased reactivation by ~150-200% over TNF+Prostratin, with minimal cytotoxicity compared to SAHA—a leading candidate which enhances reactivation (Gillespie, (1977) *J Phys Chem* 81:2340-2361) but generates substantial off-target cytotoxicity for uninfected cells (as confirmed by propidium iodine (PI) control staining (Asin et al. (2008) *AIDS Res Hum Retroviruses* 24:701-716); data not shown).

Example 10

Synergism of Noise Enhancers with PMA

Figure 18A:
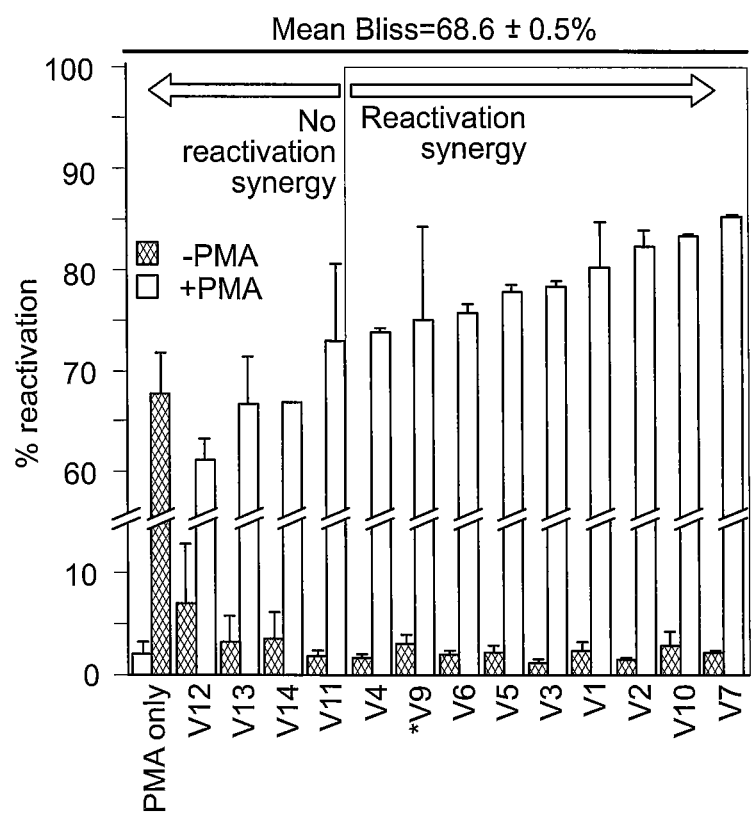
FIGS. 18A-C schematically depict that noise-enhancer cocktails improve HIV-1 reactivation with reduced toxicity and function in primary cells and that noise-suppressor cocktails limit reactivation in both cell lines and primary cells.
Figure 18B:
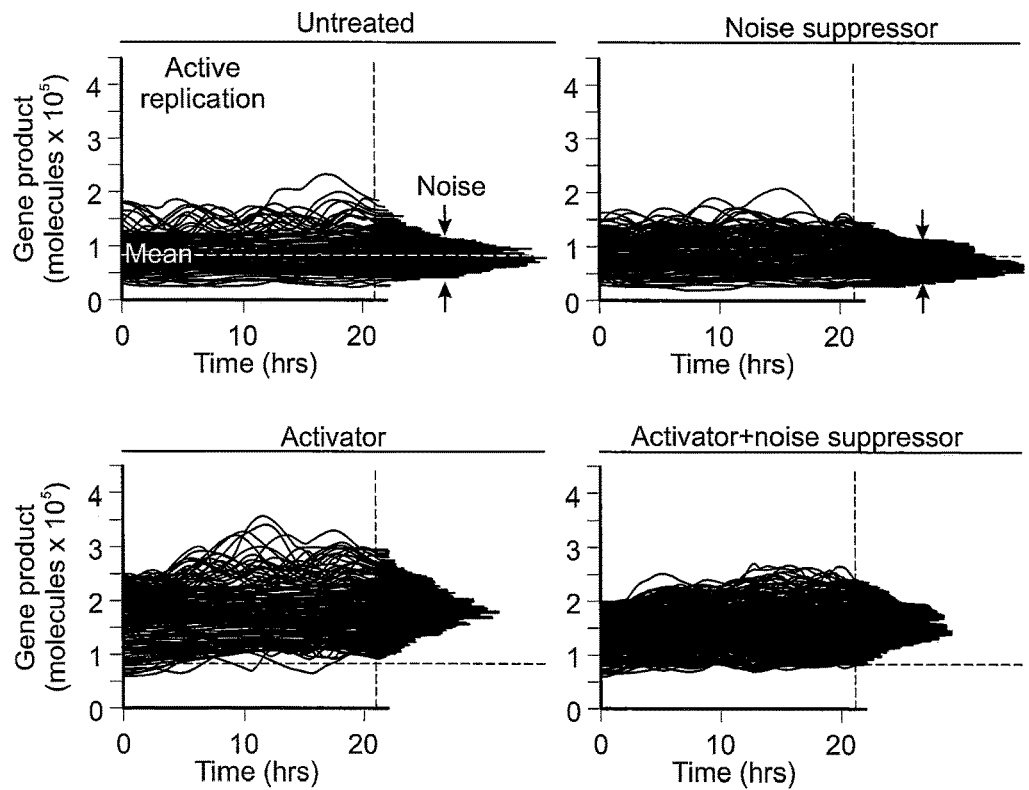
Figure 18C:
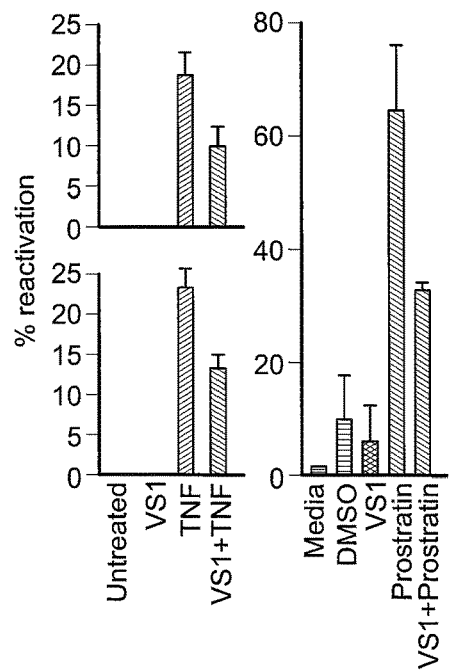

It was found herein that in a primary T-cell model of HIV-1 latency (Fernandez-Fernandez et al., (2005) *Proc Natl Acad Sci USA* 102:4735-4740) >60% of noise enhancers tested synergized with PMA (FIG. 18A), with some compounds reactivating half of the remaining cells that PMA alone did not reactivate (e.g. mebendazole, V7). Moreover, in both Jurkat and primary T-cell models, noise suppression with manidipine hydrochloride, or compound VS1, substantially reduced latent reactivation, as predicted from theory (FIGS. 18B, C). While, some considerable technical challenges in identifying noise suppressors—due to the extrinsic noise threshold have been described (e.g., see, Yang et al. (2009) *J Clin Invest* 119:3473-3486)—Applicants' surprising and unexpected findings described herein demonstrate that noise suppression can ultimately be used in strategies to limit spontaneous reactivation of latent HIV-1, to stabilize other fate-specification processes, and to identify antagonistic drug combinations.

Example 11

The Two-Reporter Method to Filter for Transcriptional Noise Enhancement

The two-color method using differential stability reporters is based upon a derived theory (9, 12). The theory shows that the transcriptional bursting component of the total noise is negligible for stable long-lived reporters.

$$CV^2_{TOTAL} = CV^2_{POISSON} + CV^2_{TRANSCRIPTIONAL\,BURSTING} + CV^2_{EXTRINSIC}$$

$$CV^2 = \frac{1}{\langle p \rangle}b + C_k\frac{(1-O)}{O} + C_{ext}$$

and $$\langle p \rangle = \frac{k_m O b}{\gamma_p};$$

$$O = \frac{k_{ON}}{k_{ON} + k_{OFF}}$$

where b is the translational burst rate (or the average number of proteins translated from each mRNA), O is the fraction of time spent in the ON state (referred to as the "on fraction"), and $C_k$ is a scaling factor that approaches 0 for fast bursting ($k_{ON}+k_{OFF} \gg \gamma_p$, e.g. long-lived mCherry) and 1 for slow bursting ($\gamma_p \gg k_{ON}+k_{OFF}$, e.g. d$_2$GFP) relative to the protein reporter stability used.

In addition to the GFP reporter in the LTR-d$_2$GFP cell line, an LTR driving a long half-life mCherry reporter was present in the cell line. This differential-stability 2-reporter system enabled the differentiation between drugs that were primarily extrinsic (global cellular resources) and post-transcriptional variability modifiers in which the noise magnitude changed significantly in both reporters. To remove compounds that altered $CV^2$ post transcriptionally, compounds that affected the $CV^2$ long-lived red reporter while conserving its mean mCherry level were removed. This method continues development of the original and decade-old 2-reporter system for intrinsic versus extrinsic noise measurements in bacteria (Elowitz et al., (2002) *Science* 297:1183-1186).

Figure 19A:
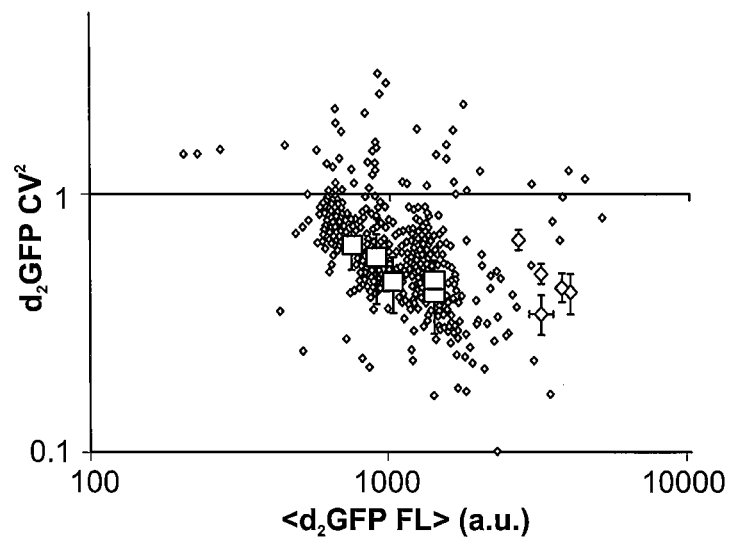
FIGS. 19A-C schematically depict the use of a two reporter method to filter for transcriptional noise enhancement.
Figure 19B:
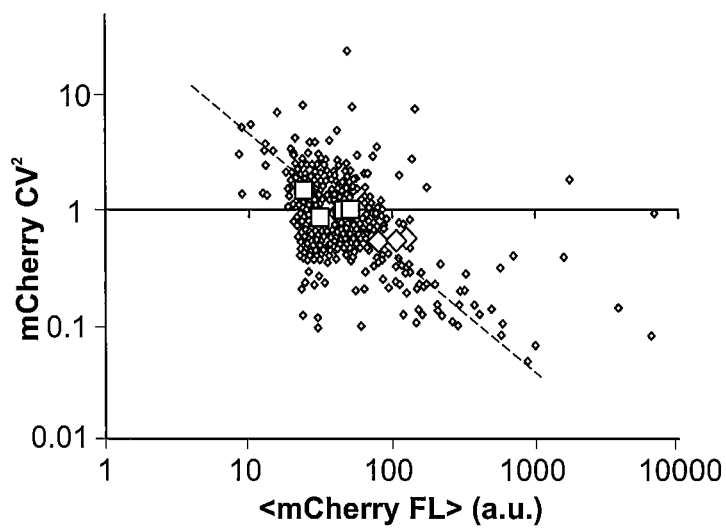
Figure 19C:
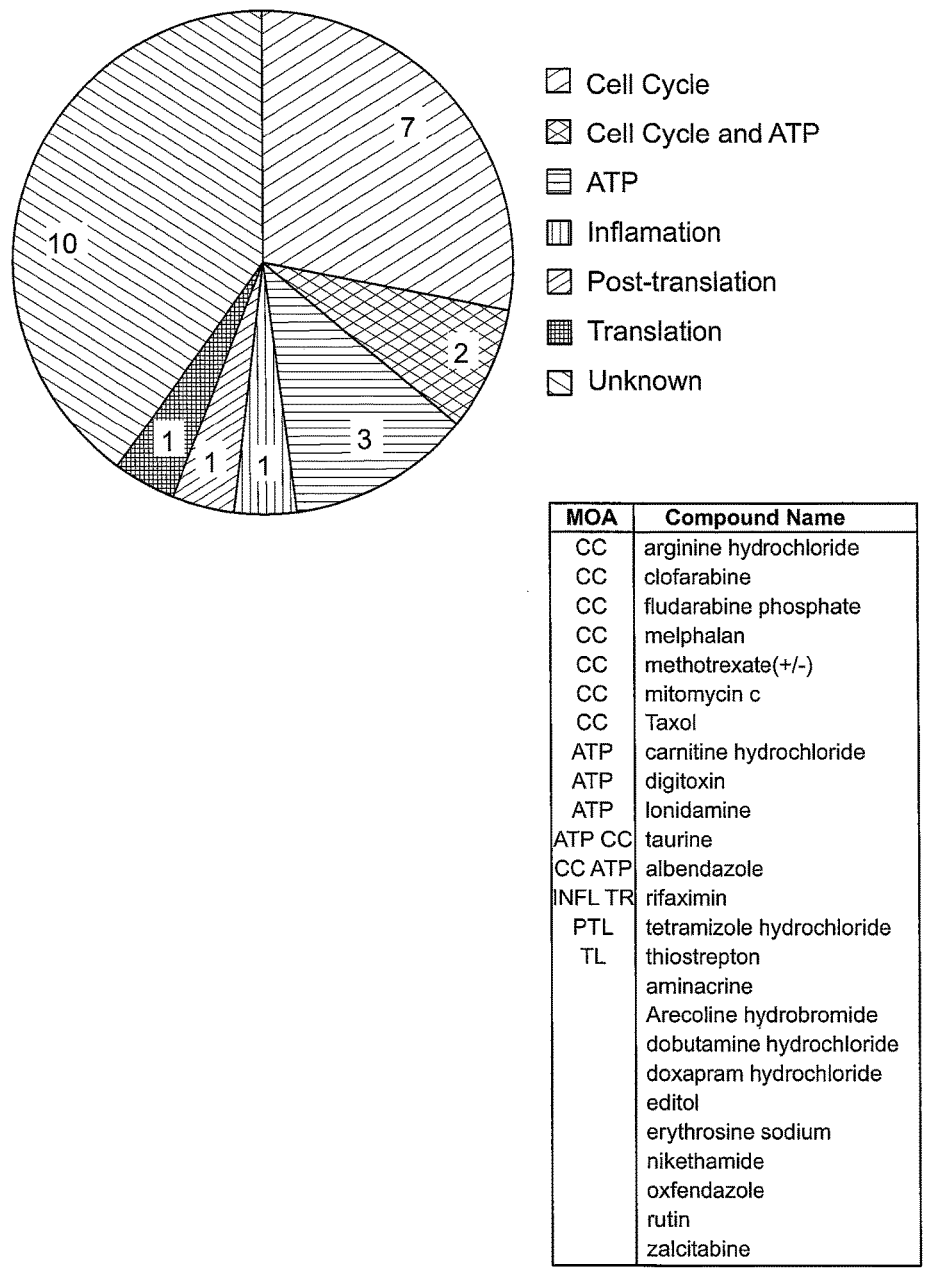

Noise versus mean fluorescence for all compounds screened on both the d$_2$GFP and mCherry channels are shown in FIG. 19A. Simultaneous changes in both d$_2$GFP and mCherry noise enabled the identification of compounds causing non-transcriptional perturbations. From 5 plate sets screened (as described above), 25 compounds were identified that enhanced noise in both reporters by more than 2–σ. Those 25 compounds are shown in FIG. 19B.

Example 12

Perspective

The data provided herein, to the Applicants' knowledge, provides the first report of a drug screen for modulating variability of gene expression of a gene promoter in a disease model whose phenotype is greatly biased at the single-cell level. Systems such as viral latency, in particular, HIV-1 latency, tumor metastasis, and fungal or bacterial persistence are statistical in nature making a variability or noise drug screen with an established theoretical underpinning suitable. Modulating a drug response distribution can aid biasing individual single-cells on the population distribution tail that can potentially rebound the disease phenotype of a patient post-treatment. Reactivation of the latent HIV-1 reservoir has been identified as the primary barrier in eradication of the virus and the latent cell sub-population were chosen as a clinically relevant model system with two main components currently required for the screen: (1) the drug exposed mechanisms that generate variability of gene expression of the gene promoter must also bias the phenotypic decision of the virus between latency and active replication (e.g. nucleosome occupancy or regulators of the promoter), and (2) the ability to decompose the full-length HIV-1 regulatory architecture into a two-stage screening process to isolate variability modulators of gene promoter expression from the promoter regulated within the context of full-length viral circuitry. Synergistic activation of the latent phenotype was only assayed in the second phase of the screen after VMs were identified.

Both variability in gene expression and mean expression level response of the HIV-1 LTR promoter to 1,600 FDA approved drugs were measured. Drugs both increased and decreased variability in gene expression and expression levels relative to the untreated LTR. To select for drugs that potentially increase transcriptional burst size a subset of 85 drugs that increased variability in gene expression in relation to their untreated LTR target (so-called variability enhancers, VEs) was identified and exposed in combination with transcriptional activators on a latency model of the virus in cell lines and in primary cells (a subset of 85 drugs only). It was found that the combination of VMs with activators can increase latent HIV-1 reactivation and further bias the viral fate decision between active replication and latency compared to activator drugs alone. Previously used transcriptional modulators such as histone deacetylase inhibitors (HDACis), methylation, and bromodomain protein inhibitors that synergize with TNFα or Prostratin significantly enhance variability in gene expression and transcriptional burst size. In cell lines reactivation was increased by more than half of the discovered VMs in combination with TNFα and Prostratin (FIG. 7A). In addition, a protective function of VM drugs was observed in dose response surfaces where similar reactivation levels can be reached by increasing VM concentration while decreasing activator drug concentrations which is currently a concern for clinical application (FIG. 7D). The use of variability suppressors was demonstrated to decrease reactivation of an assortment of activator drugs.

Integration site dependency of the drug screen target was investigated as studies have shown that local chromatin environment affects transcriptional bursting of the LTR along with burst modulation by signaling molecules (Singh et al., 2010, *Biophys J* 98:L32-L34; Dar et al., 2012, *Proc Natl Acad Sci USA* 109:17454-17459). Single-cell time-lapse microscopy of polyclonal LTR $d_2$GFP populations treated with three VMs demonstrated variability enhancement across hundreds of integration sites suggesting that the VMs are not specific to the drug screen target used in the current study. This shotgun imaging approach was implemented on the LTR treated with JQ1 (Boehm et al., 2013, *Cell Cycle* 12:452-462) and showed a global increase in noise magnitude which agrees with JQ1 as a VM on the current isoclone used in the screen (FIG. 6D). This polyclonal microscopy approach can be used to ensure that a VM hit is not exclusive to a specific drug screen target in future noise drug screens.

Screening with a two-reporter system offered an additional use of biological fluctuations for the classification of drug effects. The differential stability of the two-reporters allowed one to distinguish whether a compound treatment is more heavily post-transcriptional or global resource related (extrinsic), or a mixture of both. Known transcriptional activators provided controls for the approach. 25 variability enhancing compounds were excluded and were found to be mostly non-transcriptional and would have reduced our probability of finding novel synergistic compounds that directly affect HIV-1 transcription. According to Applicants' knowledge, this is the first report that utilizes the noise of a two-reporter system for the classification of drug compounds on a disease model in human cells and demonstrates the evolution and advancement of the original decade-old bacterial system (Elowitz et al., 2002, *Science* 297:1183-1186). The original plasmid-based two-reporter system took great care in careful positioning of the two reporter sequences for precise comparison of extrinsic and intrinsic noise contributions. Although the differential stability two-reporter system quantified expression from different integration sites, discriminating between extrinsic and intrinsic noise dominated drug effects was still possible. An alternate set of integration sites were tested using the differential stability system and demonstrated increasing transcriptional variability ($d_2$GFP) modulation with dose responses of both trichostatin A (TSA) and SAHA.

From a pharmaceutical science and drug screening perspective, Applicants have generated a new variability axis that can detect drugs which are currently overlooked by conventional screens and do not substantially change the mean expression levels of the system when used alone. Using dynamic proteomics, Cohen et al. elucidated the escape of cells from an anti-cancer drug by cell-to-cell variation in the dynamics of specific proteins (Cohen et al., 2008, *Science* 322:1511-1516). Screening for variability modulators provides an additional single-cell framework for drug characterization where detailed mechanisms of action may be enabled in the development of future noise drug screens. For HIV-1 latency, this approach will provide a novel repertoire of drugs that potentially synergize with activators for increased reactivation as the field moves away from searching for a single compound solution. The hit rate in the current study is notably higher than most HIV-1 latency drug screens. Larger screens, dose responses, and optimization of this approach may bring us closer to a clinical solution and the holy grail of purging the latent reservoir for complete eradication of HIV-1 from infected patients. Furthermore, noise drug screening methods such as those described herein can be of benefit in other systems in which a phenotype can rebound from the activity of a single cell, such as establishing or maintaining cell-fate specification of a stem cell, establishing or maintaining viral latency, establishing or maintaining tumor metastasis and establishing or maintaining fungal or bacterial persistence.

All publications, including but not limited to patents and patent applications, cited in this specification, to the extent that they provide exemplary procedural or other details supplementary to those set forth herein, are specifically incorporated herein by reference as if each individual publication were specifically and individually indicated to be incorporated by reference herein as though fully set forth

What is claimed is:

1. A method of screening for a variability modulator modulating variability of expression of a gene promoter, the method comprising the step of:
   (a) contacting a first compound to a cell comprising:
      (i) a first reporter gene comprising a gene promoter; wherein the gene promoter controls expression of the first reporter gene; and
      wherein the first compound, when compared to a control compound, modulates variability of expression of the gene promoter without substantially changing the mean expression level of the gene promoter.

2. The method according, to claim 1, further comprising the step of:
   (b) determining a first variability in gene expression of the gene promoter after step (a).

3. The method according to claim 2, further comprising the step of:
   (c) determining a second variability in gene expression of the gene promoter after contacting the cell with the control compound.

4. The method according to claim 3, further comprising the step of:
   (d) identifying the first compound as a variability modulator when the first variability in gene expression of the gene promoter is substantially different from the second variability in gene expression of the gene promoter.

5. The method according to claim 4, further comprising the step of:
   (e) identifying the variability modulator as a variability suppressor when the first variability in gene expression of the gene promoter is lower when compared to the second variability in gene expression of the gene promoter or as a variability enhancer when the first variability in gene expression of the gene promoter is higher when compared to the second variability in gene expression of the gene promoter.

6. The method according to claim 1, further comprising the step of:
   (b) contacting a second compound to the cell.

7. The method according to claim 6, further comprising the step of:
   (c) determining the mean expression level of the gene promoter after step (b).

8. The method according to claim 6, further comprising the step of:

(c) identifying the first compound as a synergistic variability enhancer when the first compound and the second compound synergistically activate gene expression from the gene promoter.

9. The method according to claim 6, further comprising the step of:
(c) identifying the first compound as a variability suppressor when the first compound and the second compound reduce the mean expression level of the gene promoter as determined either after step (a) or after contacting only the second compound to the cell.

10. The method according to claim 1, wherein the gene promoter is a promoter involved in establishing or maintaining cell-fate specification of a stem cell, establishing or maintaining viral latency, establishing or maintaining Human Immunodeficiency Virus-Type 1 (HIV-1) latency, establishing or maintaining tumor metastasis, establishing or maintaining fungal persistence or establishing or maintaining bacterial persistence.

11. The method according to claim 10, wherein the gene promoter is an HIV-1 long terminal repeat (LTR) promoter.

12. The method according to claim 1, wherein the method is a high-throughput screening method.

13. The method according to claim 1, wherein the method composes fluorescence microscopy, FISH, detection of a fluorescent protein, single-cell RNA sequencing, or flow cytometry.

14. The method according to claim 1, wherein the cell is selected from the group consisting of a prokaryotic cell, a eukaryotic cell, a fungal cell, and a mammalian cell.

15. The method according to claim 14, wherein the mammalian cell is a human cell.

16. The method according to claim 15, wherein the human cell is a human T cell.

17. The method according to claim 16, wherein the T cell is selected from the group consisting of a Jurkat cell, a MT-4 cell, a CEM cell, a SupT1 cell, and a primary T-cell.

18. The method according to claim 6, wherein the second compound is an activator of gene expression selected from the group consisting of a prokaryotic activator of gene expression, a viral activator of gene expression and a eukaryotic activator of gene expression.

19. The method according to claim 18, wherein the viral activator of gene expression is an activator of Human Immunodeficiency Virus Type 1 (HIV-1) gene expression.

20. The method according to claim 19, wherein the activator of HIV-1 gene expression is selected from the group consisting of a protein kinase C (PKC) agonist, an inhibitor of histone deacetylase, an inhibitor of methylation, an inhibitor of a bromodomain protein, and an anticancer drug.

21. The method according to claim 20, wherein the PKC agonist is selected from the group consisting of tumor necrosis factor α (TNFα), prostratin, PMA and bryostatin, single stereoisomers, mixtures of stereoisomers, pharmaceutically acceptable salts or prodrugs thereof.

22. The method according to claim 20, wherein the inhibitor of histone deacetylase is selected from the group consisting of DPP, Suberoylannilide Hydroxamic Acid (SAHA), MS-275, valproic acid) (VPA), and trichostatin A (TSA), single stereoisomers, mixtures of siereoisomers, pharmaceutically acceptable salts or prodrugs thereof.

23. The method according to claim 20, wherein the inhibitor of methylation is selected from the group consisting of azacitidine, fludarabine, and adenosine, single stereoisomers, mixtures of stereoisomers, pharmaceutically acceptable salts or prodrugs thereof.

24. The method according to claim 20, wherein the inhibitor of the bromodomain protein is selected from the group consisting of JQ1, GSK1210151A, and PFI-1, single stereoisomers, mixtures of stereoisomers, pharmaceutically acceptable salts or prodrugs thereof.

25. The method according to claim 20, wherein the anticancer drug is cytarabine single stereoisomers, mixtures of stereoisomers, pharmaceutically acceptable salts or prodrugs thereof.

26. The method according to claim 1, wherein the first compound is a member of a library.

27. The method according to claim 26, wherein the library is selected from the group consisting of a small molecule library, a fragment library, a peptide library, an RNAi library, a shRNA library, and a miRNA library.

28. The method according to claim 1, wherein the first reporter gene is a gene selected from the group consisting of a gene encoding a green fluorescent protein (GFP), a gene encoding a red fluorescent protein (RFP or mCherry) a gene encoding a cyan fluorescent protein (CFP), and a gene encoding a yellow fluorescent protein (YFP).

29. The method according to claim 28, wherein the gene is a gene encoding GFP.

30. The method according to claim 1, wherein the first reporter gene produces a reporter protein product having a half-life of between 0.1-40 hours.

31. The method according to claim 1, wherein the cell further comprises:
(ii) a second reporter gene under control of the gene promoter and wherein the second reporter gene produces a second reporter protein product having a different stability than a first reporter protein product produced by the first reporter gene.

32. The method according to claim 6, wherein the first and second compounds combined increase burst frequency and burst size of the first reporter gene.

33. The method according to claim 1, wherein the first compound is selected from the group consisting of thiamylal sodium, Estramustine, griseofulvin, telmisartan, docetaxel, riboflavin, pantothenic acid(d) na salt, mercaptopurine, pemettexed, ethinyl estradiol, irinotecan hydrochloride, dutasteride, felbinac, vincristine sulfate, thiram, bezafibrate, Indomethacin, mebendazole, ouabain, sulfaquinoxaline sodium, oxybutynin chloride, oxyphencyclimine hydrochloride, saxagliptin, phenylmercuric acetate, troclosene potassium, artemisinin, cytarabine, thioguanine, hydroquinone, acetophenazine maleate, hexylresorcinol, oxytetracycline, cefadroxil, tolnaftate, phenylbutyric acid, atorvastatin calcium, carboplatin, 5-azacytidine, levodopa, lamivudine, sotalol hydrochloride, clavulanate lithium, digoxin, sodium monofluorophosphate, dexpanthenol, rabeprazole sodium, cetirizine hydrochloride, trilostane, modafinil, thiabendazole, adapalene, sulfameter, Fluoxetine hydrochloride, trimethobenzamide hydrochloride, Metoclopramide hydrochloride, guanethidine sulfate, trichlormethine, sucralfate, valganciclovir hydrochloride, bemotrizinol, parachlorophenol (±)-Verapamil hydrochloride, oxidopamine hydrochloride, fomepizole hydrochbride, Xylazine hydrochloride, diperodon hydrochloride, zomepirac sodium, closantel, fenbendazole, finasteride, Procainamide hydrochloride, celecoxib, colistin sulfate, imipenem, cefoxitin sodium, azithromycin, clidinium bromide, Tolazamide, chlorpheniramine maleate, colesevalam hydrochloride, Pargyline hydrochloride, hydralazine hydrochloride, anastrozole, vinorelbine, bleomycin, dasatinib, busulfan, vorinostat, selamectin, idoxuridine, carvedilol, (±)-Isoproterenol hydrochloride, racephedrine hydrochloride, vardenafil hydrochloride, guaiacol, clobetasol propionate, mycophenolic acid, fludrocortisone acetate, zaleplon, nitroglycerin, riboflavin 5-phosphate sodium, acetriazoic acid, digitoxin, carnitine hydrochloride, albendazole, taurine, Taxol, mitomycin c, clofarabine, arginine hydrochloride, tetramizole hydrochloride, thiostrepton, lonidamine, melphalan, fludarabine phosphate, methotrexate(+/−),rifaximin, Arecoline hydrobromide, zalcitabine, erythrosine sodium, nikethamide, oxfendazole, editol, doxapram hydrochloride, aminacrine, dobutamine hydrochloride, rutin, single stereoisomers, mixtures of stereoisomers, pharmaceutically acceptable salts, prodrugs and functional derivatives thereof.

34. The method according to claim 1, wherein the first compound is selected from the group consisting of docetaxel, ethinyl estradiol, estramustine, felbinac, bezafibrate, mebendazole, thiamylal sodium, mercaptopurine, dutasteride, cetirizine hydrochloride, acetophenazine maleate, oxytetracycline, artemisinin, hydralazine hydrochloride, Indomethacin, atorvastatin calcium, guanethidine sulfate, pantothenic acid(d) na salt, saxagliptin, (Â±)-Verapamil hydmchloride, oxidopamine hydrochloride, trilostane, fotnepizole hydrochloride, modafinil, Xylazine hydrochloride, diperodon hydrochloride, zomepirac sodium, thiabendazole, closantel, hexylresorcinol, adapalene, finasteride, Procainarmide hydrochloride, cefadroxil, sulfameter, sulfaquinoxaiine sodium, azithromycin, imipenem, colistin sulfate, cefoxitin sodium, oxyphencyclimine hydrochloride, oxybutynin chloride, clidinium bromide, Fluoxetine hydrochloride, Tolazamide, trimethobenzamide hydrochloride, Metoclopramide hydrochloride, tolnaftate, chlorpheniramine maleate, phenylburyric acid, colesevalam hydrochloride, Pargyline hydrochloride, telmisartan, troclosene potassium, bleomycin, dasatinib, anastrozole, busulfan, carboplatin, pemetrexed, hydroquinone, selamectin, levodopa, sucralfate, valganciclovir hydrochloride, lamivudine, idoxuridine, sotalol hydrochloride, carvedilol, clavulanate lithium, (Â±)-Isoproterenol hydrochloride, racephedrine hydrochloride, sodium monofluorophosphate, dexpanthenol, vardenafil hydrochloride, guaiacol, rabeprazole sodium, clobetasol propionate, mycophenolic acid, fludrocortisone acetate, zaleplon, hemotrizinol, parachlorophenol, nitroglycerin, and acetriazoic acid, single stereoisomers, mixtures of stereoisomers, pharmaceutically acceptable salts, prodrugs and functional derivatives thereof.

35. The method according to claim 1, wherein the first compound is selected from the group consisting of docetaxel, ethinyl estradiol, estramustine, feibinac, bezafibrate, mebendazole, mercaptopurine, dutasteride, cetirizine hydrochloride, acetophenazine maleate, oxytetracycline, artemisinin, single stereoisomers, mixtures of stereoisomers, pharmaceutically acceptable salts, prodrugs and functional derivatives thereof.

36. The method according to claim 20, wherein the activator of HIV-1 gene expression is the protein kinase C (PKC) agonist.

37. The method according to claim 22, wherein, the inhibitor of histone deacetylase is valproic acid (VPA).

38. The method according to claim 21, wherein the PKC agonist is TNFα.

39. The method according to claim 23, wherein the methylation inhibitor is azacytidine.

40. The method according to claim 24, wherein the bromodomain inhibitor is GSK1210151A.

41. The method according to claim 21, wherein the PKC agonist is bryostatin.

42. The method according to claim 14, wherein the mammalian cell is in vitro.

43. The method according to claim 14, wherein the mammalian cell is in vivo.

44. The method according to claim 6, further comprising the step of:
(c) contacting the cell with a HAART compound.

45. The method according to claim 1, wherein the first compound is selected from the group consisting of manidipine hydrochloride, phenothiazine, dichlorvos, fipronil, trichlorfon, beuzydatnine hydrochloride, maprotiline hydrochloride, Papaverine hydrochloride, arsenic trioxide, phenformin hydrochloride, itraconazole, cycloheximide, hydroxyprogesterone caproate, pyrithione zinc, meeloeycline sulfosalicylate, ergotamine tartrate, adenosine phosphate, broxaldine, single stereoisomers, mixtures of stereoisomers, pharmaceutically acceptable salts, prodrugs and functional derivatives thereof.

* * * * *